US008729089B2

(12) United States Patent
Bondy et al.

(10) Patent No.: US 8,729,089 B2
(45) Date of Patent: May 20, 2014

(54) PYRIDO(3,2-D)PYRIMIDINES USEFUL FOR TREATING VIRAL INFECTIONS

(75) Inventors: Steven S. Bondy, Danville, CA (US); Chien-hung Chou, Livermore, CA (US); William John Watkins, Saratoga, CA (US); Lee S. Chong, Newark, CA (US); Jennifer R. Zhang, Foster City, CA (US); Ruchika Mishra, San Jose, CA (US)

(73) Assignee: Gilead Sciences, Inc., Foster City, CA (US)

( * ) Notice: Subject to any disclaimer, the term of this patent is extended or adjusted under 35 U.S.C. 154(b) by 1018 days.

(21) Appl. No.: 11/963,723

(22) Filed: Dec. 21, 2007

(65) Prior Publication Data

US 2008/0182870 A1 Jul. 31, 2008

Related U.S. Application Data

(60) Provisional application No. 60/871,912, filed on Dec. 26, 2006, provisional application No. 60/922,165, filed on Apr. 6, 2007.

(51) Int. Cl.
*C07D 471/04* (2006.01)
*A61K 31/519* (2006.01)
*A61P 31/12* (2006.01)

(52) U.S. Cl.
USPC ..................................... 514/264.11; 544/279

(58) Field of Classification Search
USPC ..................................... 544/279; 514/264.11
See application file for complete search history.

(56) References Cited

U.S. PATENT DOCUMENTS

| | | | |
|---|---|---|---|
| 2,512,572 A | 6/1950 | Smith, Jr. et al. |
| 2,924,599 A | 2/1960 | Oaks et al. |
| 3,843,638 A | 10/1974 | Nicki et al. |
| 3,939,268 A | 2/1976 | Nickl et al. |
| 3,952,001 A | 4/1976 | Brookes et al. |
| 3,969,268 A | 7/1976 | Fukuda et al. |
| 4,460,591 A | 7/1984 | DeGraw et al. |
| 4,492,597 A | 1/1985 | Aoki et al. |
| 4,818,819 A | 4/1989 | Taylor et al. |
| 5,167,963 A | 12/1992 | DeGraw et al. |
| 5,223,503 A | 6/1993 | Gossett et al. |
| 5,508,281 A | 4/1996 | Gangjee |
| 5,521,190 A | 5/1996 | Henri, II et al. |
| 5,547,954 A | 8/1996 | Henrie, II et al. |
| 5,654,307 A | 8/1997 | Bridges et al. |
| 5,780,462 A | 7/1998 | Lee et al. |
| 6,331,547 B1 | 12/2001 | Zhu et al. |
| 6,440,991 B1 | 8/2002 | Zhu et al. |
| 6,476,031 B1 | 11/2002 | Chakravarty et al. |
| 6,521,620 B1 | 2/2003 | Bridges et al. |
| 6,562,818 B1 | 5/2003 | Bridges |
| 6,713,484 B2 | 3/2004 | Bridges et al. |
| 6,723,726 B1 | 4/2004 | Cockerill et al. |
| 6,730,682 B2 | 5/2004 | Schnute et al. |
| 6,946,465 B2 | 9/2005 | Waer et al. |
| 6,962,920 B2 | 11/2005 | Gangjee |
| 6,974,808 B2 | 12/2005 | McCarthy |
| 7,074,799 B2 | 7/2006 | Bakthavatchalam et al. |
| 7,276,506 B2 | 10/2007 | Waer et al. |
| 7,501,513 B2 | 3/2009 | Waer et al. |
| 2002/0049207 A1 | 4/2002 | McCarthy |
| 2003/0186987 A1 | 10/2003 | Bridges et al. |
| 2003/0199526 A1 | 10/2003 | Choquette et al. |
| 2003/0236255 A1 | 12/2003 | Waer et al. |
| 2004/0039000 A1 | 2/2004 | Gangjee |
| 2004/0077859 A1 | 4/2004 | Waer et al. |
| 2004/0106616 A1 | 6/2004 | Bakthavatchalam et al. |
| 2005/0014771 A1 | 1/2005 | Hayakawa et al. |
| 2006/0189620 A1 | 8/2006 | Waer et al. |
| 2006/0287314 A1 | 12/2006 | Waer et al. |
| 2007/0004721 A1 | 1/2007 | Waer et al. |
| 2007/0032477 A1 | 2/2007 | Waer et al. |
| 2007/0043000 A1 | 2/2007 | Waer et al. |
| 2008/0004285 A1 | 1/2008 | De Jonghe et al. |
| 2008/0312227 A1 | 12/2008 | De Jonghe et al. |

(Continued)

FOREIGN PATENT DOCUMENTS

DE   2 117 657   10/1972
DE   2 202 367   8/1973

(Continued)

OTHER PUBLICATIONS

Griesser, in Chapter 8, The Importance of Solvates (pp. 211-230), in the text, Polymorphism: In the Pharmaceutical Industry, Hilfiker, 2006.*
International Search Report for International Application No. PCT/EP2007/011496 mailed Apr. 17, 2008.
U.S. Appl. No. 13/176,627, filed Jul. 5, 2011, Herdewijn et al.
Colbry et al., "Synthesis and Antimalarial Properties of 2,4-Diamino-6-[(aryl)thio, sulfinyl, and sulfonyl]pyrido[3,2- d]pyrimidines," *J. Heterocyclic Chem.* 21:1521-1525, 1984.
Di Giacomo et al., "Synthesis and Biological Activity of New Melatonin Dimeric Derivatives," *Bioorg. Med. Chem.* 15:4643-4650, 2007.

(Continued)

*Primary Examiner* — Emily Bernhardt
*Assistant Examiner* — Cecilia M Jaisle
(74) *Attorney, Agent, or Firm* — Clark & Elbing LLP

(57) ABSTRACT

Pyrido(3,2-d)pyrimidine derivatives represented by the structural formula (I):

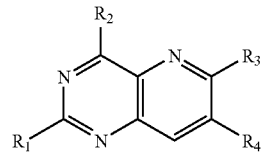

wherein:
$R_4$ is hydrogen, and
$R_1$, $R_2$ and $R_3$ together provide a specific substitution pattern,
pharmaceutical acceptable addition salts, stereochemical isomeric forms, N-oxides, solvates and pro-drugs thereof, are useful in the treatment of hepatitis C.

17 Claims, 8 Drawing Sheets

(56) References Cited

U.S. PATENT DOCUMENTS

| | | |
|---|---|---|
| 2009/0036430 A1 | 2/2009 | De Jonghe et al. |
| 2009/0131414 A1 | 5/2009 | De Jonghe et al. |
| 2009/0253696 A1 | 10/2009 | Herdewijn et al. |
| 2009/0285782 A1 | 11/2009 | Gao et al. |
| 2009/0318456 A1 | 12/2009 | Herdewijn et al. |
| 2010/0143299 A1 | 6/2010 | Gao et al. |
| 2010/0168416 A1* | 7/2010 | Goff et al. ............... 540/551 |
| 2010/0305117 A1 | 12/2010 | Herdewijn et al. |

FOREIGN PATENT DOCUMENTS

| | | |
|---|---|---|
| DE | 2 208 535 | 8/1973 |
| EP | 0 265 126 | 4/1988 |
| EP | 1 277 738 | 1/2003 |
| GB | 2 120 665 A | 12/1983 |
| WO | WO 94/27439 | 12/1994 |
| WO | WO 99/43681 | 9/1999 |
| WO | WO 99/43682 | 9/1999 |
| WO | WO 00/12497 | 3/2000 |
| WO | WO 01/83456 | 11/2001 |
| WO | WO 02/00623 | 1/2002 |
| WO | WO 02/22602 | 3/2002 |
| WO | WO 02/22607 | 3/2002 |
| WO | WO 03/062209 | 7/2003 |
| WO | WO 03/097615 | 11/2003 |
| WO | WO 2004/010929 | 2/2004 |
| WO | WO 2004/055004 | 7/2004 |
| WO | WO 2009003669 * | 6/2005 |
| WO | WO 2005/065691 | 7/2005 |
| WO | WO 2006/039718 | 4/2006 |
| WO | WO 2006/069805 | 7/2006 |
| WO | WO 2006/087229 | 8/2006 |
| WO | WO 2006/090169 | 8/2006 |
| WO | WO 2006/135993 | 12/2006 |
| WO | WO 2007/076092 | 7/2007 |
| WO | WO 2007/117394 | 10/2007 |
| WO | WO 2008/009076 | 1/2008 |
| WO | WO 2008/009079 | 1/2008 |

OTHER PUBLICATIONS

Durucasu, "Investigation of Different Synthetic Ways for Protection of 6-Bromo-5-Deazapterin," *Doga Tu J. Chem.* 13:280-292, 1989.

Griesser, "The Importance of Solvates," in *Polymorphism: in the Pharmaceutical Industry*, Ed. R. Hilfiker, Weinheim: Wiley-VCH Verlag GmbH & Co. KGaA, Ch. 8, pp. 211-233, 2006.

Hayakawa et al., "Synthesis and Biological Evaluation of 4-Morpholino-2-Phenylquinazolines and Related Derivatives as Novel PI3 Kinase p110a Inhibitors," *Bioorg. Med. Chem.* 14: 6847-6858, 2006.

Kuwada et al., "A New Synthesis of 6-Substituted Pyrido[2,3-d]Pyrimidines," *Heterocycles* 57:2081-2090, 2002.

Patani et al., "Bioisosterism: A Rational Approach in Drug Design," *Chem. Rev.* 96: 3147-3176, 1996.

Taylor et al., "A Convenient Synthesis of 6-Formyl-5-Deazapterin," *Synth. Commun.* 18:1187-1191, 1988.

Taylor et al., "Convergent and Efficient Palladium-Effected Synthesis of 5,10-Dideaza-5,6,7,8-tetrahydrofolic Acid (DDATHF)," *J. Org. Chem.* 54:3618-3624, 1989.

Taylor et al., "Protection and Deprotection of Fused 2-Amino-4(3H)-Pyrimidinones: Conversion of Pterins and 5-Deazapterins to 2,4-Diamino Derivatives," *Heterocycles* 36:1883-1895, 1993.

Temple et al., "Synthesis of Potential Antimalarial Agents. VIII. Azaquinolines. II. Preparation of Some 1, 5-Naphthyridines and Pyrido [3, 2-d] pyrimidines," *J. Heterocyclic Chem.* 7:1219-1222, 1970.

Vema et al., "Design of EGFR Kinase Inhibitors : A Ligand-Based Approach and its Confirmation with Structure-Based Studies," *Bioorg. Med. Chem.* 11:4643-4653, 2003.

Vippagunta et al., "Crystalline Solids," *Adv. Drug Del. Rev.* 48:3-26, 2001.

* cited by examiner

PYRIDO(3,2-D)PYRIMIDINES USEFUL FOR TREATING VIRAL INFECTIONS

CROSS-REFERENCE TO RELATED APPLICATIONS

This application claims benefit of U.S. provisional patent application Ser. Nos. 60/871,912 and 60/922,165, filed Dec. 26, 2006 and Apr. 6, 2007, respectively, now expired, the disclosures of each of which are incorporated herein by reference.

The present invention relates to a class of novel pyrido(3,2-d)pyrimidine derivatives. This invention also relates to pharmaceutical compositions comprising said pyrido(3,2-d)pyrimidine derivatives and one or more pharmaceutically acceptable excipients. The present invention further relates to the use of pyrido(3,2-d)pyrimidine derivatives as biologically active ingredients for manufacturing medicaments for the prevention or treatment of infection by a virus of the Flaviridae family, more specifically for inhibiting replication of hepatitis C virus.

BACKGROUND OF THE INVENTION

A huge number of pyrido(3,2-d)pyrimidine derivatives is already known in the art. For instance pyrido(3,2-d)pyrimidine derivatives with various substituents on positions 2, 4 and 6 (using the standard atom numbering for the pyrido(3,2-d)pyrimidine moiety) are known with biological activities such as competitive inhibition of pteroylglutamic acid, inhibition of thrombocyte aggregation and adhesiveness, antineoplastic activity, inhibition of dihydrofolate reductase and thymidylate synthase, e.g. from U.S. Pat. No. 2,924,599, U.S. Pat. No. 3,939,268, U.S. Pat. No. 4,460,591, U.S. Pat. No. 5,167,963 and U.S. Pat. No. 5,508,281.

Pyrido(3,2-d)pyrimidine derivatives with various substituents on positions 2, 4, 6 and 7 (using the standard atom numbering for the pyrido(3,2-d)pyrimidine moiety), some of them with biological activities, are also known e.g. from U.S. Pat. No. 5,521,190, U.S. patent application publication No. 2002/0049207, U.S. patent application publication No. 2003/0186987, U.S. patent application publication No. 2003/0199526, U.S. patent application publication No. 2004/0039000, U.S. patent application publication No. 2004/0106616, U.S. Pat. No. 6,713,484, U.S. Pat. No. 6,730,682 and U.S. Pat. No. 6,723,726.

U.S. Pat. No. 5,654,307 discloses pyrido(3,2-d)pyrimidine derivatives substituted on position 4 with monoarylamino or monobenzylamino, and on positions 6 and 7 with substituents each independently selected from the group consisting of lower alkyl, amino, lower alkoxy, mono- or dialkylamino, halogen and hydroxy. WO 01/083456 discloses pyrido(3,2-d)pyrimidine derivatives substituted on position 4 with morpholinyl and on position 2 with hydroxyphenyl or morpholinoethoxyphenyl, having PI3K and cancer inhibiting activity. U.S. Pat. No. 6,476,031 discloses substituted quinazoline derivatives, including (in reaction scheme 5) a series of pyrido(3,2-d)pyrimidine derivatives which are substituted on position 4 with hydroxy, chloro or an aryl, heteroaryl (including pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl), cycloaliphatic or cycloheteroaliphatic group being optionally spaced from the pyrido(3,2-d)pyrimidine ring by a linker such as NH. WO 02/22602 and WO 02/22607 disclose pyrazole and triazole compounds, including 2-(1-trifluoromethylphenyl)-4-fluorobenzopyrazolyl-pyrido(3,2-d)pyrimidine and 2-(1-trifluoromethylphenyl)-4-methyltriazolyl-pyrido(3,2-d)pyrimidine being useful as protein kinase inhibitors. WO 03/062209 discloses pyrido(3,2-d)pyrimidine derivatives substituted on position 7 with aryl or heteoaryl and on position 4 with monoarylamino or monoheteroarylamino and which may further be substituted on positions 2 and/or 6, being useful as capsaicin receptor modulators. WO 2006/069805 discloses pyrido(3,2-d)pyrimidine derivatives substituted on position 6 with aryl or heteoaryl and on both positions 2 and 4 with monoalkylamino, monocycloalkylamino, monoarylamino or monoarylalkylamino, and which may further be substituted on position 7, being useful in the treatment of a disease mediated by phosphodiesterase-4 activity. WO 2006/135993 discloses 2,4,6-trisubstituted pyrido(3,2-d)pyrimidine derivatives 2,4,6-trisubstituted useful in the treatment of hepatitis C.

However there is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer during the next ten years. The 15% to 45% of persons with acute hepatitis C who do recover are not subject to long-term complications and do not need treatment. Since HCV and pestiviruses belong to the same virus family and share many similarities (such as, but not limited to, organisation of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus *Flavivirus* (type species Yellow fever virus; others include West Nile virus and Dengue Fever), Genus *Hepacivirus* (type species Hepatitis C virus), and Genus *Pestivirus* (type species Bovine viral diarrhea virus (BVDV); others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease. Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and opthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anemia, which can be treated with erythropoietin. Other side effects include mood swings, irritability, anxiety, insomnia, abdominal pain, nervousness, breathlessness, rash, hair loss, dry skin, nausea, diarrhea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking other HCV-encoded proteins such as NS5A or by the conserved RNA elements employing a nucleic acid based approach including antisense oligonucleotides, ribozymes, RNA aptamers, RNA decoys, and RNA interference. A major drawback for such nucleic acid based approaches is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding that certain specific combinations of substituents on positions 2, 4 and 6 of the pyrido(3,2-d)pyrimidine core structure (using the atom numbering from standard nomenclature) which are not suggested by the available prior art are however able to meet one or more of the needs recited herein above, in particular to achieve derivatives having desirable pharmacological properties such as an activity against infection by a virus of the Flaviridae family, more particularly a significant HCV replication inhibiting activity.

Based on this finding the present invention relates, in a first embodiment, to a class of pyrido(3,2-d)pyrimidine derivatives represented by the structural formula (I):

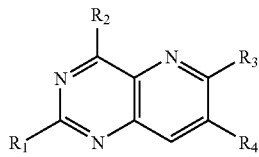

wherein:
- $R_1$ is —NH—CHR$_5$R$_6$ or —NH—R$_8$,
- $R_5$ and $R_6$ are independently selected from the group consisting of hydrogen, $C_{1-6}$ alkyl, $C_{3-10}$ cycloalkyl, aryl and heterocyclyl, wherein said aryl is substituted with one or more substituents selected from the group consisting of halogen, hydroxy, amino, nitro, cyano, trifluoromethyl, trifluoromethoxy, $C_{1-4}$ alkyl, $C_{1-4}$ alkoxy, di-$C_{1-4}$ alkylamino, mono-$C_{1-4}$ alkylamino, carboxamido, sulfamoyl, carbamoyl, sulfonamido, —SO$_2$NHR$_{13}$, —CON(R$_{13}$)$_2$, —NR$_{12}$COR$_{10}$, —SO$_2$R$_{13}$, —NHSO$_2$R$_{13}$ and phenoxy, and wherein said $C_{1-6}$ alkyl is optionally substituted with one or more substituents selected from the group consisting of halogen and $C_{1-4}$ alkoxy, and
- $R_8$ is selected from the group consisting of $C_{3-10}$ cycloalkyl, heteroaryl and aryl wherein said heteroaryl or aryl is optionally substituted with one or more substituents selected from the group consisting of halogen and $C_{1-4}$ alkyl and wherein said $C_{3-10}$ cycloalkyl is optionally substituted at the carbon position adjacent to the N atom of $R_1$ with aryl or heteroaryl wherein said aryl is optionally substituted with halogen;
- $R_2$ is XR$_7$ or is selected from the group consisting of N-morpholinyl, N-thiomorpholinyl and N-thiomorpholinyl dioxide;
- X is selected from the group consisting of O, S, NR$_{13}$ and CH$_2$;
- $R_7$ is selected from the group consisting of $C_{1-20}$ alkyl, $C_{3-10}$ cycloalkyl, aryl, heterocyclyl and aryl-$C_{1-4}$ alkyl; wherein said $C_{1-20}$ alkyl is optionally substituted with methylsulfonyl, 1-3 halogens or $C_{1-4}$ alkoxy when X is NH or said $C_{1-20}$ alkyl is optionally substituted with $C_{1-4}$ alkoxy, halo-$C_{1-4}$ alkoxy or heterocyclyloxy $C_{1-4}$ alkoxy when X is O;
- $R_4$ is hydrogen;
- $R_3$ is selected from the group consisting of optionally mono-substituted or disubstituted aryl and heterocyclyl, wherein at least one substituent of said aryl or heterocyclyl is selected from the group consisting of halogen, hydroxyl, amino, $C_{1-6}$ alkyl, $C_{1-6}$ alkoxy, —CONHR$_9$, —NR$_{12}$COR$_{10}$, —NR$_{12}$SO$_2$R$_{11}$, —SO$_2$NH$_2$, heterocyclyl and heterocyclyl substituted with one or more substituents independently selected from the group consisting of hydroxy, oxo, halogen, amino, $C_{1-6}$ alkyl and $C_{1-6}$ alkoxy;
- $R_9$ is selected from the group consisting of H, $C_{3-10}$ cycloalkyl optionally substituted with one more substituents selected from the group consisting of cyano, halogen, hydroxy, amino, $C_{1-6}$ alkyl and $C_{1-6}$ alkoxy; $C_{1-6}$ alkyl optionally substituted with one or more substituents selected from the group consisting of amino, alkylamino, cyano, dialkylamino, halogen, and heterocyclyl; $C_{1-6}$ alkoxy; heterocyclyl optionally substituted with $C_{1-6}$ alkyl; and phenyl optionally substituted with one or more halogens;
- $R_{10}$ and $R_{11}$ are each independently selected from the group consisting of $C_{1-6}$ alkyl optionally substituted with one or more substituents selected from the group consisting of amino, cyano, halogen and hydroxy; $C_{1-6}$ alkoxy optionally substituted with one or more substituents selected from the group consisting of amino, alkylamino, cyano, dialkylamino, halogen, and heterocyclyl; heterocyclyl optionally substituted with one or more substituents selected from the group consisting of $C_{1-6}$ alkyl, acylamino and oxo; $C_{3-10}$ cycloalkyl optionally substituted with one or more substituents selected from the group consisting of amino or hydroxy; and amino optionally substituted with one or more substituents selected from the group consisting of $C_{1-6}$ alkyl wherein said $C_{1-6}$ alkyl is optionally substituted with one or more substituents selected from the group consisting of amino, alkylamino, cyano, dialkylamino, halogen and heterocyclyl;
- $R_{12}$ is selected from the group consisting of H and $C_{1-6}$ alkyl, wherein said $C_{1-6}$ alkyl is optionally substituted with one or more substituents selected from the group consisting of cyano, halogen and hydroxy;
- each $R_{13}$ is independently selected from the group consisting of H and $C_{1-20}$ alkyl;

or a pharmaceutical acceptable addition salt or a stereochemical isomeric form thereof or a N-oxide thereof or a solvate thereof or a prodrug thereof.

The invention also relates, in a second embodiment, to a class of pyrido(3,2-d)pyrimidine derivatives represented by the structural formula (I):

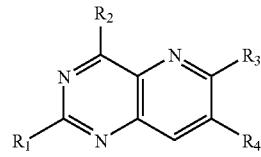

wherein:
- $R_1$ is selected from the group consisting of 2,2,2-trifluoroethylamino, 4-fluorobenzylamino, 3,4-difluorobenzylamino, 2,6-difluoro-4-methoxybenzylamino, 4-chloro-2,6-difluorobenzylamino, 4-chloro-2-fluorobenzylamino, 2,4,6-trifluorobenzylamino, 4-chloro-3-fluorobenzylamino, 2,3,4-trifluorobenzylamino, 3-chloro-4-fluorobenzylamino, 2-chloro-4-fluorobenzylamino, 3-fluoro-4-trifluoromethylamino, 3,5-difluorobenzylamino, 3,4,5-trifluorobenzylamino, 3-fluorobenzylamino, 3-chloro-2-fluorobenzylamino, 4-fluorophenylamino, phenyl-amino, 6-methylpyridazin-3-ylamino, pyridin-2-ylmethylamino, pyridin-3-ylmethylamino, 2-morpholin-4-ylethylamino, 2,2-difluoroethylamino, 2-methoxyethylamino, 4-sulfamoylbenzylamino, 3-sulfamoylbenzylamino, 1-(4-fluorophenyl)-cyclopropylamino, 2,4-difluorobenzylamino, 1-phenylethylamino, thiazol-2-ylmethylamino, oxazol-4-ylmethylamino, isoxazol-3-ylmethylamino, 4-(N-isopropylsulfamoylmethyl)benzylamino, phenethylamino, 4-methanesulfonylbenzylamino, 4-pyrrolidin-1-yl-benzylamino, 4-(4-methyl-piperazin-1-yl)benzylamino, (N,N-dimethylcarbamoyl)benzylamino, 4-[1,2,3]thiadiazol-4-ylbenzyl-amino, 2-fluoro-4-sulfamoylbenzylamino, 4-[1,3,4]oxadiazol-2-ylmethylamino, thiazol-5-ylmethylamino, 1-(4-sulfamoylphenyl)-ethylamino, 4-([1,2,4]triazol-1-yl)benzylamino, oxazol-2-ylmethylamino, 2-([1,2,4]triazol-1-yl)ethylamino, 1-(4-[1,2,4]triazol-1-yl-phenyl)-ethylamino, 2-(diethylphosphono)ethylamino, 2-sulfamoylethylamino, 2-carbamoylethylamino, 4-carbamoylbenzylamino, 4-(N,N-dimethylcarboxamido)benzylamino, 4-(N-methylmethanesulfonamido)-benzylamino, 4-methanesulfonylamino)-benzylamino, 4-(N-methylsulfomoylmethyl)benzylamino, 4-(sulfamoylmethyl)benzyl-amino, —NH—CHR$_5$R$_6$ and or —NH—R$_8$, wherein R$_5$ and R$_6$ are independently selected from the group consisting of hydrogen, C$_{1-6}$ alkyl, C$_{3-10}$ cycloalkyl, aryl and heterocyclyl, wherein said aryl is optionally substituted with one or more substituents selected from the group consisting of halogen, hydroxy, amino, nitro, cyano, trifluoromethyl, trifluoromethoxy, C$_{1-4}$ alkyl optionally substituted with SO$_2$NHR$_{13}$, C$_{1-4}$ alkoxy, di-C$_{1-4}$ alkylamino, mono-C$_{1-4}$ alkylamino, SO$_2$NHR$_{13}$, —NR$_{12}$COR$_{10}$, SO$_2$R$_{13}$, —NHSO$_2$R$_{13}$, heterocyclyl optionally substituted with C$_{1-4}$ alkyl, and phenoxy, and wherein said C$_{1-6}$ alkyl is optionally substituted with one or more substituents independently selected from the group consisting of halogen and C$_{1-4}$ alkoxy, aryl, heterocyclyl, —P(O)(OR$_{13}$)$_2$, carbamoyl, and —SO$_2$NHR$_{13}$;

R$_8$ is selected from the group consisting of C$_{3-10}$ cycloalkyl, heteroaryl and aryl wherein said heteroaryl or aryl is optionally substituted with one or more substituents independently selected from the group consisting of halogen and C$_{1-4}$ alkyl and wherein said C$_{3-10}$ cycloalkyl is optionally substituted at the carbon position adjacent to the N atom of R$_1$ with aryl or heteroaryl wherein said aryl is optionally substituted with halogen;

R$_2$ is XR$_7$ or is selected from the group consisting of tetrahydrofuran-3-yloxy, ethoxy, hydroxy, 2-carbamoylethylamino, 2-methyl-2-hydroxy-propylamino, methoxy, 3-methanesulfonyl-pyrrolidin-1-yl, N-methanesulfonylethyl-N-methylamino, 1-isopropyl-piperidin-4-ylamino, ethylamino, pyrydin-3-ylmethylamino, N-morpholin-4-ylmethylamino, 2,2,2-trifluoroethylamino, 2-methoxyethylamino, isopropylamino, dimethylamino, diethylamino, cyclopentoxy, cyclobutoxy, propyl, methanesulfonylethylamino, 2,2-difluoroethylamino, cyclopropoxy, cyclopropylamino, 4-([1,2,4]triazol-1-yl)-phenylamino, 3-fluorophenylamino, 2-methoxy-ethoxy, N-(methanesulfonylethyl)-amino, 1-propyl, tetrahydrofuran-3-ylamino, oxetan-3-yloxy, 1-methylcyclopropylamino, 2-hydroxyethylamino, 1-cyano-cyclopropylamino, N-morpholinyl, N-thiomorpholinyl, and N-thiomorpholinyl dioxide, cyclopropyl, N-piperidinyl and N-pyrrolidinyl, wherein said N-pyrrolidinyl is optionally substituted with C$_{1-4}$ alkylsulfonyl;

X is selected from the group consisting of O, S, NR$_{13}$ and CH$_2$;

R$_7$ is selected from the group consisting of C$_{1-20}$ alkyl, C$_{3-10}$ cycloalkyl, aryl, heterocyclyl and aryl-C$_{1-4}$ alkyl; wherein said C$_{1-20}$ alkyl is optionally substituted with methylsulfonyl, 1-3 halogens or one or more substituents independently selected from the group consisting of methylsulfonyl, heterocyclyl, hydroxyl, carbamoyl, halogen and C$_{1-4}$ alkoxy when X is NHNR$_{13}$ or said C$_{1-20}$ alkyl is optionally substituted with one or more substituents independently selected from the group consisting of C$_{1-4}$ alkoxy, halo-C$_{1-4}$ alkoxy and or heterocyclyl-oxy C$_{1-4}$ alkoxy when X is O; and wherein said C$_{3-10}$ cycloalkyl is optionally substituted with one or more C$_{1-20}$ alkyl or cyano; and wherein said aryl is optionally substituted with one or more halogen or with one heterocyclyl group; and wherein said heterocyclyl is optionally substituted with one or more C$_{1-20}$ alkyl;

R$_4$ is hydrogen;

R$_3$ is selected from the group consisting of halogen, 4-fluorophenyl, 5-amino-pyrazin-2-yl, 4-(N-(2-dimethylaminoethyl)carbamoyl)phenyl, 3-chloro-4-fluorophenyl, 4-(N-cyclopropyl-carbamoyl)phenyl, 3-(N-methylsulfonylamino)-phenyl, 4-(cyclopropanecarboxamido)-phenyl, 3-sulfamoyl-4-fluorophenyl, 4-(2-hydroxyacetamido)phenyl, 4-(2-amino-acetamido)phenyl, 4-[3-(2-morpholin-4-ylethyl)-ureido]phenyl, 4-(morpholin-4-carboxamido)phenyl, 4-(pyrrolidine-1-carboxamido)phenyl, 4-(3-cyclopropylureido)-phenyl, 4-ureidophenyl, 4-(4-hydroxy-2-oxo-pyrrolidin-1-yl)phenyl, 1H-indazol-5-yl, 2-oxo-indolin-5-yl, 6-cyclopropanecarboxamido-pyridin-3-yl, 2-cyclopropanecarboxamidopyrimidin-5-yl, 3-(2-pyrrolidin-1-yl-ethanesulfonamido)phenyl, 3-(cyclopropanesulfonamido)phenyl, 4-sulfamoylphenyl, 3-(dimethylaminesulfonamido)-phenyl, 3-sulfamoylphenyl, 4-(3-hydroxy-2-oxo-pyrrolidin-1-yl)phenyl, 2-fluoropyridin-5-yl, 4-(4-hydroxypyrrolidin-2-carboxamido)phenyl, 4-(pyrrolidin-2-carboxamido)phenyl, 4-[3-(2-pyrrolidin-1-yl-ethyl)ureido]phenyl, 4-(pyrrolidin-3-carboxamido)-3-fluorophenyl, 4-(pyrrolidin-3-carboxamido)phenyl, 4-(2-(pyrrolidin-1-yl)-ethoxycarbonylamino)-phenyl, 3-(4-(tert-butoxycarbonylamino)-piperidin-1-sulfonyl)-4-chlorophenyl, 3-(N-(1-(tert-butoxycarbonyl)-pyrrolidin-3-yl)-sulfamoyl)-4-fluoro-phenyl, 4-(methoxycarbonyl-amino)phenyl, 3-(N-(1-(tert-butoxycarbonyl)-piperidin-4-yl)-sulfamoyl)-4-chloro-phenyl, 3-(N-(1-(tert-butoxycarbonyl)-piperidin-4-yl)-sulfamoyl)-4-fluorophenyl, 4-(2-pyrrolidin-1-yl-ethaneureyl)phenyl, 4-(N-(2-hydroxy-1,1-dimethyl-ethyl)carbamoyl)phenyl, 4-(N-(2-(pyrrolidin-1-yl)-1,1-dimethylethyl)carbamoyl)phenyl, 2-aminothiazol-5-yl, 5-hydroxymethylfuran-2-yl, 4-(N-pyrrolidin-2-one)-phenyl, 4-(3-hydroxy-2-oxopyrrolidin-1-yl)phenyl, 4-carbamoylphenyl, 4-(N-cyclopropylcarbamoyl)phenyl, 4-(N-1-cyano-1-cyclopropylcarbamoyl)-phenyl, 4-(N-1-amino-1- cyclopropylcarbamoyl)-phenyl, 4-(N-1-hydroxy-1-cyclopropylcarboxamido)phenyl, 3-(N-(2-hydroxyethyl)methylsulfonamido)-phenyl, 4-(N-(2-(morpholin-4-yl)-1,1-dimethyl-ethyl)carbamoyl)-phenyl, 4-(2-oxo-pyrrolidin-1-yl)phenyl, 4-(2-amino-2-methylpropionamido)phenyl, 4-(N-cyclopropylcarbamoyl)phenyl, 4-(3-hydroxy-2-aminopropionamido)phenyl, 3-cyclopropanesulfonamido-4-fluorophenyl, 4-(2-amino-propionamido)-phenyl, 4-(3-hydroxy-2-amino-butyramido)phenyl, 3,5-dimethyl-isoxazol-4-yl, 1-methyl-1H-pyrazol-4-yl, 5-pyrrolidin-1-ylpyrazin-2-yl, 2-trifluoromethylpyridin-4-yl, 2-amino-pyridin-4-yl, 4-hydroxyphenyl, 2-pyrrolidin-1-yl-thiazol-4-yl, 2-methoxypyridin-4-yl, 2-cyanopyridin-4-yl, 2-amino-pyrimidin-5-yl, 3-cyanophenyl, 4-(1-methylpyrrolidine-3-carboxamido)-3-fluorophenyl, 4-(1-methylpyrrolidine-3-carboxamido)-phenyl, 3-cyclopropanesulfonamido-4-fluorophenyl, 1H-pyrazol-4-yl, 3-(N-(1-isopropyl-piperidin-4-yl)sulfamoyl)-4-chlorophenyl, 3-(N-(2-pyrrolidin-1-yl-ethyl)sulfamoyl)-4-chlorophenyl, 3-(4-isopropyl-piperazin-1-sulfonyl)-4-chlorophenyl, 3-(N-pyrrolidin-3-yl-sulfamoyl)-4-chlorophenyl, 3-(N-(2-methoxyethyl)-sulfamoyl)-4-chlorophenyl, 3-(N-piperidin-4-ylsulfamoyl)-4-chlorophenyl, pyridazin-4-yl, 4-cyanophenyl, 4-fluoro-3-(piperazin-1-sulfonyl)-phenyl, 4-fluoro-3-(4-tert-butoxycarbonyl-piperazin-1-sulfonyl)-phenyl, 4-isopropylamino-pyrazol-1-yl, [1,2,4]triazol-1-yl, imidazol-1-yl, imidazol-2-yl, 6-oxo-1,6-dihydro-pyridin-3-yl, 2-oxo-1,2-dihydro-pyridin-4-yl, 3-hydroxy-2-oxo-pyrrolidin-1-yl, 4-chlorophenyl, optionally mono-substituted or disubstituted aryl and optionally mono-substituted or disubstituted heterocyclyl, wherein at least one each substituent of said aryl or heterocyclyl is independently selected from the group consisting of halogen, hydroxy, amino, $C_{1-4}$ alkylamino, oxo, cyano, $C_{1-6}$ alkyl optionally substituted with one or more substituents independently selected from the group consisting of halogen and hydroxy, $C_{1-6}$ alkoxy, —CONHR$_9$, —NR$_{12}$COR$_{10}$, —NR$_{12}$SO$_2$R$_{11}$, —SO$_2$NH$_2$, —SO$_2$NHR$_{14}$, —SO$_2$R$_{15}$, heterocyclyl and heterocyclyl substituted with one or more substituents independently selected from the group consisting of hydroxy, oxo, halogen, amino, $C_{1-6}$ alkyl and $C_{1-6}$ alkoxy; and wherein said $C_{1-6}$ alkyl is optionally substituted with hydroxyl;

R$_9$ is selected from the group consisting of H hydrogen, $C_{3-10}$ cycloalkyl optionally substituted with one more substituents independently selected from the group consisting of cyano, halogen, hydroxy, oxo, amino, $C_{1-6}$ alkyl and $C_{1-6}$ alkoxy; $C_{1-6}$ alkyl optionally substituted with one or more substituents independently selected from the group consisting of amino, alkylamino, cyano, dialkylamino, halogen, hydroxy and heterocyclyl; $C_{1-6}$ alkoxy; heterocyclyl optionally substituted with one or more $C_{1-6}$ alkyl; and phenyl optionally and independently substituted with one or more halogens;

R$_{10}$ and R$_{11}$ are each independently selected from the group consisting of $C_{1-6}$ alkyl optionally substituted with one or more substituents independently selected from the group consisting of amino, cyano, halogen, and hydroxy and heterocyclyl; $C_{1-6}$ alkoxy optionally substituted with one or more substituents independently selected from the group consisting of amino, $C_{1-4}$ alkylamino, cyano, di-$C_{1-4}$ alkylamino, halogen, and heterocyclyl; heterocyclyl optionally substituted with one or more substituents independently selected from the group consisting of $C_{1-6}$ alkyl, acylamino, hydroxy and oxo; $C_{3-10}$ cycloalkyl optionally substituted with one or more substituents independently selected from the group consisting of cyano, amino and or hydroxy; and amino optionally substituted with one or more substituents independently selected from the group consisting of $C_{3-10}$ cycloalkyl and $C_{1-6}$ alkyl wherein said $C_{1-6}$ alkyl is optionally substituted with one or more substituents independently selected from the group consisting of amino, $C_{1-4}$ alkylamino, cyano, di-$C_{1-4}$ alkylamino, halogen and heterocyclyl;

R$_{12}$ is selected from the group consisting of H hydrogen and $C_{1-6}$ alkyl, wherein said $C_{1-6}$ alkyl is optionally substituted with one or more substituents independently selected from the group consisting of cyano, halogen and hydroxy;

each R$_{13}$ is independently selected from the group consisting of H hydrogen and $C_{1-20}$ alkyl;

R$_{14}$ is selected from the group consisting of heterocyclyl optionally substituted with one or more substituents independently selected from the group consisting of $C_{1-4}$ alkyl and $C_{1-4}$ alkyloxycarbonyl, and $C_{1-4}$ alkyl optionally substituted with one or more substituents independently selected from the group consisting of heterocyclyl and $C_{1-4}$ alkoxy; and R$_{15}$ is heterocyclyl optionally substituted with one or more substituents independently selected from the group consisting of $C_{1-4}$ alkyl, $C_{1-4}$ alkoxycarbonyl and $C_{1-4}$ alkyloxycarbonylamino;

or a pharmaceutically acceptable addition salt or a stereochemical isomeric form thereof or a N-oxide thereof or a solvate thereof or a prodrug thereof.

The present invention also relates to a sub-group of tri-substituted pyrido(3,2-d)pyrimidines having represented by the above structural formula (I), but wherein R$_3$ is halogen and all other substituents are as specified above, which are useful as intermediates for making biologically-active pyrido (3,2-d)pyrimidine derivatives wherein R$_3$ is other than halogen. The present invention also relates to another sub-group of tri-substituted pyrido(3,2-d)pyrimidines represented by the structural formula (II) as shown in the detailed description below.

In another embodiment, the present invention relates to the unexpected finding that desirable pharmacological properties such as an antiviral activity, especially against infection by a virus of the Flaviridae family, more specifically the ability to inhibit hepatitis C virus (HCV) replication, is present in a sub-group of compounds having represented by the above structural formula (I) with the proviso that R$_3$ is not halogen, or by the structural formula (II) below.

As a consequence, the invention relates to the manufacture of pharmaceutical compositions comprising one or more pharmaceutically acceptable carriers and, as a biologically active principle, a therapeutically effective amount of at least one pyrido(3,2-d)pyrimidine derivative having represented by the above structural formula (I), with the proviso that R$_3$ is not halogen, or by the structural formula (II) below, and/or a pharmaceutically acceptable addition salt thereof and/or a stereochemical isomeric form thereof and/or a N-oxide thereof and/or a solvate thereof and/or a pro-drug thereof.

As a result of their biological properties mentioned hereinabove, compounds having represented by the above structural formula (I), with the proviso that R$_3$ is not halogen, or having by the structural formula (II) below, are highly active anti-flaviridae agents, especially anti-HCV agents which, together with one or more pharmaceutically acceptable carriers, may be formulated into pharmaceutical compositions for the prevention or treatment of pathologic conditions such as, but not limited to, hepatitis C infection. It has furthermore been surprisingly found that their activity is virus-specific.

In a further embodiment, the present invention relates to combined preparations containing at least one compound represented by the above structural formula (I), with the proviso that $R_3$ is not halogen, or the structural formula (II) below, and one or more antiviral agents, especially one or more other anti-flaviridae agents. In a further embodiment, the present invention relates to the prevention or treatment of the above-cited pathologic conditions or infections by administering to the patient in need thereof a therapeutically effective amount of a compound having the structural formula (I), with the proviso that $R_3$ is not halogen, optionally in the form of a pharmaceutical composition or a combined preparation with one or more other suitable drugs, in particular antiviral agents.

In another embodiment, the present invention relates to various processes and methods for making the novel pyrido(3,2-d)pyrimidine derivatives defined by the structural formulae (I) and (II) as well as their pharmaceutically acceptable salts, N-oxides, solvates, pro-drugs and/or stereochemical isomeric forms, e.g. via one or more groups of tri-substituted pyrido(3,2-d)pyrimidine intermediates.

DEFINITIONS

Figure 1:
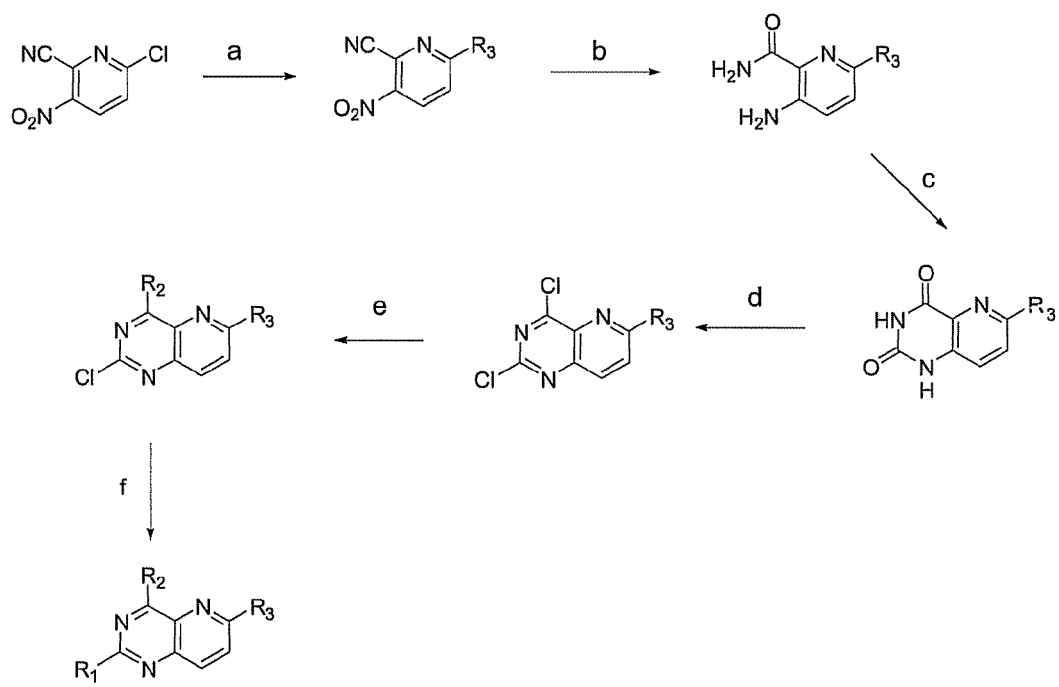
FIG. 1 schematically shows a first method for making 2,4,6-tri-substituted pyrido(3,2-d)pyrimidine derivatives having represented by the structural formula (I), as well as intermediates therefor wherein the substituent in position 2 is chloro.

Unless otherwise stated herein, the term "tri-substituted" means that three of the carbon atoms being in positions 2, 4 and 6 of the pyrido(3,2-d)pyrimidine core structure (according to standard atom numbering for the pyrido(3,2-d)pyrimidine moiety) are substituted with an atom or group of atoms other than hydrogen.

As used herein with respect to a substituting radical, and unless otherwise stated, the term "$C_{1-6}$ alkyl" means straight and branched chain saturated acyclic hydrocarbon monovalent radicals having from 1 to 6 carbon atoms such as, for example, methyl, ethyl, propyl, n-butyl, 1-methylethyl (isopropyl), 2-methylpropyl (isobutyl), 1,1-dimethylethyl (tert-butyl), 2-methylbutyl, n-pentyl, dimethylpropyl, n-hexyl, 2-methylpentyl, 3-methylpentyl, and the like. By analogy, the term "$C_{1-4}$ alkyl" refers to such radicals having from 1 to 4 carbon atoms, the term "$C_{1-10}$ alkyl" refers to such radicals having from 1 to 10 carbon atoms and the term "$C_{1-20}$ alkyl" refers to such radicals having from 1 to 20 carbon atoms, including n-octyl, n-decyl, n-dodecyl, n-hexadecyl and the like.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids or sulphonic acids, are designated herein as aliphatic or cycloaliphatic acyl and sulfonyl groups and include, but are not limited to, the following:
  alkanoyl (for example formyl, acetyl, propionyl, butyryl, isobutyryl, valeryl, isovaleryl, pivaloyl and the like);
  cycloalkanoyl (for example cyclobutanecarbonyl, cyclopentanecarbonyl, cyclohexanecarbonyl, 1-adamantanecarbonyl and the like);
  cycloalkyl-alkanoyl (for example cyclohexylacetyl, cyclopentylacetyl and the like);
  alkenoyl (for example acryloyl, methacryloyl, crotonoyl and the like);
  alkylthioalkanoyl (for example methylthioacetyl, ethylthioacetyl and the like);
  alkanesulfonyl (for example mesyl, ethanesulfonyl, propanesulfonyl and the like);
  alkoxycarbonyl (for example methoxycarbonyl, ethoxycarbonyl, propoxycarbonyl, isopropoxycarbonyl, butoxycarbonyl, isobutoxycarbonyl and the like);
  alkylcarbamoyl (for example methylcarbamoyl and the like);
  (N-alkyl)-thiocarbamoyl (for example (N-methyl)-thiocarbamoyl and the like);
  alkylcarbamidoyl (for example methylcarbamidoyl and the like); and
  alkoxyalkyl (for example methoxyalkyl, ethoxyalkyl, propoxyalkyl and the like);

Acyl and sulfonyl groups may also originate from aromatic monocarboxylic acids or sulphonic acids, and include, but are not limited to, the following:
  aroyl (for example benzoyl, toluoyl, xyloyl, 1-naphthoyl, 2-naphthoyl and the like);
  arylalkanoyl (for example phenylacetyl and the like);
  arylalkenoyl (for example cinnamoyl and the like);

aryloxyalkanoyl (for example phenoxyacetyl and the like);
arylthioalkanoyl (for example phenylthioacetyl and the like);
arylaminoalkanoyl (for example N-phenylglycyl, and the like);
arylsulfonyl (for example benzenesulfonyl, toluenesulfonyl, naphthalene sulfonyl and the like);
aryloxycarbonyl (for example phenoxycarbonyl, naphthyloxycarbonyl and the like);
arylalkoxycarbonyl (for example benzyloxycarbonyl and the like);
arylcarbamoyl (for example phenylcarbamoyl, naphthylcarbamoyl and the like);
arylglyoxyloyl (for example phenylglyoxyloyl and the like).
arylthiocarbamoyl (for example phenylthiocarbamoyl and the like); and
arylcarbamidoyl (for example phenylcarbamidoyl and the like).

Acyl groups may also originate from an heterocyclic monocarboxylic acids or sulphonic acids, and include, but are not limited to, the following:
heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and
heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenanthracyl, fluoranthenyl, chrysenyl, pyrenyl, biphenyyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical (including the combination of substituents in certain positions of the pyrido(3,2-d)pyrimidine ring together with the carbon atoms in the same positions of said ring), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; depending upon the number of unsaturations in the 3 to 10 atoms ring, heterocyclic radicals are conventionally sub-divided into heteroaromatic (or "heteroaryl") radicals and non-aromatic heterocyclic radicals.

As used herein with respect to a substituting radical, and unless otherwise stated, the terms "$C_{1-6}$ alkoxy" and "heterocyclic-oxy" refer to substituents wherein a carbon atom of a $C_{1-6}$ alkyl or heterocyclic radical (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, and various isomers of piperidinoxy, methylpiperidinoxy, pyrrolidinoxy, pyridinoxy, tetrahydrofuranyloxy, and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "arylalkyl" refers to an aliphatic saturated hydrocarbon monovalent radical (preferably a $C_{1-6}$ alkyl or $C_{1-4}$ alkyl radical such as defined above, alternatively a $C_{1-4}$ alkyl radical such as defined above) onto which an aryl radical (such as defined above) is attached via a carbon atom, and wherein the said aliphatic radical and/or the said aryl radical may be optionally substituted with one or more substituents independently selected from the group consisting of halogen, amino, hydroxyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, and the like.

As used herein with respect to a substituting radical, and unless otherwise stated, the term "alkylamino" means that one (thus monosubstituted amino or monoalkylamino) or respectively two (thus disubstituted amino or dialkylamino) $C_{1-6}$ alkyl or $C_{1-4}$ alkyl radical(s) (as defined herein, respectively, is/are attached to a nitrogen atom through a single bond such as, but not limited to, methylamino, dimethylamino, ethylamino, diethylamino, isopropylamino, n-butylamino, tert-butylamino, dibutylamino. Alternatively, the alkyl groups that are part of the mono- or di-alkylamino substituting radical may be $C_{1-4}$ alkyl groups.

As used herein with respect to a substituting radical, and unless otherwise stated, the term "carboxamido" refers to a substituting radical having the structural formula —$NR_{12}COR_{10}$ wherein $R_{10}$ and $R_{12}$ are as defined herein.

As used herein with respect to a substituting radical, and unless otherwise stated, the term "sulfonamido" refers to a substituting radical having the structural formula —NR$_{12}$SO$_2$R$_{11}$ wherein R$_{11}$ and R$_{12}$ are as defined herein.

As used herein and unless otherwise stated, the term "stereochemical isomeric form" refers to all possible different isomeric as well as conformational forms which the compounds of formula (I) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90890% of one enantiomer and at most 10210% of the other enantiomer), preferably at least 90% and more preferably at least 98%.

As used herein and unless otherwise stated, the term "solvate" includes any combination which may be formed by a pyrido(3,2-d)pyrimidine derivative of this invention with a suitable inorganic solvent (e.g. hydrates) or organic solvent, such as but not limited to alcohols, ketones, esters, ethers, nitriles and the like.

DETAILED DESCRIPTION OF THE INVENTION

In a first embodiment of the present invention, the novel trisubstituted pyrido(3,2-d)pyrimidine derivatives are as defined in the structural formula (I), wherein X and each of the substituents R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$ and/or R$_{158}$ may independently correspond to any of the definitions given above, in particular with any of the individual meanings (such as illustrated above) of generic terms used for substituting groups such as, but not limited to, "C$_{1-20}$ alkyl", "C$_{3-10}$ cycloalkyl", "aryl", "heterocyclic", "halogen", "arylalkyl", "monoalkylamino", "dialkylamino", "C$_{1-4}$ alkoxy", "C$_{1-4}$ alkylthio" and the like.

Within the broad class of trisubstituted pyrido(3,2-d)pyrimidine derivatives represented by the above structural formula (I) or the structural formula (II) below, a useful sub-group of compounds is one wherein R$_3$ is a mono-substituted or di-substituted phenyl group, wherein at least one substituent of said phenyl group is located in para position with respect to the pyrido(3,2-d)pyrimidinyl core.

Within the broad class of trisubstituted pyrido(3,2-d)pyrimidine derivatives represented by the above structural formula (I) or the structural formula (II) below, a useful sub-group of compounds is one wherein R$_3$ is a di-substituted phenyl group wherein one substituent is halogen.

Within the broad class of trisubstituted pyrido(3,2-d)pyrimidine derivatives represented by the structural formula (I) or the structural formula (II) below, a useful sub-group of compounds is one wherein R$_3$ is a mono-substituted or di-substituted phenyl group, wherein at least one substituent of said phenyl group is located in meta position with respect to the pyrido(3,2-d)pyrimidinyl core.

Within the broad class of trisubstituted pyrido(3,2-d)pyrimidine derivatives represented by the above structural formula (I) or the structural formula (II) below, a useful sub-group of compounds is one wherein R$_2$ is selected from the group consisting of mono-C$_{2-20}$ alkyl-amino, mono-C$_{3-10}$ cycloalkyl-amino, benzylamino, C$_{1-4}$ alkoxy and C$_{1-4}$ alkylthio.

Within the broad class of trisubstituted pyrido(3,2-d)pyrimidine derivatives represented by the above structural formula (I), a useful sub-group of compounds is one wherein both R$_5$ and R$_6$ are hydrogen atoms.

Within the broad class of trisubstituted pyrido(3,2-d)pyrimidine derivatives represented by the above structural formula (I), a useful sub-group of compounds is one wherein R$_8$ is selected from the group consisting of phenyl, pyridazinyl and pyrazolyl and wherein said R$_8$ is optionally substituted with a substituent selected from the group consisting of halogen and methyl.

Within the broad class of trisubstituted pyrido(3,2-d)pyrimidine derivatives represented by the above structural formula (I), a useful sub-group of compounds is one wherein R$_5$ is hydrogen and R$_6$ is selected from the group consisting of trifluoromethyl, naphthyl, imidazol-2-yl and thien-2-yl.

Within the broad class of trisubstituted pyrido(3,2-d)pyrimidine derivatives represented by the above structural formula (I), a useful sub-group of compounds is one wherein R$_5$ is hydrogen and R$_6$ is selected from the group consisting of C$_{1-4}$ alkyl, C$_{3-10}$ cycloalkyl, heterocyclic and phenyl, wherein said phenyl is optionally substituted with one or more substituents selected from the group consisting of halogen, hydroxy, amino, nitro, cyano, trifluoromethyl, trifluoromethoxy, C$_{1-4}$ alkyl, C$_{1-4}$ alkoxy, dimethylamino, diethylamino and phenoxy.

In another embodiment, the present invention relates to a pyrido(3,2-d)pyrimidine derivative having represented by the structural formula (II):

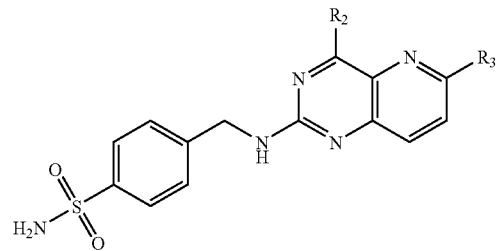

wherein:
R$_2$ is XR$_7$;
X is selected from the group consisting of O and NR$_{13}$;
R$_7$ is selected from the group consisting of C$_{1-20}$ alkyl wherein said C$_{1-20}$ alkyl is optionally substituted with methylsulfonyl or 1-3 halogens when X is NH;
R$_3$ is selected from the group consisting of optionally mono-substituted or disubstituted aryl and heterocyclyl, wherein at least one substituent of said aryl or heterocyclyl is selected from the group consisting of halogen, amino, —CONHR$_9$, —NR$_{12}$COR$_{10}$, —NR$_{12}$SO$_2$R$_{11}$, —SO$_2$NH$_2$, heterocyclyl, and heterocyclyl optionally substituted with one or more substituents selected from the group consisting of hydroxy, oxo, amino, halogen, C$_{1-6}$ alkyl and C$_{1-6}$ alkoxy;
R$_9$ is selected from the group consisting of H; C$_{3-10}$ cycloalkyl optionally substituted with amino, alkylamino, cyano, dialkylamino, halogen, or heterocyclyl; C$_{1-6}$ alkoxy; heterocyclyl optionally substituted with C$_{1-6}$ alkyl; and phenyl optionally substituted with halogen;
R$_{10}$ and R$_{11}$ are each independently selected from the group consisting of C$_{1-6}$ alkyl optionally substituted with one or more substituents selected from the group consisting of cyano, halogen and hydroxy; C$_{1-6}$ alkoxy optionally substituted with one or more substituents selected from the group consisting of amino, alkylamino, cyano, dialkylamino, halogen, and heterocyclyl; heterocyclyl optionally substituted with one or more substituents selected from the group consisting of $C_{1-6}$ alkyl, acylamino and oxo; $C_{3-10}$ cycloalkyl optionally substituted with one or more substituents selected from the group consisting of amino or hydroxy; and amino optionally substituted with one or more substituents selected from the group consisting of $C_{1-6}$ alkyl wherein said $C_{1-6}$ alkyl is optionally substituted with one or more substituents selected from the group consisting of amino, alkylamino, cyano, dialkylamino, halogen and heterocyclyl;

$R_{12}$ is selected from the group consisting of H and $C_{1-6}$ alkyl, wherein said $C_{1-6}$ alkyl is optionally substituted with one or more substituents selected from the group consisting of cyano, halogen and hydroxy;

$R_{13}$ is selected from the group consisting of H and $C_{1-20}$ alkyl;

or a pharmaceutical acceptable addition salt or a stereochemical isomeric form thereof or a N-oxide thereof or a solvate thereof or a prodrug thereof.

The present invention further provides various processes and methods for making the novel pyrido(3,2-d)pyrimidine derivatives represented by the structural formulae (I) or (II). As a general rule, the preparation of these compounds is based on the principle that, starting from a suitable pyrido(3,2-d)pyrimidine precursor (e.g. method shown in FIG. 5) or from a 2,4-dichloro-pyrido(3,2-d)pyrimidine (method shown in FIG. 4), each of the desirable substituents $R_2$ and $R_3$ may be introduced separately without adversely influencing the presence of one or more substituents already introduced at other positions on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound). For instance, the synthesis of mono- and di-N-oxides of the pyrido(3,2-d)pyrimidine derivatives of this invention can easily be achieved by treating the said derivatives with an oxidizing agent such as, but not limited to, hydrogen peroxide (e.g. in the presence of acetic acid) or a peracid such as chloroperbenzoic acid. The methods for making the pyrido(3,2-d)pyrimidine derivatives of the present invention will now be explained in more details by reference to the appended FIGS. 1 and 2 to 8 wherein, unless otherwise stated hereinafter, each of the substituting groups or atoms $R_2$, $R_3$, $R_4$ and $R_1$ is as defined in formula (I) of the summary of the invention and, more specifically, may correspond to any of the individual meanings disclosed above-herein.

In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

Most of the present methods make use of a boronic acid, or a pinacol ester thereof, for introducing substituent $R_3$ onto the core structure. In the following methods, suitable aryl-boronic acids include, but are not limited to, the following commercially available materials wherein the aryl group is 3-acetamidophenyl, 4-acetamidophenyl, 4-acetylphenyl, 3-acetylphenyl, 2-acetylphenyl, 5-acetyl-2-chlorophenyl, 4-acetyl-3-fluorophenyl, 5-acetyl-2-fluorophenyl, 3-aminophenyl, 4-aminomethylphenyl, 3-aminophenyl, 4-benzyloxybenzene, 3-benzyloxybenzene, 4-benzyloxy-2-fluorophenyl, 4-benzyloxy-3-fluorophenyl, biphenyl-3-, 3,5-bis(trifluoromethyl)benzene, 4-bromophenyl, 3-bromophenyl, 4-bromo-2,5-dimethylphenyl, 2-bromo-5-fluorophenyl, 2-Bromo-6-fluorophenyl, 4-carboxyphenyl, 2-carboxyphenyl, 2-carboxy-5-fluorophenyl, 4-carboxy-2-chlorophenyl, 5-carboxy-2-chlorophenyl, 4-carboxy-3-chlorophenyl, 3-carboxyphenyl, 2-chloro-5-formylphenyl, 2-chloro-5-hydroxyphenyl, 3-chloro-4-fluorophenyl, 2-chloro-4-fluorophenyl, 4-chloro-2-fluorophenyl, 3-chloro-5-methoxyphenyl, 2-chloro-4-methylphenyl, 2-chloro-5-methylphenyl, 2-chloro-5-trifluoromethoxyphenyl, 3-chloro-5-trifluoromethylphenyl, 4-chloro-2-trifluoromethylphenyl, 4-chlorophenyl, 3-chlorophenyl, 2-chlorophenyl, 4-cyanophenyl, 3-cyanophenyl, 2-cyanophenyl, 3,5-dibromophenyl, 2,6-dichlorophenyl, 3,4-dichlorophenyl, 2,4-dichlorophenyl, 2,3-dichlorophenyl, 3,5-dichlorophenyl, 3,5-difluorophenyl, 3,5-difluoro-2-methoxyphenyl, 3,4-difluorophenyl, 2,6-difluorophenyl, 2,5-difluorophenyl, 2,4-difluorophenyl, 2,3-difluorophenyl, 2,3-dihydro-1,4-benzodioxin-6-yl, 2,4-dimethoxybenzene, 4-(N,N-dimethylamino)phenyl, 2-(N,N-dimethylaminomethyl)phenyl, 3,5-dimethylphenyl, 3,4-dimethylphenyl, 2,6-dimethylphenyl, 2,6-dimethoxyphenyl, 2,5-dimethoxyphenyl, 2,4-dimethoxyphenyl, 4-ethoxyphenyl, 2-ethoxyphenyl, 4-ethoxycarbonylphenyl, 3-ethoxycarbonylphenyl, 4-ethylphenyl, 4-fluorophenyl, 3-fluorophenyl, 2-fluorophenyl, 3-fluoro-4-formylphenyl, 4-fluoro-2-methylphenyl, 2-fluoro-5-methylphenyl, 4-fluoro-3-formylphenyl, 2-fluoro-5-methoxyphenyl, 5-fluoro-2-methoxycarbonylphenyl, 2-formyl-5-methoxyphenyl, 5-formyl-2-methoxyphenyl, 2-formyl-5-methylphenyl, 4-formylphenyl, 3-formylphenyl, 2-formylphenyl, 3-hydroxy-4-methoxycarbonylphenyl, 4-(hydroxymethyl)phenyl, 3-(hydroxymethyl)phenyl, 4-hydroxyphenyl, 3-hydroxyphenyl, 4-iodophenyl, 3-iodophenyl, 3-isopropoxycarbonylphenyl, 4-isopropoxycarbonylphenyl, 4-methanesulfonylphenyl, 2-methoxy-5-formylphenyl, 5-methoxy-2-formylphenyl, 4-methoxy-2-formylphenyl, 4-methoxycarbonylphenyl, 3-methoxycarbonylphenyl, 4-methoxyphenyl, 3-methoxyphenyl, 2-methoxyphenyl, 3,4-methylenedioxyphenyl, 4-methylphenyl, 2-methylphenyl, 4-(methylthio)phenyl, 3-(methylthio)phenyl, 4-morpholinophenyl, 3-nitrophenyl, 4-phenoxyphenyl, 4-(tert-butoxycarbonylamino)-3-methoxyphenyl, 2-(tert-butoxycarbonyl)phenyl, 3-(tert-butoxycarbonyl)phenyl, 4-(tert-butoxycarbonyl)phenyl, 4-tert-butylphenyl, 4-(tetrahydro-2H-pyran-2-yloxy)phenyl, 4-(2-thienyl)phenyl, trans-β-styrene, 4-tolyl, 3-tolyl, 2-tolyl, 4-trifluoromethoxyphenyl, 4-(trimethylammonium)methylphenyl, 2,4,6-trimethylphenyl, 3,4,5-trifluorophenyl, 3-trifluoromethylphenyl, 4-trifluoromethoxyphenyl, 3-trifluoromethoxyphenyl, 3-trifluoromethylphenyl, 2-trifluoromethylphenyl, 3,4,5-trimethoxyphenyl, 4-vinylphenyl, 6-benzyloxy-2-naphthyl, 1-naphthalene, 2-naphthalene, or 1-biphenylenyl.

In the following methods, suitable heterocyclic-boronic acids include, but are not limited to, the following commercially available materials wherein the heterocyclic group is 2-acetamidopyridin-5-yl, 2-benzothienyl, 1-benzothiophen-3-yl, 1-benzothiophen-2-yl, 2-bromo-3-chloropyridin-4-yl, 5-bromo-2,3-dihydrobenzo[b]furan-7-yl, 2-bromo-3-methylpyridin-5-yl, 2-bromopyridin-5-yl, 5-bromothien-2-yl, 2-chloro-6-isopropylpyridin-3-yl, 2-chloro-3-methylpyridin-5-yl, 5-chlorothien-2-yl, dibenzo[b,d]furan-4-yl, 2-chloro-3-fluoropyridin-4-yl, dibenzo[b,d]thien-4-yl, 3,4-dihydro-2H-1,5-benzodioxepin-7-yl, 2,5-dibromo-3-pyridinyl, 2,6-dichloro-pyridin-3-yl, 2,3-dihydro-1-benzofuran-5-yl, 2,4-dimethoxypyrimidin-5-yl, 3,5-dimethylisoxazol-4-yl, 1-[1,3]dioxolan-2-ylmethyl-4-1H-pyrazolyl, 2,4-dioxo-1,2,34-tetrahydro-5-pyrimidinyl, 2,4-di(tert-butoxy)pyrimidin-5-yl, 2-ethoxypyridin-3-yl, 2-fluoro-3-methylpyridin-5-yl, 2-fluoropyridin-3-yl, 2-fluoropyridin-5-yl, 5-formyl-2-furyl, 5-formylthiophen-2-yl, furan-3-yl, furan-2-yl, 5-indolyl, isoquinolin-4-yl, 2-methoxypyrimidin-5-yl, 5-methyl-1-benzothiophen-2-yl, 5-methylfuran-2-yl, 5-methyl-3-phenyl-4-isoxazolyl, 5-(methylsulfanyl)-2-thienyl, 3-methyl-pyridin-2-yl, (5-methyl)thien-2-yl, 5-methylpyridin-2-yl, 5-methylpyridin-3-yl, 2-methoxypyridine-3-yl, (4-methyl)thien-2-yl, 2-methoxypyridin-5-yl, 1-(phenylsulfonyl)-1H-indol-3-yl, 1-(phenylsulfonyl)-1H-indol-3-yl, 5-phenyl-2-thienyl, pyridin-4-yl, pyridin-3-yl, 5-pyrimidinyl, 4-phenoxathiinyl, 8-quinolinyl, 3-quinolinyl, 1-tert-butoxycarbonyl-2-pyrrolyl, 1-(tert-butoxycarbonyl)-5-bromo-1H-indol-2-yl, 1-(tert-butoxycarbonyl)-1H-indol-2-yl, 1-(tert-butoxycarbonyl)-5-methoxy-1H-indol-2-yl, 1-thianthrenyl-3-thienyl, or 2-thienyl.

FIG. 1 schematically shows a first method for making 2-amino-4,6-di-substituted pyrido(3,2-d)pyrimidine derivatives represented by the structural formula (I) through a series of intermediates. In step (a), 6-chloro-2-cyano-3-nitropyridine is subjected to a palladium-catalyzed reaction such as, but not limited to, a Suzuki reaction with an aryl boronic acid to yield the corresponding biaryl derivative or, alternatively, a Heck reaction with a terminal alkene leading to the formation of an alkenyl derivative. Alternatively, a Sonogashira reaction with a terminal alkyne might lead to the formation of alkynyl derivatives. In step (b), the 3-nitro group is reduced, either catalytically (e.g. by using platinum or palladium under an atmosphere of hydrogen) or chemically (e.g. by using iron or tin under acidic conditions) and at the same time the cyano group is hydrolyzed into a carboxamide function. Ring closure reaction leading to the formation of the pyrido[3,2-d] pyrimidine scaffold occurs in step (c) by treatment of a 6-$R_3$-substituted-2-carboxamido-3-aminopyridine derivative either with a phosgene derivative in an aprotic solvent or with a carbonate (such as, but not limited to, dimethylcarbonate or diethylcarbonate) in a protic or aprotic solvent. Activation of the tautomeric hydroxyl groups at positions 2 and 4 of the pyrido[3,2-d]pyrimidine scaffold for the subsequent nucleophilic displacement reaction occurs in step (d) by preparing the corresponding 2,4-dichloro-pyrido[3,2-d]pyrimidine derivative, e.g. by treating the 2,4-di-oxo-pyrido[3,2-d]pyrimidine derivative with thionyl chloride or $POCl_3$. Selective nucleophilic displacement of the chlorine at position 4 occurs in step (e) by reaction with an appropriate nucleophile having the general formula $R_2H$ in a polar protic or aprotic solvent at an appropriate temperature. In step (f), the 2-chloro derivative is then treated with an appropriate nucleophile having the general formula $R_1H$ in a polar protic or aprotic solvent at an appropriate temperature in order to afford the desired 2,4,6-trisubstituted derivative. Suitable examples of nucleophilic reagents include, but are not limited to, sodium or potassium alkoxides, sodium or potassium alkenyl oxides, sodium or potassium cycloalkyl oxides, sodium or potassium cycloalkenyl oxides, sodium or potassium aryl oxides, sodium or potassium arylalkyl oxides, sodium or potassium cycloalkylalkyl oxides, sodium or potassium heterocyclic oxides, sodium or potassium heterocyclic-substituted alkyl oxides, sodium or potassium thiolates, and primary or secondary amines.

Figure 2:
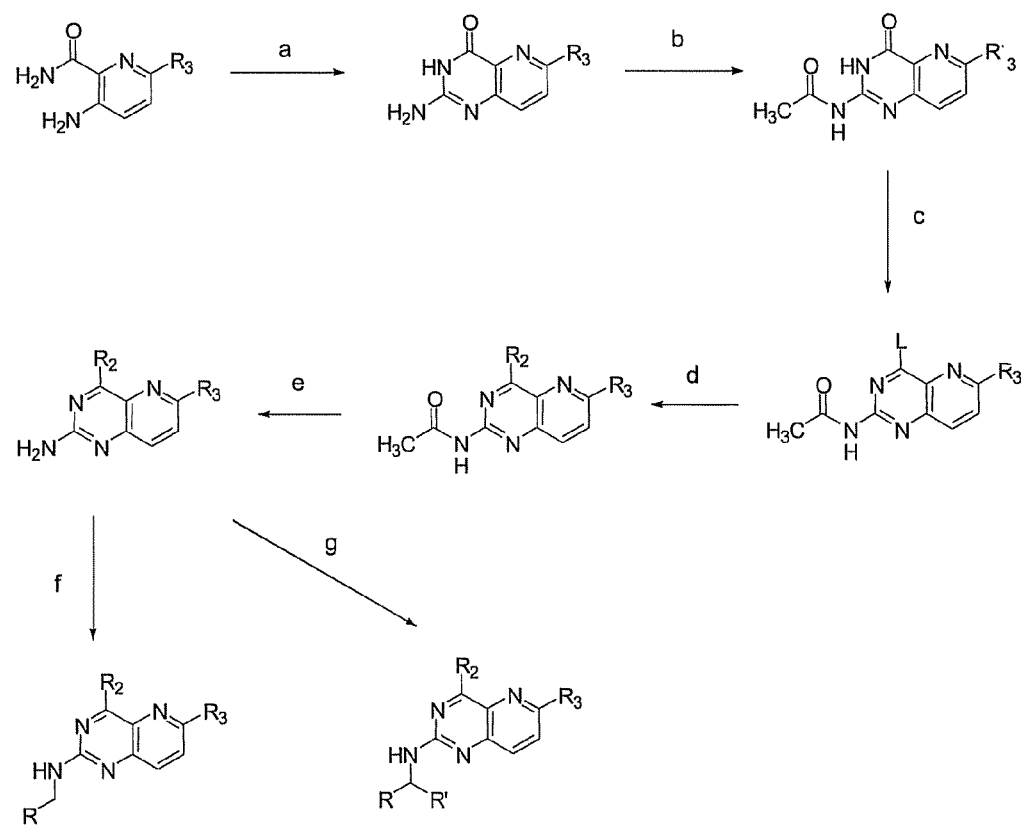
FIG. 2 schematically shows a second method for making 2,4,6-tri-substituted pyrido(3,2-d)pyrimidine derivatives having represented by the structural formula (I), as well as intermediates therefor wherein the substituent in position 2 is acetylamino or amino.

FIG. 2 schematically shows another method for making 2,4,6-tri-substituted pyrido(3,2-d)pyrimidine derivatives, as well as intermediates therefor wherein the substituent in position 2 is a N-protected amino such as acetamido and/or wherein the substituent in position 4 is hydroxy, chloro or triazolyl. A ring closure reaction leading to the formation of the pyrido[3,2-d]pyrimidine scaffold occurs in step (a) by treatment of 6-chloro-2-cyano-3-aminopyridine with a ring closure reagent such as, but not limited to, chloroformamidine or guanidine. In step (b), the amino group at position 2 is protected, for example by a pivaloyl (not shown in FIG. 2) or acetyl group, by reaction with acetic anhydride or pivaloyl anhydride in pyridine as a solvent, thus resulting into the introduction of a N-protected amino group at position 2 such as, but not limited to, acetamido or pivalamido. Activation of the tautomeric hydroxyl group at position 4 of the pyrido[3,2-d]pyrimidine scaffold for the subsequent nucleophilic displacement reaction occurs in step (c) by preparing the corresponding 4-(1,2,4-triazolyl)-pyrido[3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The chlorine atom or triazolyl group is designated as L in FIG. 2. Nucleophilic displacement of the triazolyl group or chlorine atom occurs in step (d) by reaction with an appropriate nucleophile having the general formula $R_2H$ in a polar aprotic solvent. Examples of suitable nucleophiles include sodium and potassium alkoxides, sodium or potassium thiolates, primary and secondary amines. In order to introduce a carbon linker at position 4 of the pyrido(3,2-d) pyrimidine scaffold, a nucleophilic displacement reaction can be effected by mixing the 2-(protected amino)-4-chloro-6-substituted or 2-(protected amino)-4-(1,2,4-triazolyl)-6-substituted pyrido(3,2-d)pyrimidine derivative with an appropriate Grignard reagent in a dry, polar, aprotic solvent such as for example 1,4-dioxane, diethyl ether or tetrahydrofuran. A broad range of suitable Grignard reagents is commercially available such as, but not limited to, benzylmagnesium chloride, methylmagnesium bromide, methylmagnesium chloride, methylmagnesium iodide, ethylmagnesium bromide, ethylmagnesium chloride, propylmagnesium chloride, n-butylmagnesium chloride, sec-butylmagnesium chloride, tert-butylmagnesium chloride, pentylmagnesium bromide, allylmagnesium bromide, allylmagnesium chloride, ethynylmagnesium chloride, (trimethylsilyl)methylmagnesium chloride, phenylmagnesium bromide, 4-methoxyphenylmagnesium bromide, 4-chlorophenylmagnesium bromide, 4-fluorophenylmagnesium bromide, 1-naphthylmagnesium bromide, phenyl-magnesium chloride, vinylmagnesium bromide, vinylmagnesium chloride, cyclohexylmagnesium chloride, and the like. Alternatively, the above-listed Grignard reagents as well as those which are not commercially available are obtainable using methods well known to the skilled person, or can advantageously be made in situ if desired. Alternatively, 2-(protected amino)-4-chloro-6-substituted pyrido(3,2-d)pyrimidine derivatives can also serve as excellent starting materials for a wide variety of organometallic cross-coupling reactions, which are well known in the art. Examples of cross-coupling reactions include, but are not limited to, a Negishi reaction (i.e. a nickel or palladium catalyzed coupling of organozinc compounds with an aryl- or heteroarylhalide), Stille coupling (i.e. a palladium catalysed coupling reaction between an aryl- or heteroaryl halide and a stannane), Suzuki coupling (i.e. a palladium catalysed cross coupling reaction between an organoboronic acid and an aryl- or heteroaryl-halide), Kumada coupling (which is a palladium or nickel catalyzed coupling of a Grignard reagent with an aryl- or heteroarylhalide), Heck reaction (which is the palladium-catalyzed C—C coupling between an aryl- or heteroaryl halide and an activated alkene in the presence of a base), Sonogashira reaction (i.e. the coupling of a terminal alkyne with an aryl- or heteroarylhalide with a palladium catalyst, a copper (I) co-catalyst, and an amine base). In each of the above types of reaction, the 4-chloro-pyrido(3,2-d)pyrimidine moiety will serve as the heteroaryl halide. In step (e), the amino protecting group is cleaved off by using standard cleavage conditions such as acidic or basic hydrolysis. In step (f), a reductive amination reaction, the 2-amino-4,6-disubstituted pyrido(3,2-d)pyrimidine derivative is condensed with an aldehyde having the structural formula RC(O)H in an appropriate solvent and in the presence of a suitable reducing agent. Suitable (and preferably commercially available) aldehydes include, but are not limited to, acetaldehyde, benzaldehyde, propionaldehyde, naphthaldehyde, salicylaldehyde and the like. Suitable solvents are for example methanol and acetonitrile. Suitable reducing agents include, but are not limited to, sodium cyanoborohydride, sodium triacetoxyborohydride and sodium borohydride. Alternatively, this reductive amination reaction can also be carried out in step (g) by means of a ketone having the structural formula RC(O)R', wherein R and R' may be the same or different. Suitable ketones include, but are not limited to, acetone, methylethylketone and acetophenone.

Figure 3:
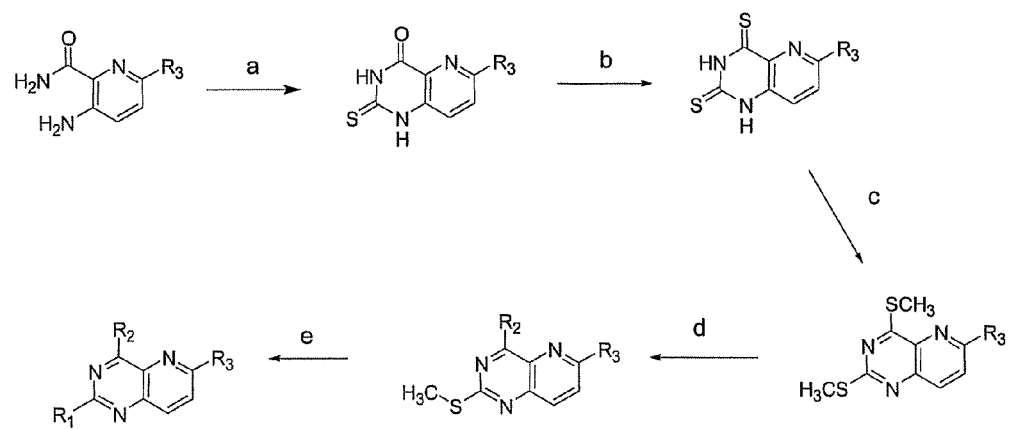
FIG. 3 schematically shows a third method for making 2,4,6-tri-substituted pyrido(3,2-d)pyrimidine derivatives having represented by the structural formula (I), as well as intermediates therefor wherein the substituent in position 2 is methylthio.

FIG. 3 schematically shows another method for making 2,4,6-tri-substituted pyrido(3,2-d)pyrimidine derivatives. In step (a), treatment of a 6-$R_3$-substituted-2-carboxamido-3-aminopyridine derivative either with a thiophosgene derivative in an aprotic solvent or with a thiocarbonate (such as, but not limited to, dimethylthiocarbonate or diethylthiocarbonate) in a protic or aprotic solvent leads to the formation of the pyrido[3,2-d]pyrimidine scaffold. In step (b), the tautomeric hydroxyl group at position 4 is converted to its corresponding 4-thio derivative by treatment with phosphorus pentasulfide or Lawesson's reagent. The resulting 6-$R_6$-substituted pyrido (3,2-d)pyrimidin-2(1H)-4(3H)dithione is then alkylated by treatment with iodomethane under alkaline conditions (e.g. use of a 1 N NaOH solution). The thiomethyl group at position 4 can selectively be displaced by a nucleophile bearing the general formula $R_2H$. In step (e), a second nucleophile bearing the general formula $R_1H$ can be introduced at position 2 of the pyrido(3,2-d)pyrimidine scaffold. In some cases (not shown in FIG. 3), for example when less reactive nucleophiles such as aniline derivatives are used, it may be desirable to oxidize the sulfur atom of the thiomethyl group beforehand to the corresponding sulfoxide or sulfone. This may be achieved by using an oxidizing agent, such as, but not limited to, hydrogen peroxide, sodium periodate or m-chloro-perbenzoic acid. Examples of suitable nucleophiles include sodium and potassium alkoxides, sodium or potassium thiolates, primary and secondary amines.

Figure 4:
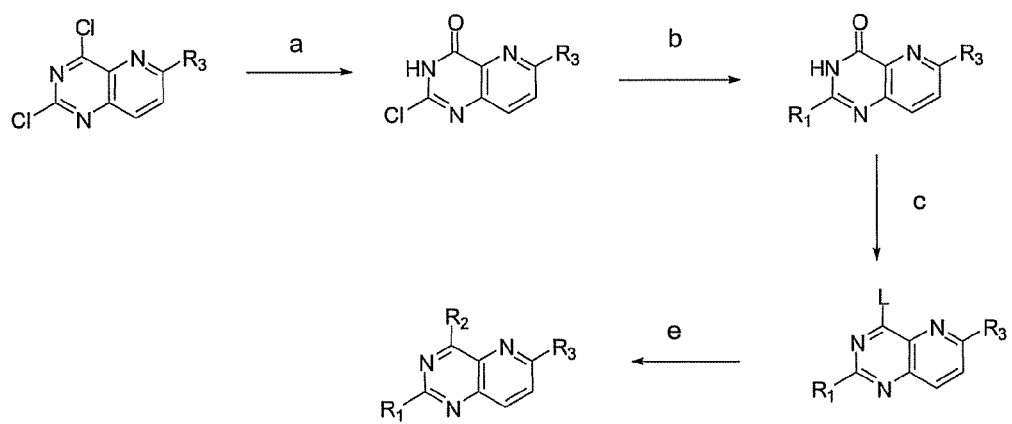
FIG. 4 schematically shows a fourth method for making 2,4,6-tri-substituted pyrido(3,2-d)pyrimidine derivatives having represented by the structural formula (I), as well as intermediates therefor wherein the substituent in position 2 is chloro, or wherein the substituent in position 4 is hydroxyl, chloro or triazolyl.

FIG. 4 shows another method for preparing 2,4,6-trisubstituted pyrido(3,2-d)pyrimidines of this invention. In step (a), selective hydrolysis under aqueous alkaline conditions of the chlorine at position 4 gives rise to the 2-chloro-4-hydroxy-6-$R_6$-pyrido(3,2-d)pyrimidine derivative. The chlorine at position 2 can be displaced by a nucleophile bearing the general formula $R_1H$ in an aprotic solvent (such as for example dioxane or tetrahydrofuran) at an appropriate temperature. Activation of the tautomeric hydroxyl group at position 4 of the pyrido[3,2-d]pyrimidine scaffold for the subsequent nucleophilic displacement reaction occurs in step (c) by preparing the corresponding 4-(1,2,4-triazolyl)-pyrido[3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The chlorine atom or triazolyl group is designated as L in FIG. 4. Nucleophilic displacement of the triazolyl group or chlorine atom occurs in step (d) by reaction with an appropriate nucleophile having the general formula $R_2H$ in a polar aprotic solvent. Examples of suitable nucleophiles include sodium and potassium alkoxides, sodium or potassium thiolates, primary and secondary amines. In case, it is desirable to introduce a carbon linker at position 4 of the pyrido(3,2-d)pyrimidine scaffold, a similar strategy as outlined in FIG. 2 can be used.

Figure 5:
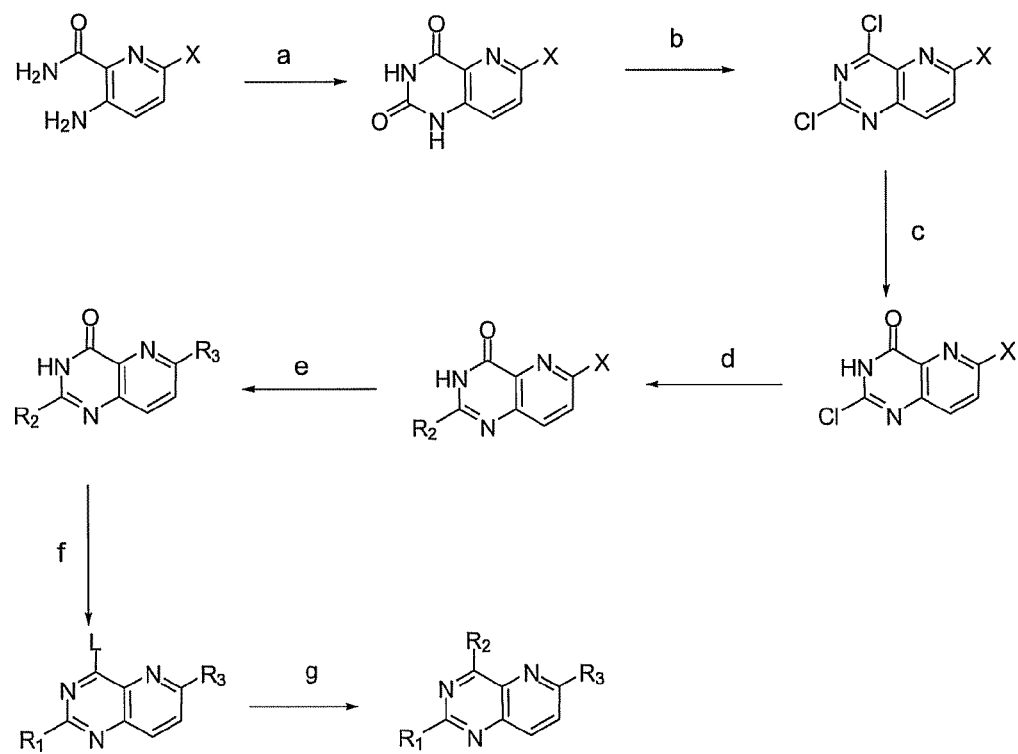
FIG. 5 schematically shows a fifth method for making 2,4,6-tri-substituted pyrido(3,2-d)pyrimidine derivatives having represented by the structural formula (I), as well as intermediates therefor wherein the substituent in position 2 is chloro, or wherein the substituent in position 4 is hydroxyl, chloro or triazolyl.

FIG. 5 schematically shows an alternative method for making the 2,4,6-trisubstituted 8-deazapteridines of this invention. In step (a), treatment of a 3-amino-6-halo-pyridine-2-carboxylic acid amide (X is preferably chlorine, bromine or iodine) either with phosgene or a phosgene derivative in an aprotic solvent gives the 2,4-dioxo-pteridine scaffold. In step (b), the tautomeric hydroxyl groups at position 2 and 4 are chlorinated by treatment with phosphorus oxychloride. In step (c), the chloride atom at position 4 is selectively hydrolyzed to the corresponding tautomeric 4-hydroxy compound. In step (d), a nucleophile, bearing the general formula $R_1H$, can be easily introduced at position 2 of the pteridine scaffold, yielding 2-$R_1$-4-oxo-6-$R_3$-pteridine derivatives. Palladium-mediated aryl-aryl cross coupling (Suzuki type) occurs in step (e) by treating the 2-$R_1$-4-oxo-6-halopteridine with an aryl- or heterocyclic boronic acid, or a pinacol ester thereof, in the presence of aqueous base and a palladium(0) catalyst such as $Pd(PPh_3)_4$ to give 2-$R_1$-4-oxo-6-$R_3$-pteridines. Activation of the tautomeric hydroxyl group at position 4 of the pteridine scaffold for the subsequent nucleophilic displacement reaction occurs in step (f) by preparing the corresponding 4-(1,2,4-triazolyl)-pteridine or 4-chloro-pteridine derivatives. The 4-triazolyl derivative can be obtained by treating the 4-oxo-pteridine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pteridine derivative with thionyl chloride or $POCl_3$. The chlorine atom or triazolyl group is designated as L in FIG. 5. Nucleophilic displacement of the triazolyl group or chlorine atom occurs in step (g) by reaction with an appropriate nucleophile having the general formula $R_2H$ in a polar aprotic solvent. Suitable examples of nucleophilic reagents include sodium or potassium alkoxides, sodium or potassium thiolates, and primary or secondary amines. In order to introduce a carbon linker at position 4 of the pteridine scaffold, a similar synthetic method as that outlined in FIG. 2 can be used.

Figure 6:
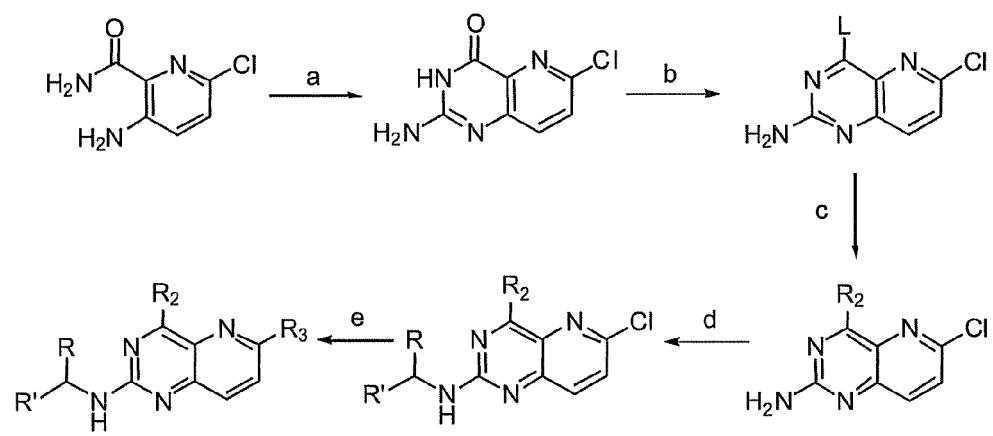
FIG. 6 schematically shows another method for making 2,4,6-tri-substituted pyrido(3,2-d)pyrimidine derivatives according to an embodiment of the present invention.

FIG. 6 schematically shows another method for making 2,4,6-tri-substituted pyrido(3,2-d)pyrimidine derivatives. A ring closure reaction leading to the formation of the pyrido [3,2-d]pyrimidine scaffold occurs in step (a) by treatment of 6-chloro-3-amino-2-pyridylcarboxamide or 3-amino-2-cyano-6-chloropyridine with a ring closure reagent such as, but not limited to, chloroformamidine or guanidine. In step (b), a leaving group (L), such as a chlorine or 1,2,4-triazol-1-yl, can be introduced at position 4 of the pyrido(3,2-d)pyrimidine ring. The 4-chloro derivatives can be obtained by treating the product obtained from step (a) with a reagent such as, but is not limited to, thionyl chloride or phosphorus oxychloride. The 4-triazole derivatives can be obtained by treating the product obtained from step (a) with a reagent such as, but is not limited to, thionyl chloride or phosphorus oxychloride plus 1,2,4-triazole. A base such as trialkylamine, DBU, etc. may be added to facilitate the reaction. The chlorine atom or triazolyl group is designated as L in FIG. 6. Nucleophilic displacement of the triazolyl group or chlorine atom occurs in step (c) by reaction with an appropriate nucleophile having the general formula $R_2M$ wherein M may be selected from the group comprising hydrogen, Li, Na, K and others, in a polar aprotic solvent. Examples of suitable nucleophiles include lithium, sodium or potassium alkoxides, lithium, sodium or potassium thiolates, primary and secondary amines. In particular when M is hydrogen, a suitable base may also be added to facilitate the reaction. Such bases include, but are not limited to potassium t-butoxide, trialkylamines, DBU. In step (d), the —$NH_2$ group at position 2 of the pyrido(3,2-d)pyrimidine ring is substituted with a group R. This can be accomplished by reaction such as, but not limited to, reductive amination. In a reductive amination reaction, the product obtained from step (c) reacts with an aldehyde or ketone of the general formula RC(O)R', in the presence of a reducing agent in a solvent such as, but is not limited to, diethyl ether, THF, acetonitrile, toluene, DMF, dichloromethane, dichloroethane, methanol etc. Suitable aldehydes include, but are not limited to, acetaldehyde, benzaldehyde, propionaldehyde, naphthaldehyde, salicylaldehyde and the like. Alternatively, this reductive amination reaction can also be carried out in step (g) by means of a ketone having the structural formula RC(O)R', wherein R and R' may be the same or different. Suitable ketones include, but are not limited to, acetone, methylethylketone and acetophenone. There are a variety of reagents or reagent combinations suitable for the reductive amination reaction. Some examples include, but are not limited to, hydrogen in the presence of a transition metal catalyst (Pd, Pt, Ni, etc.), $NaBH(OAc)_3$ in the presence of AcOH, $NaBH_4$, $i\text{-}Bu_2AlH$. One can consult texts such as *Comprehensive Organic Transformation*, $2^{nd}$ ed by Richard C. Larock, Wiley-VCH, (1999) and the references cited therein for more complete list of suitable reducing agents and further details. In step (e), the product obtained from step (d) is subjected to a palladium-catalyzed coupling reaction such as, but not limited to, a Stille coupling reaction with an aryl tin reagent or a Suzuki reaction with an aryl boronic acid to yield the corresponding biaryl derivative or, alternatively, a Heck reaction with a terminal alkene leading to the formation of an alkenyl derivative. Alternatively, a Sonogashira reaction with a terminal alkyne can lead to the formation of alkynyl derivatives.

Figure 7:
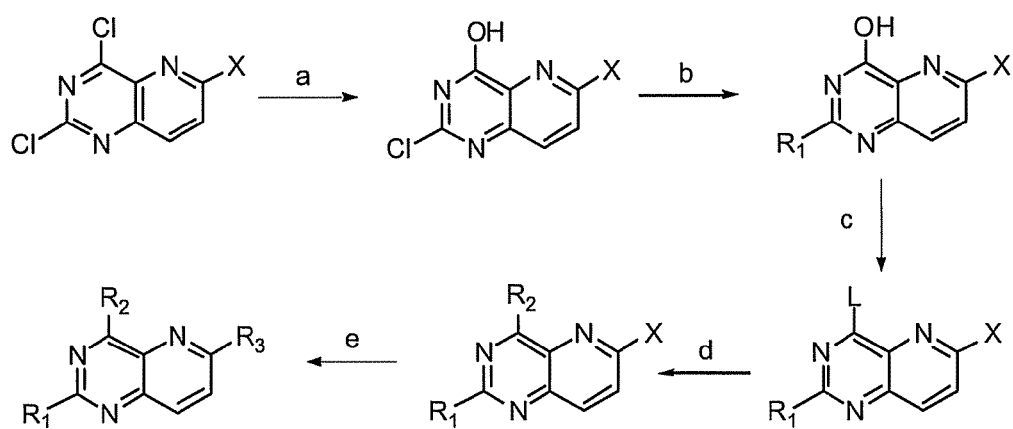
FIG. 7 schematically shows an alternative method for making the 2,4,6-tri-substituted pyrido(3,2-d)pyrimidine derivatives of this according to an embodiment of the present invention.

FIG. 7 schematically shows an alternative method for making the 2,4,6-tri-substituted pyrido(3,2-d)pyrimidine derivatives of this invention. In step (a), the chloride atom at position 4 of 2,4-dichloro-6-halo-pyrido(3,2-d)pyrimidine (see FIG. 5 and corresponding text for general method of its preparation) is selectively hydrolyzed to the corresponding tautomeric 4-hydroxy compound. In step (b), the chlorine at position 2 of the pyrido(3,2-d)pyrimidine ring can be displaced by a nucleophile bearing the general formula $R_1H$ in an aprotic solvent (such as for example dioxane or tetrahydrofuran) in the presence of a suitable base at an appropriate temperature. Representative $R_1H$ includes, but is not limited to, alcohol, primary amine, or secondary amine. Suitable base includes, but is not limited to, trialkyl amine, potassium t-butoxide, DBU, etc. In step (c), a leaving group (L), such as a chlorine or 1,2,4-triazol-1-yl group, can be introduced at the 4 position of the pyrido(3,2-d)pyrimidine ring. The 4-chloro derivatives can be obtained by treating the product obtained from step (b) with a reagent such as, but is not limited to, thionyl chloride or phosphorus oxychloride. The 4-triazole derivatives can be obtained by treating the product obtained from step (b) with a reagent such as, but is not limited to, thionyl chloride or phosphorus oxychloride plus 1,2,4-triazole. A base such as trialkylamine, DBU, etc. can be added to facilitate the reaction. The chlorine atom or triazolyl group is designated as L in FIG. 7. Nucleophilic displacement of the triazolyl group or chlorine atom occurs in step (d) by reaction with an appropriate nucleophile having the general formula $R_2M$ wherein M is selected from the group comprising hydrogen, Li, Na and K, in a polar aprotic solvent. Examples of suitable nucleophiles include lithium, sodium or potassium alkoxides, lithium, sodium or potassium thiolates, primary and secondary amines. In particular when M is H, a suitable base may also be added to facilitate the reaction. Such bases include, but are not limited to potassium t-butoxide, trialkylamines, DBU. In step (e), the product obtained from step (d) is subjected to a palladium-catalyzed coupling reaction such as, but not limited to, a Stille coupling reaction with an aryl tin reagent or a Suzuki reaction with an aryl boronic acid to yield the corresponding biaryl derivative or, alternatively, a Heck reaction with a terminal alkene leading to the formation of an alkenyl derivative. Alternatively, a Sonogashira reaction with a terminal alkyne can lead to the formation of alkynyl derivatives.

Figure 8:
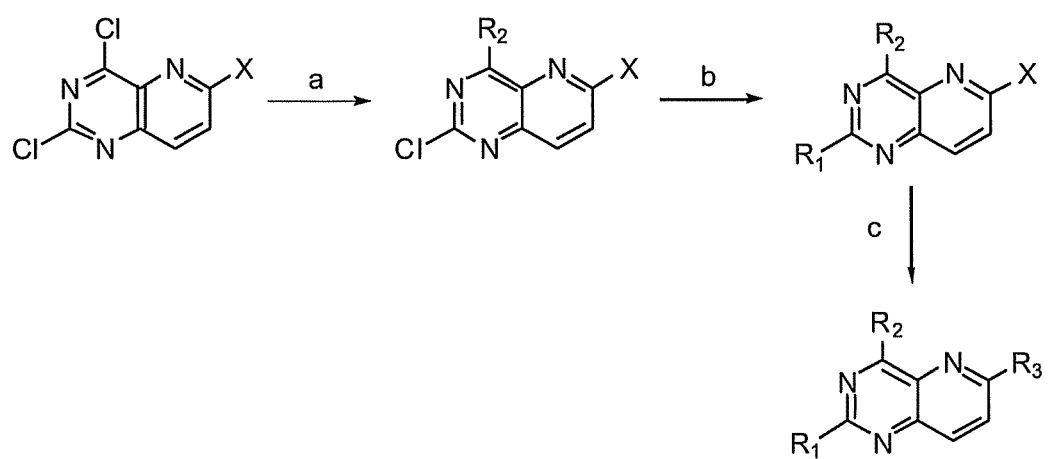
FIG. 8 schematically shows yet another method for making the 2,4,6-tri-substituted pyrido(3,2-d)pyrimidine derivatives of this according to an embodiment of the present invention.

FIG. 8 schematically shows an alternative method for making the 2,4,6-tri-substituted pyrido(3,2-d)pyrimidine derivatives of this invention. In step (a), nucleophilic displacement of the chloride atom at 4 position of the 2,4-dichloro-6-halo-pyrido(3,2-d)pyrimidine (see FIG. 5 and corresponding text for general method of its preparation) is done by reaction with an appropriate nucleophile having the general formula $R_2M$ wherein M selected from the group comprising hydrogen, Li, Na, K, magnesium halide, trialkyltin and $B(OH)_2$, in a polar aprotic solvent. Examples of suitable nucleophiles include alcohols, lithium, sodium or potassium alkoxides, lithium, sodium or potassium thiolates, primary and secondary amines. In particular when M is hydrogen, a suitable base may also be added to facilitate the reaction. Such bases include, but are not limited to potassium t-butoxide, trialkylamines, DBU. In order to introduce a carbon linker at position 4 of the pyrido(3,2-d)pyrimidine scaffold, a nucleophilic displacement reaction can be effected by mixing 2,4-dichloro-6-halo-pyrido(3,2-d)pyrimidine with an appropriate Grignard reagent in a dry, polar, aprotic solvent such as for example 1,4-dioxane, diethyl ether or tetrahydrofuran. A broad range of suitable Grignard reagents is commercially available such as, but not limited to, benzylmagnesium chloride, methylmagnesium bromide, methylmagnesium chloride, methylmagnesium iodide, ethylmagnesium bromide, ethylmagnesium chloride, propylmagnesium chloride, n-butylmagnesium chloride, sec-butylmagnesium chloride, tert-butylmagnesium chloride, pentylmagnesium bromide, allylmagnesium bromide, allylmagnesium chloride, ethynylmagnesium chloride, (trimethylsilyl)methylmagnesium chloride, phenylmagnesium bromide, 4-methoxyphenylmagnesium bromide, 4-chlorophenylmagnesium bromide, 4-fluorophenylmagnesium bromide, 1-naphthylmagnesium bromide, phenyl-magnesium chloride, vinylmagnesium bromide, vinylmagnesium chloride, cyclohexylmagnesium chloride, and the like. Alternatively, the above-listed Grignard reagents as well as those which are not commercially available are obtainable using methods well known to the skilled person, or can advantageously be made in situ if desired. Alternatively, 2,4-dichloro-6-halopyrido(3,2-d)pyrimidine can also serve as a starting materials for a wide variety of organometallic cross-coupling reactions, which are well known in the art. Examples of cross-coupling reactions include, but are not limited to, a Negishi reaction (i.e. a nickel or palladium catalyzed coupling of organozinc compounds with an aryl- or heteroarylhalide), Stille coupling (i.e. a palladium catalysed coupling reaction between an aryl- or heteroaryl halide and a stannane), Suzuki coupling (i.e. a palladium catalysed cross coupling reaction between an organoboronic acid and an aryl- or heteroaryl-halide), Kumada coupling (which is a palladium or nickel catalyzed coupling of a Grignard reagent with an aryl- or heteroarylhalide), Heck reaction (which is the palladium-catalyzed C—C coupling between an aryl- or heteroaryl halide and an activated alkene in the presence of a base), Sonogashira reaction (i.e. the coupling of a terminal alkyne with an aryl- or heteroarylhalide with a palladium catalyst, a copper (I) co-catalyst, and an amine base). In each of the above types of reaction, the 4-chloro-pyrido(3,2-d)pyrimidine moiety will serve as the heteroaryl halide. In step (b), the chlorine at position 2 of the pyrido(3,2-d)pyrimidine ring can be displaced by a nucleophile bearing the general formula $R_1H$ in an aprotic solvent (such as for example dioxane or tetrahydrofuran) in the presence of a suitable base at an appropriate temperature. Representative $R_1H$ includes, but is not limited to, alcohol, primary amine, or secondary amine. Suitable base includes, but is not limited to, trialkyl amine, potassium t-butoxide, DBU, etc. In step (c), the product obtained from step (b) is subjected to a palladium-catalyzed coupling reaction such as, but not limited to, a Stille coupling reaction with an aryl tin reagent or a Suzuki reaction with an aryl boronic acid to yield the corresponding biaryl derivative or, alternatively, a Heck reaction with a terminal alkene leading to the formation of an alkenyl derivative. Alternatively, a Sonogashira reaction with a terminal alkyne can lead to the formation of alkynyl derivatives.

In another particular embodiment, the invention relates to a group of trisubstituted pyrido(3,2-d)pyrimidine derivatives, as well as pharmaceutical compositions comprising such pyrido(3,2-d)pyrimidine derivatives as active principle, having the above general formula (I) or (II), and being in the form of a pharmaceutically acceptable salt. The latter include any therapeutically active non-toxic addition salt which compounds having the general formula (I), especially these wherein $R_3$ is not halogen, or (II) are able to form with a salt-forming agent. Such addition salts may conveniently be obtained by treating the trisubstituted pyrido(3,2-d)pyrimidine derivatives of the invention with an appropriate salt-forming acid or base. For instance, pyrido(3,2-d)pyrimidine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic mono- or di-acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-amino-salicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like.

Trisubstituted pyrido(3,2-d)pyrimidine derivatives of the general formula (I), especially these wherein $R_3$ is not halogen, or general formula (II), having acidic properties may be converted in a similar manner into the corresponding therapeutically active, non-toxic base addition salt form. Examples of appropriate salt-forming bases include, for instance, inorganic bases like metallic hydroxides such as, but not limited to, those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the trisubstituted pyrido (3,2-d)pyrimidine derivatives having the general formula (I) or (II) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water solubility, lower toxicity, greater stability and/or slower dissolution rate to the pyrido(3,2-d)pyrimidine derivative of this invention.

The present invention further provides the use of a trisubstituted pyrido(3,2-d)pyrimidine derivative represented by the structural formula (I), especially these wherein $R_3$ is not halogen, or general formula (II), or a pharmaceutically acceptable salt or a solvate thereof, as a biologically-active ingredient, i.e. active principle, especially as a medicine or for the manufacture of a medicament for the treatment of a Flaviridae viral infection such as, but not limited to, hepatitis C.

In another embodiment, the present application provides for methods of treating a viral infection in a patient, comprising: administering to the patient a therapeutically effective amount of a compound of Formula (I) or (II), or a pharmaceutically acceptable salt, solvate, and/or ester thereof.

In another embodiment, the present application provides for methods of treating a viral infection in a patient, comprising: administering to the patient a therapeutically effective amount of a compound of Formula I or II, or a pharmaceutically acceptable salt, solvate, and/or ester thereof, and at least one additional active agent.

In another embodiment, the present application provides for methods of treating HCV in a patient, comprising: administering to the patient a therapeutically effective amount of a compound of Formula I or II, or a pharmaceutically acceptable salt, solvate, and/or ester thereof.

In another embodiment, the present application provides for methods of treating HCV in a patient, comprising: administering to the patient a therapeutically effective amount of a compound of Formula I or II, or a pharmaceutically acceptable salt, solvate, and/or ester thereof, and at least one additional active agent, whereby HCV polymerase is inhibited.

In another embodiment, the present application provides for methods of treating HCV in a patient, comprising: administering to the patient a therapeutically effective amount of a compound of Formula I or II, or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In another embodiment, the present application provides for the use of a compound of the present invention, or a pharmaceutically acceptable salt, solvate, and/or ester thereof, for the preparation of a medicament for treating a viral infection, e.g., an HBV/HCV infection.

In yet another embodiment, the present application provides a method for treating or preventing a viral infection comprising co-administering, to a patient in need thereof, a therapeutically effective amount of at least one compound of Formula (I) or (II) and at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

The invention further relates to a pharmaceutical composition comprising:

(a) one or more pyrido(3,2-d)pyrimidine derivatives represented by the structural formula (I), wherein $R_3$ is not halogen, or general formula (II), and (b) one or more pharmaceutically acceptable carriers.

In another embodiment, the compounds of the present invention are used in combination with other active therapeutic ingredients or agents. Combinations of the compounds of Formula (I) or (II) and additional active agents may be selected to treat patients with a viral infection, e.g., HBV, HCV, or HIV infection. In this embodiment, the this invention further provides combinations, preferably synergistic combinations, of one or more pyrido(3,2-d)pyrimidine derivatives represented by the general formula (I), wherein $R_3$ is not halogen, or general formula (II), with one or more antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of biologically desirable effects such as, but not limited to, an anti-viral activity against a Flaviridae virus, e.g. HCV.

Preferably, the other active therapeutic ingredients or agents are interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Combinations of the compounds of Formula (I) or (II) are typically selected based on the condition to be treated, cross-reactivities of ingredients and pharmaco-properties of the combination. For example, when treating an infection (e.g., HCV), the compositions of the invention are combined with other active agents (such as those described herein).

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In an embodiment, the present invention discloses pharmaceutical compositions comprising one or more compounds of the present invention, or a pharmaceutically acceptable salt, solvate, and/or ester thereof, in combination with at least one additional active agent, and a pharmaceutically acceptable carrier or excipient.

According to the present invention, the active agent used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In particular, Tthe invention further relates to a pharmaceutical composition or combined prepa-ration having synergistic effects against a hepatitis C infection and containing:
(a) one or more anti-viral agents, and
(b) at least one pyrido(3,2-d)pyrimidine derivative represented by the general formula (I), wherein $R_3$ is not halogen, and
(c) optionally one or more pharmaceutical excipients or pharmaceutically acceptable carriers,
for simultaneous, separate or sequential use in the treatment of HCV infection.

Alternatively, the present invention provides a combination pharmaceutical composition comprising:
a) a first pharmaceutical composition comprising a compound of the present invention, or a pharmaceutically acceptable salt, solvate, or ester thereof; and
b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Suitable anti-viral agents for inclusion into the synergistic antiviral compositions or combined preparations of this invention include, for instance, ribavirin, (pegylated)interferon, and retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

In particular suitable active agents or ingredients which can be combined with the compounds of Formula (I) or (II) can include interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

Especially relevant to this aspect of the invention is the inhibition of the replication of viruses selected from the group consisting of picorna-, toga-, bunya, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV). Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical compositions or combined preparations with synergistic activity against viral infection according to this invention may contain the trisubstituted pyrido(3, 2-d)pyrimidine derivative represented by the structural formula (I), wherein $R_3$ is not halogen, or structural formula (II) over a broad content range depending on the contemplated use and the expected effect of the preparation. The pyrido(3,2-d)pyrimidine derivative content of the combined preparation may be within a range of from about 1 to about 99% by weight, preferably from about 5 to about 95% by weight, more preferably from about 20 to 80% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperiteneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the pyrido(3,2-d)pyrimidine derivative represented by the general formula (I), wherein $R_3$ is not halogen, or by general formula (II) and optionally the additional one or more antiviral agents, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the pyrido(3,2-d)pyrimidine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. The compositions may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antiseftle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gailate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including a pyrido(3,2-d)pyrimidine derivative of this invention and an additional active agent, in particular an antiviral agent, both ingredients do not necessarily bring out their synergistic therapeutic effect against the pathologic condition (viral infection) directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating hepatitis C in a patient, preferably a mammal, more preferably a human being. The method of this invention consists of administering to the patient in need thereof an effective amount of a trisubstituted pyrido(3,2-d)pyrimidine derivative having the general formula (I), wherein $R_3$ is not halogen, optionally together with an effective amount of an antiviral agent, or a pharmaceutical composition comprising the same, such as disclosed above in extensive details. The effective amount is usually in the range of about 0.01 mg to 20 mg, preferably about 0.1 mg to 5 mg, per day per kg bodyweight for humans. Depending upon the pathologic condition to be treated and the patient's condition, the said effective amount may be divided into several sub-units per day or may be administered at more than one day intervals. The patient to be treated may be any warm-blooded animal, preferably a mammal, more preferably a human being, suffering from said pathologic condition.

The preferred compounds of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in *Toxicology* (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an antiviral amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals.

Another embodiment of this invention includes the various precursors or "pro-drug" forms of the trisubstituted pyrido(3,2-d)pyrimidine derivatives having the general formula (I), wherein $R_3$ is not halogen, or formula (II) of the present invention. It may be desirable, under specific circumstances, to formulate the compounds of the present invention in the form of a chemical species which itself is not significantly biologically-active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purpose of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

In another embodiment, the present application provides for methods of inhibiting a viral polymerase in a cell, in particular HCV polymerase. The method comprises the step of contacting a cell infected with a virus, in particular HCV, with an effective amount of a compound of Formula I or II, or a pharmaceutically acceptable salt, solvate, and/or ester thereof, whereby HCV polymerase is inhibited.

In another embodiment, the present application provides for methods of inhibiting a viral polymerase in a cell, in particular HCV polymerase, comprising: contacting a cell infected with a virus, in particular HCV with an effective amount of a compound of Formula I or II, or a pharmaceutically acceptable salt, solvate, and/or ester thereof, and at least one additional active agent, whereby HCV polymerase is inhibited.

In a particular embodiment, the present application provides for methods of inhibiting HCV polymerase in a cell, comprising: contacting a cell infected with HCV with an effective amount of a compound of Formula (I) or (II), or a pharmaceutically acceptable salt, solvate, and/or ester thereof, and at least one additional active agent selected from the group consisting of interferons, ribavirin analogs, HCV NS3 protease inhibitors; alpha-glucosidase 1 inhibitors, hepatoprotectants, non-nucleoside inhibitors of HCV, and other drugs for treating HCV.

The present invention will be further described with reference to certain more specific embodiments, detailed schemes and examples, but the present invention is not limited thereto but only by the attached claims. The following examples are given by way of illustration only.

EXAMPLE 1

Synthesis of 2-acetamido-6-(4-fluorophenyl)-pyrido[3,2-d]pyrimidin-4(3H)-one

A suspension of 2-amino-6-(4-fluorophenyl)-pyrido[3,2-d]pyrimidin-4(3H)-one (2.0 g) in acetic anhydride (180 ml) and acetic acid (20 ml) was refluxed for 16 hours. The hot suspension was filtered and the filtrate was concentrated under reduced pressure until crystallization started. The precipitate was filtered off to give the pure title compound in 78% yield. The compound was characterized by its mass spectrum as follows: MS (m/z): 299 ([M+H]$^+$, 100).

EXAMPLE 2

Synthesis of 2-acetamido-4-(1,2,4-triazolyl)-6-(4-fluorophenyl)-pyrido[3,2-d]pyrimidine A suspension of 1,2,4-triazole (120 mmol) and phosphorus oxychloride (36 mmol) in dry acetonitrile (150 ml) was added to a stirred suspension of the 2-acetamido-6-(4-fluorophenyl)-pyrido[3,2-d]pyrimidin-4(3H)-one of example 1 (12 mmol) and triethylamine (36 mmol) in dry acetonitrile (150 ml). The mixture was stirred at room temperature under nitrogen for 70 hours (or, alternatively, at 50° C. for 24 hours) and the yellow precipitate formed was filtered off, then successively washed with ethanol and ether, and further dried over P$_2$O$_5$ under vacuum. Solvents were evaporated in vacuo, then the crude residue was dissolved in dichloromethane and extracted with a diluted hydrochloric acid solution (HCl 0.01 N). The combined organic layers were dried over anhydrous MgSO$_4$ and evaporated, thus providing the crude title compound in 72% yield, which was characterized by its mass spectrum as follows: MS (m/z): 350 ([M+H]$^+$, 100).

EXAMPLE 3

Synthesis of 2-acetamido-4-(N-isopropylamino)-6-(4-fluorophenyl)-pyrido[3,2-d]pyrimidine To a suspension of the 2-acetamido-4-(1,2,4-triazolyl)-6-(4-fluorophenyl)-pyrido[3,2-d]pyrimidine of example 2 (70 mg) in dioxane (5 ml) was added isopropylamine (0.4 mmol). The reaction was stirred at room temperature for 24 hours.

The solvents were evaporated in vacuo, yielding the crude title compound which was purified by preparative TLC on silica, using a mixture of methanol and dichloromethane, in a ratio of 10:90 as mobile phase, thus providing the title compound in 73% yield. The pure title compound was characterized by its mass spectrum as follows: MS (m/z): 340 ([M+H]$^+$, 100).

EXAMPLE 4

Synthesis of 2-amino-4-(N-isopropylamino)-6-(4-fluorophenyl)pyrido-[3,2-d]pyrimidine The crude 2-acetamido-4-(N-isopropylamino)-6-(4-fluorophenyl)pyrido[3,2-d]pyrimidine of example 3 (0.5 mmol) was suspended in a mixture of dichloromethane (10 ml) and 0.5 N sodium ethoxide (10 ml). The reaction mixture was stirred for 16 hours at room temperature. The solvents were evaporated in vacuo and the crude residue was purified by preparative thin layer chromatography on silica, using a mixture of methanol and dichloromethane (in a volume ratio of 10:90) as a mobile phase providing, in a yield of 61%, the pure title compound which was characterized by its mass spectra as follows: MS (m/z): 298 ([M+H]$^+$, 100).

EXAMPLES 5 AND 6

Synthesis of 2-monoethylamino-4-isopropylamino-6-(4-fluorophenyl)-pyrido(3,2-d)pyrimidine and 2-monobenzylamino-4-isopropylamino-6-(4-fluorophenyl)-pyrido(3,2-d)pyrimidine To a solution of the 2-amino-4-(N-isopropylamino)-6-(4-fluorophenyl)-pyrido(3,2-d)pyrimidine of example 4 (80 mg) in methanol (10 ml) was added sodium cyanoborohydride (1.25 mmol, 80 mg) and an appropriate aldehyde (3 mmol). The reaction mixture was stirred at room temperature for 2 days. The solvents were evaporated in vacuo and the crude residue was purified by preparative thin layer chromatography on silica plates (using methanol and dichloromethane as mobile phase in a volume ratio of 5:95). If necessary a second purification step was performed by HPLC on a C18-RP column (100×30 mm Gemini 5 um) with a gradient of H$_2$O, 0.05% TEA-acetonitrile. In this way were obtained, and characterized by their mass spectrum MS:

2-monoethylamino-4-isopropylamino-6-(4-fluorophenyl)-pyrido(3,2-d)pyrimidine (example 5) from acetaldehyde, MS (m/z): 326 ([M+H]$^+$, 100).

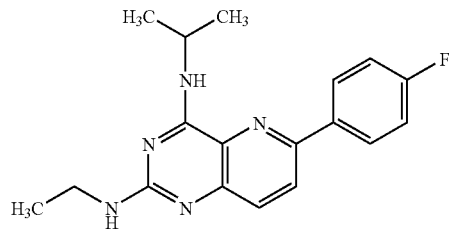 [SMILES: CCNc1nc(NC(C)C)c2nc(-c3ccc(F)cc3)ccc2n1]

2-benzylamino-4-isopropylamino-6-(4-fluorophenyl)-pyrido(3,2-d)pyrimidine (example 6) from benzaldehyde; MS (m/z): 389 ([M+H]$^+$, 100).

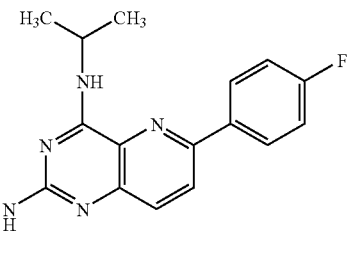

EXAMPLE 7

Synthesis of 2-amino-6-(4-fluorophenyl)-pyrido(3,2-d)pyrimidin-4(3H)thione

A suspension of 2-amino-6-(4-fluorophenyl)-pyrido(3,2-d)pyrimidin-4(3H) one (2.56 g) and phosphorus pentasulfide (2.5 g) in pyridine (200 ml) was refluxed for 4 hours. The reaction mixture was cooled down and the precipitate was filtered off, yielding 2 g of the pure title compound (yield: 73%) which was characterized by its mass spectrum as follows: MS (m/z): 273 ([M+H]$^+$, 100).

EXAMPLE 8

Synthesis of 2-amino-4-methylthio-6-(4-fluorophenyl)-pyrido(3,2-d)pyrimidine

To a solution of the 2-amino-6-(4-fluorophenyl)-pyrido(3,2-d)pyrimidin-4(3H)thione of example 7 (55 mg) in a 1 N NaOH solution (10 ml) was added methyl iodide (0.2 mmol). The reaction was stirred at room temperature for 12 hours. The reaction mixture was diluted with diethyl ether and the organic layer was extracted with water. The combined organic layers were evaporated in vacuo and the crude residue was purified by preparative thin layer chromatography on silica, the mobile phase being a mixture of methanol and dichloromethane, in a volume ratio of 5:95, providing 41 mg of the pure title compound (yield: 72%) which was characterized by its mass spectrum as follows: MS (m/z): 287 ([M+H]$^+$, 100).

EXAMPLE 9

Synthesis of 2-amino-4-ethoxy-6-(4-fluorophenyl)-pyrido(3,2-d)pyrimidine

To a solution of the 2-amino-4-methylthio-6-(4-fluorophenyl)-pyrido(3,2-d)pyrimidine of example 8 (700 mg) in ethanol (20 ml) was added 276 mg sodium. The reaction mixture was refluxed for 5 hours and then cooled down. The solvents were evaporated in vacuo and the crude residue was purified by silica gel flash chromatography, the mobile phase being a mixture of ethanol and dichloromethane, in a volume ratio gradually ranging from 3% to 5% ethanol, thus providing 490 mg of the pure title compound (72% yield), which was characterized by its mass spectrum as follows: MS (m/z): 285 ([M+H]$^+$, 100).

EXAMPLES 10 TO 19

Synthesis of 2-monoalkylamino-4-ethoxy-6-(4-fluorophenyl)-pyrido(3,2-d)pyrimidines To a solution of the 2-amino-4-ethoxy-6-(4-fluorophenyl)-pyrido(3,2-d)pyrimidine of example 9 (35 mg) in ethanol (5 ml) were added molecular sieves, acetic acid (5 drops), sodium cyanoborohydride (0.6 mmol) and an appropriate aldehyde (3 mmol). The reaction mixture was stirred at room temperature for 3 days. The solvent was evaporated in vacuo and the crude residue was purified by preparative thin layer chromatography on silica plates (using ethyl acetate and hexane as mobile phase in a volume ratio of 1:1). If desired a second purification was performed by HPLC on a C18-RP column (100×30 mm Gemini 5 um) with a gradient of $H_2O$, 0.05% TEA-acetonitrile. The following compounds were obtained in yields ranging from 20% to 40%, depending upon the specific aldehyde used, and were characterized by their mass spectrum MS.

2-monoethylamino-4-ethoxy-6-(4-fluorophenyl)-pyrido(3, 2-d)pyrimidine (example 10) from acetaldehyde; MS (m/z): 313 ([M+H]$^+$, 100).

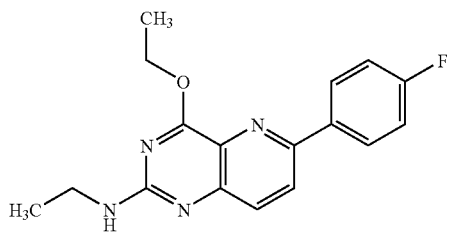 [SMILES: CCNc1nc(OCC)c2nc(-c3ccc(F)cc3)ccc2n1]

2-monobenzylamino-4-ethoxy-6-(4-fluorophenyl)-pyrido(3, 2-d)pyrimidine (example 11) from benzaldehyde; MS (m/z): 375 ([M+H]$^+$, 100).

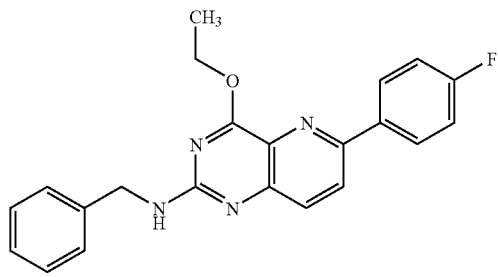 [SMILES: CCOc1nc(NCc2ccccc2)nc2ccc(-c3ccc(F)cc3)nc12]

2-mono[(3-methyl)butylamino]-4-ethoxy-6-(4-fluorophenyl)-pyrido(3,2-d)pyrimidine (example 12) from 3-methylbutyraldehyde; MS (m/z): 355 ([M+H]$^+$, 100).

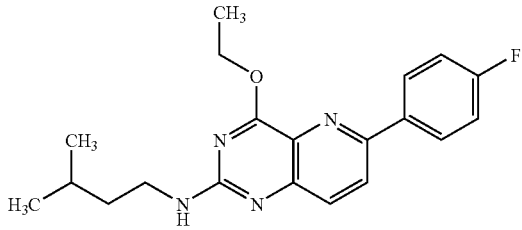 [SMILES: CCOc1nc(NCCC(C)C)nc2ccc(-c3ccc(F)cc3)nc12]

2-mono(cyclopropylmethylamino)-4-ethoxy-6-(4-fluorophenyl)-pyrido(3,2-d)-pyrimidine (example 13) from cyclopropanecarboxaldehyde; MS (m/z): 339 ([M+H]$^+$, 100).

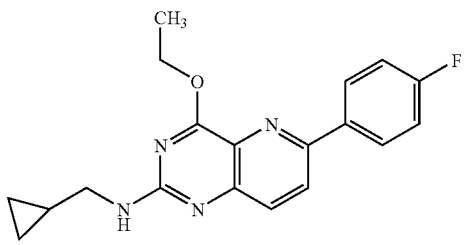 [SMILES: CCOc1nc(NCC2CC2)nc2ccc(-c3ccc(F)cc3)nc12]

2-mono(n-propylamino)-4-ethoxy-6-(4-fluorophenyl)-pyrido(3,2-d)pyrimidine (example 14) from propionaldehyde; MS (m/z): 327 ([M+H]$^+$, 100).

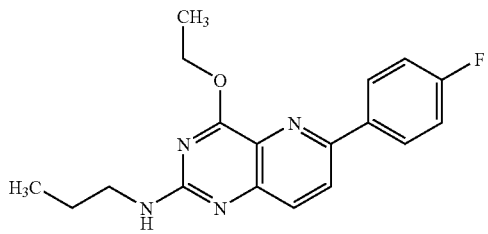 [SMILES: CCCNc1nc(OCC)c2nc(-c3ccc(F)cc3)ccc2n1]

2-mono(4-methoxy-benzylamino)-4-ethoxy-6-(4-fluorophenyl)-pyrido(3,2-d)-pyrimidine (example 15) was obtained from p-anisaldehyde; MS (m/z): 405 ([M+H]$^+$, 100).

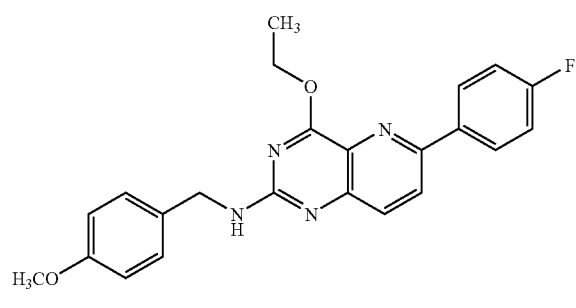 [SMILES: CCOc1nc(NCc2ccc(OC)cc2)nc2ccc(-c3ccc(F)cc3)nc12]

2-mono(4-fluoro-benzylamino)-4-ethoxy-6-(4-fluorophenyl)-pyrido(3,2-d)pyrimidine (example 16) from 4-fluorobenzaldehyde; MS (m/z): 393 ([M+H]$^+$, 100).

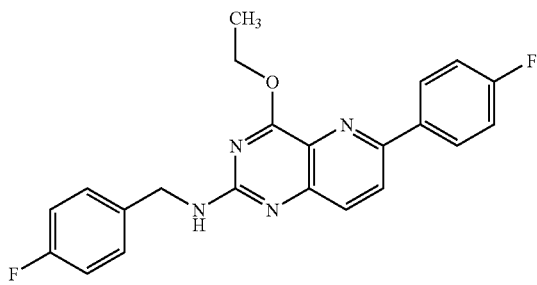 [SMILES: CCOc1nc(NCc2ccc(F)cc2)nc2ccc(-c3ccc(F)cc3)nc12]

2-mono(4-N,N-dimethylaminobenzylamino)-4-ethoxy-6-(4-fluorophenyl)-pyrido(3,2-d)pyrimidine (example 17) from 4-dimethylaminobenzaldehyde; MS (m/z): 419 ([M+H]$^+$, 100).

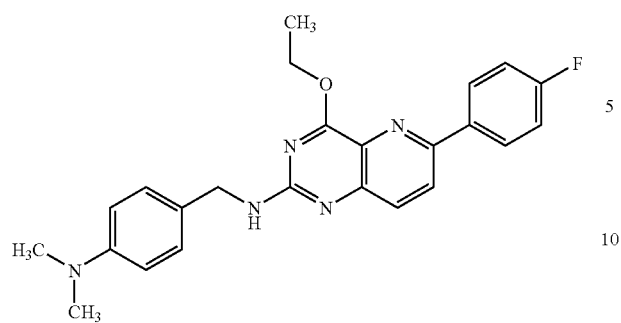

2-mono[2-(imidazolyl)-methylamino]-4-ethoxy-6-(4-fluorophenyl)-pyrido(3,2-d)pyrimidine (example 18) from imidazole-2-carboxaldehyde; MS (m/z): 365 ([M+H]$^+$, 100).

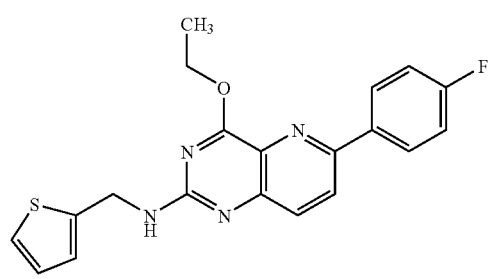

EXAMPLES 20 TO 48

Synthesis of 2-monoalkylamino-4-alkoxy-6-(4-fluorophenyl)-pyrido(3,2-d)pyrimidines and 2-monoalkylamino-4-substituted amino-6-(4-fluorophenyl)-pyrido(3,2-d)-pyrimidines 2-monoalkylamino-4-alkoxy-6-(4-fluorophenyl)-pyrido(3,2-d)-pyrimidines and 2-monoalkylamino-4-substituted amino-6-(4-fluorophenyl)-pyrido(3,2-d)pyrimidines have been synthesized from 3-amino-6-chloropicolinamide according to the principles set forth in FIG. 4 and outlined in more details in two alternative embodiments shown in Scheme 1 below.

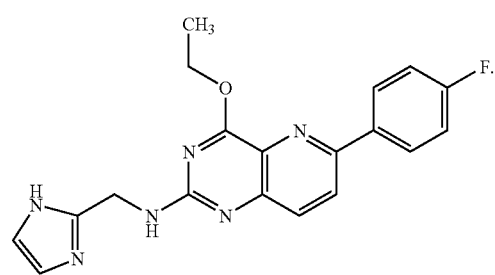 [SMILES: CCOc1nc(NCc2ncc[nH]2)nc2ccc(-c3ccc(F)cc3)nc12]

2-[2-(thienyl)methylamino]-4-ethoxy-6-(4-fluorophenyl)-pyrido(3,2-d)pyrimidine (example 19) from 2-thiophenecarboxaldehyde; MS (m/z): 381 ([M+H]$^+$, 100).

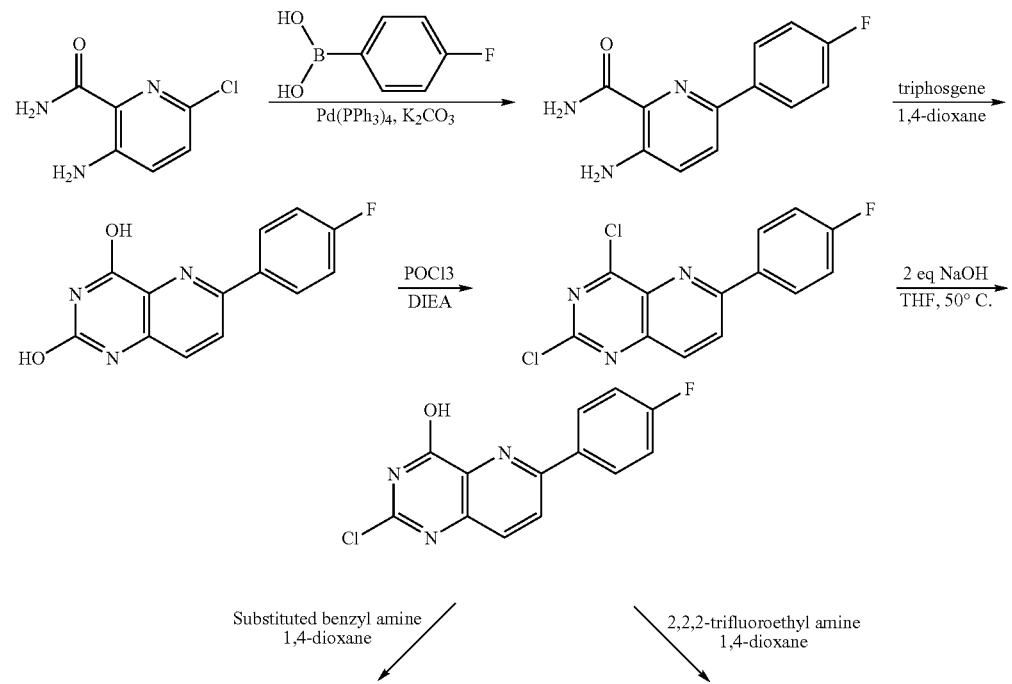

-continued

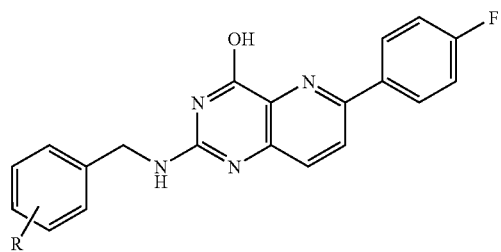
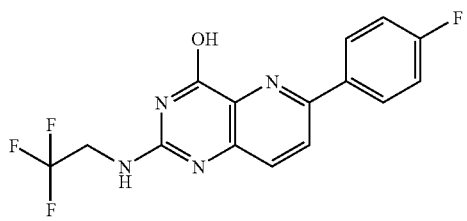

ACN | POCl₃, triazole

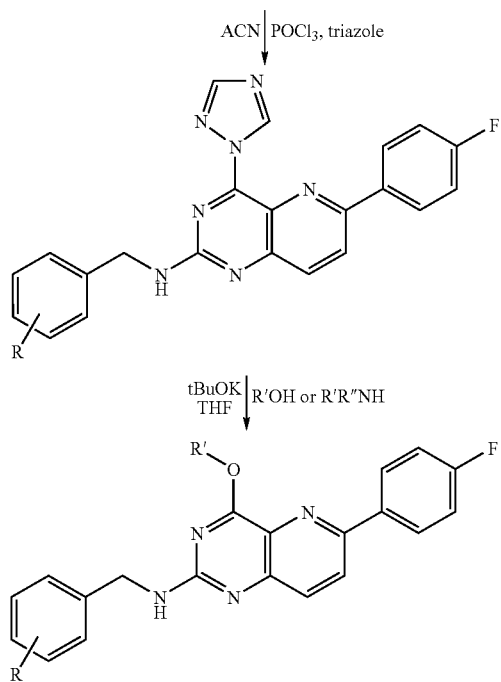
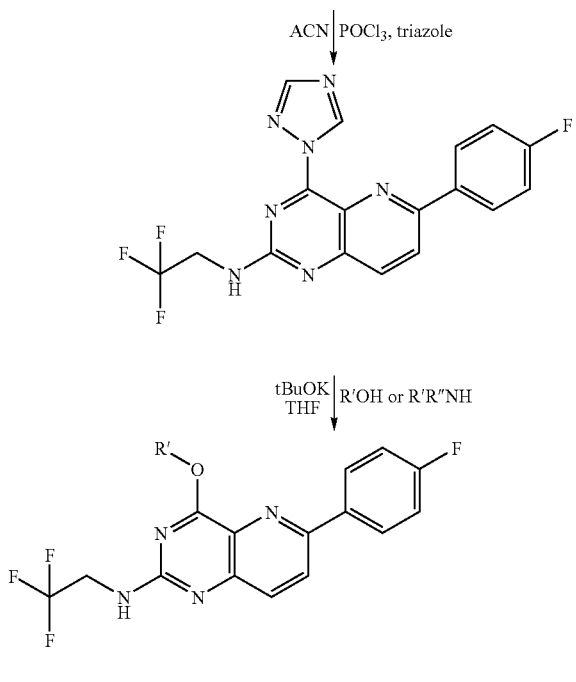

tBuOK / THF | R'OH or R'R"NH

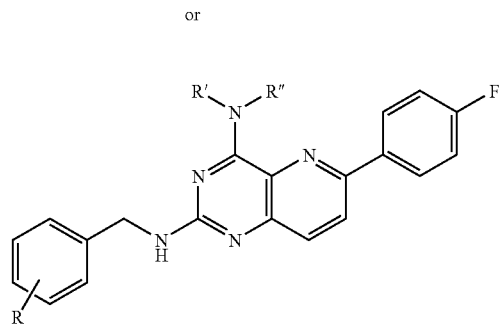
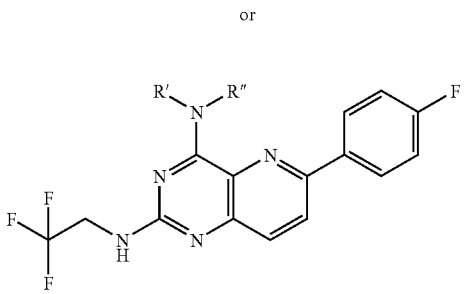

A mixture of 3-amino-6-chloropicolinamide (2 g), potassium carbonate (3.2 g), tetrakis(triphenylphosphine) palladium (0.674 g) and 4-fluorophenylboronic acid (1.79 g) in DMF (50 mL) and water (10 mL) was heated to 120° C. for 16 hours. Solvents were removed and 1N HCl (30 ml) was added to the mixture. The resulting solid was filtered to provide 2.48 g of 3-amino-6-(4-fluorophenyl)picolinamide which was characterized by its mass spectrum as follows: MS (m/z) 232 [M+H]⁺.

A solution of 3-amino-6-(4-fluorophenyl)picolinamide (2.48 g) and triphosgene in 1,4-dioxane (50 mL) was heated to 100° C. for 1 hour. Cooling and filtration provided 2.2 g of 6-(4-fluorophenyl)pyrido[3,2-d]pyrimidine-2,4-diol which was characterized by its mass spectrum as follows: MS (m/z) 258 [M+H]⁺.

A solution of 6-(4-fluorophenyl)pyrido[3,2-d]pyrimidine-2,4-diol (19), POCl₃ (20 ml) and DIEA (2.0 ml) was heated to reflux for 16 hours. POCl₃ was removed and the residue was dissolved in ethyl acetate. The organic layer was extracted with brine three times. It was dried and concentrated to provide 0.97 g of 2,4-dichloro-6-(4-fluorophenyl)pyrido[3,2-d]pyrimidine which was characterized by its mass spectrum as follows: MS (m/z) 294 [M+H]⁺.

A solution of 2,4-dichloro-6-(4-fluorophenyl)pyrido[3,2-d]pyrimidine (0.76 g, 2.58 mmol) and sodium hydroxide (2.6 ml, 1N) in THF (30 mL) was heated at 50° C. for 1 hour. 1N HCl (3 ml) was added and the mixture was extracted with ethyl acetate. The organic layer was dried and concentrated to provide 0.73 g of 2-chloro-6-(4-fluorophenyl)pyrido[3,2-d]pyrimidin-4-ol which was characterized by its mass spectrum as follows: MS (m/z) 276 [M+H]⁺.

A solution of 2-chloro-6-(4-fluorophenyl)pyrido[3,2-d]pyrimidin-4-ol (730 mg) and 4-fluorobenzyl amine (398 mg) in 1,4-dioxane (20 mL) was heated at 80° C. overnight. 1N HCl (5 ml) was added to the mixture and the resulting solid was filtered to provide 0.9 g of 2-(4-fluorobenzylamino)-6-(4-fluorophenyl)-pyrido[3,2-d]pyrimidin-4-ol which was characterized by its mass spectrum as follows: MS (m/z) 365 [M+H]$^+$.

A solution of 2-(4-fluorobenzylamino)-6-(4-fluorophenyl) pyrido[3,2-d]pyrimidin-4-ol (2 g), 1,2,4-triazole (1.52 g), DIEA (3.55 g) and POCl$_3$ (3.4 g) in acetonitrile (20 mL) was stirred at room temperature for 1 hour. Ethyl acetate was added to the mixture, which was then washed twice with brine. The organic layer was dried and concentrated to provide 2.1 g of N-(4-fluorobenzyl)-6-(4-fluorophenyl)-4-(1H-1,2,4-triazol-1-yl)pyrido[3,2-d]pyrimidin-2-amine which was characterized by its mass spectrum as follows: MS (m/z) 416 [M+H]$^+$.

A solution of N-(4-fluorobenzyl)-6-(4-fluorophenyl)-4-(1H-1,2,4-triazol-1-yl)pyrido[3,2-d]pyrimidin-2-amine (26 mg), (S)-tetrahydrofuran-3-ol (13.77 mg, 0.56 mmol) and potassium tert-butoxide (0.156 mmol) in THF (1 mL) was stirred at room temperature for 1 hour. Solvents were concentrated in vacuo and the residue was purified by RP HPLC using a C18 column with a gradient of H$_2$O, 0.1% TFA-acetonitrile to provide Example 24 (41 mg).

A solution of 2-chloro-6-(4-fluorophenyl)pyrido[3,2-d]pyrimidin-4-ol (130 mg 9, 0.47 mmol) and 2,2,2-trifluoroethyl amine (1 ml) in 1,4-dioxane (20 mL) was heated at 80° C. for 72 hrs. 1N HCl (3 ml) was added to the mixture, which was then extracted with ethyl acetate. The organic layer was dried and concentrated to provide 230 mg of crude product which was used without further purification. MS (m/z) 339 [M+H]$^+$.

A solution of 6-(4-fluorophenyl)-2-(2,2,2-trifluoroethylamino)pyrido[3,2-d]pyrimidin-4-ol (230 mg, 0.68 mmol), 1,2,4-triazole (187 mg, 2.7 mmol), DIEA (439 mg, 3.4 mmol) and POCl$_3$ (416 mg, 2.7 mmol) in acetonitrile (2 mL) was stirred at room temperature for 1 hour. Ethyl acetate was added and the mixture was washed twice with brine. The organic layer was dried and concentrated to provide 200 mg of crude product which was used without further purification. MS (m/z) 390 [M+H]$^+$.

A solution of 6-(4-fluorophenyl)-4-(1H-1,2,4-triazol-1-yl)-N-(2,2,2-trifluoro-ethyl)pyrido[3,2-d]pyrimidin-2-amine (100 mg g, 0.247 mmol), (S)-tetrahydrofuran-3-ol (26.1 mg, 0.296 mmol) and potassium tert-butoxide (0.543 mmol) or sodium ethoxide (0.565 mmol) in THF (1 mL) was stirred at room temperature for 1 hour. Solvents were concentrated in vacuo and the residue was purified by RP HPLC using a C18 column with a gradient of H$_2$O, 0.1% TFA-acetonitrile, to provide Example 20. The following pure final compounds were characterized by their mass spectra as indicated in Table 1.

Other examples in Table 1 with a substituted benzylamino group at the 2-position of the pyrido[3,2-d]pyrimidine ring were synthesized using an analogous method as described for Example 24 above. In each case, a suitable alcohol or amine was used in place of (S)-tetrahydrofuran-3-ol.

Other examples in Table 1 with a trifluoroethyl group at the 2-position of the pyrido[3,2-d]pyrimidine ring were synthesized using an analogous method as described for Example 20 above. In each case, a suitable alcohol or amine was used in place of (S)-tetrahydrofuran-3-ol.

TABLE 1

| No. | Structure | Name | Mass M$^{+1}$ |
|---|---|---|---|
| 20 | 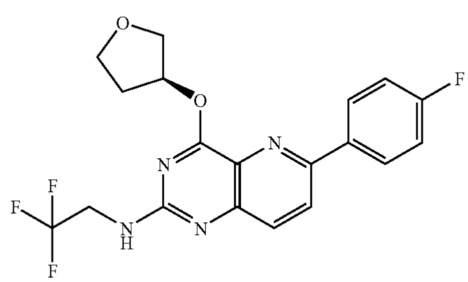 [SMILES: Fc1ccc(-c2ccc3nc(NCC(F)(F)F)nc(O[C@H]4CCOC4)c3n2)cc1] | [6-(4-Fluoro-phenyl)-4-(tetrahydro-furan-3-yloxy)-pyrido[3,2-d]pyrimidin-2-yl]-(2,2,2-trifluoro-ethyl)-amine | 408.9 |
| 21 | 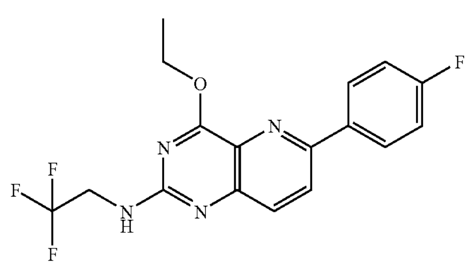 [SMILES: CCOc1nc(NCC(F)(F)F)nc2ccc(-c3ccc(F)cc3)nc12] | [4-Ethoxy-6-(4-fluoro-phenyl)-pyrido[3,2-d]pyrimidin-2-yl]-(2,2,2-trifluoro-ethyl)-amine | 367 |

TABLE 1-continued

| No. | Structure | Name | Mass M+1 |
|---|---|---|---|
| 22 | 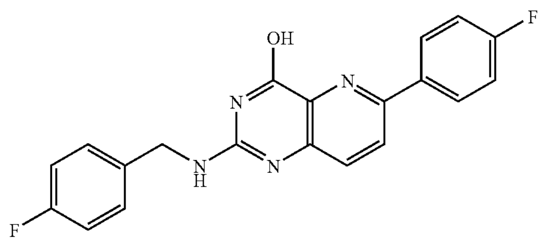 [SMILES: Oc1nc(NCc2ccc(F)cc2)nc2ccc(-c3ccc(F)cc3)nc12] | 2-(4-Fluoro-benzylamino)-6-(4-fluoro-phenyl)-pyrido[3,2-d]pyrimidin-4-ol | 365.1 |
| 23 | 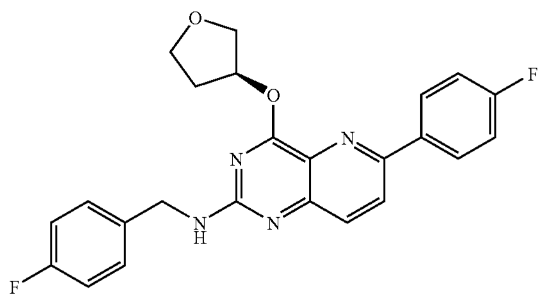 [SMILES: Fc1ccc(CNc2nc(O[C@H]3CCOC3)c3nc(-c4ccc(F)cc4)ccc3n2)cc1] | (4-Fluoro-benzyl)-[6-(4-fluoro-phenyl)-4-(tetrahydro-furan-3-yloxy)-pyrido[3,2-d]pyrimidin-2-yl]amine | 435 |
| 24 | 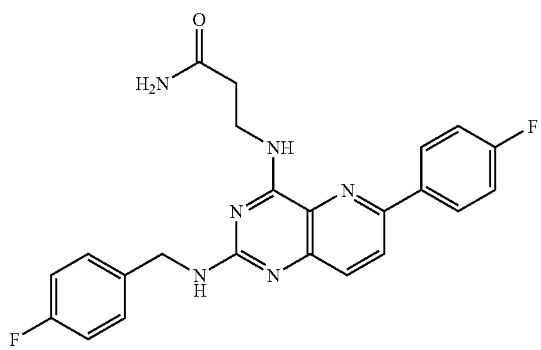 [SMILES: NC(=O)CCNc1nc(NCc2ccc(F)cc2)nc2ccc(-c3ccc(F)cc3)nc12] | 3-[2-(4-Fluoro-benzylamino)-6-(4-fluoro-phenyl)-pyrido[3,2-d]pyrimidin-4-ylamino]-propionamide | 435 |
| 25 | 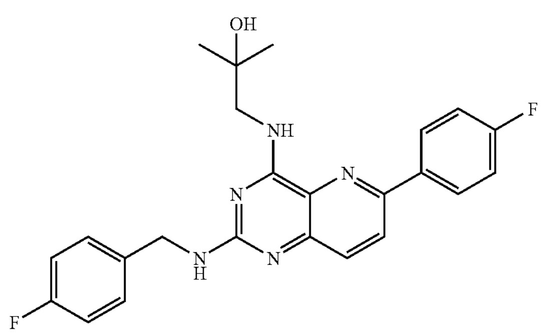 [SMILES: CC(C)(O)CNc1nc(NCc2ccc(F)cc2)nc2ccc(-c3ccc(F)cc3)nc12] | 1-[2-(4-Fluoro-benzylamino)-6-(4-fluoro-phenyl)-pyrido[3,2-d]pyrimidin-4-ylamino]-2-methyl-propan-2-ol | 436 |
| 26 | 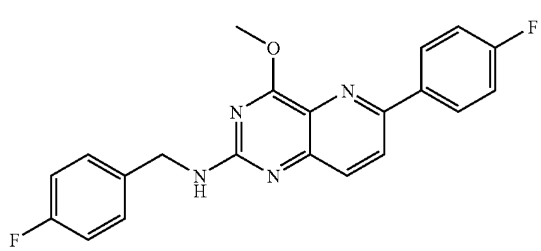 [SMILES: COc1nc(NCc2ccc(F)cc2)nc2ccc(-c3ccc(F)cc3)nc12] | (4-Fluoro-benzyl)-[6-(4-fluoro-phenyl)-4-methoxy-pyrido[3,2-d]pyrimidin-2-yl]-amine | 379 |

TABLE 1-continued

| No. | Structure | Name | Mass M+1 |
|---|---|---|---|
| 27 | 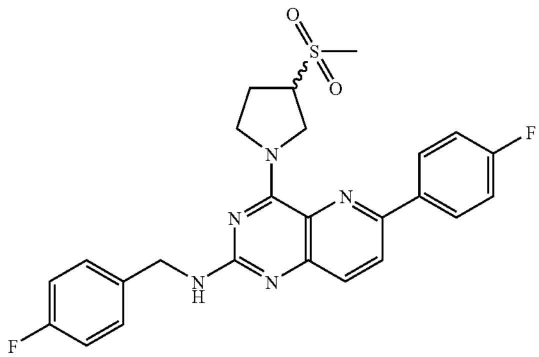 [SMILES: CS(=O)(=O)C1CCN(c2nc(NCc3ccc(F)cc3)nc3ccc(-c4ccc(F)cc4)nc23)C1] | (4-Fluoro-benzyl)-[6-(4-fluoro-phenyl)-4-(3-methanesulfonyl-pyrrolidin-1-yl)-pyrido[3,2-d]pyrimidin-2-yl]-amine | 496 |
| 28 | 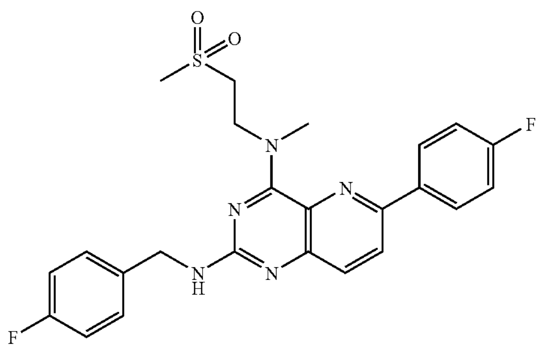 [SMILES: CN(CCS(C)(=O)=O)c1nc(NCc2ccc(F)cc2)nc2ccc(-c3ccc(F)cc3)nc12] | N2-(4-Fluoro-benzyl)-6-(4-fluoro-phenyl)-N4-(2-methanesulfonyl-ethyl)-N4-methyl-pyrido[3,2-d]pyrimidine-2,4-diamine | 484 |
| 29 | 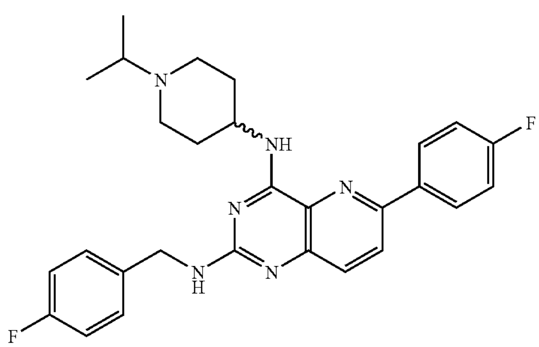 [SMILES: CC(C)N1CCC(Nc2nc(NCc3ccc(F)cc3)nc3ccc(-c4ccc(F)cc4)nc23)CC1] | N2-(4-Fluoro-benzyl)-6-(4-fluoro-phenyl)-N4-(1-isopropyl-piperidin-4-yl)-pyrido[3,2-d]pyrimidine-2,4-diamine | 489 |
| 30 | 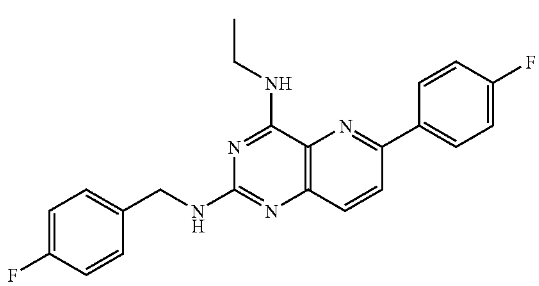 [SMILES: CCNc1nc(NCc2ccc(F)cc2)nc2ccc(-c3ccc(F)cc3)nc12] | N4-Ethyl-N2-(4-fluoro-benzyl)-6-(4-fluoro-phenyl)-pyrido[3,2-d]pyrimidine-2,4-diamine | 392 |

TABLE 1-continued

| No. | Structure | Name | Mass M⁺¹ |
|---|---|---|---|
| 31 | 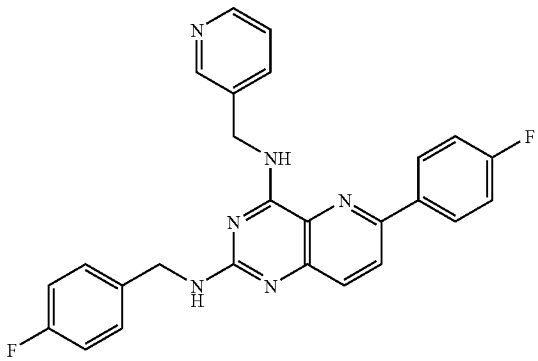 [SMILES: Fc1ccc(CNc2nc(NCc3cccnc3)c3nc(-c4ccc(F)cc4)ccc3n2)cc1] | N2-(4-Fluoro-benzyl)-6-(4-fluoro-phenyl)-N4-pyridin-3-ylmethyl-pyrido[3,2-d]pyrimidine-2,4-diamine | 455 |
| 32 | 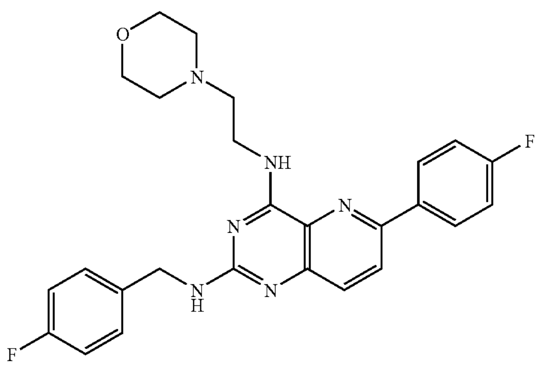 [SMILES: Fc1ccc(CNc2nc(NCCN3CCOCC3)c3nc(-c4ccc(F)cc4)ccc3n2)cc1] | N2-(4-Fluoro-benzyl)-6-(4-fluoro-phenyl)-N4-(2-morpholin-4-yl-ethyl)-pyrido[3,2-d]pyrimidine-2,4-diamine | 477 |
| 33 | 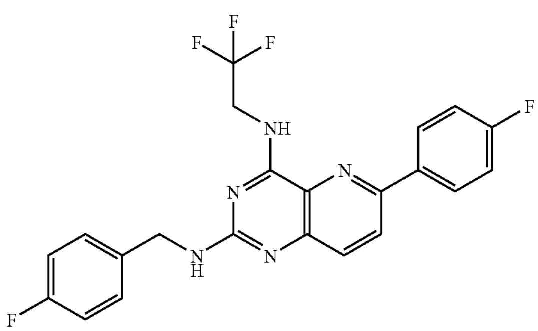 [SMILES: Fc1ccc(CNc2nc(NCC(F)(F)F)c3nc(-c4ccc(F)cc4)ccc3n2)cc1] | N2-(4-Fluoro-benzyl)-6-(4-fluoro-phenyl)-N4-(2,2,2-trifluoro-ethyl)-pyrido[3,2-d]pyrimidine-2,4-diamine | 446 |
| 34 | 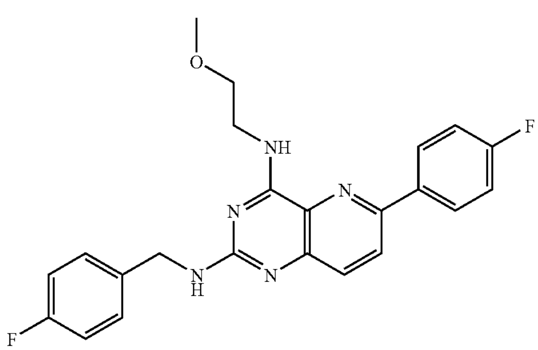 [SMILES: COCCNc1nc(NCc2ccc(F)cc2)nc2ccc(-c3ccc(F)cc3)nc12] | N2-(4-Fluoro-benzyl)-6-(4-fluoro-phenyl)-N4-(2-methoxy-ethyl)-pyrido[3,2-d]pyrimidine-2,4-diamine | 422 |

TABLE 1-continued

| No. | Structure | Name | Mass M+1 |
|---|---|---|---|
| 35 | 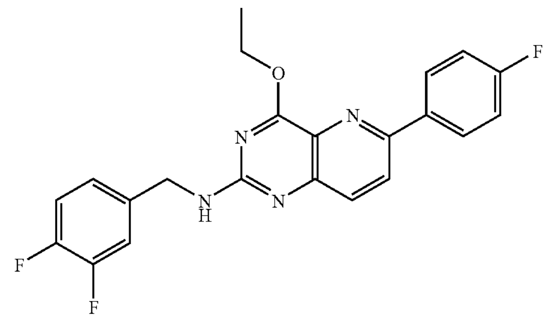 | (3,4-Difluoro-benzyl)-[4-ethoxy-6-(4-fluoro-phenyl)-pyrido[3,2-d]pyrimidin-2-yl]-amine | 411 |
| 36 | 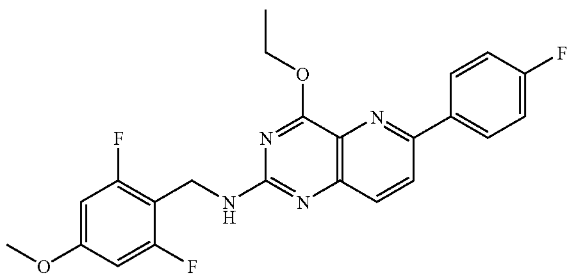 [SMILES: CCOc1nc(NCc2c(F)cc(OC)cc2F)nc2ccc(-c3ccc(F)cc3)nc12] | (2,6-Difluoro-4-methoxy-benzyl)-[4-ethoxy-6-(4-fluoro-phenyl)-pyrido[3,2-d]pyrimidin-2-yl]-amine | 441 |
| 37 | 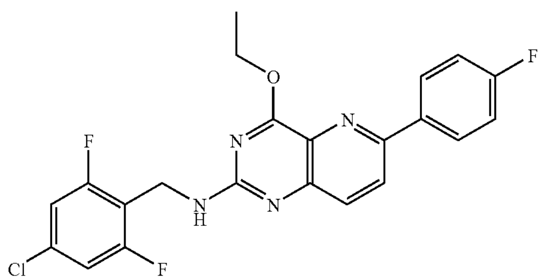 | (4-Chloro-2,6-difluoro-benzyl)-[4-ethoxy-6-(4-fluoro-phenyl)-pyrido[3,2-d]pyrimidin-2-yl]-amine | 445 |
| 38 | 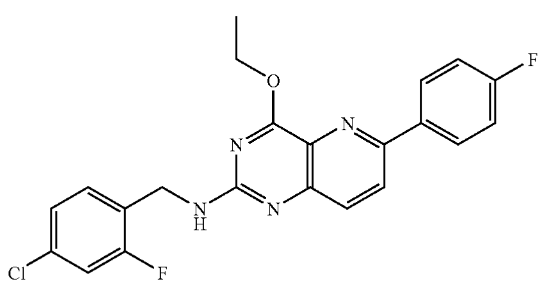 [SMILES: CCOc1nc(NCc2c(F)cc(F)cc2F)nc2ccc(-c3ccc(F)cc3)nc12] | (4-Chloro-2-fluoro-benzyl)-[4-ethoxy-6-(4-fluoro-phenyl)-pyrido[3,2-d]pyrimidin-2-yl]-amine | 427 |
| 39 | 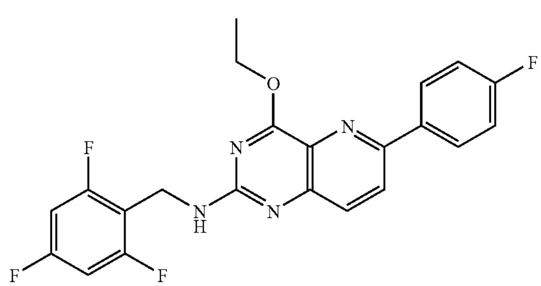 | (4-Ethoxy-6-(4-fluoro-phenyl)-pyrido[3,2-d]pyrimidin-2-yl]-(2,4,6-trifluoro-benzyl)-amine | 429 |

TABLE 1-continued

| No. | Structure | Name | Mass M⁺¹ |
|---|---|---|---|
| 40 | 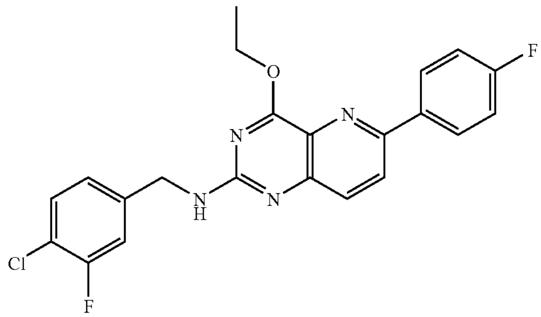 | (4-Chloro-3-fluoro-benzyl)-[4-ethoxy-6-(4-fluoro-phenyl)-pyrido[3,2-d]pyrimidin-2-yl]-amine | 427 |
| 41 | 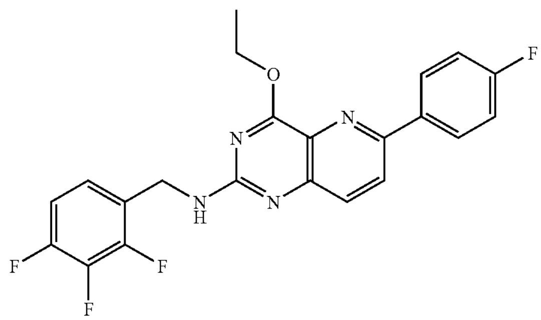 [SMILES: CCOc1nc(NCc2ccc(F)c(F)c2F)nc2ccc(-c3ccc(F)cc3)nc12] | [4-Ethoxy-6-(4-fluoro-phenyl)-pyrido[3,2-d]pyrimidin-2-yl]-(2,3,4-trifluoro-benzyl)-amine | 429 |
| 42 | 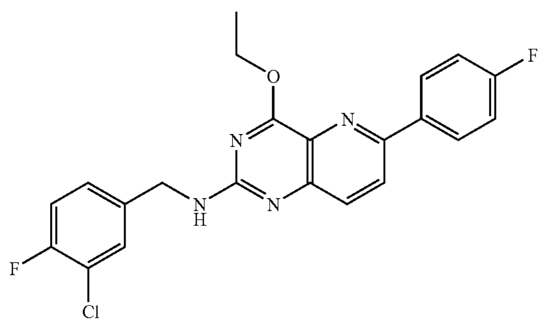 [SMILES: CCOc1nc(NCc2ccc(F)c(Cl)c2)nc2ccc(-c3ccc(F)cc3)nc12] | (3-Chloro-4-fluoro-benzyl)-[4-ethoxy-6-(4-fluoro-phenyl)-pyrido[3,2-d]pyrimidin-2-yl]-amine | 427 |
| 43 | 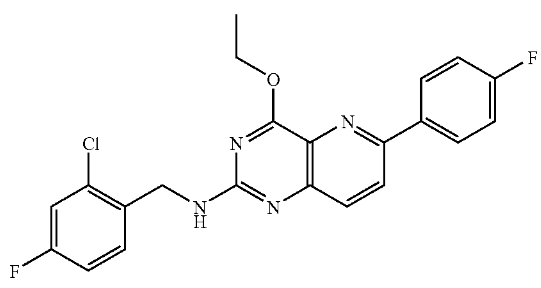 | (2-Chloro-4-fluoro-benzyl)-[4-ethoxy-6-(4-fluoro-phenyl)-pyrido[3,2-d]pyrimidin-2-yl]-amine | 427 |
| 44 | 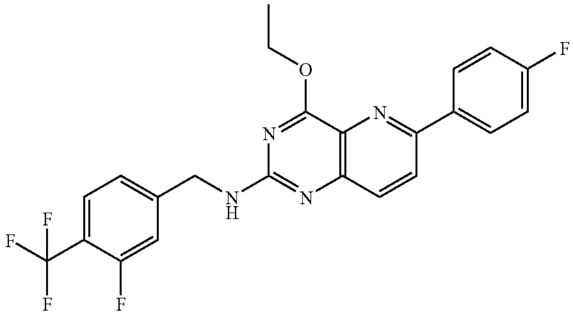 [SMILES: CCOc1nc(NCc2ccc(C(F)(F)F)c(F)c2)nc2ccc(-c3ccc(F)cc3)nc12] | [4-Ethoxy-6-(4-fluoro-phenyl)-pyrido[3,2-d]pyrimidin-2-yl]-(3-fluoro-4-trifluoromethyl-benzyl)-amine | 461 |

TABLE 1-continued

| No. | Structure | Name | Mass M$^{+1}$ |
|---|---|---|---|
| 45 | 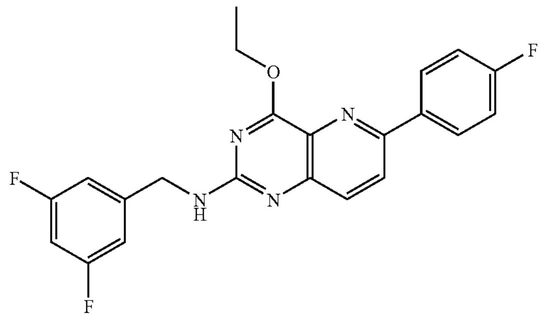 [SMILES: CCOc1nc(NCc2cc(F)cc(F)c2)nc2ccc(-c3ccc(F)cc3)nc12] | (3,5-Difluoro-benzyl)-[4-ethoxy-6-(4-fluoro-phenyl)-pyrido[3,2-d]pyrimidin-2-yl]-amine | 411 |
| 46 | 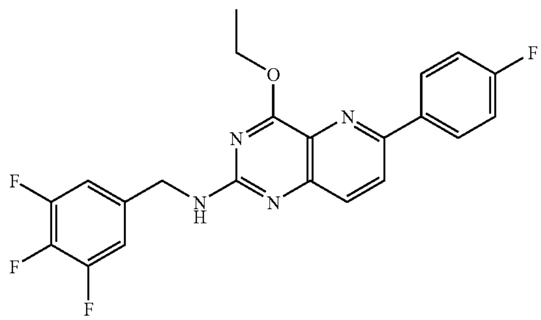 [SMILES: CCOc1nc(NCc2cc(F)c(F)c(F)c2)nc2ccc(-c3ccc(F)cc3)nc12] | [4-Ethoxy-6-(4-fluoro-phenyl)-pyrido[3,2-d]pyrimidin-2-yl]-(3,4,5-trifluoro-benzyl)-amine | 429 |
| 47 | 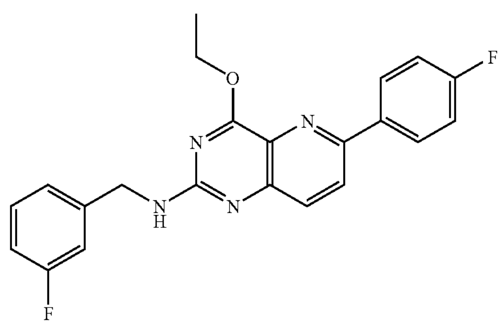 [SMILES: CCOc1nc(NCc2cccc(F)c2)nc2ccc(-c3ccc(F)cc3)nc12] | [4-Ethoxy-6-(4-fluoro-phenyl)-pyrido[3,2-d]pyrimidin-2-yl]-(3-fluoro-benzyl)-amine | 393 |
| 48 | 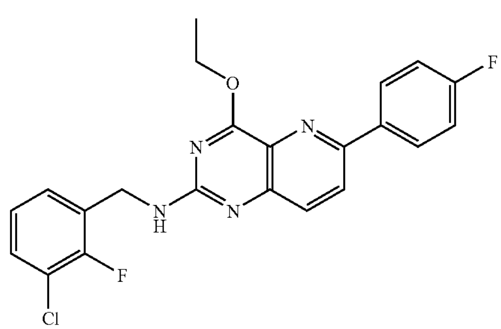 [SMILES: CCOc1nc(NCc2cccc(Cl)c2F)nc2ccc(-c3ccc(F)cc3)nc12] | (3-Chloro-2-fluoro-benzyl)-[4-ethoxy-6-(4-fluoro-phenyl)-pyrido[3,2-d]pyrimidin-2-yl]-amine | 427 |

EXAMPLES 49 TO 60

Synthesis of 2-mono(hetero)arylamino-4-monoalkylamino-6-(4-fluorophenyl)-pyrido(3,2-d)pyrimidines and 2-monoalkylamino-4-alkylamino-6-(4-fluorophenyl)-pyrido(3,2-d)pyrimidines 2-(substituted amino)-4-monoalkylamino-6-(4-fluorophenyl)-pyrido(3,2-d)pyrimidines and 2-(substituted amino)-4-bisalkylamino-6-(4-fluorophenyl)-pyrido(3,2-d)pyrimidines have been synthesized from 2,4-dichloro-6-(4-fluorophenyl) pyrido[3,2-d]pyrimidine according to the principles set forth in FIG. 1 and outlined in more details in the embodiments shown in Scheme 2 below.

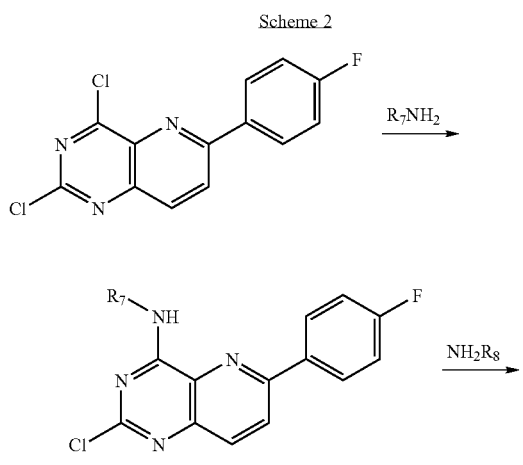

Scheme 2

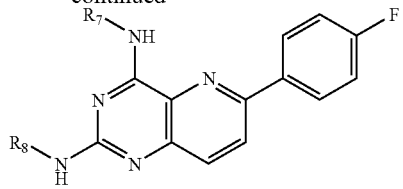

The procedure used in the first step was as follows: a mixture of 2,4-dichloro-6-(4-fluorophenyl)pyrido[3,2-d]pyrimidine (2.0 g), isopropylamine (2 ml) or cyclopropylamine (2 ml) in 2,6-dioxane (20 mL) was stirred for 1 hour. Solvents were concentrated in vacuo and the residue was dissolved in DCM (20 ml). The solid was filtered to provide 2-chloro-6-(4-fluorophenyl)-N-isopropylpyrido[3,2-d]pyrimidin-4-amine and 2-chloro-6-(4-fluorophenyl)-N-cyclopropylpyrido[3,2-d]pyrimidin-4-amine respectively, which were characterized by their mass spectra as follows: MS (m/z) 317 $[M+H]^+$ and MS (m/z) 315 $[M+H]^+$, respectively.

The general procedure used in the second step was as follows: a mixture of 2-chloro-6-(4-fluorophenyl)-N-isopropylpyrido[3,2-d]pyrimidin-4-amine or 2-chloro-6-(4-fluorophenyl)-N-cyclopropylpyrido[3,2-d]pyrimidin-4-amine, potassium carbonate (20 mg) and a suitable amine (0.19 mmol) in 2,6-dioxane (1.0 mL) or DMF (1.0 mL) was heated at 80° C. for 16 hours. Solvents were concentrated in vacuo and the residue was purified by RP HPLC, using a C18 column with a gradient of $H_2O$, 0.1% TFA-acetonitrile, to provide, with yields ranging from 20% to 70%, the pure desired compounds, which were characterized by their mass spectra as indicated in the following table 2.

Other examples in Table 2 with different substituents on the 4-amino group of the pyrido[3,2-d]pyrimidine ring were synthesized using an analogous method as described above. In each case, a suitable amine was used in place of isopropyl amine or cyclopropyl amine.

TABLE 2

| No. | Structure | Name | Mass $M^{+1}$ |
|---|---|---|---|
| 49 | 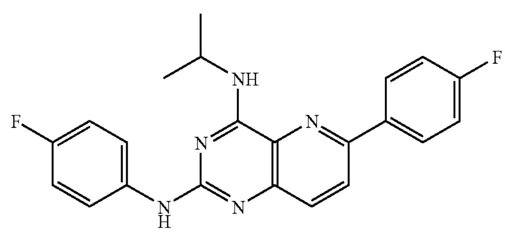 [SMILES: CC(C)Nc1nc(Nc2ccc(F)cc2)nc2ccc(-c3ccc(F)cc3)nc12] | 6-(4-Fluoro-phenyl)-N4-isopropyl-N2-(4-fluoro-phenyl)-pyrido[3,2-d]pyrimidine-2,4-diamine | 392 |
| 50 | 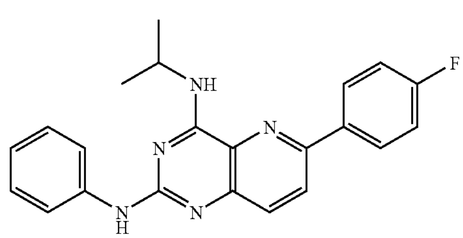 [SMILES: CC(C)Nc1nc(Nc2ccccc2)nc2ccc(-c3ccc(F)cc3)nc12] | 6-(4-Fluoro-phenyl)-N4-isopropyl-N2-phenyl-pyrido[3,2-d]pyrimidine-2,4-diamine | 374 |

TABLE 2-continued

| No. | Structure | Name | Mass M$^{+1}$ |
|---|---|---|---|
| 51 | 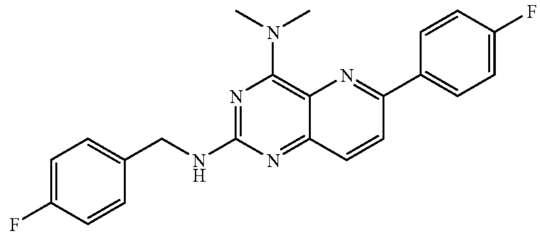 [SMILES: CN(C)c1nc(NCc2ccc(F)cc2)nc2ccc(-c3ccc(F)cc3)nc12] | 6-(4-Fluoro-phenyl)-N4-(N,N-dimethyl)-N2-(4-fluoro-benzyl)-pyrido[3,2-d]pyrimidine-2,4-diamine | 392 |
| 52 | 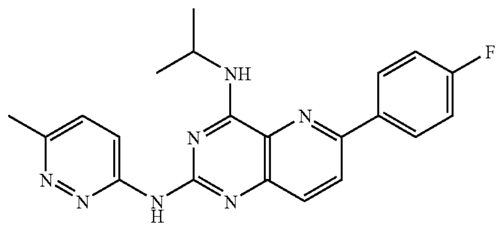 [SMILES: Cc1ccc(Nc2nc(NC(C)C)c3nc(-c4ccc(F)cc4)ccc3n2)nn1] | 6-(4-Fluoro-phenyl)-N4-isopropyl-N2-(6-methyl-pyridazin-3-yl)-pyrido[3,2-d]pyrimidine-2,4-diamine | 390.3 |
| 53 | 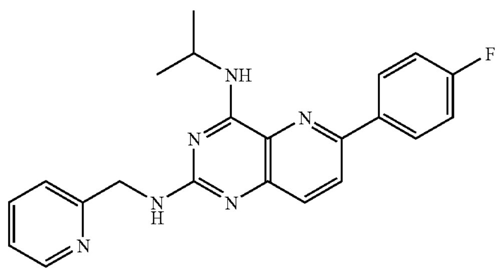 [SMILES: CC(C)Nc1nc(NCc2ccccn2)nc2ccc(-c3ccc(F)cc3)nc12] | 6-(4-Fluoro-phenyl)-N4-isopropyl-N2-pyridin-2-ylmethyl-pyrido[3,2-d]pyrimidine-2,4-diamine | 389.3 |
| 54 | 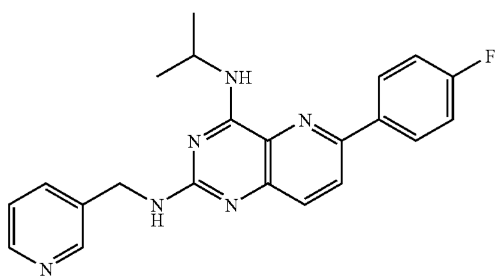 [SMILES: CC(C)Nc1nc(NCc2cccnc2)nc2ccc(-c3ccc(F)cc3)nc12] | 6-(4-Fluoro-phenyl)-N4-isopropyl-N2-pyridin-3-ylmethyl-pyrido[3,2-d]pyrimidine-2,4-diamine | 389.3 |
| 55 | 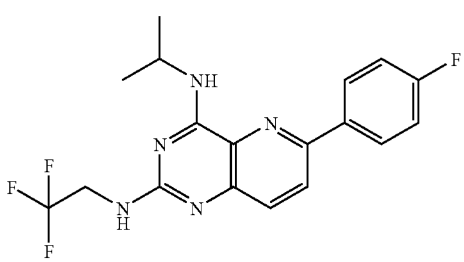 | 6-(4-Fluoro-phenyl)-N4-isopropyl-N2-(2,2,2-trifluoro-ethyl)-pyrido[3,2-d]pyrimidine-2,4-diamine | 380.3 |
| 56 | 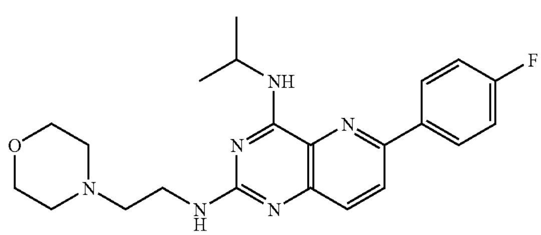 [SMILES: CC(C)Nc1nc(NCCN2CCOCC2)nc2ccc(-c3ccc(F)cc3)nc12] | 6-(4-Fluoro-phenyl)-N4-isopropyl-N2-(2-morpholin-4-yl-ethyl)-pyrido[3,2-d]pyrimidine-2,4-diamine | 411.3 |

TABLE 2-continued

| No. | Name | Mass M+1 |
|---|---|---|
| 57 | N2-(2,2-Difluoro-ethyl)-6-(4-fluoro-phenyl)-N4-isopropyl-pyrido[3,2-d]pyrimidine-2,4-diamine | 362.1 |
| 58 | 6-(4-Fluoro-phenyl)-N4-isopropyl-N2-(2-methoxy-ethyl)-pyrido[3,2-d]pyrimidine-2,4-diamine | 356.3 |
| 59 | 4-{[4-Diethylamino-6-(4-fluoro-phenyl)-pyrido[3,2-d]pyrimidin-2-ylamino]-methyl}-benzenesulfonamide | 481.1 |
| 60 | 6-(4-Fluoro-phenyl)-2,4-bis(2,2,2-trifluoro-ethylamino)-pyrido[3,2-d]pyrimidine | 420 |

EXAMPLES 61 TO 105

Synthesis of 6-aryl-4-ethoxy-pyrido[3,2-d]pyrimidin-2-yl)-(4-fluorobenzyl)-amines and 6-heteroaryl-4-ethoxy-pyrido[3,2-d]pyrimidin-2-yl)-(4-fluorobenzyl)-amines These compounds were synthesized from 2-amino-4-ethoxy-6-chloro-pyrido[3,2-d]pyrimidine according to the to the principles set forth in FIG. 6 and outlined in more details in the embodiment shown in Scheme 3 below.

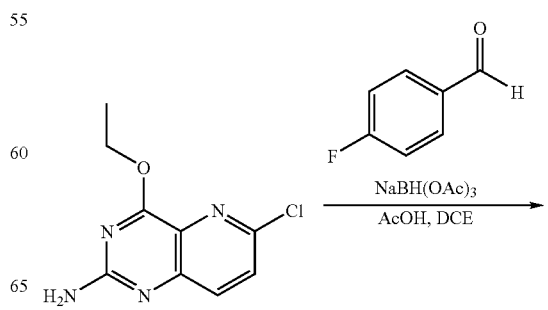

Scheme 3

-continued

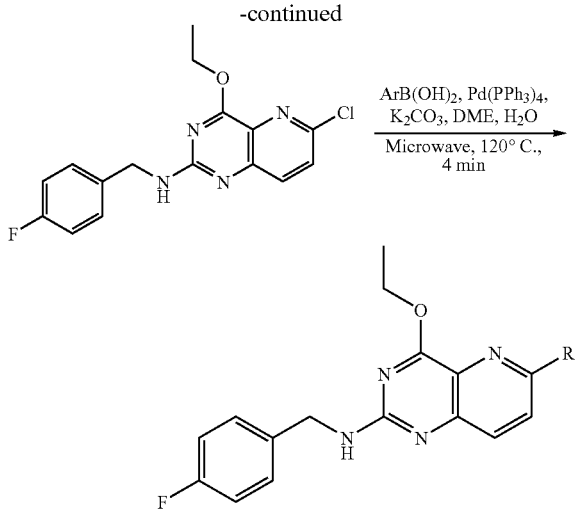

ArB(OH)₂, Pd(PPh₃)₄,
K₂CO₃, DME, H₂O
─────────────────→
Microwave, 120° C.,
4 min A mixture of 6-chloro-4-ethoxy-pyrido[3,2-d]pyrimidin-2-ylamine (0.22 g), 4-fluorobenzaldehyde (2.0 mmol), acetic acid 5.0 mmol) and molecular sieves (10 mg) in DCE (3 mL) was stirred at room temperature for 30 minutes. NaBH(OAc)₃ was added portion by portion. The mixture was stirred for 16 hours, and then quenched by adding saturated aqueous NaHCO₃. The solution was partitioned with DCM. The organic layer was dried over Na₂SO₄ and concentrated to afford the crude product which was purified by flash chromatography using hexane/ethyl acetate as eluting solvent. 0.33 g of 6-chloro-4-ethoxy-pyrido[3,2-d]pyrimidin-2-yl)-(4-fluoro-benzyl)-amine (Example 61) was obtained (yield: 50%) as a white solid which was characterized by its mass spectrum as follows: MS (m/z) 333.1 [M+H]⁺.

Then a mixture of the 6-chloro-4-ethoxy-pyrido[3,2-d]pyrimidin-2-yl)-(4-fluoro-benzyl)-amine from Example 61 (33 mg), potassium carbonate (50 mg), tetrakis(triphenylphosphine)palladium (10 mg) and a suitable aryl-boronic acid or heteroaryl-boronic acid, or a pinacol ester thereof (0.1 mmol) in DME (2 mL) and water (1 mL) was heated to 120° C. for 4 minutes by microwave. Solvents were concentrated in vacuo and the residue was purified by RP HPLC using a C18 column with a gradient of H₂O, 0.05% TFA-acetonitrile, to provide, with yields ranging from 30% to 60% depending upon the aryl or heteroaryl group introduced at the 6-position of the pyrido[3,2-d]pyrimidine ring, the following pure compounds which were characterized by their mass spectrum MS as indicated in Table 3 below.

TABLE 3

| No. | Structure | Name | Mass M⁺¹ |
|---|---|---|---|
| 62 | 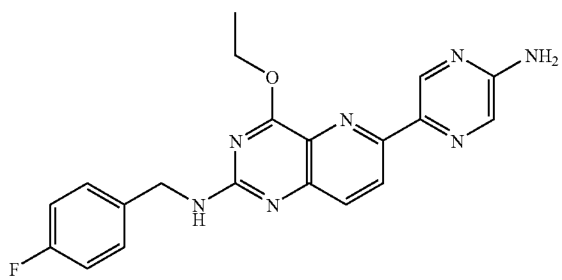 [SMILES: CCOc1nc(NCc2ccc(F)cc2)nc2ccc(-c3cnc(N)cn3)nc12] | [6-(5-Amino-pyrazin-2-yl)-4-ethoxy-pyrido[3,2-d]pyrimidin-2-yl]-(4-fluoro-benzyl)-amine | 392.1 |
| 63 | 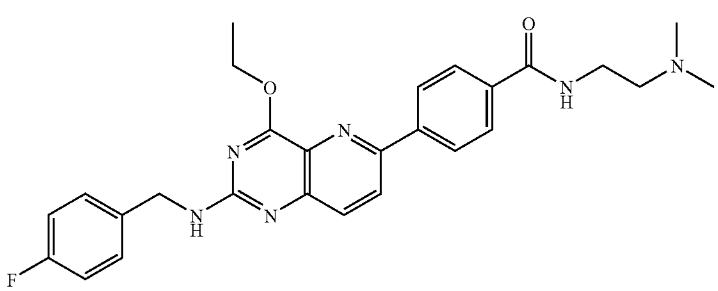 [SMILES: CCOc1nc(NCc2ccc(F)cc2)nc2ccc(-c3ccc(C(=O)NCCN(C)C)cc3)nc12] | N-(2-Dimethylamino-ethyl)-4-[4-ethoxy-2-(4-fluoro-benzylamino)-pyrido[3,2-d]pyrimidin-6-yl]-benzamide | 489.2 |
| 64 | 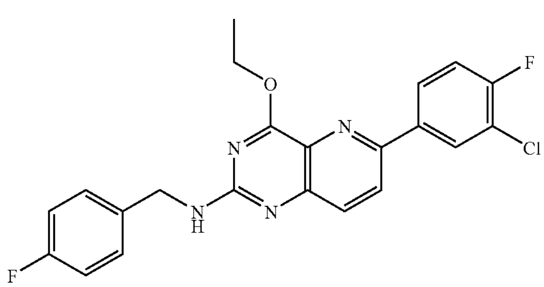 [SMILES: CCOc1nc(NCc2ccc(F)cc2)nc2ccc(-c3ccc(F)c(Cl)c3)nc12] | [6-(3-Chloro-4-fluoro-phenyl)-4-ethoxy-pyrido[3,2-d]pyrimidin-2-yl]-(4-fluoro-benzyl)-amine | 427 |

TABLE 3-continued

| No. | Structure | Name | Mass M+1 |
|---|---|---|---|
| 65 | 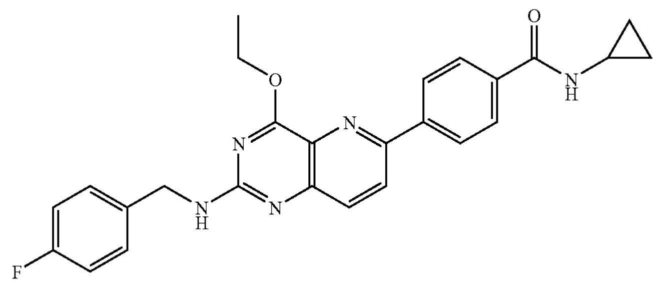 [SMILES: CCOc1nc(NCc2ccc(F)cc2)nc2ccc(-c3ccc(C(=O)NC4CC4)cc3)nc12] | N-Cyclopropyl-4-[4-ethoxy-2-(4-fluoro-benzylamino)-pyrido[3,2-d]pyrimidin-6-yl]-benzamide | 458.1 |
| 66 | 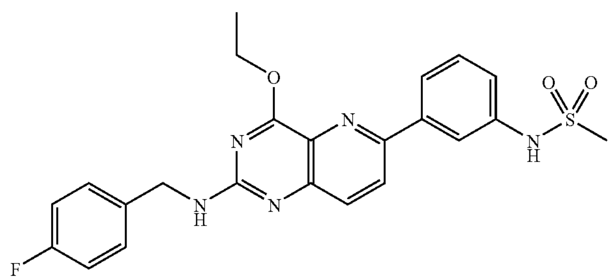 [SMILES: CCOc1nc(NCc2ccc(F)cc2)nc2ccc(-c3cccc(NS(C)(=O)=O)c3)nc12] | N-{3-[4-Ethoxy-2-(4-fluoro-benzylamino)-pyrido[3,2-d]pyrimidin-6-yl]-phenyl}-methanesulfonamide | 468.1 |
| 67 | 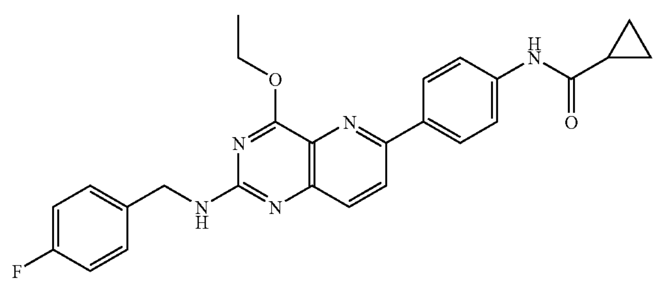 [SMILES: CCOc1nc(NCc2ccc(F)cc2)nc2ccc(-c3ccc(NC(=O)C4CC4)cc3)nc12] | Cyclopropanecarboxylic acid {4-[4-ethoxy-2-(4-fluoro-benzylamino)-pyrido[3,2-d]pyrimidin-6-yl]-phenyl}-amide | 458.1 |
| 68 | 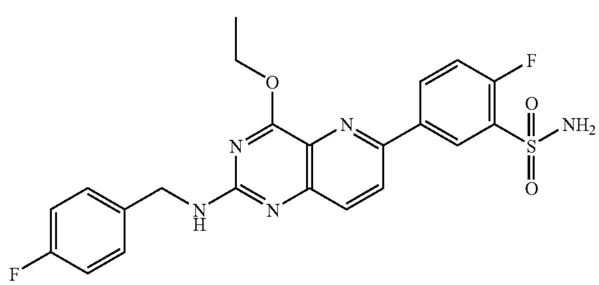 [SMILES: CCOc1nc(NCc2ccc(F)cc2)nc2ccc(-c3ccc(F)c(S(N)(=O)=O)c3)nc12] | 5-[4-Ethoxy-2-(4-fluoro-benzylamino)-pyrido[3,2-d]pyrimidin-6-yl]-2-fluoro-benzenesulfonamide | 472 |
| 69 | 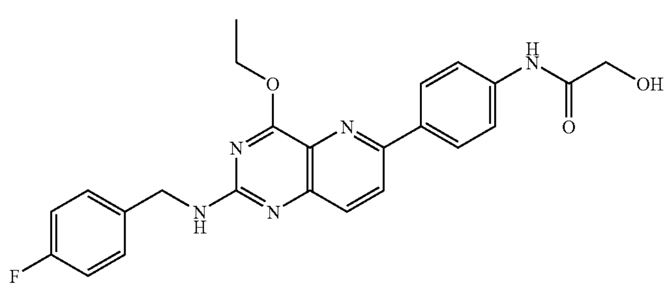 [SMILES: CCOc1nc(NCc2ccc(F)cc2)nc2ccc(-c3ccc(NC(=O)CO)cc3)nc12] | N-{4-[4-Ethoxy-2-(4-fluoro-benzylamino)-pyrido[3,2-d]pyrimidin-6-yl]-phenyl}-2-hydroxy-acetamide | 448.2 |

TABLE 3-continued

| No. | Structure | Name | Mass M+1 |
|---|---|---|---|
| 70 | 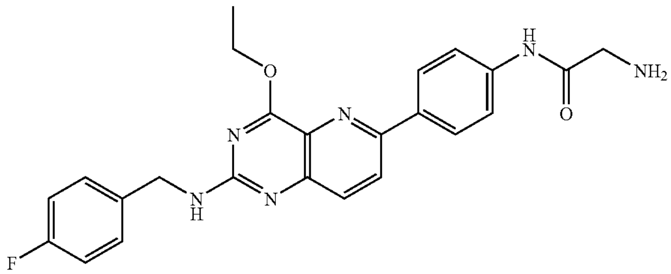 [SMILES: CCOc1nc(NCc2ccc(F)cc2)nc2ccc(-c3ccc(NC(=O)CN)cc3)nc12] | 2-Amino-N-{4-[4-ethoxy-2-(4-fluoro-benzylamino)-pyrido[3,2-d]pyrimidin-6-yl]-phenyl}-acetamide | 447.2 |
| 71 | 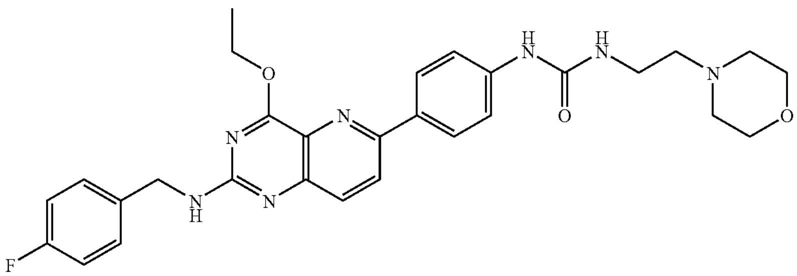 [SMILES: CCOc1nc(NCc2ccc(F)cc2)nc2ccc(-c3ccc(NC(=O)NCCN4CCOCC4)cc3)nc12] | 1-{4-[4-Ethoxy-2-(4-fluoro-benzylamino)-pyrido[3,2-d]pyrimidin-6-yl]-phenyl}-3-(2-morpholin-4-yl-ethyl)-urea | 546 |
| 72 | 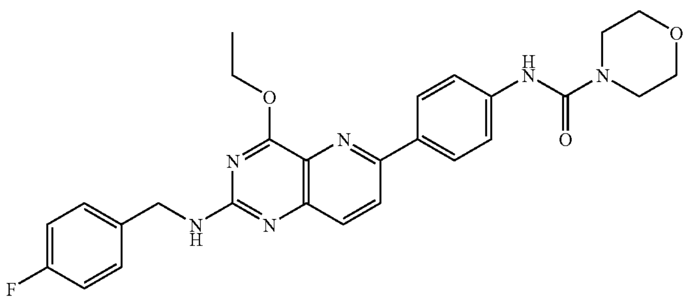 [SMILES: CCOc1nc(NCc2ccc(F)cc2)nc2ccc(-c3ccc(NC(=O)N4CCOCC4)cc3)nc12] | Morpholine-4-carboxylic acid {4-[4-ethoxy-2-(4-fluoro-benzylamino)-pyrido[3,2-d]pyrimidin-6-yl]-phenyl}-amide | 503 |
| 73 | 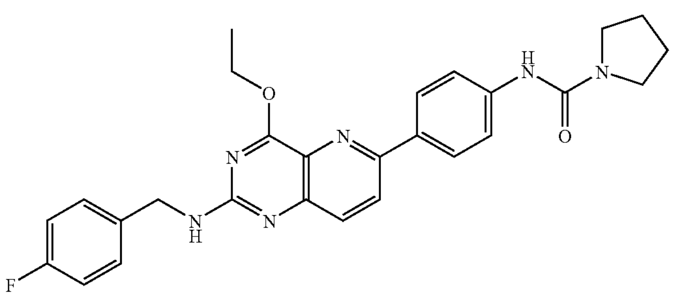 [SMILES: CCOc1nc(NCc2ccc(F)cc2)nc2ccc(-c3ccc(NC(=O)N4CCCC4)cc3)nc12] | Pyrrolidine-1-carboxylic acid {4-[4-ethoxy-2-(4-fluoro-benzylamino)-pyrido[3,2-d]pyrimidin-6-yl]-phenyl}-amide | 487 |
| 74 | 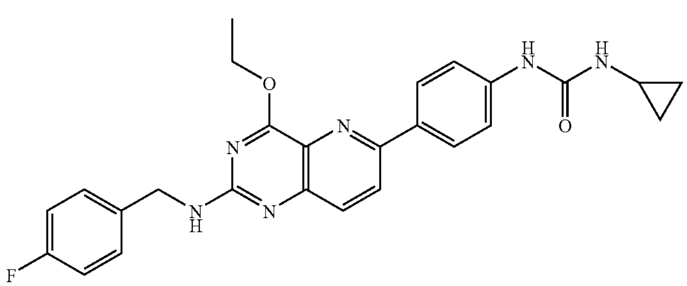 [SMILES: CCOc1nc(NCc2ccc(F)cc2)nc2ccc(-c3ccc(NC(=O)NC4CC4)cc3)nc12] | 1-Cyclopropyl-3-{4-[4-ethoxy-2-(4-fluoro-benzylamino)-pyrido[3,2-d]pyrimidin-6-yl]-phenyl}-urea | 473 |

TABLE 3-continued

| No. | Structure | Name | Mass M$^{+1}$ |
|---|---|---|---|
| 75 | 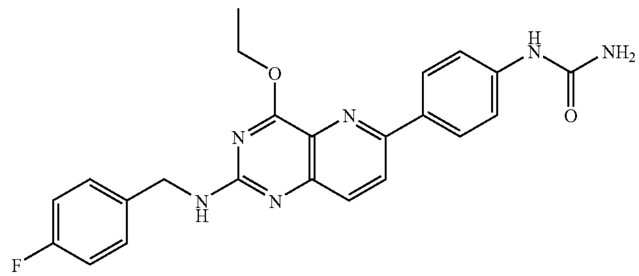 [SMILES: CCOc1nc(NCc2ccc(F)cc2)nc2ccc(-c3ccc(NC(N)=O)cc3)nc12] | {4-[4-Ethoxy-2-(4-fluoro-benzylamino)-pyrido[3,2-d]pyrimidin-6-yl]-phenyl}-urea | 433 |
| 76 | 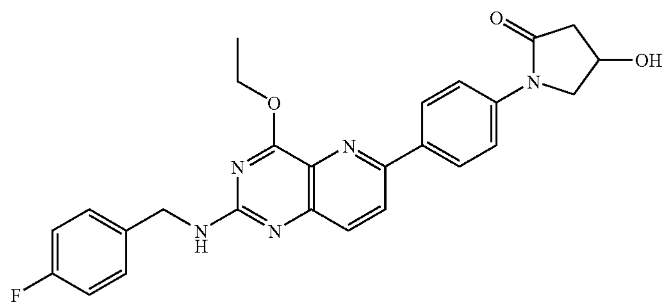 [SMILES: CCOc1nc(NCc2ccc(F)cc2)nc2ccc(-c3ccc(N4CC(O)CC4=O)cc3)nc12] | 1-{4-[4-Ethoxy-2-(4-fluoro-benzylamino)-pyrido[3,2-d]pyrimidin-6-yl]-phenyl}-4-hydroxy-pyrrolidin-2-one | 474.3 |
| 77 | 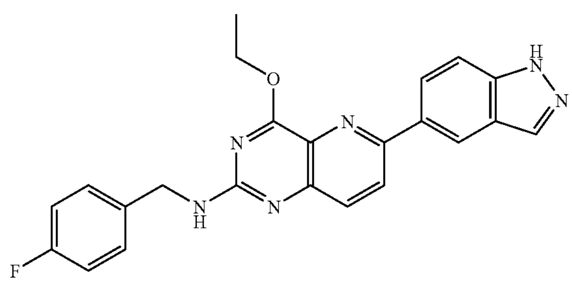 [SMILES: CCOc1nc(NCc2ccc(F)cc2)nc2ccc(-c3ccc4[nH]ncc4c3)nc12] | [4-Ethoxy-6-(1H-indazol-5-yl)-pyrido[3,2-d]pyrimidin-2-yl]-(4-fluoro-benzyl)-amine | 415.2 |
| 78 | 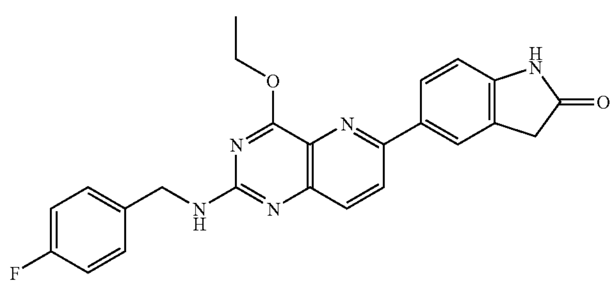 [SMILES: CCOc1nc(NCc2ccc(F)cc2)nc2ccc(-c3ccc4c(c3)CC(=O)N4)nc12] | 5-[4-Ethoxy-2-(4-fluoro-benzylamino)-pyrido[3,2-d]pyrimidin-6-yl]-1,3-dihydro-indol-2-one | 430.2 |
| 79 | 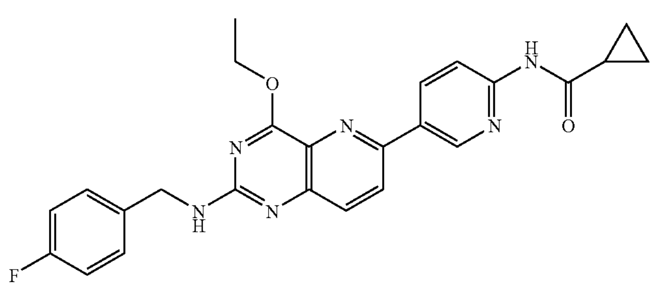 [SMILES: CCOc1nc(NCc2ccc(F)cc2)nc2ccc(-c3ccc(NC(=O)C4CC4)nc3)nc12] | Cyclopropanecarboxylic acid {5-[4-ethoxy-2-(4-fluoro-benzylamino)-pyrido[3,2-d]pyrimidin-6-yl]-pyridin-2-yl}-amide | 459 |

TABLE 3-continued

| No. | Structure | Name | Mass M+1 |
|---|---|---|---|
| 80 | 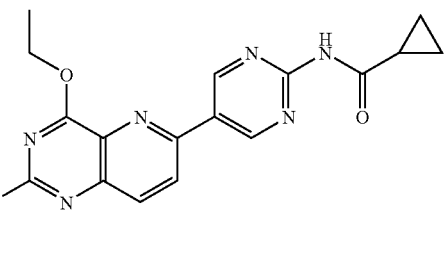 | Cyclopropanecarboxylic acid {5-[4-ethoxy-2-(4-fluoro-benzylamino)-pyrido[3,2-d]pyrimidin-6-yl]-pyrimidin-2-yl}-amide | 460 |
| 81 | 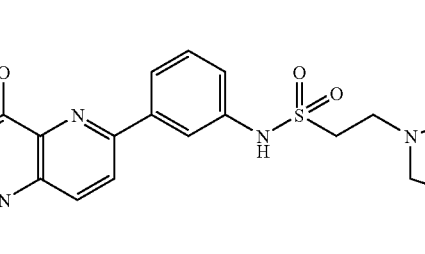 | 2-Pyrrolidin-1-yl-ethanesulfonic acid {3-[4-ethoxy-2-(4-fluoro-benzylamino)-pyrido[3,2-d]pyrimidin-6-yl]-phenyl}-amide | 551 |
| 82 | 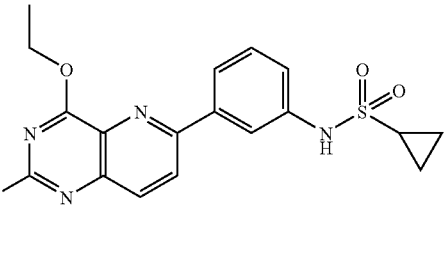 | Cyclopropanesulfonic acid {3-[4-ethoxy-2-(4-fluoro-benzylamino)-pyrido[3,2-d]pyrimidin-6-yl]-phenyl}-amide | 494 |
| 83 | 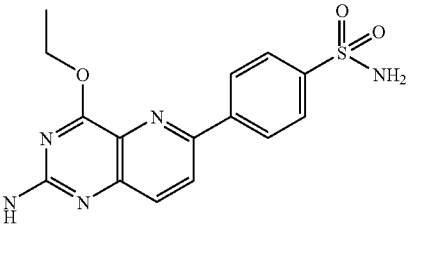 | 4-[4-Ethoxy-2-(4-fluoro-benzylamino)-pyrido[3,2-d]pyrimidin-6-yl]-benzenesulfonamide | 454 |
| 84 | 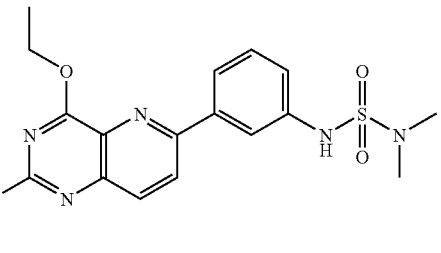 | N'-{3-[4-Ethoxy-2-(4-fluoro-benzylamino)-pyrido[3,2-d]pyrimidin-6-yl]-phenyl}-N,N-dimethyl methanesulfonyl urea | 497 |

TABLE 3-continued

| No. | Structure | Name | Mass M⁺¹ |
|---|---|---|---|
| 85 | 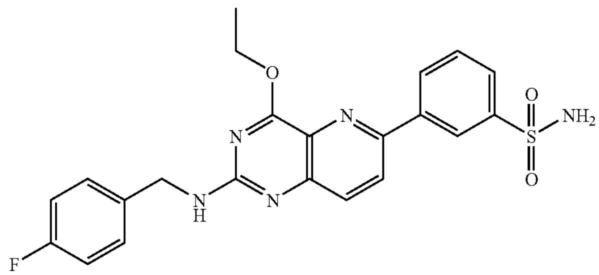 [SMILES: CCOc1nc(NCc2ccc(F)cc2)nc2ccc(-c3cccc(S(N)(=O)=O)c3)nc12] | 3-[4-Ethoxy-2-(4-fluoro-benzylamino)-pyrido[3,2-d]pyrimidin-6-yl]-benzenesulfonamide | 454 |
| 86 | 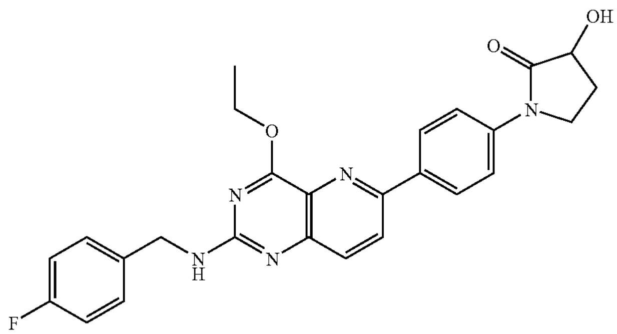 [SMILES: CCOc1nc(NCc2ccc(F)cc2)nc2ccc(-c3ccc(N4CCC(O)C4=O)cc3)nc12] | 1-{4-[4-Ethoxy-2-(4-fluoro-benzylamino)-pyrido[3,2-d]pyrimidin-6-yl]-phenyl}-3-hydroxy-pyrrolidin-2-one | 474.2 |
| 87 | 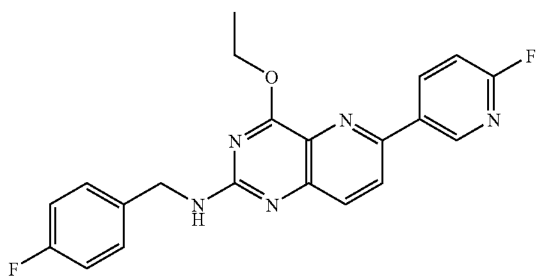 [SMILES: CCOc1nc(NCc2ccc(F)cc2)nc2ccc(-c3ccc(F)nc3)nc12] | [4-Ethoxy-6-(6-fluoro-pyridin-3-yl)-pyrido[3,2-d]pyrimidin-2-yl]-(4-fluoro-benzyl)-amine | 394 |
| 88 | 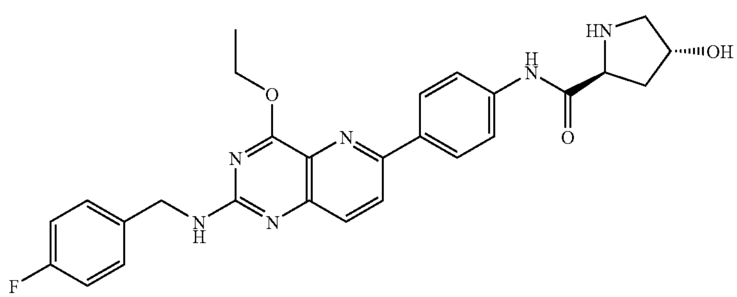 [SMILES: CCOc1nc(NCc2ccc(F)cc2)nc2ccc(-c3ccc(NC(=O)[C@@H]4C[C@@H](O)CN4)cc3)nc12] | 4-Hydroxy-pyrrolidine-2-carboxylic acid {4-[4-ethoxy-2-(4-fluoro-benzylamino)-pyrido[3,2-d]pyrimidin-6-yl]-phenyl}-amide | 503.3 |
| 89 | 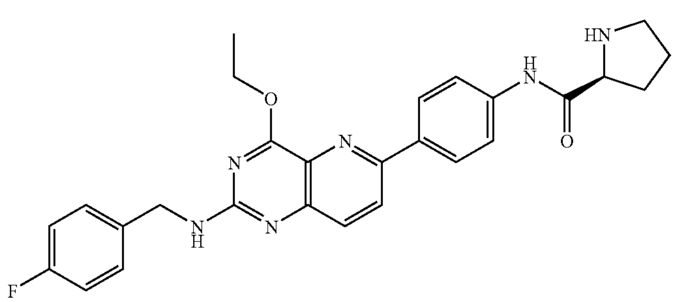 [SMILES: CCOc1nc(NCc2ccc(F)cc2)nc2ccc(-c3ccc(NC(=O)[C@@H]4CCCN4)cc3)nc12] | Pyrrolidine-2-carboxylic acid {4-[4-ethoxy-2-(4-fluoro-benzylamino)-pyrido[3,2-d]pyrimidin-6-yl]-phenyl}-amide | 487.2 |

TABLE 3-continued

| No. | Structure | Name | Mass M+1 |
|---|---|---|---|
| 90 | 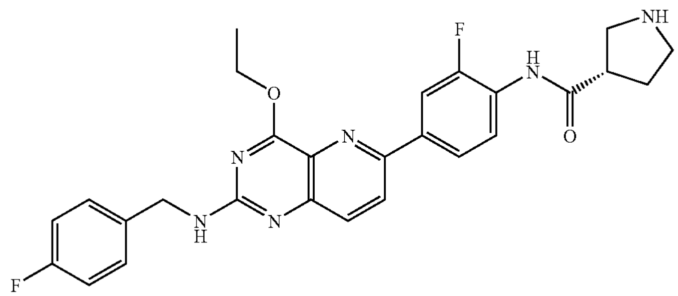 [SMILES: CCOc1nc(NCc2ccc(F)cc2)nc2ccc(-c3ccc(NC(=O)[C@H]4CCNC4)c(F)c3)nc12] | Pyrrolidine-3-carboxylic acid {4-[4-ethoxy-2-(4-fluoro-benzylamino)-pyrido[3,2-d]pyrimidin-6-yl]-2-fluoro-phenyl}-amide | 505.3 |
| 91 | 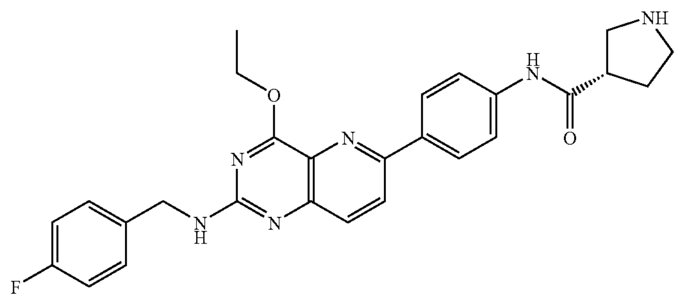 [SMILES: CCOc1nc(NCc2ccc(F)cc2)nc2ccc(-c3ccc(NC(=O)[C@H]4CCNC4)cc3)nc12] | Pyrrolidine-3-carboxylic acid {4-[4-ethoxy-2-(4-fluoro-benzylamino)-pyrido[3,2-d]pyrimidin-6-yl]-phenyl}-amide | 487.3 |
| 92 | 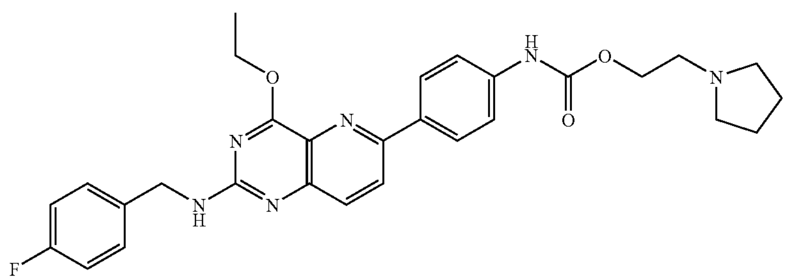 [SMILES: CCOc1nc(NCc2ccc(F)cc2)nc2ccc(-c3ccc(NC(=O)OCCN4CCCC4)cc3)nc12] | {4-[4-Ethoxy-2-(4-fluoro-benzylamino)-pyrido[3,2-d]pyrimidin-6-yl]-phenyl}-carbamic acid 2-pyrrolidin-1-yl-ethyl ester | 531 |
| 93 | 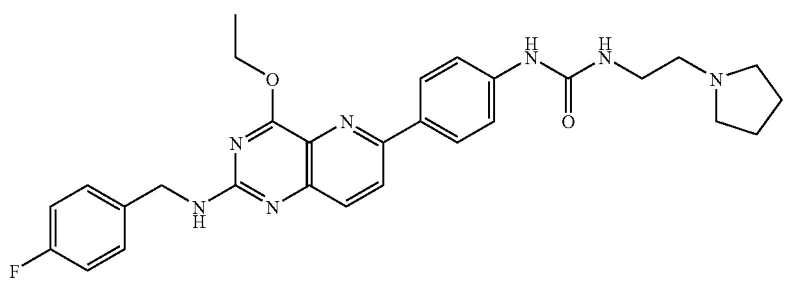 [SMILES: CCOc1nc(NCc2ccc(F)cc2)nc2ccc(-c3ccc(NC(=O)NCCN4CCCC4)cc3)nc12] | 1-{4-[4-Ethoxy-2-(4-fluoro-benzylamino)-pyrido[3,2-d]pyrimidin-6-yl]-phenyl}-3-(2-pyrrolidin-1-yl-ethyl)-urea | 530 |
| 94 | 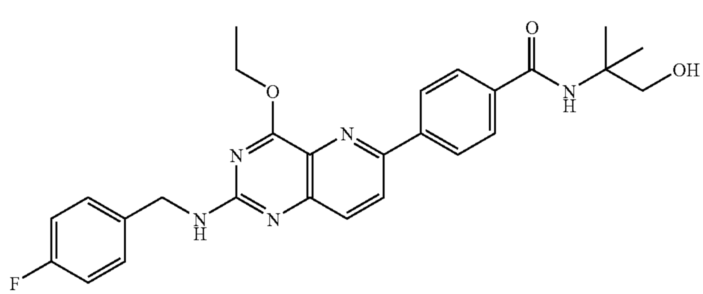 [SMILES: CCOc1nc(NCc2ccc(F)cc2)nc2ccc(-c3ccc(C(=O)NC(C)(C)CO)cc3)nc12] | 4-[4-Ethoxy-2-(4-fluoro-benzylamino)-pyrido[3,2-d]pyrimidin-6-yl]-N-(2-hydroxy-1,1-dimethyl-ethyl)-benzamide | 490 |

TABLE 3-continued

| No. | Structure | Name | Mass M+1 |
|---|---|---|---|
| 95 | 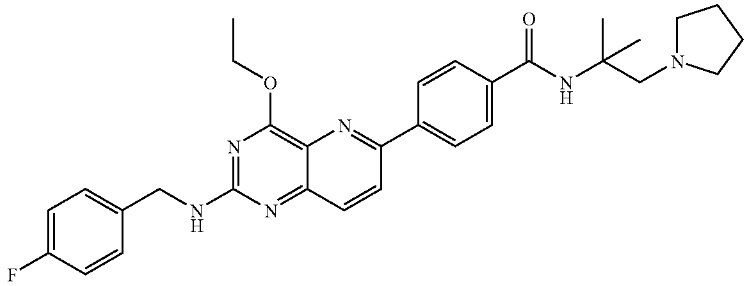 [SMILES: CCOc1nc(NCc2ccc(F)cc2)nc2ccc(-c3ccc(C(=O)NC(C)(C)CN4CCCC4)cc3)nc12] | N-(1,1-Dimethyl-2-pyrrolidin-1-yl-ethyl)-4-[4-ethoxy-2-(4-fluoro-benzylamino)-pyrido[3,2-d]pyrimidin-6-yl]-benzamide | 543 |
| 96 | 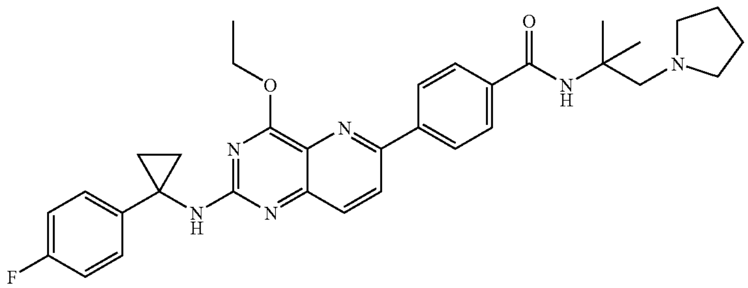 [SMILES: CCOc1nc(NC2(c3ccc(F)cc3)CC2)nc2ccc(-c3ccc(C(=O)NC(C)(C)CN4CCCC4)cc3)nc12] | N-(1,1-Dimethyl-2-pyrrolidin-1-yl-ethyl)-4-{4-ethoxy-2-[1-(4-fluoro-phenyl)-cyclopropylamino]-pyrido[3,2-d]pyrimidin-6-yl}-benzamide | 569 |
| 97 | 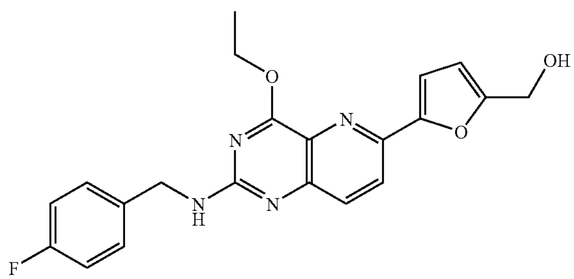 [SMILES: CCOc1nc(NCc2ccc(F)cc2)nc2ccc(-c3ccc(CO)o3)nc12] | {5-[4-Ethoxy-2-(4-fluoro-benzylamino)-pyrido[3,2-d]pyrimidin-6-yl]-furan-2-yl}-methanol | 395.1 |
| 98 | 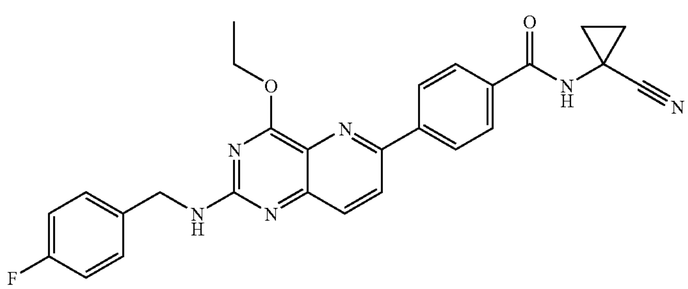 [SMILES: CCOc1nc(NCc2ccc(F)cc2)nc2ccc(-c3ccc(C(=O)NC4(C#N)CC4)cc3)nc12] | N-(1-Cyano-cyclopropyl)-4-[4-ethoxy-2-(4-fluoro-benzylamino)-pyrido[3,2-d]pyrimidin-6-yl]-benzamide | 483 |
| 99 | 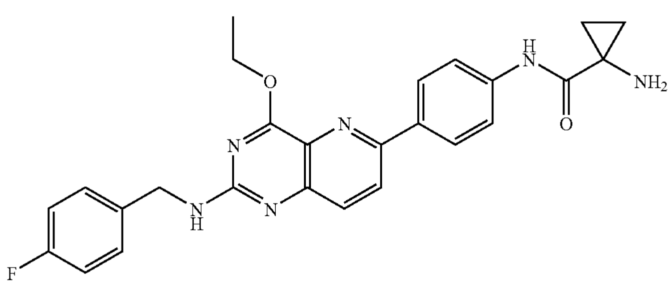 [SMILES: CCOc1nc(NCc2ccc(F)cc2)nc2ccc(-c3ccc(NC(=O)C4(N)CC4)cc3)nc12] | 1-Amino-cyclopropanecarboxylic acid {4-[4-ethoxy-2-(4-fluoro-benzylamino)-pyrido[3,2-d]pyrimidin-6-yl]-phenyl}-amide | 473.1 |

TABLE 3-continued

| No. | Structure | Name | Mass M+1 |
|---|---|---|---|
| 100 | 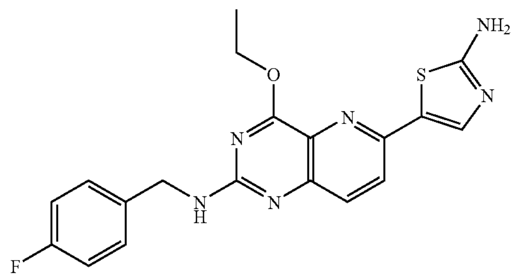 [SMILES: CCOc1nc(NCc2ccc(F)cc2)nc2ccc(-c3cnc(N)s3)nc12] | [6-(2-Amino-thiazol-5-yl)-4-ethoxy-pyrido[3,2-d]pyrimidin-2-yl]-(4-fluoro-benzyl)-amine | 397.1 |
| 101 | 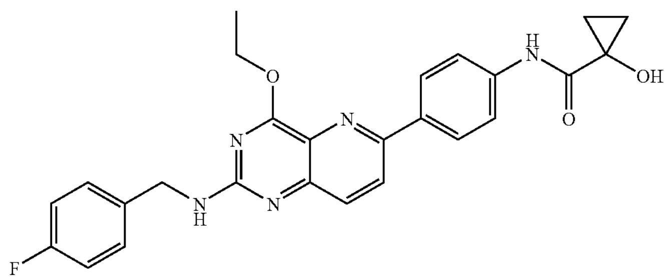 [SMILES: CCOc1nc(NCc2ccc(F)cc2)nc2ccc(-c3ccc(NC(=O)C4(O)CC4)cc3)nc12] | 1-Hydroxy-cyclopropanecarboxylic acid {4-[4-ethoxy-2-(4-fluoro-benzylamino)-pyrido[3,2-d]pyrimidin-6-yl]-phenyl}-amide | 474.1 |
| 102 | 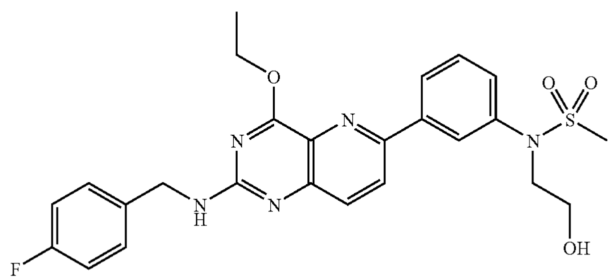 [SMILES: CCOc1nc(NCc2ccc(F)cc2)nc2ccc(-c3cccc(N(CCO)S(C)(=O)=O)c3)nc12] | N-{3-[4-Ethoxy-2-(4-fluoro-benzylamino)-pyrido[3,2-d]pyrimidin-6-yl]-phenyl}-N-(2-hydroxy-ethyl)-methanesulfonamide | 512.2 |
| 103 | 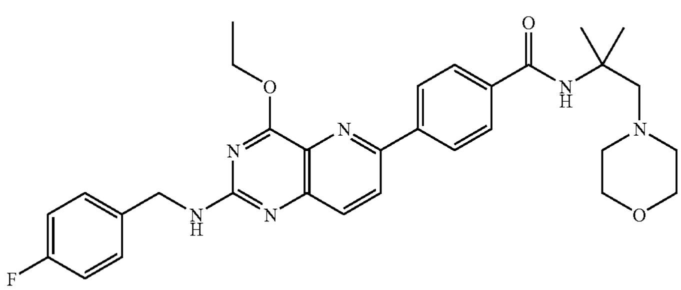 [SMILES: CCOc1nc(NCc2ccc(F)cc2)nc2ccc(-c3ccc(C(=O)NC(C)(C)CN4CCOCC4)cc3)nc12] | N-(1,1-Dimethyl-2-morpholin-4-yl-ethyl)-4-[4-ethoxy-2-(4-fluoro-benzylamino)-pyrido[3,2-d]pyrimidin-6-yl]-benzamide | 559.2 |
| 104 | 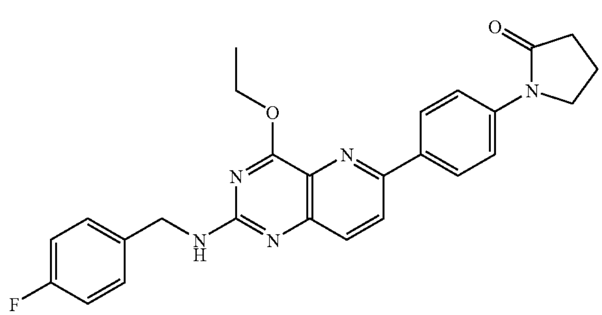 [SMILES: CCOc1nc(NCc2ccc(F)cc2)nc2ccc(-c3ccc(N4CCCC4=O)cc3)nc12] | 1-{4-[4-Ethoxy-2-(4-fluoro-benzylamino)-pyrido[3,2-d]pyrimidin-6-yl]-phenyl}-pyrrolidin-2-one | 458.2 |

TABLE 3-continued

| No. | Structure | Name | Mass M+1 |
|---|---|---|---|
| 105 | 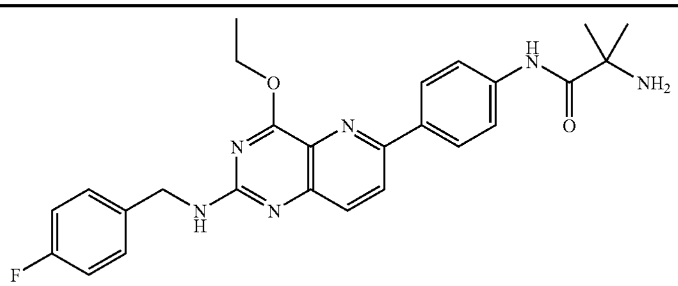 | 2-Amino-N-{4-[4-ethoxy-2-(4-fluoro-benzylamino)-pyrido[3,2-d]pyrimidin-6-yl]-phenyl}-2-methyl-propionamide | 475.2 |

EXAMPLES 106 TO 108

Synthesis of 6-aryl-4-ethoxy-pyrido[3,2-d]pyrimidin-2-yl)-(2,4-difluoro-benzyl)-amines These compounds were synthesized from 2-amino-4-ethoxy-6-chloro-pyrido[3,2-d]pyrimidine according to the to the principles set forth in FIG. 6 and outlined in more details in the embodiment shown in Scheme 4 below.

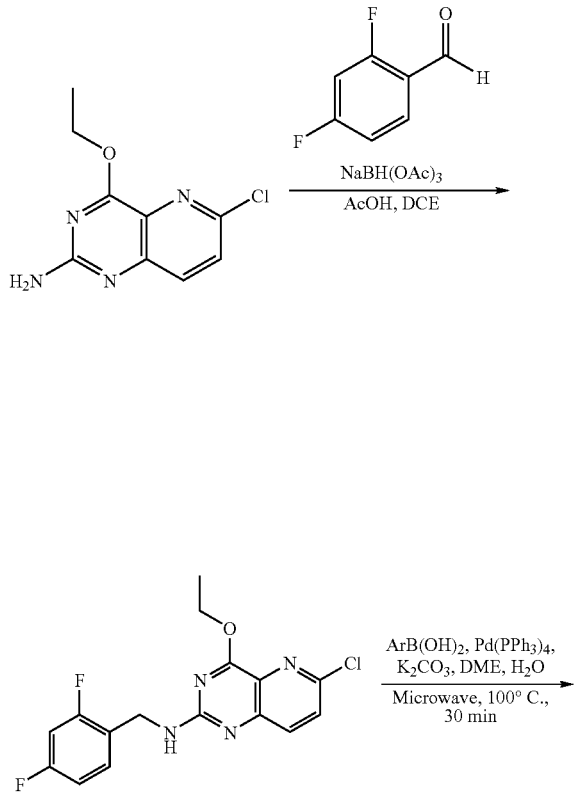

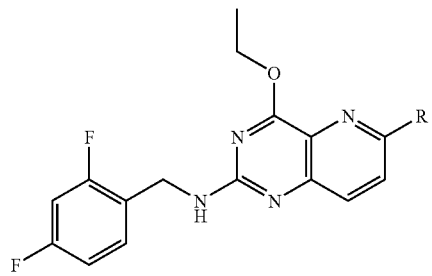

In a first step, the procedure of Example 61 was repeated, except for the use of 2,4-difluorobenzaldehyde instead of 4-fluorobenzaldehyde, thus resulting in 6-chloro-4-ethoxy-pyrido[3,2-d]pyrimidin-2-yl)-(2,4-difluoro-benzyl)-amine (Example 106) which was characterized by its mass spectrum as follows: MS (m/z) 351.1 [M+H]+.

Then a mixture of the 6-chloro-4-ethoxy-pyrido[3,2-d]pyrimidin-2-yl)-(2,4-difluoro-benzyl)-amine (33 mg), potassium carbonate (50 mg), tetrakis(triphenylphosphine) palladium (10 mg) and a suitable aryl-boronic acid, or a pinacol ester of aryl-boronic acid thereof (0.1 mmol) in DME (2 mL) and water (1 mL) was heated to 120° C. for 4 minutes by microwave. Solvents were concentrated in vacuo and the residue was purified by RP HPLC using a C18 column with a gradient of $H_2O$, 0.05% TFA-acetonitrile, to provide the desired product. This procedure provided, with yields ranging from 40% to 70% depending upon the aryl group introduced at the 6-position of the pyrido[3,2-d]pyrimidine ring, the following pure compounds which were characterized by their mass spectrum MS as indicated in Table 4.

TABLE 4

| No. | Structure | Name | Mass M+1 |
|---|---|---|---|
| 107 | 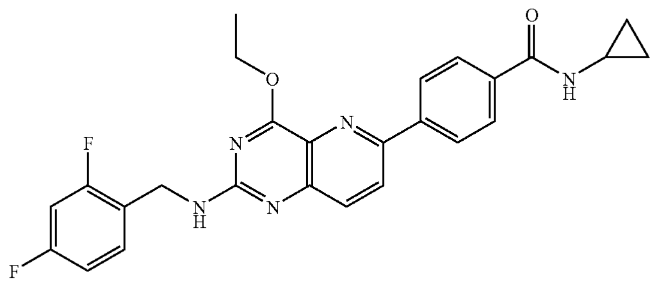 [SMILES: CCOc1nc(NCc2ccc(F)cc2F)nc2ccc(-c3ccc(C(=O)NC4CC4)cc3)nc12] | N-Cyclopropyl-4-[2-(2,4-difluoro-benzylamino)-4-ethoxy-pyrido[3,2-d]pyrimidin-6-yl]-benzamide | 476.1 |
| 108 | 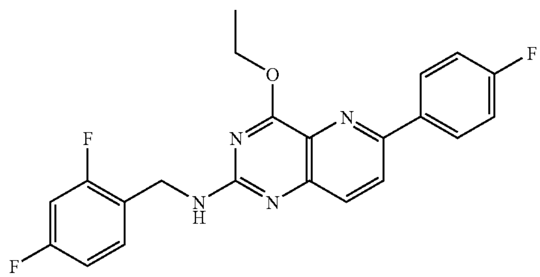 [SMILES: CCOc1nc(NCc2ccc(F)cc2F)nc2ccc(-c3ccc(F)cc3)nc12] | (2,4-Difluoro-benzyl)-{4-ethoxy-6-(4-fluoro-phenyl)-pyrido[3,2-d]pyrimidin-2-yl}-amine | 411.1 |

EXAMPLE 109

Synthesis of 4-{[4-ethoxy-6-(4-fluoro-phenyl)-pyrido[3,2-d]pyrimidin-2-ylamino]-methyl}-benzenesulfonamide This compound was synthesized according to the synthetic sequence outlined in Scheme 5 below.

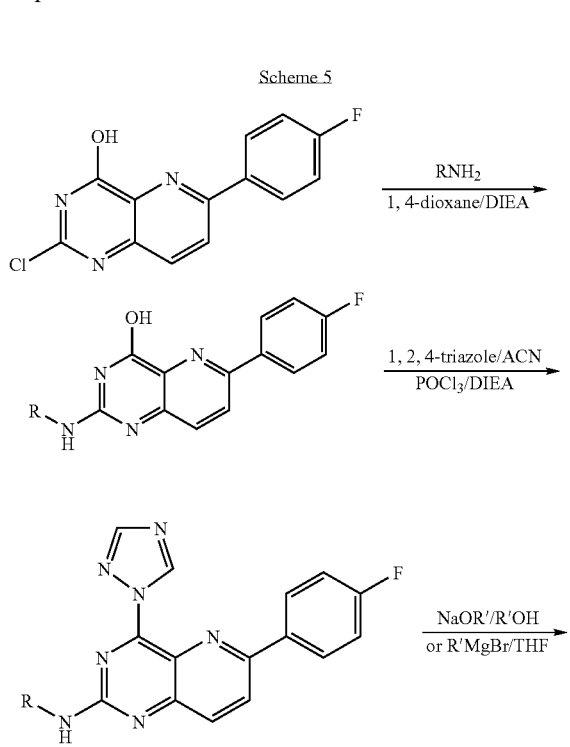

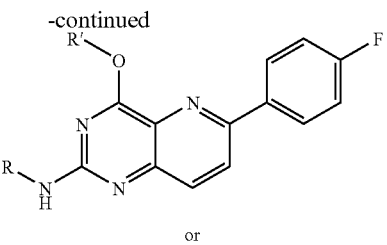

or

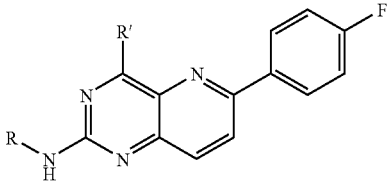

A solution of 2-chloro-6-(4-fluorophenyl)pyrido[3,2-d]pyrimidin-4-ol (1 g, 3.63 mmol), 4-(aminomethyl)benzenesulfonamide hydrochloride (808 mg, 3.63 mmol) and diisopropylethylamine (1.90 ml, 10.89 mmol) in 1,4-dioxane (40 mL) was heated at 90° C. for 4 hrs. The reaction was cooled to room temperature and concentrated in vacuo. The residue was partitioned between EtOAc and H₂O. The aqueous layer was extracted twice with EtOAc. The combined organic layers were then washed with H₂O and saturated aqueous NaCl solution. The organic phase was then dried over solid MgSO₄, filtered and concentrated in vacuo. This gave 4-{[6-(4-fluorophenyl)-4-hydroxy-pyrido[3,2-d]pyrimidin-2-ylamino]-methyl}-benzenesulfonamide as a brown solid after drying on high vacuum. MS (m/z) 426 [M+H]⁺.

A solution of 4-{[6-(4-fluoro-phenyl)-4-hydroxy-pyrido[3,2-d]pyrimidin-2-ylamino]-methyl}-benzenesulfonamide (735 mg, 1.73 mmol), 1,2,4-triazole (478 mg, 6.92 mmol), diisopropylethylamine (1.21 ml, 6.92 mmol) and POCl₃ (0.633 ml, 6.92 mmol) in acetonitrile (20 mL) was stirred at room temperature for 15 min. The reaction was concentrated in vacuo. The solid was triturated with H₂O and dried in vacuo overnight. This gave 638 mg of 4-{[6-(4-fluoro-phenyl)-4-[1,2,4]triazol-4-yl-pyrido[3,2-d]pyrimidin-2-ylamino]-methyl}-benzenesulfonamide as a greenish solid. MS (m/z) 476 [M+H]$^+$.

A suspension of 4-{[6-(4-fluoro-phenyl)-4-[1,2,4]triazol-4-yl-pyrido[3,2-d]pyrimidin-2-ylamino]-methyl}-benzenesulfonamide (638 mg, 1.34 mmol) in 10 ml THF was added to a solution of 21% (w/w) NaOEt in EtOH (1.50 ml, 4.03 mmol) in 20 ml of dry THF over 5 min. The triazole flask was rinsed once with 5 ml THF and the rinse was added to the reaction flask. The reaction was stirred at room temperature for 15 min. Analysis by reversed phase HPLC/MS indicated the reaction was complete. The pH was adjusted to 7 with 10% acetic acid/EtOAc and then concentrated in vacuo. The residue was partitioned between EtOAc and H$_2$O. The aqueous layer was extracted twice with EtOAc. The combined organics were washed twice with water and once with brine, dried over MgSO$_4$, filtered and concentrated. The solid was absorbed onto SiO$_2$, and purified by eluting onto a 30 g SiO$_2$ column with CH$_2$Cl$_2$/MeOH. The fractions containing the desired compound as determined by LC/MS were combined and concentrated. The solid thus obtained was dissolved in DMF and re-purified by reverse phase HPLC using acetonitrile/H$_2$O in 4 runs. The pure fractions from each run were combined and the acetonitrile was removed in vacuo. The resulting aqueous suspension was neutralized with excess saturated aqueous NaHCO$_3$, and extracted three times with EtOAc. The organics were dried over MgSO$_4$, filtered and concentrated. The material was solidified by addition of MeOH. The solid was dried at high vacuum for 24 hrs, giving 110 mg of 4-{[4-ethoxy-6-(4-fluoro-phenyl)-pyrido[3,2-d]pyrimidin-2-ylamino]-methyl}-benzenesulfonamide (Example 109) as a white powder. MS (m/z) 454 [M+H]$^+$.

EXAMPLES 110-118

Synthesis of 2-(substituted amino)-4-alkoxy-6-(4-fluorophenyl)-Pyrido[3,2-d]pyrimidines These compounds were synthesized from 2-chloro-4-hydroxy-6-(4-fluorophenyl)-pyrido[3,2-d]pyrimidine according to the to the principles set forth in FIG. 4 and outlined in more details in the embodiment shown in Scheme 5 above. Further details were derived from the procedures described for Example 109 by varying the reagents in the first and third steps as necessary, e.g. in Example 112 the n-propyl substituent was introduced using n-propyl magnesium bromide in THF in place of the sodium ethoxide/ethanol combination.

TABLE 5

| No. | Structure | Name | Mass M$^{+1}$ |
|---|---|---|---|
| 110 | 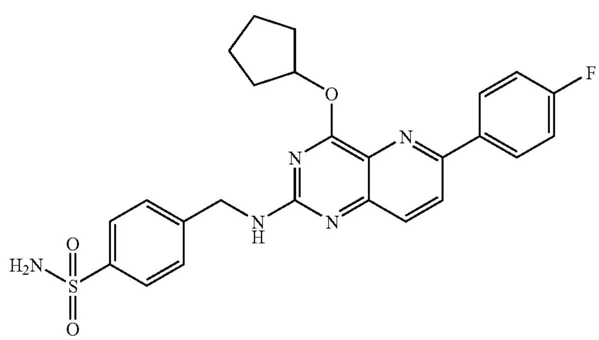 [SMILES: NS(=O)(=O)c1ccc(CNc2nc(OC3CCCC3)c3nc(-c4ccc(F)cc4)ccc3n2)cc1] | 4-{[4-Cyclopentyloxy-6-(4-fluoro-phenyl)-pyrido[3,2-d]pyrimidin-2-ylamino]-methyl}-benzenesulfonamide | 494 |
| 111 | 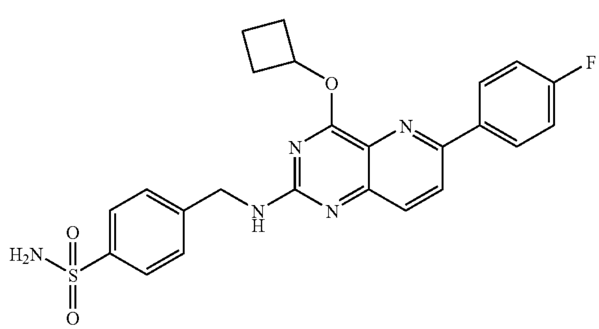 [SMILES: NS(=O)(=O)c1ccc(CNc2nc(OC3CCC3)c3nc(-c4ccc(F)cc4)ccc3n2)cc1] | 4-{[4-Cyclobutoxy-6-(4-fluorophenyl)-pyrido[3,2-d]pyrimidin-2-ylamino]-methyl}-benzenesulfonamide | 480 |

TABLE 5-continued

| No. | Structure | Name | Mass M+1 |
|---|---|---|---|
| 112 | 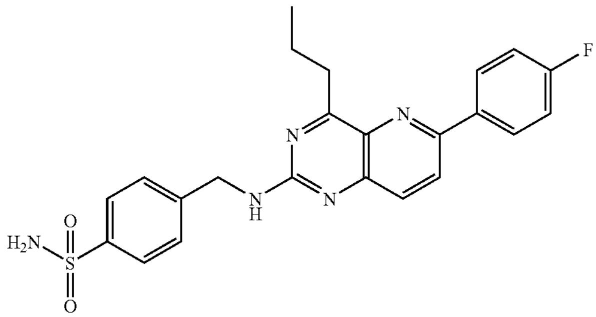 [SMILES: CCCc1nc(NCc2ccc(S(N)(=O)=O)cc2)nc2ccc(-c3ccc(F)cc3)nc12] | 4-{[6-(4-Fluoro-phenyl)-4-propyl-pyrido[3,2-d]pyrimidin-2-ylamino]-methyl}-benzenesulfonamide | 452 |
| 113 | 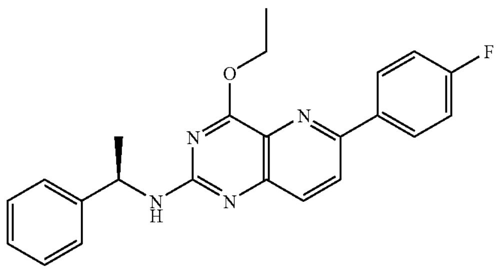 [SMILES: CCOc1nc(N[C@H](C)c2ccccc2)nc2ccc(-c3ccc(F)cc3)nc12] | [4-Ethoxy-6-(4-fluoro-phenyl)-pyrido[3,2-d]pyrimidin-2-yl]-(1-phenyl-ethyl)-amine | 389.4 |
| 114 | 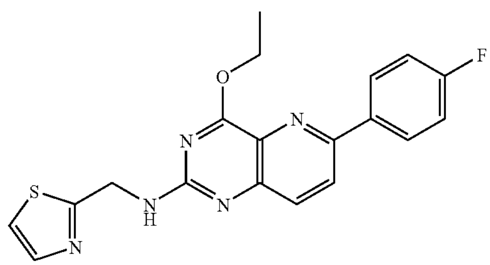 [SMILES: CCOc1nc(NCc2nccs2)nc2ccc(-c3ccc(F)cc3)nc12] | [4-Ethoxy-6-(4-fluoro-phenyl)-pyrido[3,2-d]pyrimidin-2-yl]-thiazol-2-ylmethyl-amine | 382.4 |
| 115 | 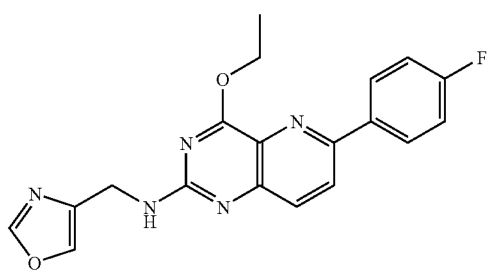 [SMILES: CCOc1nc(NCc2cocn2)nc2ccc(-c3ccc(F)cc3)nc12] | [4-Ethoxy-6-(4-fluoro-phenyl)-pyrido[3,2-d]pyrimidin-2-yl]-oxazol-4-ylmethyl-amine | 366.3 |
| 116 | 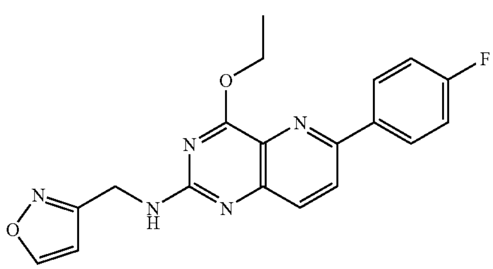 [SMILES: CCOc1nc(NCc2ccon2)nc2ccc(-c3ccc(F)cc3)nc12] | [4-Ethoxy-6-(4-fluoro-phenyl)-pyrido[3,2-d]pyrimidin-2-yl]-isoxazol-3-ylmethyl-amine | 366.3 |

TABLE 5-continued

| No. | Structure | Name | Mass M+1 |
|---|---|---|---|
| 117 | 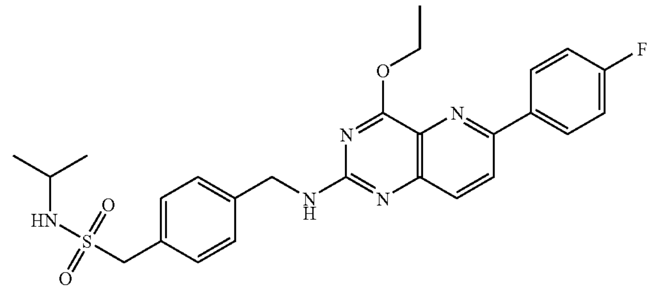 [SMILES: CCOc1nc(NCc2ccc(CS(=O)(=O)NC(C)C)cc2)nc2ccc(-c3ccc(F)cc3)nc12] | C-(4-{[4-Ethoxy-6-(4-fluoro-phenyl)-pyrido[3,2-d]pyrimidin-2-ylamino]-methyl}-phenyl)-N-isopropyl-methanesulfonamide | 510.5 |
| 118 | 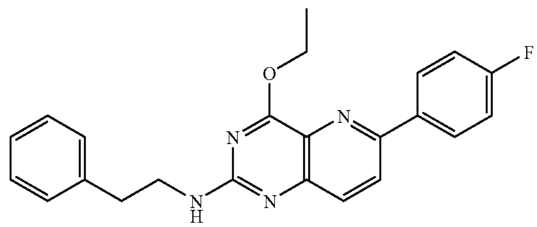 [SMILES: CCOc1nc(NCCc2ccccc2)nc2ccc(-c3ccc(F)cc3)nc12] | [4-Ethoxy-6-(4-fluoro-phenyl)-pyrido[3,2-d]pyrimidin-2-yl]-phenethyl-amine | 389.4 |
| 119 | 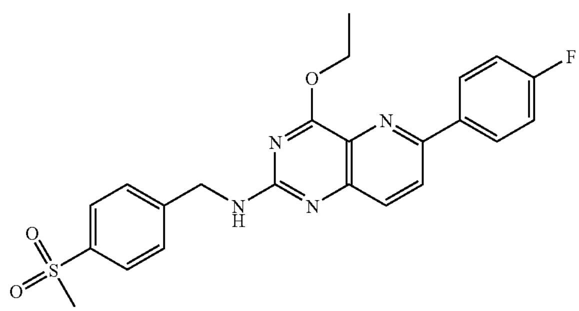 [SMILES: CCOc1nc(NCc2ccc(S(C)(=O)=O)cc2)nc2ccc(-c3ccc(F)cc3)nc12] | [4-Ethoxy-6-(4-fluoro-phenyl)-pyrido[3,2-d]pyrimidin-2-yl]-(4-methanesulfonyl-benzyl)-amine | 453.5 |

EXAMPLE 120 TO 147

Synthesis of 4-{[4-ethoxy-6-substituted-pyrido[3,2-d]pyrimidin-2-ylamino]-methyl}-benzenesulfonamide

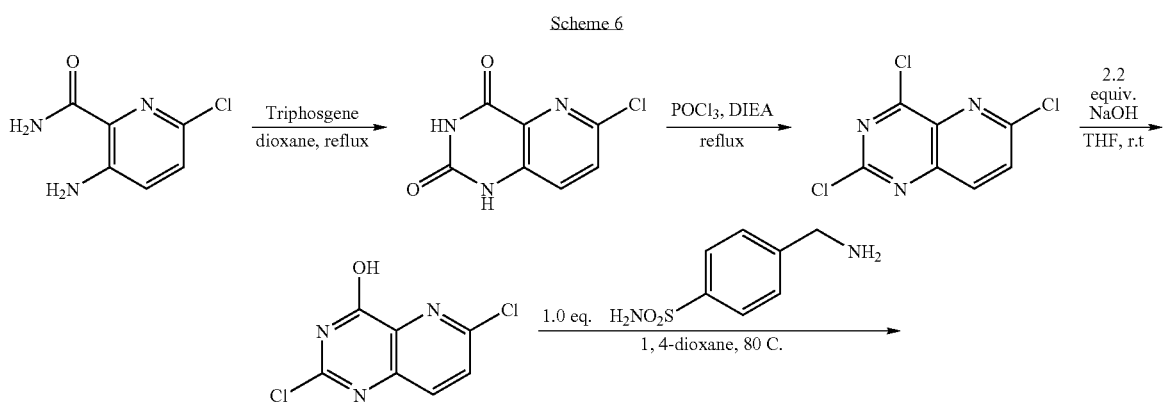

Scheme 6

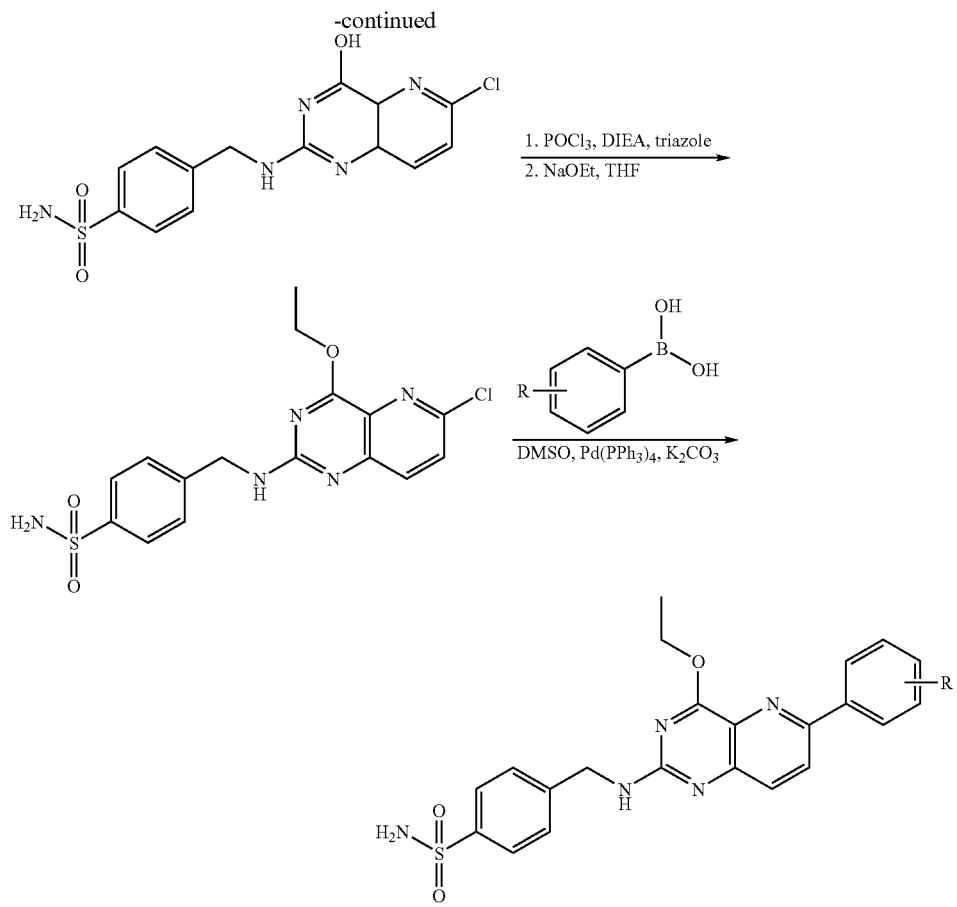

The compounds in Table 6 were synthesized from 3-amino-6-chloropicolinamide according to the to the principles set forth in FIG. 7 and outlined in more details in the embodiment shown in Scheme 6 above.

The procedures used for each compound was analogous to the one described below for 4-{[4-ethoxy-6-(4-fluorophenyl)-pyrido[3,2-d]pyrimidin-2-ylamino]-methyl}-benzenesulfonamide (Example 109). In each case, a suitable boronic acid or boronate ester was used in place of 4-fluorophenyl boronic acid to introduce the corresponding substitution at 6 position of the pyrido[3,2-d]pyrimidine ring.

To a solution mixture of 3-amino-6-chloro-pyridine-2-carboxylic acid amide (10 g, 58.3 mmol) in 1,4-dioxane (300 mL), was added triphosgene (6.9 g, 23.3 mmol). The reaction was heated to 100° C. for 1.5 hours. It was then cooled to RT and 3 ml of water was added to quench excess triphosgene. The solid was filtered and washed with EtOAc twice to provide 11 g of crude product which used without further purification.

A mixture of 6-chloro-1H-pyrido[3,2-d]pyrimidine-2,4-dione (11 g, 55.7 mmol), POCl₃ (100 ml) and DIEA (20 ml) was heated to reflux overnight. The POCl₃ was removed in vacuo and the residue was dissolved in ether. The organic layer was extracted with brine five times. The organic layer was dried and concentrated to provide 11 g of crude product which used without further purification.

A mixture of 2,4,6-trichloro-pyrido[3,2-d]pyrimidine (16 g, 68.3 mmol), and sodium hydroxide (6 g in 20 ml of water) in THF (100 mL) at room temperature was stirred for 1 hour. The reaction was neutralized with HCl (1N) and extracted with ethyl acetate twice. The organic layer was dried and concentrated to provide 12 g of crude product.

To a solution mixture of 2,6-dichloro-pyrido[3,2-d]pyrimidin-4-ol (1.94 g, 8.9 mmol) and 4-aminomethyl-benzenesulfonamide (4.0 g, 17.8 mmol) in 1,4-dioxane (30 mL) and DIEA (6.7 ml, 38.5 mmol) was added to the solution. Then it was heated up to 90° C. overnight. Acidified by 1N HCl to pH 2~3. The solid was filtered and dried in vacuo to provide 2.48 g (6.8 mm, 76%) of crude product.

To a solution of 4-[(6-chloro-4-hydroxy-pyrido[3,2-d]pyrimidin-2-ylamino)-methyl]-benzenesulfonamide (0.5 g, 1.37 mmol), 1,2,4-triazole (0.377 g, 5.46 mmol), DIEA (0.95 ml, 5.46 mmol) and POCl₃(0.5 g, 5.46 mmol) in dioxane (10 mL) was stirred at room temperature for 1 hour. The reaction mixture was transferred to a solution of NaOEt (7.6 ml, 21%, 20.6 mmol) in THF (10 ml). The reaction was stirred for 10 min, then diluted with ethyl acetate (200 ml) and washed with brine (50 ml) twice. The organic layer was concentrated and purified by flash column ($R_f$: 0.3, ethyl acetate/hexanes: 70%). The yield was 200 mg.

A mixture of 4-[(6-chloro-4-ethoxy-pyrido[3,2-d]pyrimidin-2-ylamino)-methyl]-benzenesulfonamide (170 mg, 0.433 mmol), potassium carbonate (119.3 mg, 0.86 mmol), tetrakis(triphenylphosphine) palladium (0) (25 mg) and 4-fluorophenyl boronic acid (61 mg, o.433 mmol) in DMSO (4 mL) and water (1 mL) was heated to 120° C. for 5 minutes by microwave. The reaction mixture was diluted with ethyl acetate (200 ml) and washed with brine (100 ml) twice. The organic layer was concentrated and purified with flash column ($R_f$: 0.32, ethyl acetate/hexanes: 70%). The yield of Example 109 was 180 mg, 91.6%.

TABLE 6

| No. | Structure | Name | Mass M+1 |
|-----|-----------|------|----------|
| 120 | 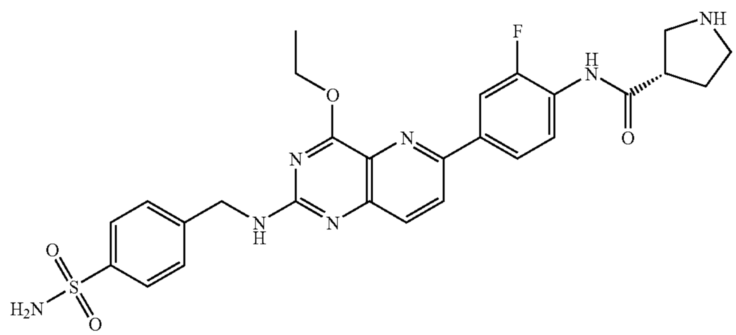 [SMILES: CCOc1nc(NCc2ccc(S(N)(=O)=O)cc2)nc2ccc(-c3ccc(NC(=O)[C@H]4CCNC4)c(F)c3)nc12] | (S)-4-{[4-Ethoxy-6-(3-fluoro-4-(pyrrolidine-3-carboxamido)-phenyl)-pyrido[3,2-d]pyrimidin-2-ylamino]-methyl}-benzenesulfonamide | 566 |
| 121 | 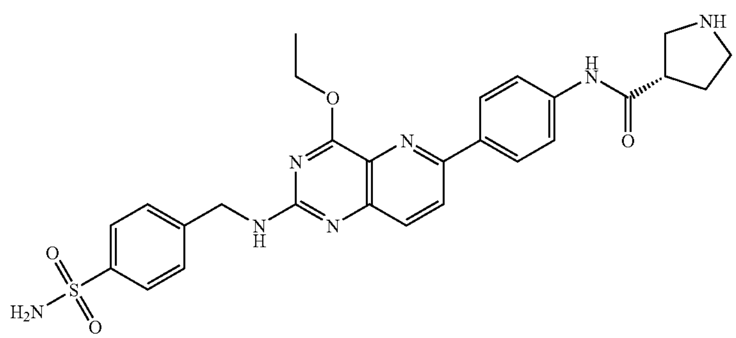 [SMILES: CCOc1nc(NCc2ccc(S(N)(=O)=O)cc2)nc2ccc(-c3ccc(NC(=O)[C@H]4CCNC4)cc3)nc12] | (S)-4-{[4-Ethoxy-6-(4-(pyrrolidine-3-carboxamido)-phenyl)-pyrido[3,2-d]pyrimidin-2-ylamino]-methyl}-benzenesulfonamide | 548 |
| 122 | 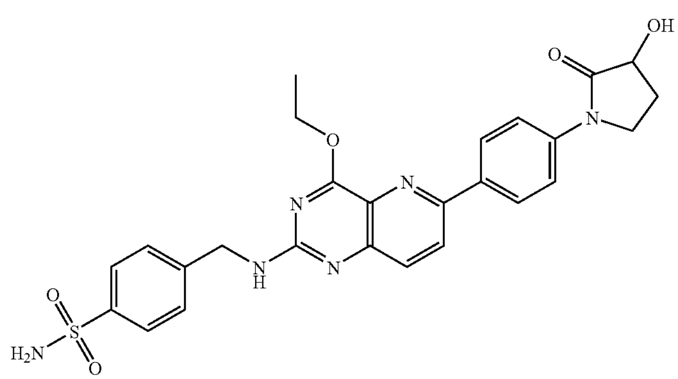 [SMILES: CCOc1nc(NCc2ccc(S(N)(=O)=O)cc2)nc2ccc(-c3ccc(N4CCC(O)C4=O)cc3)nc12] | 4-{[4-Ethoxy-6-(4-(3-hydroxy-2-oxopyrrolidin-1-yl)-phenyl)-pyrido[3,2-d]pyrimidin-2-ylamino]-methyl}-benzenesulfonamide | 535 |
| 123 | 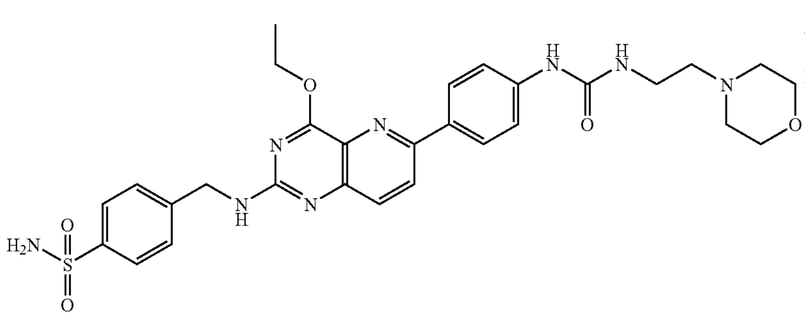 [SMILES: CCOc1nc(NCc2ccc(S(N)(=O)=O)cc2)nc2ccc(-c3ccc(NC(=O)NCCN4CCOCC4)cc3)nc12] | 4-{[4-Ethoxy-6-(4-(3-(2-(morpholin-4-yl)ethyl)ureido)-phenyl)-pyrido[3,2-d]pyrimidin-2-ylamino]-methyl}-benzenesulfonamide | 607 |

TABLE 6-continued

| No. | Structure | Name | Mass M⁺¹ |
|---|---|---|---|
| 124 | 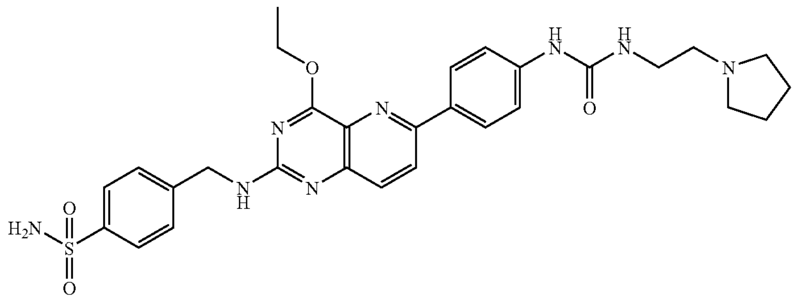 [SMILES: CCOc1nc(NCc2ccc(S(N)(=O)=O)cc2)nc2ccc(-c3ccc(NC(=O)NCCN4CCCC4)cc3)nc12] | 4-{[4-Ethoxy-6-(4-(3-(2-(pyrrolidin-1-yl)ethyl)ureido)-phenyl)-pyrido[3,2-d]pyrimidin-2-ylamino]-methyl}-benzenesulfonamide | 591 |
| 125 | 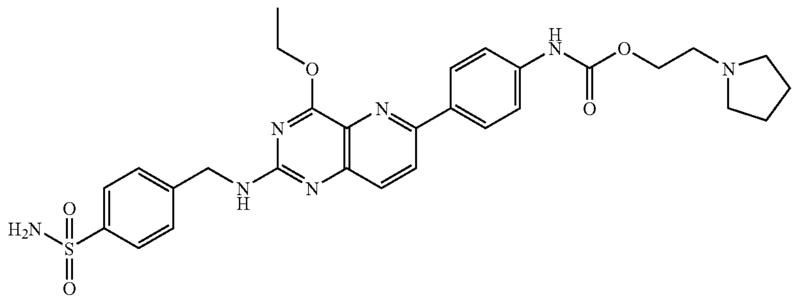 [SMILES: CCOc1nc(NCc2ccc(S(N)(=O)=O)cc2)nc2ccc(-c3ccc(NC(=O)OCCN4CCCC4)cc3)nc12] | 4-{[4-Ethoxy-6-(4-(2-(pyrrolidin-1-yl)ethoxycarbonyl)-phenyl)-pyrido[3,2-d]pyrimidin-2-ylamino]-methyl}-benzenesulfonamide | 592 |
| 126 | 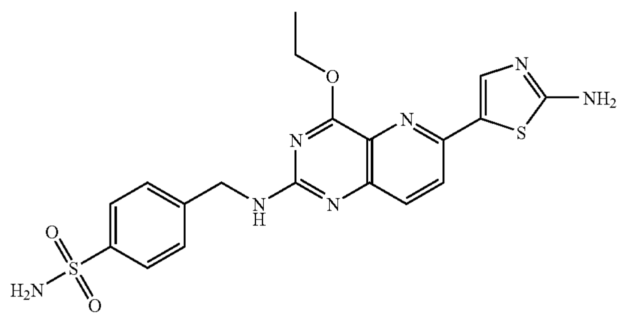 [SMILES: CCOc1nc(NCc2ccc(S(N)(=O)=O)cc2)nc2ccc(-c3cnc(N)s3)nc12] | 4-{[4-Ethoxy-6-(2-aminothiazole-5-yl)-pyrido[3,2-d]pyrimidin-2-ylamino]-methyl}-benzenesulfonamide | 458 |
| 127 | 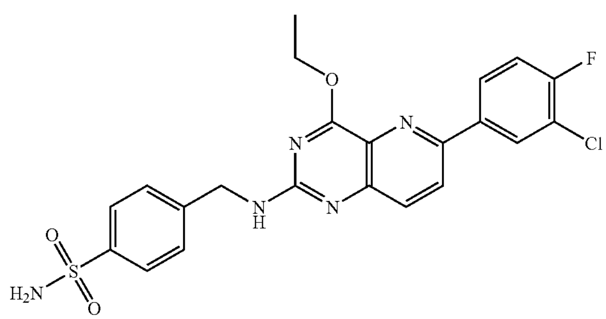 [SMILES: CCOc1nc(NCc2ccc(S(N)(=O)=O)cc2)nc2ccc(-c3ccc(F)c(Cl)c3)nc12] | 4-{[4-Ethoxy-6-(3-chloro-4-fluorophenyl)-pyrido[3,2-d]pyrimidin-2-ylamino]-methyl}-benzenesulfonamide | 488 |
| 128 | 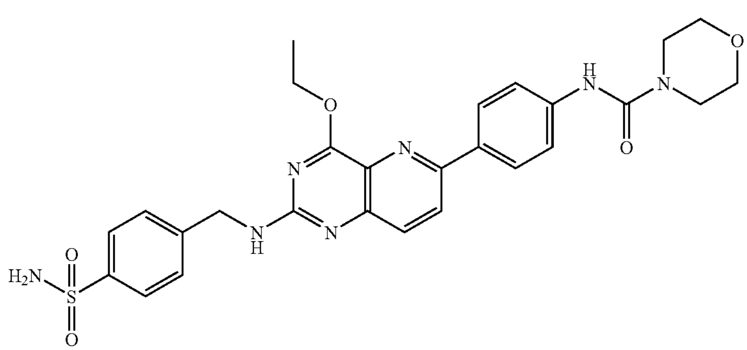 [SMILES: CCOc1nc(NCc2ccc(S(N)(=O)=O)cc2)nc2ccc(-c3ccc(NC(=O)N4CCOCC4)cc3)nc12] | 4-{[4-Ethoxy-6-(4-(morpholine-4-carboxamido)-phenyl)-pyrido[3,2-d]pyrimidin-2-ylamino]-methyl}-benzenesulfonamide | 564 |

TABLE 6-continued

| No. | Structure | Name | Mass M+1 |
|---|---|---|---|
| 129 | 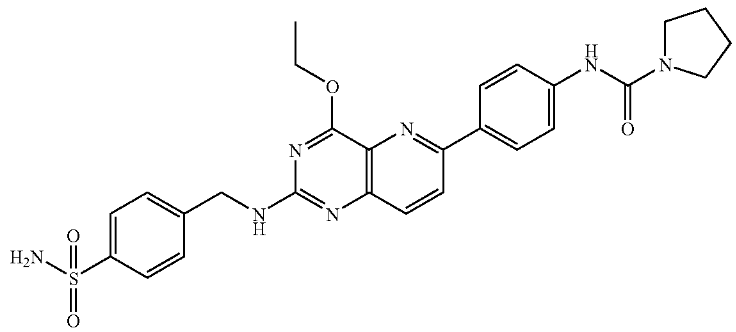 [SMILES: CCOc1nc(NCc2ccc(S(N)(=O)=O)cc2)nc2ccc(-c3ccc(NC(=O)N4CCCC4)cc3)nc12] | 4-{[4-Ethoxy-6-(4-(pyrrolidine-1-carboxamido)-phenyl)-pyrido[3,2-d]pyrimidin-2-ylamino]-methyl}-benzenesulfonamide | 548 |
| 130 | 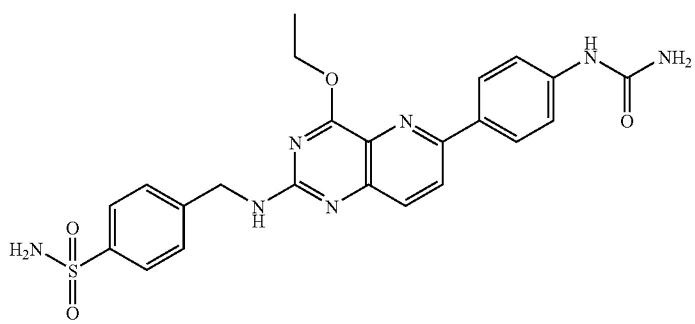 [SMILES: CCOc1nc(NCc2ccc(S(N)(=O)=O)cc2)nc2ccc(-c3ccc(NC(N)=O)cc3)nc12] | 4-{[4-Ethoxy-6-(4-ureidophenyl)-pyrido[3,2-d]pyrimidin-2-ylamino]-methyl}-benzenesulfonamide | 494 |
| 131 | 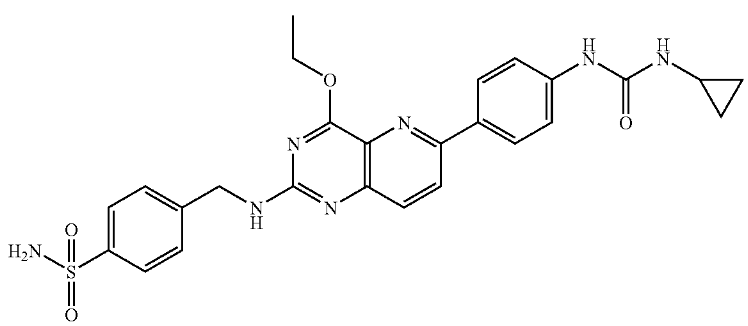 [SMILES: CCOc1nc(NCc2ccc(S(N)(=O)=O)cc2)nc2ccc(-c3ccc(NC(=O)NC4CC4)cc3)nc12] | 4-{[4-Ethoxy-6-(4-(3-cyclopropylureido)-phenyl)-pyrido[3,2-d]pyrimidin-2-ylamino]-methyl}-benzenesulfonamide | 534 |
| 132 | 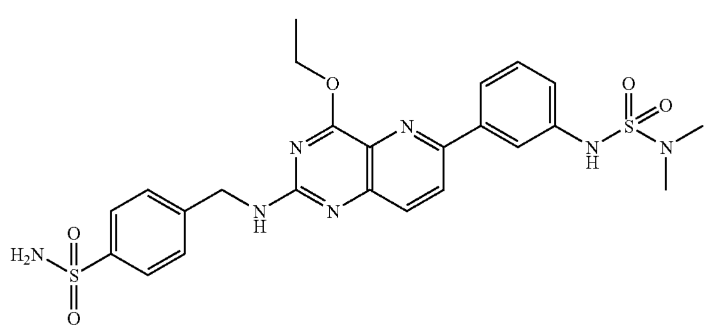 [SMILES: CCOc1nc(NCc2ccc(S(N)(=O)=O)cc2)nc2ccc(-c3cccc(NS(=O)(=O)N(C)C)c3)nc12] | 4-{[4-Ethoxy-6-(3-(aminosulfonylamido)-phenyl)-pyrido[3,2-d]pyrimidin-2-ylamino]-methyl}-benzenesulfonamide | 558 |

TABLE 6-continued

| No. | Structure | Name | Mass M⁺¹ |
|---|---|---|---|
| 133 | 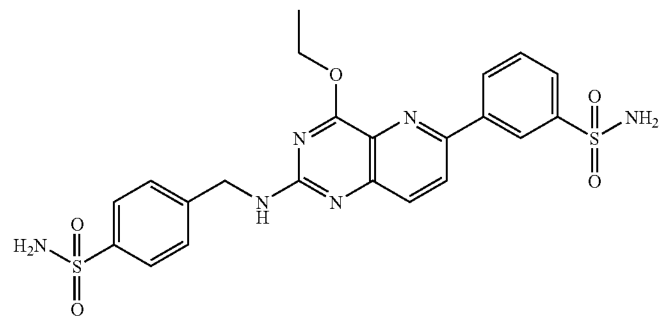 [SMILES: CCOc1nc(NCc2ccc(S(N)(=O)=O)cc2)nc2ccc(-c3cccc(S(N)(=O)=O)c3)nc12] | 4-{[4-Ethoxy-6-(3-(aminosulfonyl)-phenyl)-pyrido[3,2-d]pyrimidin-2-ylamino]-methyl}-benzenesulfonamide | 515 |
| 134 | 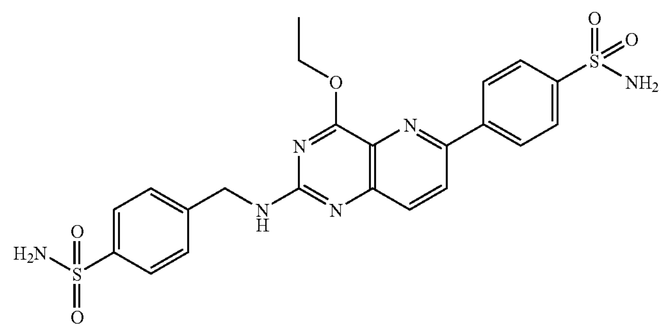 [SMILES: CCOc1nc(NCc2ccc(S(N)(=O)=O)cc2)nc2ccc(-c3ccc(S(N)(=O)=O)cc3)nc12] | 4-{[4-Ethoxy-6-(4-(aminosulfonyl)-phenyl)-pyrido[3,2-d]pyrimidin-2-ylamino]-methyl}-benzenesulfonamide | 515 |
| 135 | 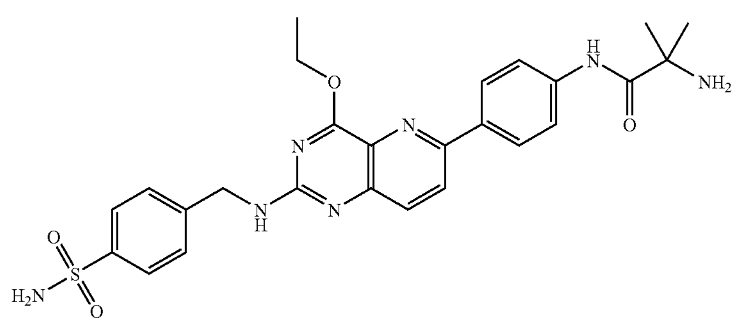 [SMILES: CCOc1nc(NCc2ccc(S(N)(=O)=O)cc2)nc2ccc(-c3ccc(NC(=O)C(C)(C)N)cc3)nc12] | 4-{[4-Ethoxy-6-(4-((2-amino-2-propyl)-carboxamido)-phenyl)-pyrido[3,2-d]pyrimidin-2-ylamino]-methyl}-benzenesulfonamide | 536 |
| 136 | 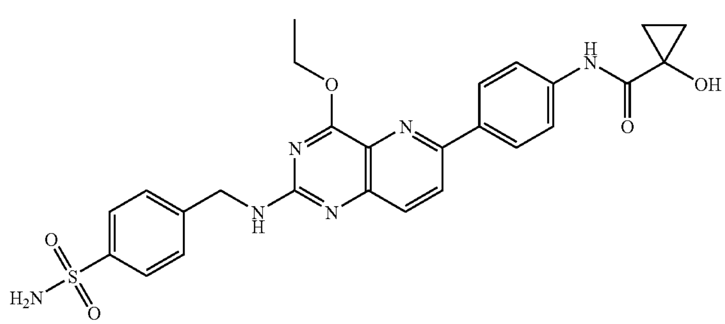 [SMILES: CCOc1nc(NCc2ccc(S(N)(=O)=O)cc2)nc2ccc(-c3ccc(NC(=O)C4(O)CC4)cc3)nc12] | 4-{[4-Ethoxy-6-(4-((1-hydroxy-1-cyclopropyl)-carboxamido)-phenyl)-pyrido[3,2-d]pyrimidin-2-ylamino]-methyl}-benzenesulfonamide | 535 |

| No. | Structure | Name | Mass M+1 |
|---|---|---|---|
| 137 | 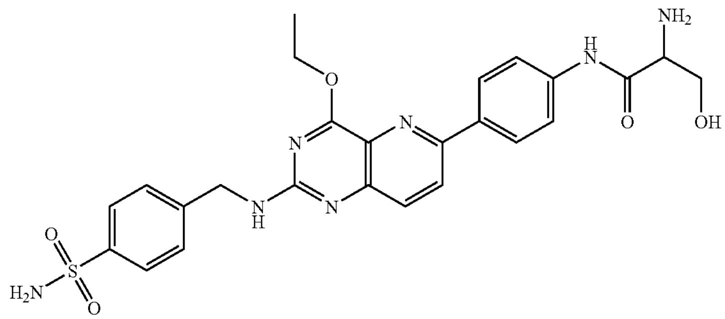 [SMILES: CCOc1nc(NCc2ccc(S(N)(=O)=O)cc2)nc2ccc(-c3ccc(NC(=O)C(N)CO)cc3)nc12] | (S)-4-{[4-Ethoxy-6-(4-((2-hydroxy-1-aminoethyl)-carboxamido)-phenyl)-pyrido[3,2-d]pyrimidin-2-ylamino]-methyl}-benzenesulfonamide | 538 |
| 138 | 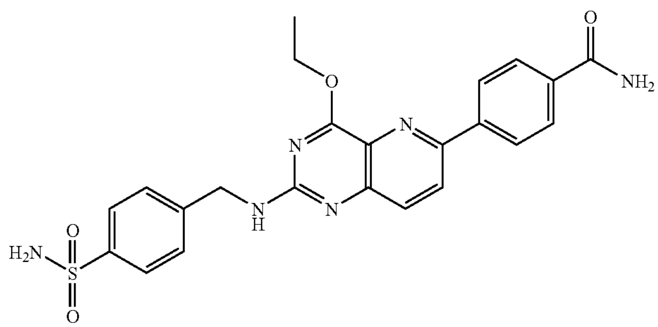 [SMILES: CCOc1nc(NCc2ccc(S(N)(=O)=O)cc2)nc2ccc(-c3ccc(C(N)=O)cc3)nc12] | 4-{[4-Ethoxy-6-(4-carbamoylphenyl)-pyrido[3,2-d]pyrimidin-2-ylamino]-methyl}-benzenesulfonamide | 479 |
| 139 | 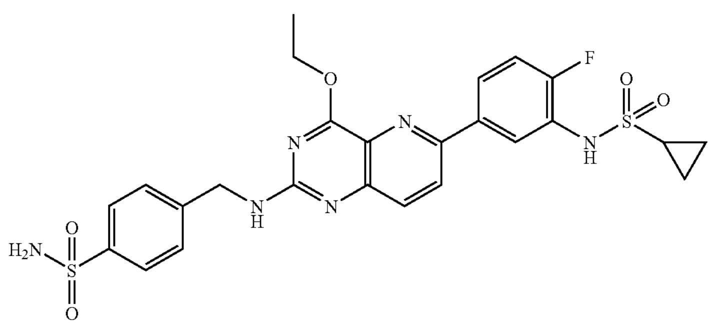 [SMILES: CCOc1nc(NCc2ccc(S(N)(=O)=O)cc2)nc2ccc(-c3ccc(F)c(NS(=O)(=O)C4CC4)c3)nc12] | 4-{[4-Ethoxy-6-(4-(3-cyclopropanesulfonamido-4-fluoro)-phenyl)-pyrido[3,2-d]pyrimidin-2-ylamino]-methyl}-benzenesulfonamide | 573 |
| 140 | 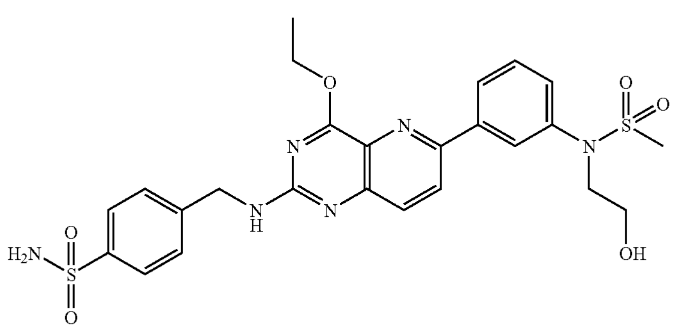 [SMILES: CCOc1nc(NCc2ccc(S(N)(=O)=O)cc2)nc2ccc(-c3cccc(N(CCO)S(C)(=O)=O)c3)nc12] | 4-{[4-Ethoxy-6-(4-(3-(N-2-hydroxy-ethyl)methanesulfonamido)-phenyl)-pyrido[3,2-d]pyrimidin-2-ylamino]-methyl}-benzenesulfonamide | 573 |

TABLE 6-continued

| No. | Structure | Name | Mass M[+1] |
|---|---|---|---|
| 141 | 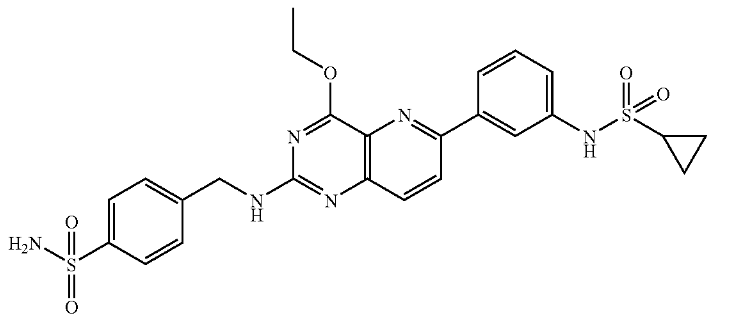 [SMILES: CCOc1nc(NCc2ccc(S(N)(=O)=O)cc2)nc2ccc(-c3cccc(NS(=O)(=O)C4CC4)c3)nc12] | 4-{[4-Ethoxy-6-(4-(3-cyclopropanesulfonamido)-phenyl)-pyrido[3,2-d]pyrimidin-2-ylamino]-methyl}-benzenesulfonamide | 555 |
| 142 | 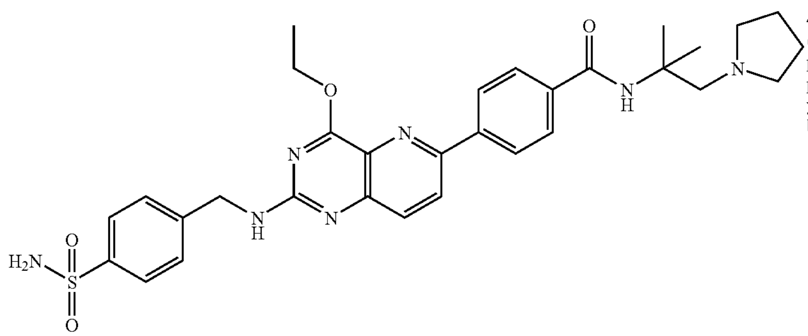 [SMILES: CCOc1nc(NCc2ccc(S(N)(=O)=O)cc2)nc2ccc(-c3ccc(C(=O)NC(C)(C)CN4CCCC4)cc3)nc12] | 4-{[4-Ethoxy-6-(4-(N-(2-(pyrrolidin-1-yl)methyl-2-propyl)-carbamoyl)phenyl)-pyrido[3,2-d]pyrimidin-2-ylamino]-methyl}-benzenesulfonamide | 604 |
| 143 | 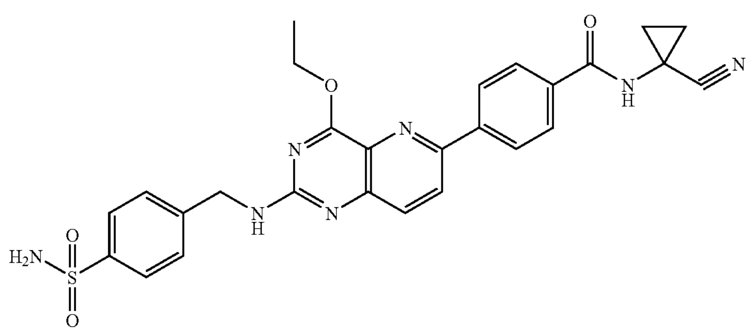 [SMILES: CCOc1nc(NCc2ccc(S(N)(=O)=O)cc2)nc2ccc(-c3ccc(C(=O)NC4(C#N)CC4)cc3)nc12] | 4-{[4-Ethoxy-6-(4-(N-(1-cyano-1-cyclopropyl)-carbamoyl)phenyl)-pyrido[3,2-d]pyrimidin-2-ylamino]-methyl}-benzenesulfonamide | 544 |
| 144 | 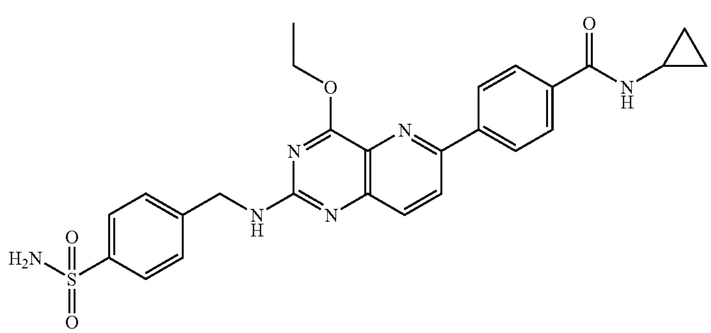 [SMILES: CCOc1nc(NCc2ccc(S(N)(=O)=O)cc2)nc2ccc(-c3ccc(C(=O)NC4CC4)cc3)nc12] | 4-{[4-Ethoxy-6-(4-(N-cyclopropylcarbamoyl)phenyl)-pyrido[3,2-d]pyrimidin-2-ylamino]-methyl}-benzenesulfonamide | 519 |

TABLE 6-continued

| No. | Structure | Name | Mass M+1 |
|---|---|---|---|
| 145 | 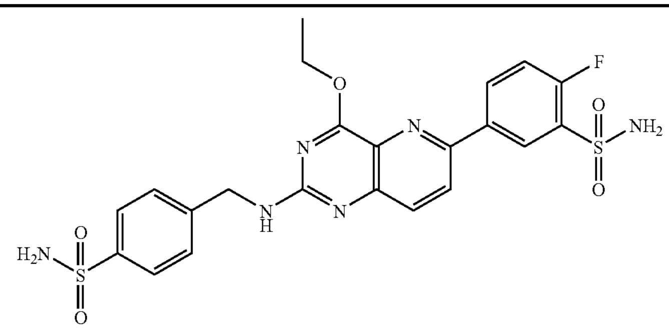 | 5-[4-Ethoxy-2-(4-sulfamoyl-benzylamino)-pyrido[3,2-d]pyrimidin-6-yl]-2-fluoro-benzenesulfonamide | 533 |
| 146 | 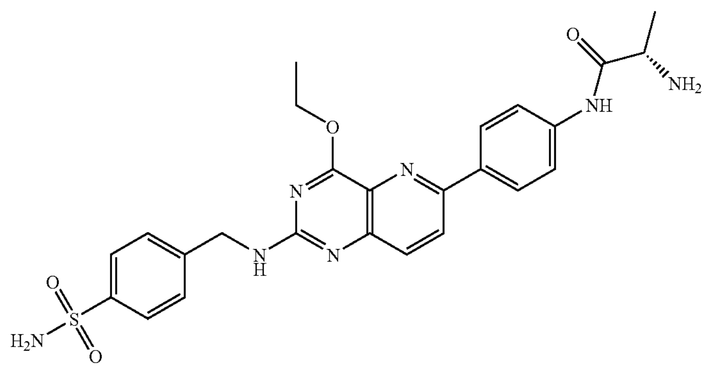 [SMILES: CCOc1nc(NCc2ccc(S(N)(=O)=O)cc2)nc2ccc(-c3ccc(NC(=O)[C@H](C)N)cc3)nc12] | 2-Amino-N-{4-[4-ethoxy-2-(4-sulfamoyl-benzylamino)-pyrido[3,2-d]pyrimidin-6-yl]-phenyl}-propionamide | 522.3 |
| 147 | 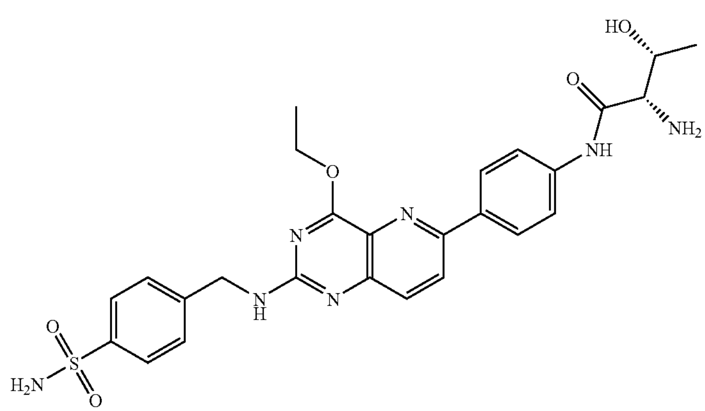 [SMILES: CCOc1nc(NCc2ccc(S(N)(=O)=O)cc2)nc2ccc(-c3ccc(NC(=O)[C@@H](N)[C@@H](C)O)cc3)nc12] | 2-Amino-N-{4-[4-ethoxy-2-(4-sulfamoyl-benzylamino)-pyrido[3,2-d]pyrimidin-6-yl]-phenyl}-3-hydroxy-butyramide | 552.2 |

EXAMPLES 148 TO 237

Synthesis of 4-[(6-substituted-4-(substituted amino)-pyrido[3,2-d]pyrimidin-2-ylamino)-methyl]-benzenesulfonamide The compounds in Table 7 were synthesized from 4-[(6-chloro-4-hydroxypyrido[3,2-d]pyrimidin-2-ylamino)-methyl]-benzenesulfonamide according to the to the principles set forth in FIG. 7 and outlined in more details in the embodiment shown in Scheme 7 below.

In a first step, 4-[(6-chloro-4-hydroxy-pyrido[3,2-d]pyrimidin-2-ylamino)-methyl]-benzenesulfonamide (3 g, 8.0 mmol) and PyBOP (8.32 g, 16.0 mmol) were mixed in THF (120 mL) and DIEA (2 mL, 12.0 mmol) was added. The reaction mixture was stirred at room temperature for 2 hours. This solution was then transferred to a stirred solution of sodium ethoxide (11.9 mL, 32.0 mmol, 21 wt % in ethanol) in THF (25 mL) using an addition funnel. After stirring at room temperature for 30 min, the THF was removed in vacuo and the residue diluted with ethyl acetate (100 mL) and washed with water and brine. The organic layer was dried over sodium sulfate and concentrated to afford an oily residue. Dichloromethane (50 mL) was added to the residue whereupon 4-[(6-chloro-4-ethoxy-pyrido[3,2-d]pyrimidin-2-ylamino)-methyl]-benzenesulfonamide precipitated as a yellow solid and was filtered, washed with dichloromethane and dried overnight. (1.9 g, yield: 61%) MS (m/z) 394.0 [M+H]+; HPLC R$_t$=1.39 min.

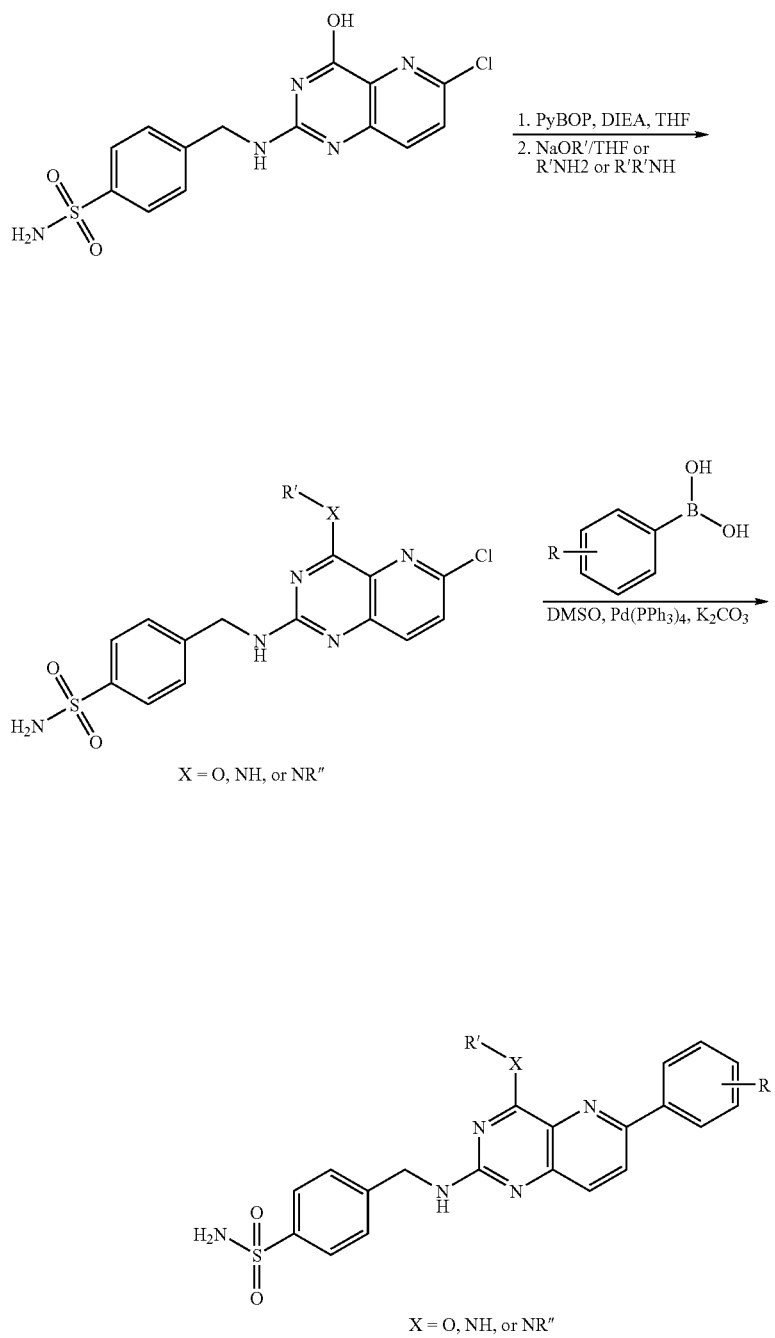

Other alkoxy groups at 4 position of the pyrido[3,2-d] pyrimidine ring were introduced using a suitable alkoxide in a suitable solvent in place of sodium ethoxide in ethanol. The corresponding products, 4-[(6-chloro-4-alkoxy-pyrido[3,2-d]pyrimidin-2-ylamino)-methyl]-benzenesulfonamide were isolated either by precipitation or normal phase chromatography.

For X=NH or NR", analogous procedures were used by substituting sodium ethoxide with a suitable amine after the initial activation of 4-[(6-chloro-4-hydroxypyrido[3,2-d]pyrimidin-2-ylamino)-methyl]-benzenesulfonamide with PyBOP. The corresponding products, 4-[(6-chloro-4-(substituted amino)-pyrido[3,2-d]pyrimidin-2-ylamino)-methyl]-benzenesulfonamide were isolated either by precipitation or normal phase chromatography.

In the next step, the compounds in Table 7 were synthesized by introducing the substituents at the 6 position of the pyrido[3,2-d]pyrimidine ring using procedure outlined in Scheme 7. The detailed procedure for the synthesis of Example 109 outlined in the last step of Scheme 6 was adapted. In each case, a suitable boronic acid or boronate ester was used in place of 4-fluorophenyl boronic acid to introduce the corresponding substitution at 6 position of the pyrido[3,2-d]pyrimidine ring.

TABLE 7

| No. | Structure | Name | Mass M$^{+1}$ |
|---|---|---|---|
| 148 | 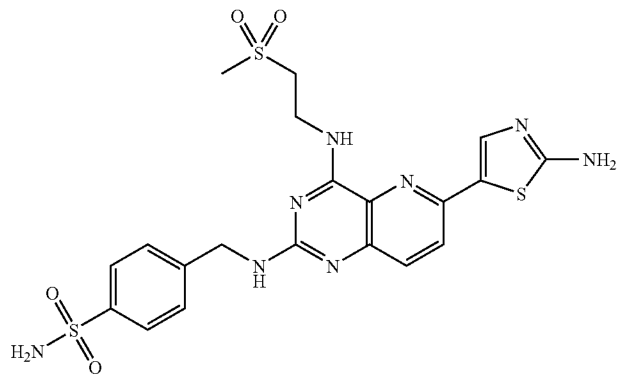 [SMILES: CS(=O)(=O)CCNc1nc(NCc2ccc(S(N)(=O)=O)cc2)nc2ccc(-c3cnc(N)s3)nc12] | 4-{[4-(2-Methanesulfonylethyl)-amino-6-(2-aminothiazole-5-yl)-pyrido[3,2-d]pyrimidin-2-ylamino]-methyl}-benzenesulfonamide | 535 |
| 149 | 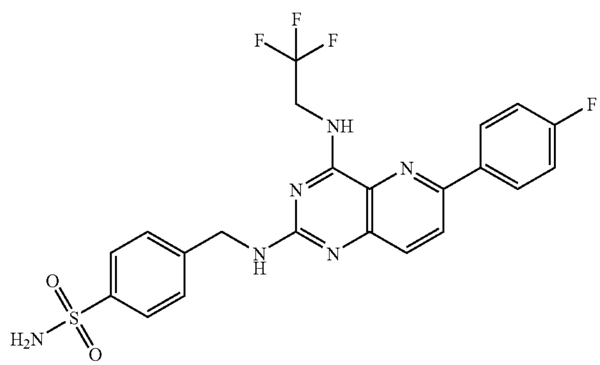 [SMILES: NS(=O)(=O)c1ccc(CNc2nc(NCC(F)(F)F)c3nc(-c4ccc(F)cc4)ccc3n2)cc1] | 4-{[4-(2,2,2-Trifluoroethyl)-amino-6-(4-fluorophenyl)-pyrido[3,2-d]pyrimidin-2-ylamino]-methyl}-benzenesulfonamide | 507 |
| 150 | 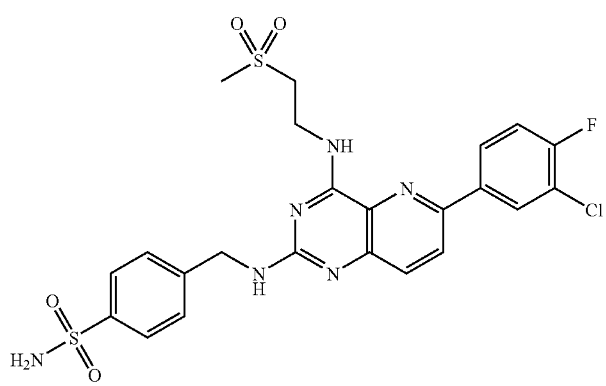 [SMILES: CS(=O)(=O)CCNc1nc(NCc2ccc(S(N)(=O)=O)cc2)nc2ccc(-c3ccc(F)c(Cl)c3)nc12] | 4-{[4-(2-Methanesulfonylethyl)-amino-6-(3-chloro-4-fluorophenyl)-pyrido[3,2-d]pyrimidin-2-ylamino]-methyl}-benzenesulfonamide | 566 |
| 151 | 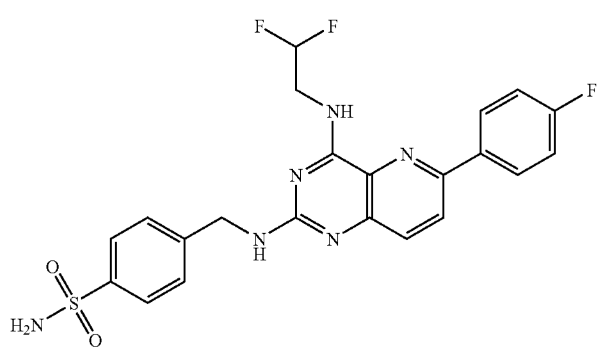 [SMILES: NS(=O)(=O)c1ccc(CNc2nc(NCC(F)F)c3nc(-c4ccc(F)cc4)ccc3n2)cc1] | 4-{[4-(2,2-Difluoroethyl)-amino-6-(4-fluorophenyl)-pyrido[3,2-d]pyrimidin-2-ylamino]-methyl}-benzenesulfonamide | 489 |

| No. | Structure | Name | Mass M+1 |
|---|---|---|---|
| 152 | 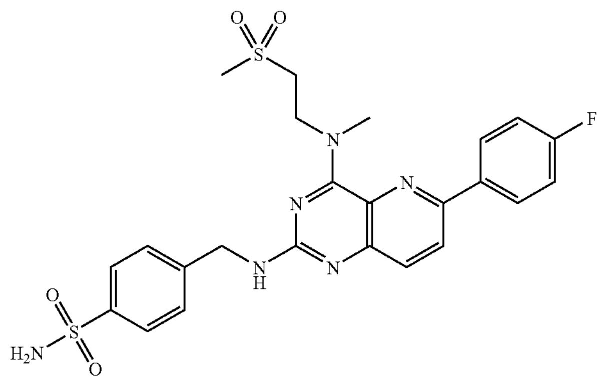 [SMILES: CN(CCS(C)(=O)=O)c1nc(NCc2ccc(S(N)(=O)=O)cc2)nc2ccc(-c3ccc(F)cc3)nc12] | 4-{[4-(N-(2-Methanesulfonylethyl)-N-methyl)-amino-6-(4-fluorophenyl)-pyrido[3,2-d]pyrimidin-2-ylamino]-methyl}-benzenesulfonamide | 545 |
| 153 | 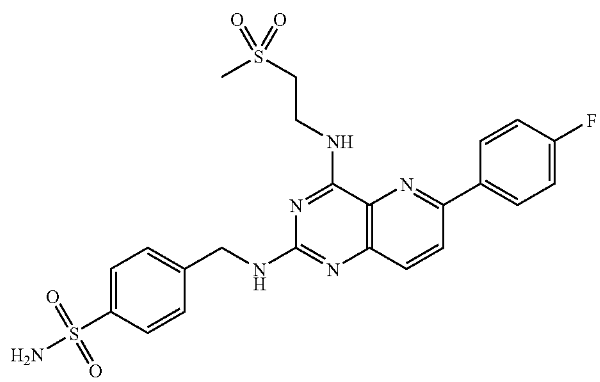 [SMILES: CS(=O)(=O)CCNc1nc(NCc2ccc(S(N)(=O)=O)cc2)nc2ccc(-c3ccc(F)cc3)nc12] | 4-{[4-(2-Methanesulfonylethyl)-amino-6-(4-fluorophenyl)-pyrido[3,2-d]pyrimidin-2-ylamino]-methyl}-benzenesulfonamide | 531 |
| 154 | 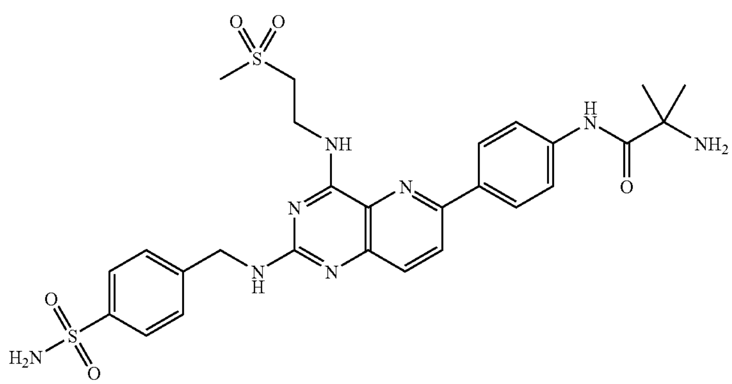 [SMILES: CC(C)(N)C(=O)Nc1ccc(-c2ccc3nc(NCc4ccc(S(N)(=O)=O)cc4)nc(NCCS(C)(=O)=O)c3n2)cc1] | 4-{[4-(2-Methanesulfonylethyl)-amino-6-(4-((2-amino-2-propyl)-carboxamido)-phenyl)-pyrido[3,2-d]pyrimidin-2-ylamino]-methyl}-benzenesulfonamide | 613 |
| 155 | 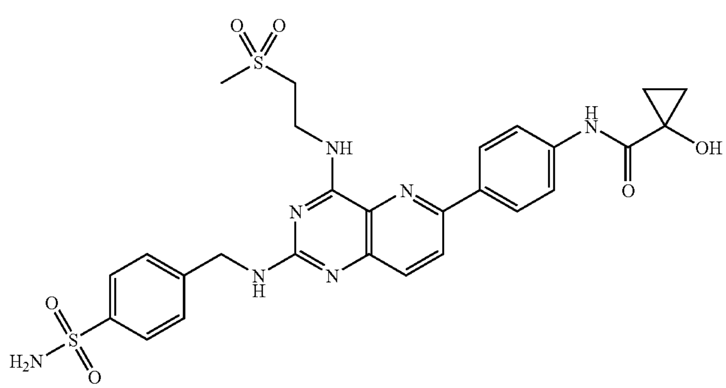 [SMILES: CS(=O)(=O)CCNc1nc(NCc2ccc(S(N)(=O)=O)cc2)nc2ccc(-c3ccc(NC(=O)C4(O)CC4)cc3)nc12] | 4-{[4-(2-Methanesulfonylethyl)-amino-6-(4-((1-hydroxy-1-cyclopropyl)-carboxamido)-phenyl)-pyrido[3,2-d]pyrimidin-2-ylamino]-methyl}-benzenesulfonamide | 612 |

TABLE 7-continued

| No. | Structure | Name | Mass M+1 |
|---|---|---|---|
| 156 | 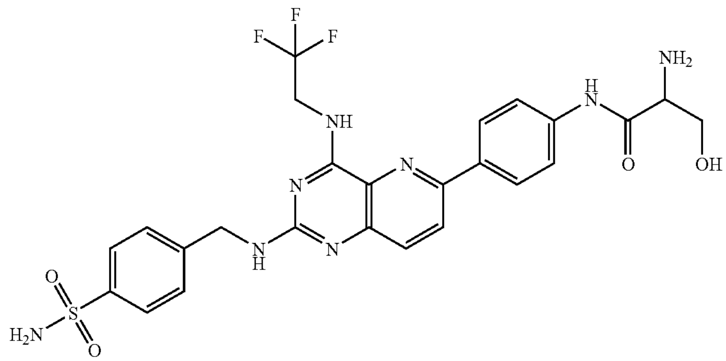 [SMILES: NC(CO)C(=O)Nc1ccc(-c2ccc3nc(NCc4ccc(S(N)(=O)=O)cc4)nc(NCC(F)(F)F)c3n2)cc1] | (S)-4-{[4-(2,2,2-Trifluoroethyl)-amino-6-(4-((2-hydroxy-1-aminoethyl)-carboxamido)-phenyl)-pyrido[3,2-d]pyrimidin-2-ylamino]-methyl}-benzenesulfonamide | 591 |
| 157 | 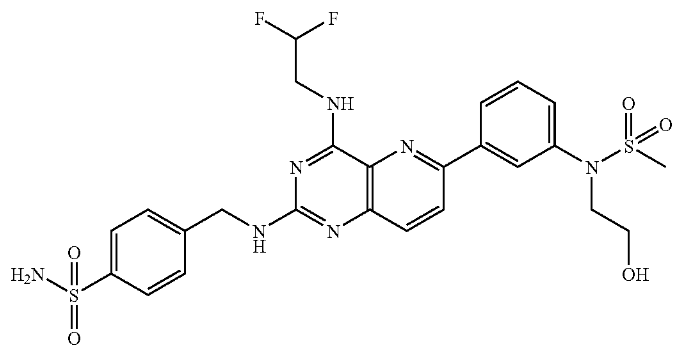 [SMILES: CS(=O)(=O)N(CCO)c1cccc(-c2ccc3nc(NCc4ccc(S(N)(=O)=O)cc4)nc(NCC(F)F)c3n2)c1] | 4-{[4-(2,2-Difluoroethyl)-amino-6-(4-(3-(N-2-hydroxyethyl)methane-sulfonamido)-phenyl)-pyrido[3,2-d]pyrimidin-2-ylamino]-methyl}-benzenesulfonamide | 608 |
| 158 | 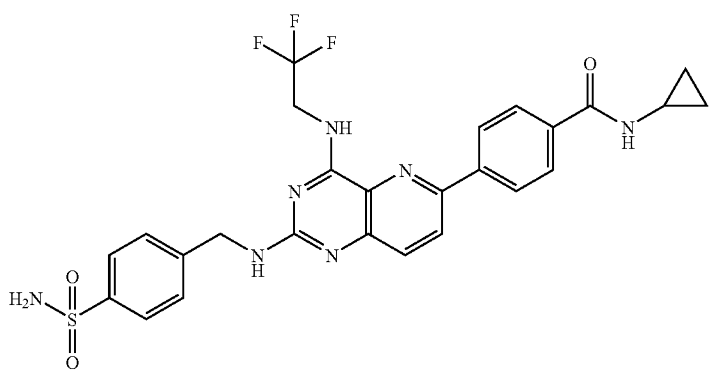 [SMILES: NS(=O)(=O)c1ccc(CNc2nc(NCC(F)(F)F)c3nc(-c4ccc(C(=O)NC5CC5)cc4)ccc3n2)cc1] | 4-{[4-(2,2,2-Trifluoroethyl)-amino-6-(4-(N-cyclopropylcarbamoyl)-phenyl)-pyrido[3,2-d]pyrimidin-2-ylamino]-methyl}-benzenesulfonamide | 572 |
| 159 | 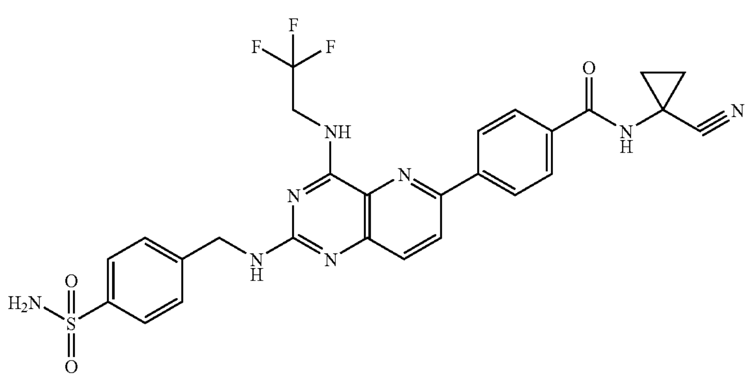 [SMILES: N#CC1(NC(=O)c2ccc(-c3ccc4nc(NCc5ccc(S(N)(=O)=O)cc5)nc(NCC(F)(F)F)c4n3)cc2)CC1] | 4-{[4-(2,2,2-Trifluoroethyl)-amino-6-(4-(N-(1-cyano-1-cyclopropyl)-carbamoyl)phenyl)-pyrido[3,2-d]pyrimidin-2-ylamino]-methyl}-benzenesulfonamide | 597 |

TABLE 7-continued

| No. | Structure | Name | Mass M$^{+1}$ |
|---|---|---|---|
| 160 | 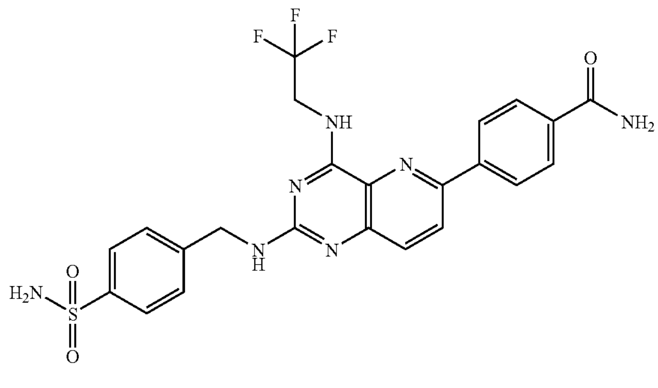 [SMILES: NC(=O)c1ccc(-c2ccc3nc(NCc4ccc(S(N)(=O)=O)cc4)nc(NCC(F)(F)F)c3n2)cc1] | 4-{[4-(2,2,2-Trifluoroethyl)-amino-6-carbamoyl)phenyl)-pyrido[3,2-d]pyrimidin-2-ylamino]-methyl}-benzenesulfonamide | 532 |
| 161 | 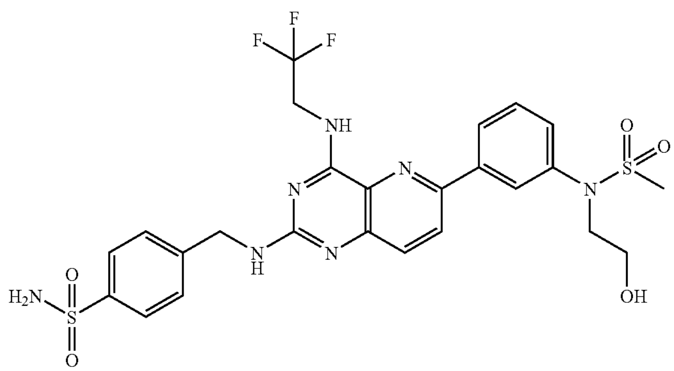 [SMILES: CS(=O)(=O)N(CCO)c1cccc(-c2ccc3nc(NCc4ccc(S(N)(=O)=O)cc4)nc(NCC(F)(F)F)c3n2)c1] | 4-{[4-(2,2,2-Trifluoroethyl)-amino-6-(4-(3-(N-2-hydroxyethyl)methane-sulfonamido)-phenyl)-pyrido[3,2-d]pyrimidin-2-ylamino]-methyl}-benzenesulfonamide | 626 |
| 162 | 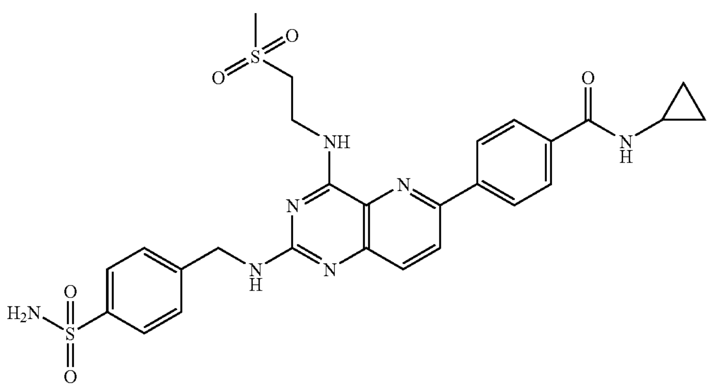 [SMILES: CS(=O)(=O)CCNc1nc(NCc2ccc(S(N)(=O)=O)cc2)nc2ccc(-c3ccc(C(=O)NC4CC4)cc3)nc12] | 4-{[4-(2-Methanesulfonylethyl)-amino-6-(4-(N-cyclopropylcarbamoyl)-phenyl)-pyrido[3,2-d]pyrimidin-2-ylamino]-methyl}-benzenesulfonamide | 596 |
| 163 | 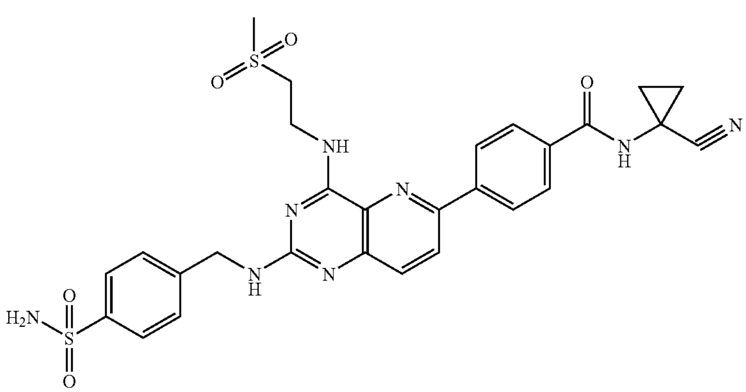 [SMILES: CS(=O)(=O)CCNc1nc(NCc2ccc(S(N)(=O)=O)cc2)nc2ccc(-c3ccc(C(=O)NC4(C#N)CC4)cc3)nc12] | 4-{[4-(2-Methanesulfonylethyl)-amino-6-(4-(N-(1-cyano-1-cyclopropyl)-carbamoyl)-phenyl)-pyrido[3,2-d]pyrimidin-2-ylamino]-methyl}-benzenesulfonamide | 621 |

TABLE 7-continued

| No. | Structure | Name | Mass M$^{+1}$ |
|---|---|---|---|
| 164 | 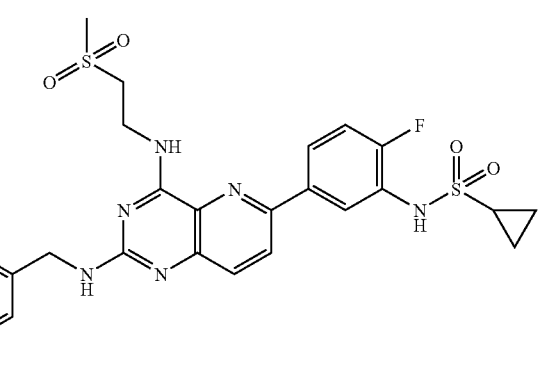 | 4-{[4-(2-Methanesulfonylethyl)-amino-6-(4-(3-cyclopropanesulfonamido-4-fluoro)-phenyl)-pyrido[3,2-d]pyrimidin-2-ylamino]-methyl}-benzenesulfonamide | 650 |
| 165 | 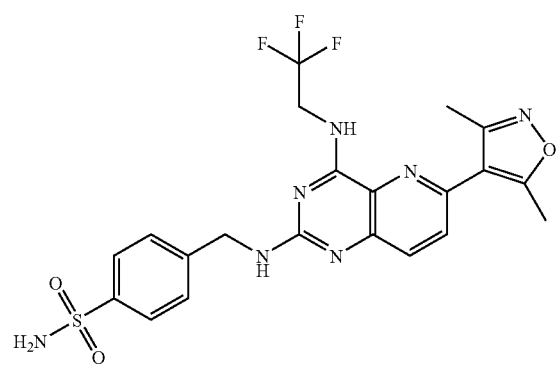 [SMILES: Cc1noc(C)c1-c1ccc2nc(NCc3ccc(S(N)(=O)=O)cc3)nc(NCC(F)(F)F)c2n1] | 4-{[6-(3,5-Dimethyl-isoxazol-4-yl)-4-(2,2,2-trifluoro-ethylamino)-pyrido[3,2-d]pyrimidin-2-ylamino]-methyl}-benzenesulfonamide | 508.2 |
| 166 | 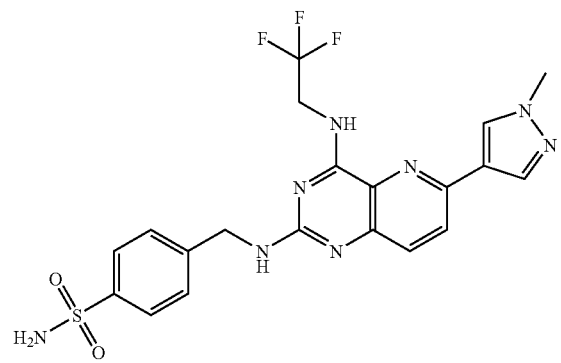 [SMILES: Cn1cc(-c2ccc3nc(NCc4ccc(S(N)(=O)=O)cc4)nc(NCC(F)(F)F)c3n2)cn1] | 4-{[6-(1-Methyl-1H-pyrazol-4-yl)-4-(2,2,2-trifluoro-ethylamino)-pyrido[3,2-d]pyrimidin-2-ylamino]-methyl}-benzenesulfonamide | 493.2 |
| 167 | 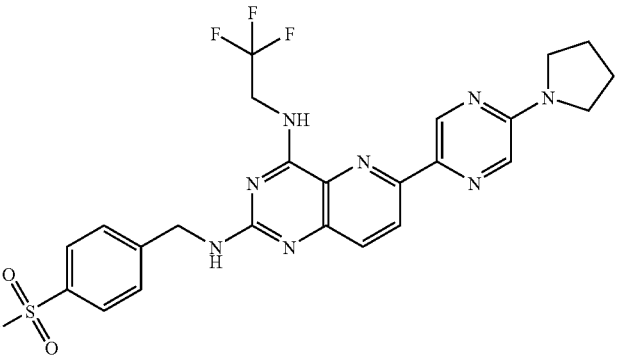 | 4-{[6-(5-Pyrrolidin-1-yl-pyrazin-2-yl)-4-(2,2,2-trifluoro-ethylamino)-pyrido[3,2-d]pyrimidin-2-ylamino]-methyl}-benzenesulfonamide | 560.2 |

TABLE 7-continued

| No. | Structure | Name | Mass M⁺¹ |
|---|---|---|---|
| 168 | 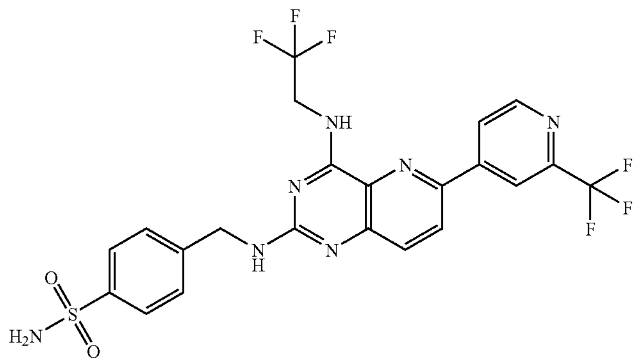 [SMILES: NS(=O)(=O)c1ccc(CNc2nc(NCC(F)(F)F)c3nc(-c4ccnc(C(F)(F)F)c4)ccc3n2)cc1] | 4-{[4-(2,2,2-Trifluoro-ethylamino)-6-(2-trifluoromethyl-pyridin-4-yl)-pyrido[3,2-d]pyrimidin-2-ylamino]-methyl}-benzenesulfonamide | 558.2 |
| 169 | 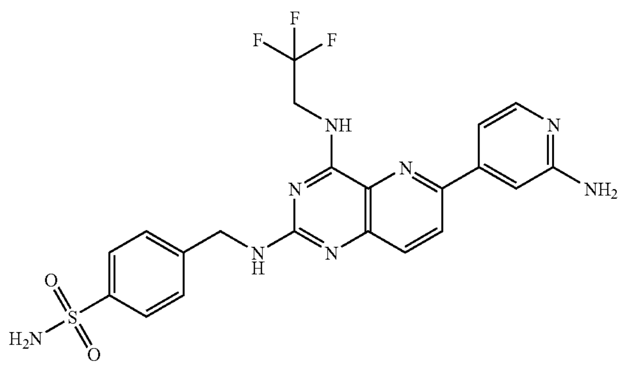 [SMILES: Nc1cc(-c2ccc3nc(NCc4ccc(S(N)(=O)=O)cc4)nc(NCC(F)(F)F)c3n2)ccn1] | 4-{[6-(2-Amino-pyridin-4-yl)-4-(2,2,2-trifluoro-ethylamino)-pyrido[3,2-d]pyrimidin-2-ylamino]-methyl}-benzenesulfonamide | 505.2 |
| 170 | 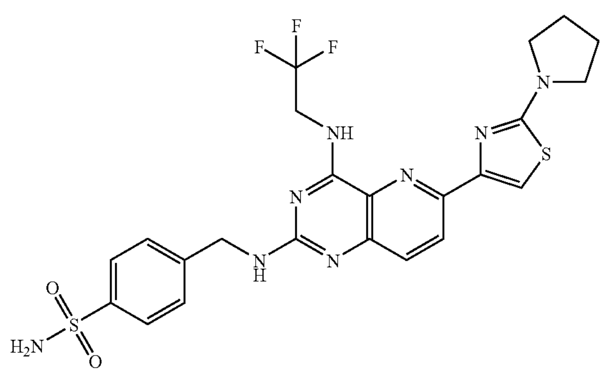 [SMILES: NS(=O)(=O)c1ccc(CNc2nc(NCC(F)(F)F)c3nc(-c4csc(N5CCCC5)n4)ccc3n2)cc1] | 4-{[6-(2-Pyrrolidin-1-yl-thiazol-4-yl)-4-(2,2,2-trifluoro-ethylamino)-pyrido[3,2-d]pyrimidin-2-ylamino]-methyl}-benzenesulfonamide | 565.2 |
| 171 | 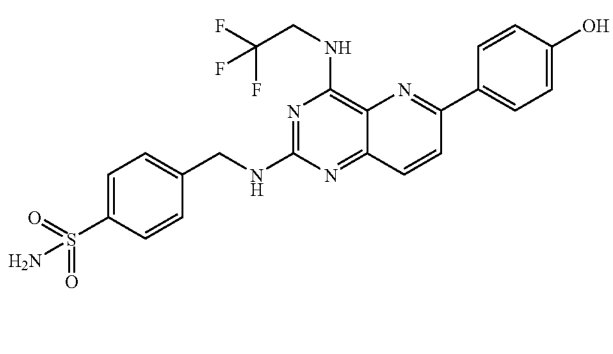 [SMILES: NS(=O)(=O)c1ccc(CNc2nc(NCC(F)(F)F)c3nc(-c4ccc(O)cc4)ccc3n2)cc1] | 4-{[6-(4-Hydroxy-phenyl)-4-(2,2,2-trifluoro-ethylamino)-pyrido[3,2-d]pyrimidin-2-ylamino]-methyl}-benzenesulfonamide | 505.2 |

TABLE 7-continued

| No. | Structure | Name | Mass M+1 |
|---|---|---|---|
| 172 | 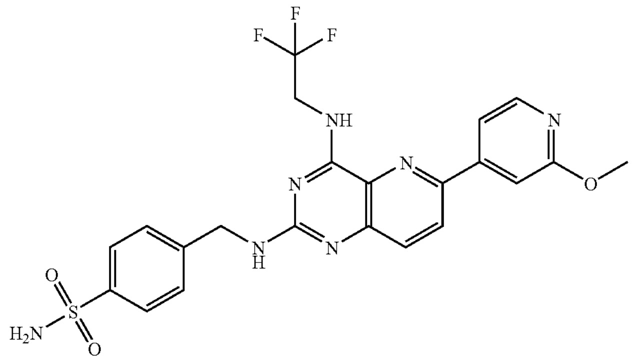 [SMILES: COc1cc(-c2ccc3nc(NCc4ccc(S(N)(=O)=O)cc4)nc(NCC(F)(F)F)c3n2)ccn1] | 4-{[6-(2-Methoxy-pyridin-4-yl)-4-(2,2,2-trifluoro-ethylamino)-pyrido[3,2-d]pyrimidin-2-ylamino]-methyl}-benzenesulfonamide | 520.2 |
| 173 | 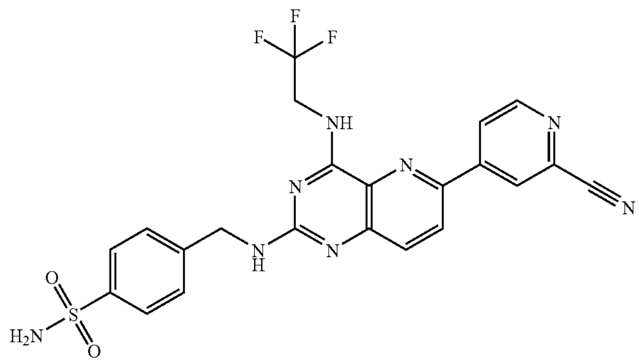 [SMILES: N#Cc1cc(-c2ccc3nc(NCc4ccc(S(N)(=O)=O)cc4)nc(NCC(F)(F)F)c3n2)ccn1] | 4-{[6-(2-Cyano-pyridin-4-yl)-4-(2,2,2-trifluoro-ethylamino)-pyrido[3,2-d]pyrimidin-2-ylamino]-methyl}-benzenesulfonamide | 515.1 |
| 174 | 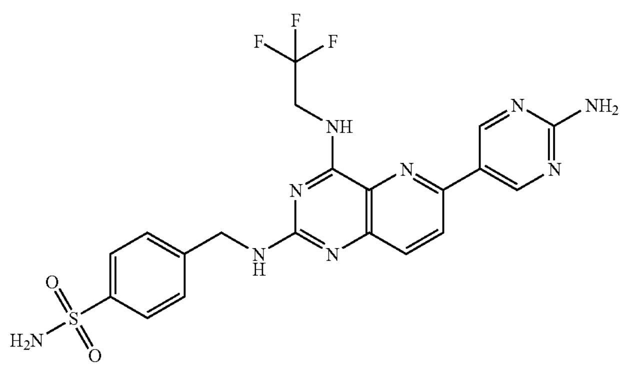 [SMILES: Nc1ncc(-c2ccc3nc(NCc4ccc(S(N)(=O)=O)cc4)nc(NCC(F)(F)F)c3n2)cn1] | 4-{[6-(2-Amino-pyrimidin-5-yl)-4-(2,2,2-trifluoro-ethylamino)-pyrido[3,2-d]pyrimidin-2-ylamino]-methyl}-benzenesulfonamide | 506.2 |
| 175 | 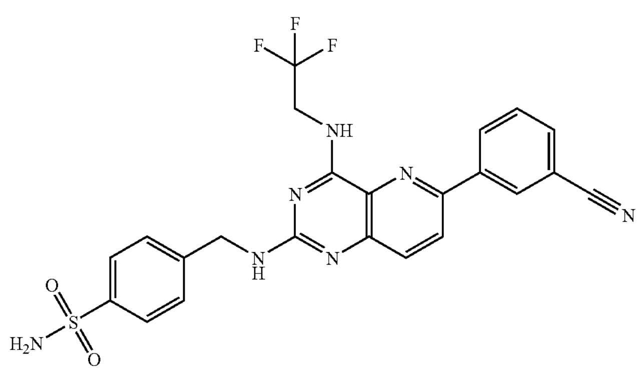 [SMILES: N#Cc1cccc(-c2ccc3nc(NCc4ccc(S(N)(=O)=O)cc4)nc(NCC(F)(F)F)c3n2)c1] | 4-{[6-(3-Cyano-phenyl)-4-(2,2,2-trifluoro-ethylamino)-pyrido[3,2-d]pyrimidin-2-ylamino]-methyl}-benzenesulfonamide | 514 |

TABLE 7-continued

| No. | Structure | Name | Mass M⁺¹ |
|---|---|---|---|
| 176 | 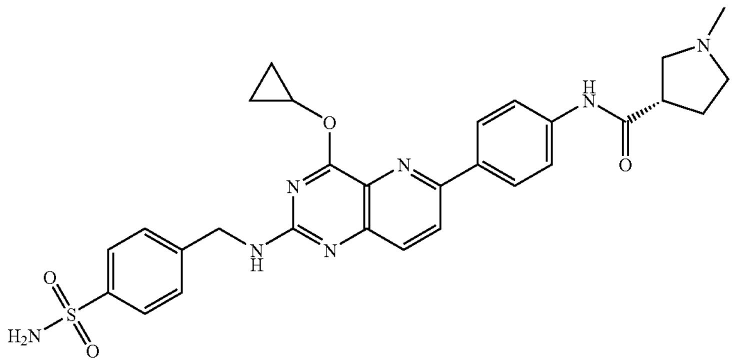 [SMILES: CN1CC[C@H](C(=O)Nc2ccc(-c3ccc4nc(NCc5ccc(S(N)(=O)=O)cc5)nc(OC5CC5)c4n3)cc2)C1] | 1-Methyl-pyrrolidine-3-carboxylic acid {4-[4-cyclopropoxy-2-(4-sulfamoyl-benzylamino)-pyrido[3,2-d]pyrimidin-6-yl]-phenyl}-amide | 574.3 |
| 177 | 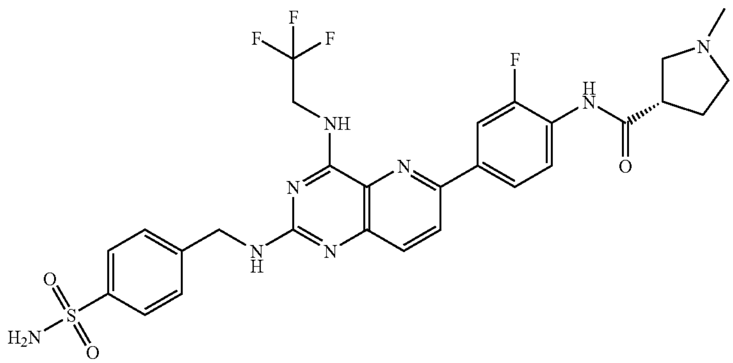 [SMILES: CN1CC[C@H](C(=O)Nc2ccc(-c3ccc4nc(NCc5ccc(S(N)(=O)=O)cc5)nc(NCC(F)(F)F)c4n3)cc2F)C1] | 1-Methyl-pyrrolidine-3-carboxylic acid {2-fluoro-4-[2-(4-sulfamoyl-benzylamino)-4-(2,2,2-trifluoro-ethylamino)-pyrido[3,2-d]pyrimidin-6-yl]-phenyl}-amide | 633.3 |
| 178 | 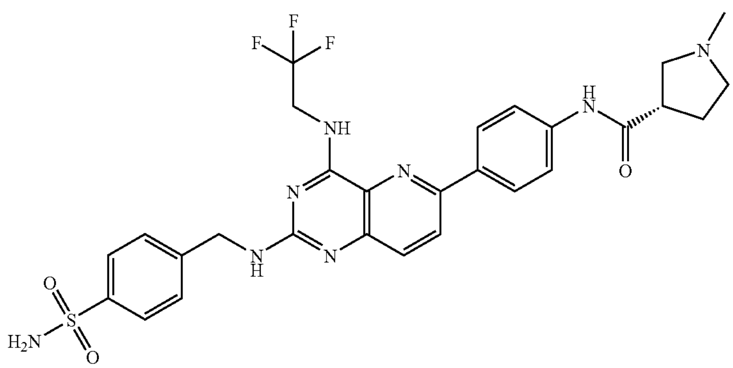 [SMILES: CN1CC[C@H](C(=O)Nc2ccc(-c3ccc4nc(NCc5ccc(S(N)(=O)=O)cc5)nc(NCC(F)(F)F)c4n3)cc2)C1] | 1-Methyl-pyrrolidine-3-carboxylic acid {4-[2-(4-sulfamoyl-benzylamino)-4-(2,2,2-trifluoro-ethylamino)-pyrido[3,2-d]pyrimidin-6-yl]-phenyl}-amide | 615.3 |
| 179 | 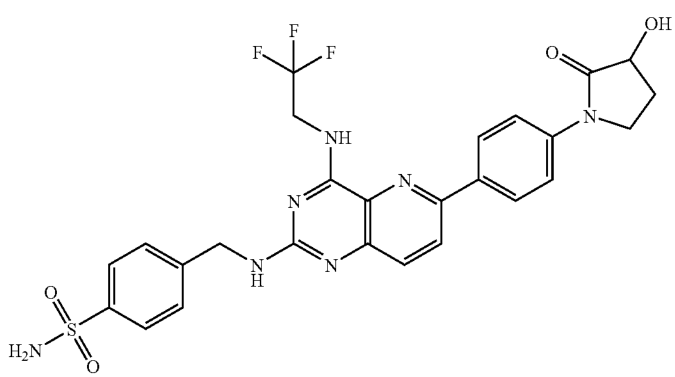 [SMILES: NS(=O)(=O)c1ccc(CNc2nc(NCC(F)(F)F)c3nc(-c4ccc(N5CCC(O)C5=O)cc4)ccc3n2)cc1] | 4-{[6-[4-(3-Hydroxy-2-oxo-pyrrolidin-1-yl)-phenyl]-4-(2,2,2-trifluoro-ethylamino)-pyrido[3,2-d]pyrimidin-2-ylamino]-methyl}-benzenesulfonamide | 588.2 |

TABLE 7-continued

| No. | Structure | Name | Mass M⁺¹ |
|---|---|---|---|
| 180 | 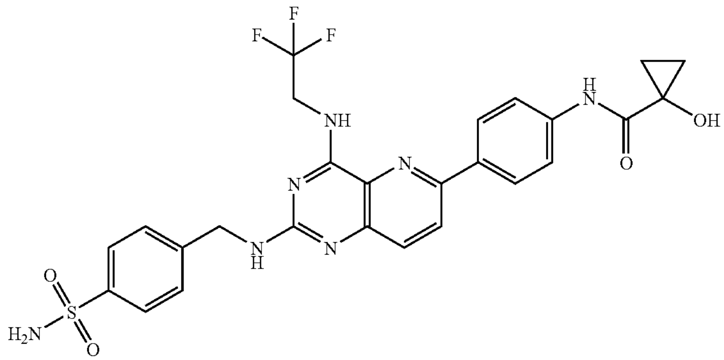 [SMILES: NS(=O)(=O)c1ccc(CNc2nc(NCC(F)(F)F)c3nc(-c4ccc(NC(=O)C5(O)CC5)cc4)ccc3n2)cc1] | 1-Hydroxy-cyclopropanecarboxylic acid {4-[2-(4-sulfamoyl-benzylamino)-4-(2,2,2-trifluoro-ethylamino)-pyrido[3,2-d]pyrimidin-6-yl]-phenyl}-amide | 588.2 |
| 181 | 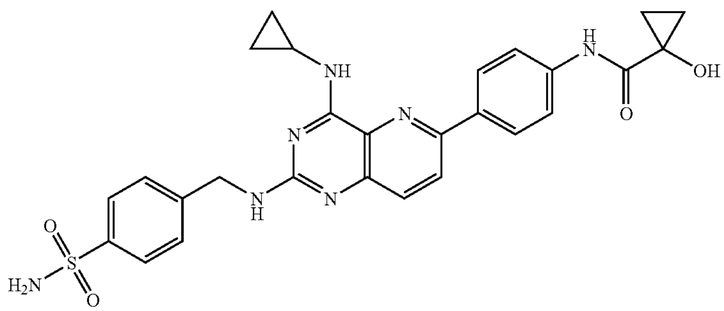 [SMILES: NS(=O)(=O)c1ccc(CNc2nc(NC3CC3)c3nc(-c4ccc(NC(=O)C5(O)CC5)cc4)ccc3n2)cc1] | 1-Hydroxy-cyclopropanecarboxylic acid {4-[4-cyclopropylamino-2-(4-sulfamoyl-benzylamino)-pyrido[3,2-d]pyrimidin-6-yl]-phenyl}-amide | 546.1 |
| 182 | 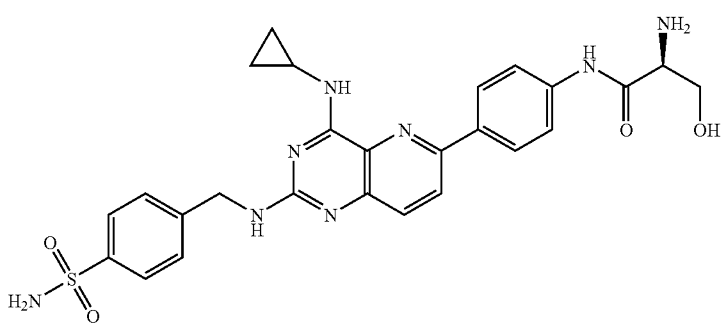 [SMILES: N[C@@H](CO)C(=O)Nc1ccc(-c2ccc3nc(NCc4ccc(S(N)(=O)=O)cc4)nc(NC4CC4)c3n2)cc1] | 2-Amino-N-{4-[4-cyclopropylamino-2-(4-sulfamoyl-benzylamino)-pyrido[3,2-d]pyrimidin-6-yl]-phenyl}-3-hydroxy-propionamide | 549.3 |
| 183 | 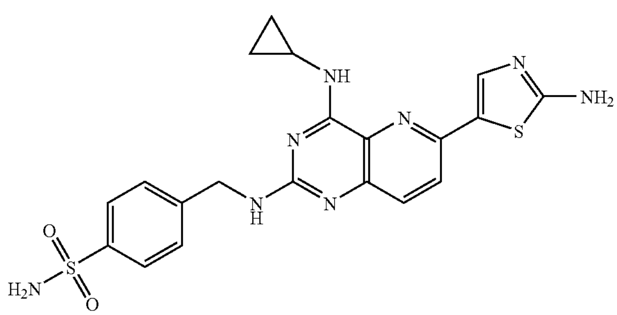 [SMILES: Nc1ncc(-c2ccc3nc(NCc4ccc(S(N)(=O)=O)cc4)nc(NC4CC4)c3n2)s1] | 4-{[6-(2-Amino-thiazol-5-yl)-4-cyclopropylamino-pyrido[3,2-d]pyrimidin-2-ylamino]-methyl}-benzenesulfonamide | 469.2 |

TABLE 7-continued

| No. | Structure | Name | Mass M+1 |
|---|---|---|---|
| 184 | 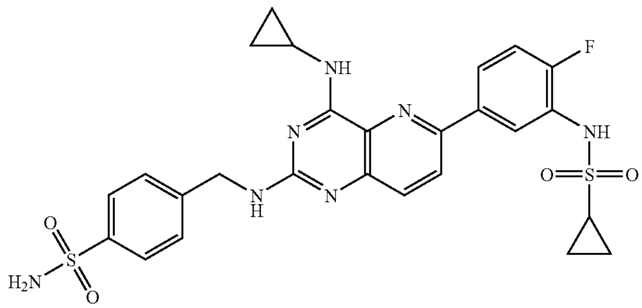 [SMILES: NS(=O)(=O)c1ccc(CNc2nc(NC3CC3)c3nc(-c4ccc(F)c(NS(=O)(=O)C5CC5)c4)ccc3n2)cc1] | 4-{[6-(3-Cyclopropanesulfonylamino-4-fluoro-phenyl)-4-cyclopropylamino-pyrido[3,2-d]pyrimidin-2-ylamino]-methyl}-benzenesulfonamide | 584.2 |
| 185 | 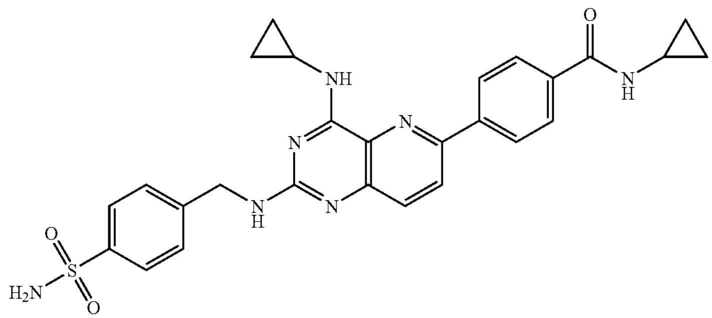 [SMILES: NS(=O)(=O)c1ccc(CNc2nc(NC3CC3)c3nc(-c4ccc(C(=O)NC5CC5)cc4)ccc3n2)cc1] | N-Cyclopropyl-4-[4-cyclopropylamino-2-(4-sulfamoyl-benzylamino)-pyrido[3,2-d]pyrimidin-6-yl]-benzamide | 530.1 |
| 186 | 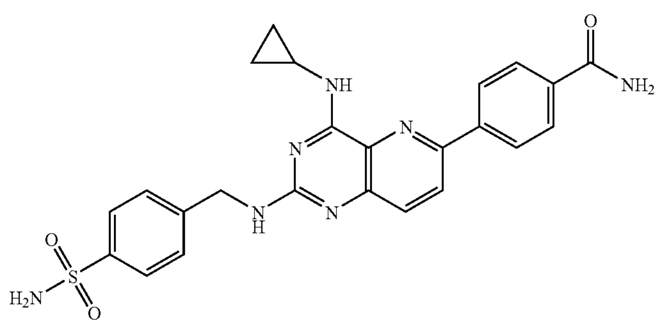 [SMILES: NC(=O)c1ccc(-c2ccc3nc(NCc4ccc(S(N)(=O)=O)cc4)nc(NC4CC4)c3n2)cc1] | 4-[4-Cyclopropylamino-2-(4-sulfamoyl-benzylamino)-pyrido[3,2-d]pyrimidin-6-yl]-benzamide | 490.2 |
| 187 | 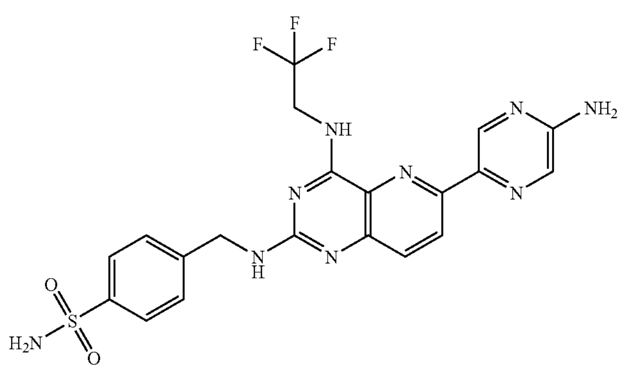 [SMILES: Nc1cnc(-c2ccc3nc(NCc4ccc(S(N)(=O)=O)cc4)nc(NCC(F)(F)F)c3n2)cn1] | 4-{[6-(5-Amino-pyrazin-2-yl)-4-(2,2,2-trifluoro-ethylamino)-pyrido[3,2-d]pyrimidin-2-ylamino]-methyl}-benzenesulfonamide | 506.2 |

TABLE 7-continued

| No. | Structure | Name | Mass M+1 |
|---|---|---|---|
| 188 | 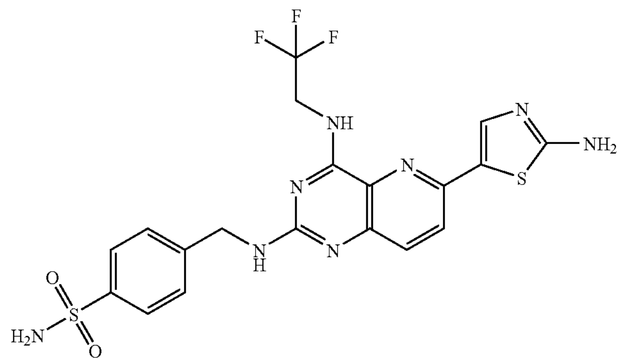 [SMILES: Nc1ncc(-c2ccc3nc(NCc4ccc(S(N)(=O)=O)cc4)nc(NCC(F)(F)F)c3n2)s1] | 4-{[6-(2-Amino-thiazol-5-yl)-4-(2,2,2-trifluoro-ethylamino)-pyrido[3,2-d]pyrimidin-2-ylamino]-methyl}-benzenesulfonamide | 511.2 |
| 189 | 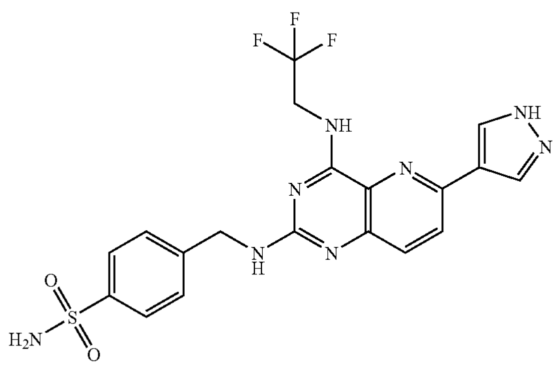 [SMILES: NS(=O)(=O)c1ccc(CNc2nc(NCC(F)(F)F)c3nc(-c4cn[nH]c4)ccc3n2)cc1] | 4-{[6-(1H-Pyrazol-4-yl)-4-(2,2,2-trifluoro-ethylamino)-pyrido[3,2-d]pyrimidin-2-ylamino]-methyl}-benzenesulfonamide | 479.2 |
| 190 | 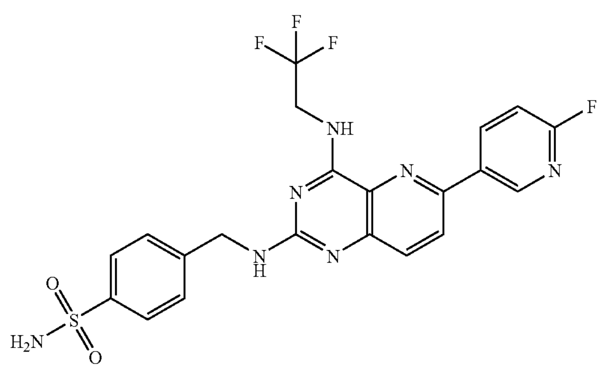 [SMILES: NS(=O)(=O)c1ccc(CNc2nc(NCC(F)(F)F)c3nc(-c4ccc(F)nc4)ccc3n2)cc1] | 4-{[6-(6-Fluoro-pyridin-3-yl)-4-(2,2,2-trifluoro-ethylamino)-pyrido[3,2-d]pyrimidin-2-ylamino]-methyl}-benzenesulfonamide | 508.1 |
| 191 | 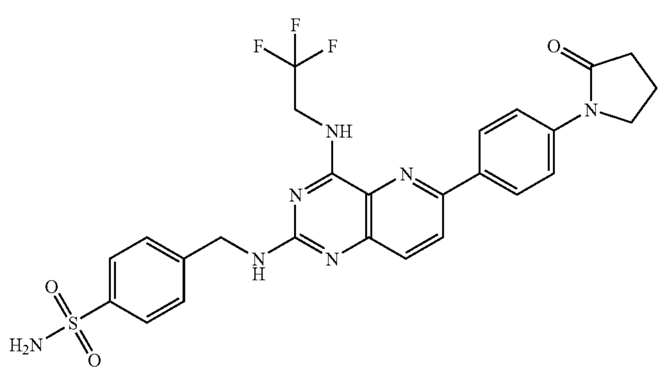 [SMILES: NS(=O)(=O)c1ccc(CNc2nc(NCC(F)(F)F)c3nc(-c4ccc(N5CCCC5=O)cc4)ccc3n2)cc1] | 4-{[6-[4-(2-Oxo-pyrrolidin-1-yl)-phenyl]-4-(2,2,2-trifluoro-ethylamino)-pyrido[3,2-d]pyrimidin-2-ylamino]-methyl}-benzenesulfonamide | 572.4 |

TABLE 7-continued

| No. | Structure | Name | Mass M+1 |
|---|---|---|---|
| 192 | 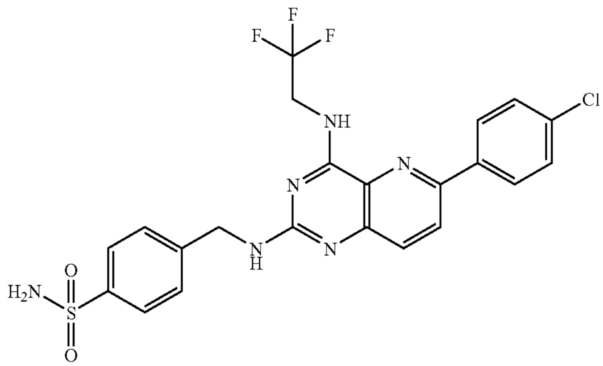 [SMILES: NS(=O)(=O)c1ccc(CNc2nc(NCC(F)(F)F)c3nc(-c4ccc(Cl)cc4)ccc3n2)cc1] | 4-{[6-(4-Chloro-phenyl)-4-(2,2,2-trifluoro-ethylamino)-pyrido[3,2-d]pyrimidin-2-ylamino]-methyl}-benzenesulfonamide | 523 |
| 193 | 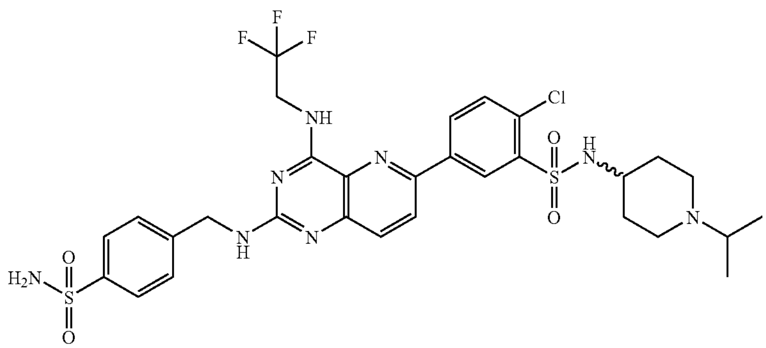 [SMILES: CC(C)N1CCC(NS(=O)(=O)c2cc(-c3ccc4nc(NCc5ccc(S(N)(=O)=O)cc5)nc(NCC(F)(F)F)c4n3)ccc2Cl)CC1] | 2-Chloro-N-(1-isopropyl-piperidin-4-yl)-5-[2-(4-sulfamoyl-benzylamino)-4-(2,2,2-trifluoro-ethylamino)-pyrido[3,2-d]pyrimidin-6-yl]-benzenesulfonamide | 727 |
| 194 | 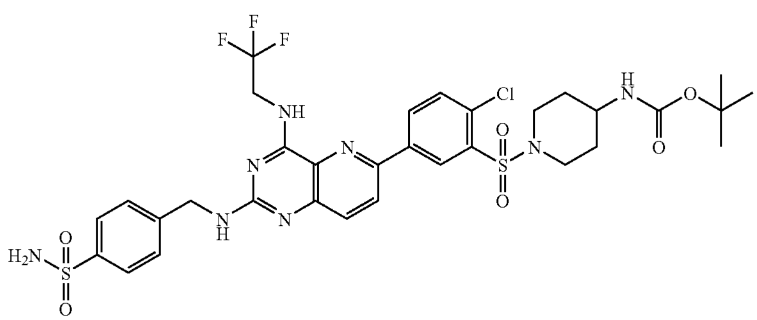 [SMILES: CC(C)(C)OC(=O)NC1CCN(S(=O)(=O)c2cc(-c3ccc4nc(NCc5ccc(S(N)(=O)=O)cc5)nc(NCC(F)(F)F)c4n3)ccc2Cl)CC1] | (1-{2-Chloro-5-[2-(4-sulfamoyl-benzylamino)-4-(2,2,2-trifluoro-ethylamino)-pyrido[3,2-d]pyrimidin-6-yl]-benzenesulfonyl}-piperidin-4-yl)-carbamic acid tert-butyl ester | 785 |
| 195 | 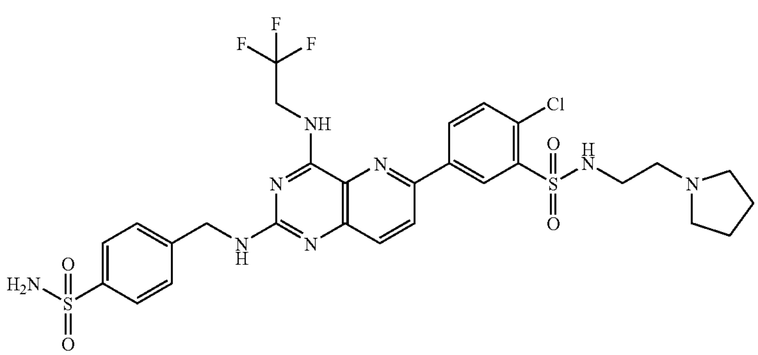 [SMILES: NS(=O)(=O)c1ccc(CNc2nc(NCC(F)(F)F)c3nc(-c4ccc(Cl)c(S(=O)(=O)NCCN5CCCC5)c4)ccc3n2)cc1] | 2-Chloro-N-(2-pyrrolidin-1-yl-ethyl)-5-[2-(4-sulfamoyl-benzylamino)-4-(2,2,2-trifluoro-ethylamino)-pyrido[3,2-d]pyrimidin-6-yl]-benzenesulfonamide | 699 |

TABLE 7-continued

| No. | Structure | Name | Mass M+1 |
|---|---|---|---|
| 196 | 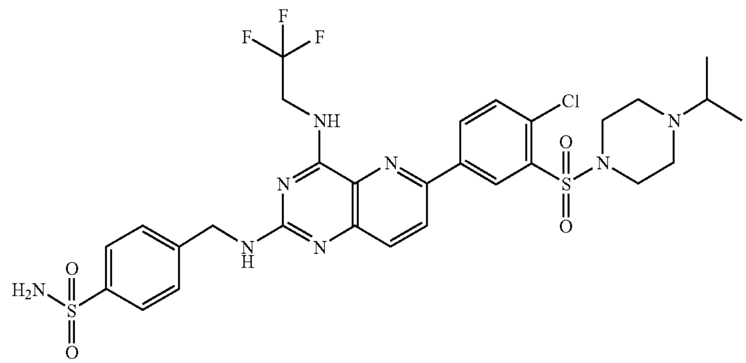 [SMILES: CC(C)N1CCN(S(=O)(=O)c2cc(-c3ccc4nc(NCc5ccc(S(N)(=O)=O)cc5)nc(NCC(F)(F)F)c4n3)ccc2Cl)CC1] | 4-{[6-[4-Chloro-3-(4-isopropyl-piperazine-1-sulfonyl)-phenyl]-4-(2,2,2-trifluoro-ethylamino)-pyrido[3,2-d]pyrimidin-2-ylamino]-methyl}-benzenesulfonamide | 713 |
| 197 | 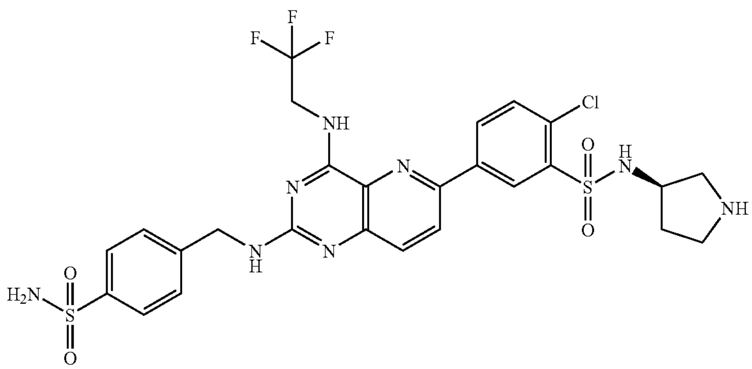 | 2-Chloro-N-pyrrolidin-3-yl-5-[2-(4-sulfamoyl-benzylamino)-4-(2,2,2-trifluoro-ethylamino)-pyrido[3,2-d]pyrimidin-6-yl]-benzenesulfonamide | 671 |
| 198 | 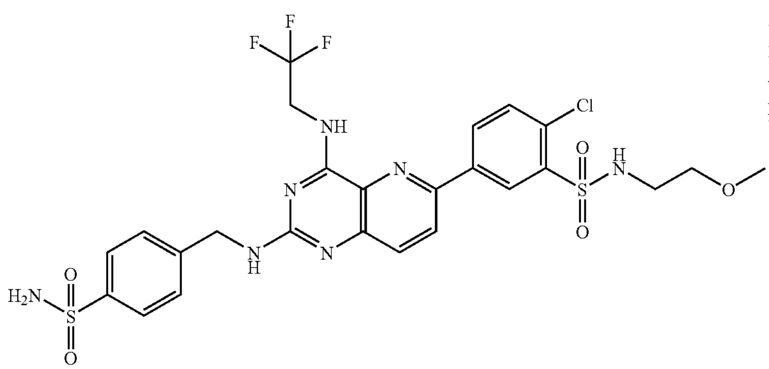 [SMILES: COCCNS(=O)(=O)c1cc(-c2ccc3nc(NCc4ccc(S(N)(=O)=O)cc4)nc(NCC(F)(F)F)c3n2)ccc1Cl] | 2-Chloro-N-(2-methoxy-ethyl)-5-[2-(4-sulfamoyl-benzylamino)-4-(2,2,2-trifluoro-ethylamino)-pyrido[3,2-d]pyrimidin-6-yl]-benzenesulfonamide | 660 |
| 199 | 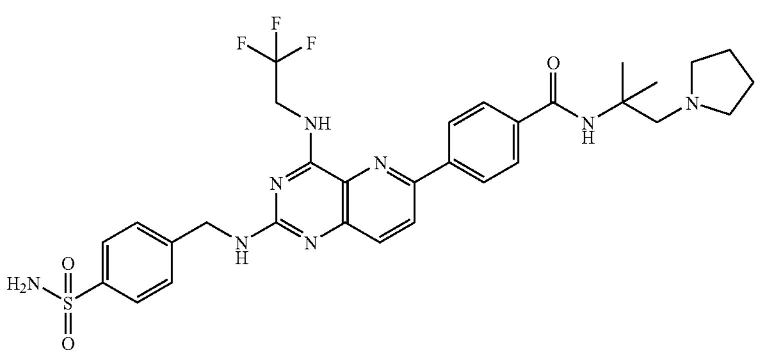 [SMILES: CC(C)(CN1CCCC1)NC(=O)c1ccc(-c2ccc3nc(NCc4ccc(S(N)(=O)=O)cc4)nc(NCC(F)(F)F)c3n2)cc1] | N-(1,1-Dimethyl-2-pyrrolidin-1-yl-ethyl)-4-[2-(4-sulfamoyl-benzylamino)-4-(2,2,2-trifluoro-ethylamino)-pyrido[3,2-d]pyrimidin-6-yl]-benzamide | 657 |

TABLE 7-continued

| No. | Structure | Name | Mass M$^{+1}$ |
|---|---|---|---|
| 200 | 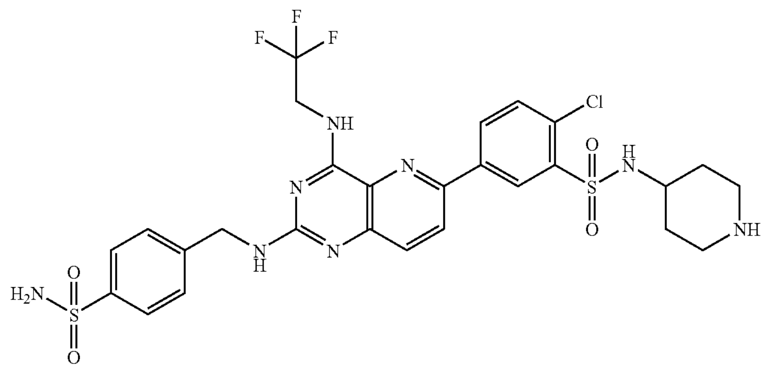 | 2-Chloro-N-piperidin-4-yl-5-[2-(4-sulfamoyl-benzylamino)-4-(2,2,2-trifluoro-ethylamino)-pyrido[3,2-d]pyrimidin-6-yl]-benzenesulfonamide | 685 |
| 201 | 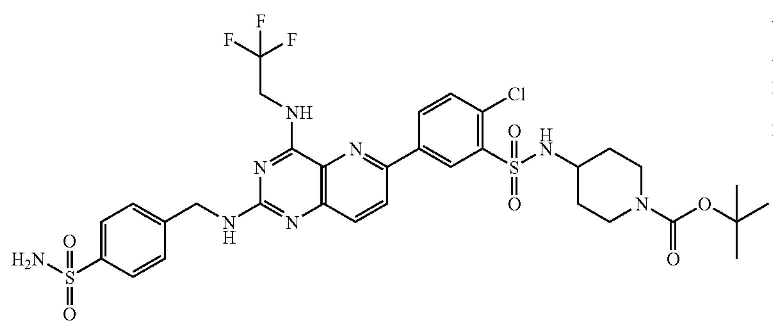 | 4-{2-Chloro-5-[2-(4-sulfamoyl-benzylamino)-4-(2,2,2-trifluoro-ethylamino)-pyrido[3,2-d]pyrimidin-6-yl]-benzenesulfonylamino}-piperidine-1-carboxylic acid tert-butyl ester | 785 |
| 202 | 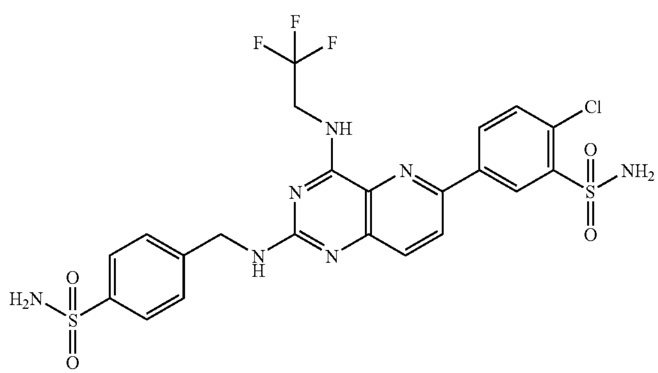 | 2-Chloro-5-[2-(4-sulfamoyl-benzylamino)-4-(2,2,2-trifluoro-ethylamino)-pyrido[3,2-d]pyrimidin-6-yl]-benzenesulfonamide | 602 |
| 203 | 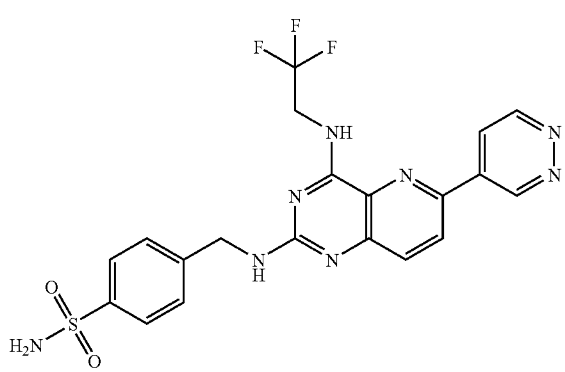 [SMILES: NS(=O)(=O)c1ccc(CNc2nc(NCC(F)(F)F)c3nc(-c4ccnnc4)ccc3n2)cc1] | 4-{[6-Pyridazin-4-yl-4-(2,2,2-trifluoro-ethylamino)-pyrido[3,2-d]pyrimidin-2-ylamino]-methyl}-benzenesulfonamide | 491.2 |

| No. | Structure | Name | Mass M+1 |
|---|---|---|---|
| 204 | 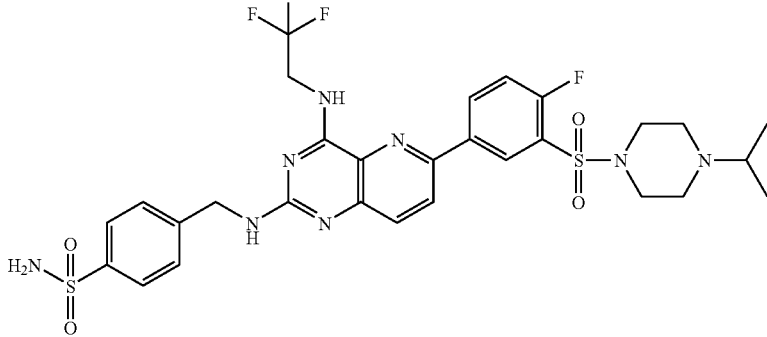 | 4-{[6-[4-Fluoro-3-(4-isopropyl-piperazine-1-sulfonyl)-phenyl]-4-(2,2,2-trifluoro-ethylamino)-pyrido[3,2-d]pyrimidin-2-ylamino]-methyl}-benzenesulfonamide | 697 |
| 205 | 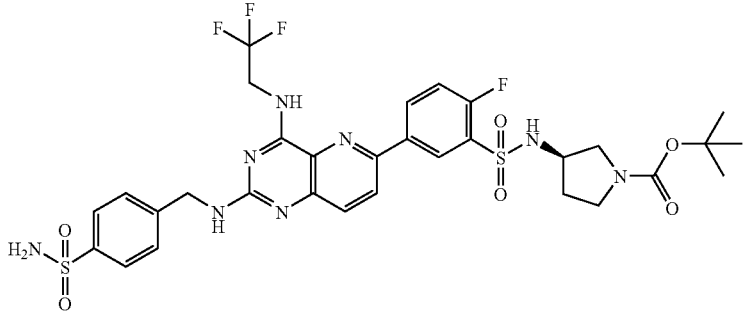 [SMILES: CC(C)(C)OC(=O)N1CC[C@@H](NS(=O)(=O)c2cc(-c3ccc4nc(NCc5ccc(S(N)(=O)=O)cc5)nc(NCC(F)(F)F)c4n3)ccc2F)C1] | 3-{2-Fluoro-5-[2-(4-sulfamoyl-benzylamino)-4-(2,2,2-trifluoro-ethylamino)-pyrido[3,2-d]pyrimidin-6-yl]-benzenesulfonylamino}-pyrrolidine-1-carboxylic acid tert-butyl ester | 755 |
| 206 | 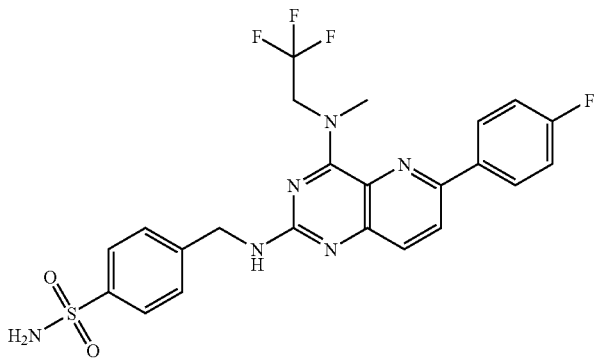 [SMILES: CN(CC(F)(F)F)c1nc(NCc2ccc(S(N)(=O)=O)cc2)nc2ccc(-c3ccc(F)cc3)nc12] | 4-({6-(4-Fluoro-phenyl)-4-[methyl-(2,2,2-trifluoro-ethyl)-amino]-pyrido[3,2-d]pyrimidin-2-ylamino}-methyl)-benzenesulfonamide | 521.2 |
| 207 | 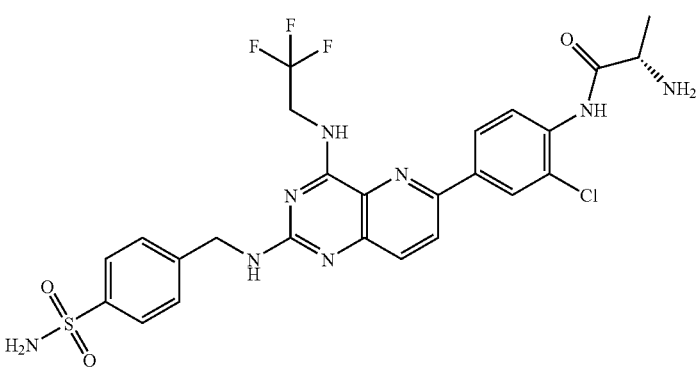 | 2-Amino-N-{2-chloro-4-[2-(4-sulfamoyl-benzylamino)-4-(2,2,2-trifluoro-ethylamino)-pyrido[3,2-d]pyrimidin-6-yl]-phenyl}-propionamide | 609.2 |

TABLE 7-continued

| No. | Name | Mass M⁺¹ |
|---|---|---|
| 208 | N-{2-Chloro-4-[2-(4-sulfamoyl-benzylamino)-4-(2,2,2-trifluoro-ethylamino)-pyrido[3,2-d]pyrimidin-6-yl]-phenyl}-2-hydroxy-propionamide | 610.1 |
| 209 | N-{2-Fluoro-4-[2-(4-sulfamoyl-benzylamino)-4-(2,2,2-trifluoro-ethylamino)-pyrido[3,2-d]pyrimidin-6-yl]-phenyl}-2-hydroxy-propionamide | 594 |
| 210 | 2-Hydroxy-N-{4-[2-(4-sulfamoyl-benzylamino)-4-(2,2,2-trifluoro-ethylamino)-pyrido[3,2-d]pyrimidin-6-yl]-phenyl}-propionamide | 576.2 |
| 211 | {4-[2-(4-Sulfamoyl-benzylamino)-4-(2,2,2-trifluoro-ethylamino)-pyrido[3,2-d]pyrimidin-6-yl]-phenyl}-carbamic acid methyl ester | 562 |

TABLE 7-continued

| No. | Structure | Name | Mass M+1 |
|---|---|---|---|
| 212 | 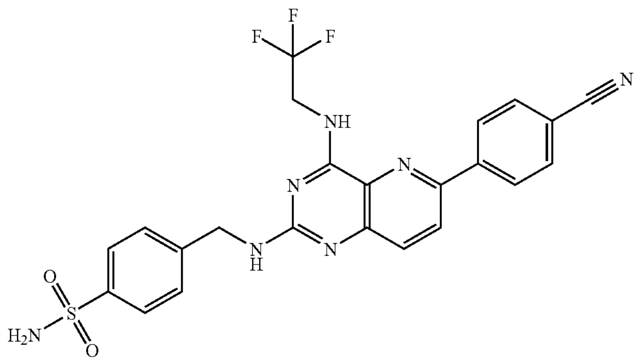 [SMILES: N#Cc1ccc(-c2ccc3nc(NCc4ccc(S(N)(=O)=O)cc4)nc(NCC(F)(F)F)c3n2)cc1] | 4-{[6-(4-Cyano-phenyl)-4-(2,2,2-trifluoro-ethylamino)-pyrido[3,2-d]pyrimidin-2-ylamino]-methyl}-benzenesulfonamide | 513.9 |
| 213 | 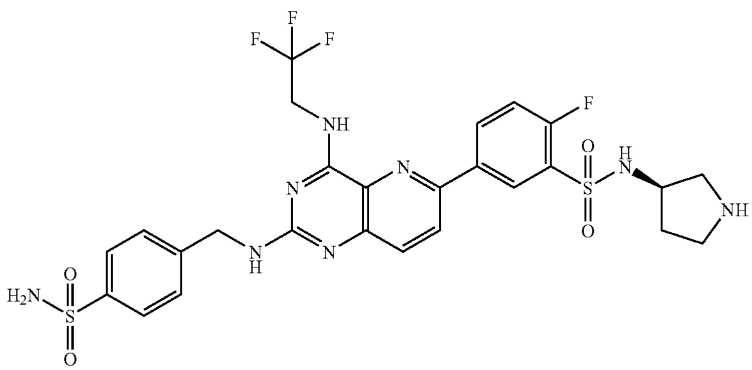 [SMILES: NS(=O)(=O)c1ccc(CNc2nc(NCC(F)(F)F)c3nc(-c4ccc(F)c(S(=O)(=O)N[C@@H]5CCNC5)c4)ccc3n2)cc1] | 2-Fluoro-N-pyrrolidin-3-yl-5-[2-(4-sulfamoyl-benzylamino)-4-(2,2,2-trifluoro-ethylamino)-pyrido[3,2-d]pyrimidin-6-yl]-benzenesulfonamide | 655 |
| 214 | 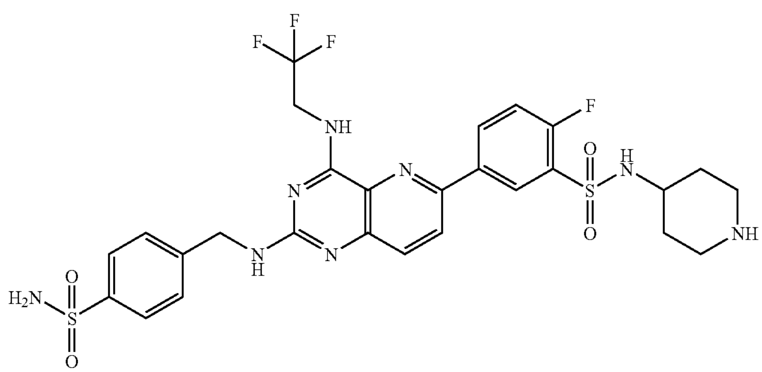 [SMILES: NS(=O)(=O)c1ccc(CNc2nc(NCC(F)(F)F)c3nc(-c4ccc(F)c(S(=O)(=O)NC5CCNCC5)c4)ccc3n2)cc1] | 2-Fluoro-N-piperidin-4-yl-5-[2-(4-sulfamoyl-benzylamino)-4-(2,2,2-trifluoro-ethylamino)-pyrido[3,2-d]pyrimidin-6-yl]-benzenesulfonamide | 669 |
| 215 | 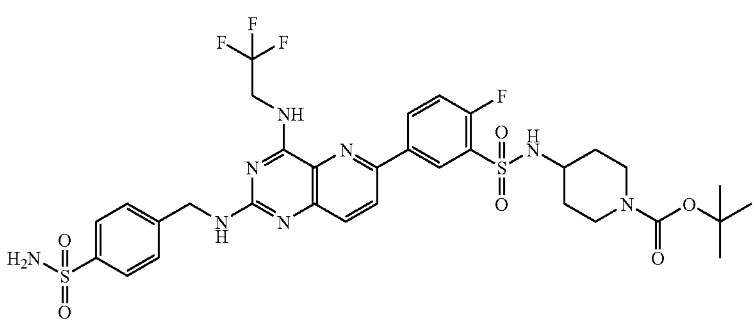 | 4-{2-Fluoro-5-[2-(4-sulfamoyl-benzylamino)-4-(2,2,2-trifluoro-ethylamino)-pyrido[3,2-d]pyrimidin-6-yl]-benzenesulfonylamino}-piperidine-1-carboxylic acid tert-butyl ester | 769 |

TABLE 7-continued

| No. | Structure | Name | Mass M+1 |
|---|---|---|---|
| 216 | 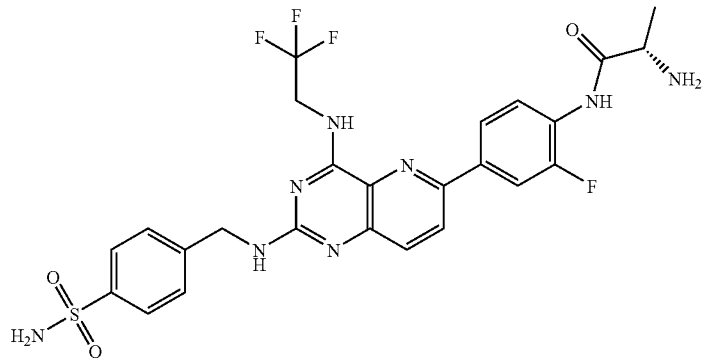 [SMILES: C[C@H](N)C(=O)Nc1ccc(-c2ccc3nc(NCc4ccc(S(N)(=O)=O)cc4)nc(NCC(F)(F)F)c3n2)cc1F] | 2-Amino-N-{2-fluoro-4-[2-(4-sulfamoyl-benzylamino)-4-(2,2,2-trifluoro-ethylamino)-pyrido[3,2-d]pyrimidin-6-yl]-phenyl}-propionamide | 593.2 |
| 217 | 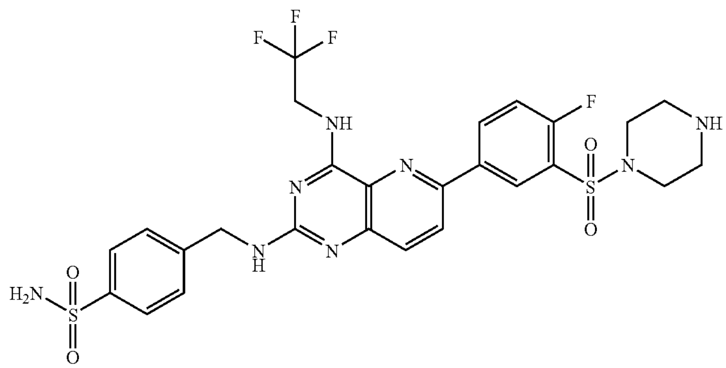 [SMILES: NS(=O)(=O)c1ccc(CNc2nc(NCC(F)(F)F)c3nc(-c4ccc(F)c(S(=O)(=O)N5CCNCC5)c4)ccc3n2)cc1] | 4-{[6-[4-Fluoro-3-(piperazine-1-sulfonyl)-phenyl]-4-(2,2,2-trifluoro-ethylamino)-pyrido[3,2-d]pyrimidin-2-ylamino]-methyl}-benzenesulfonamide | 655 |
| 218 | 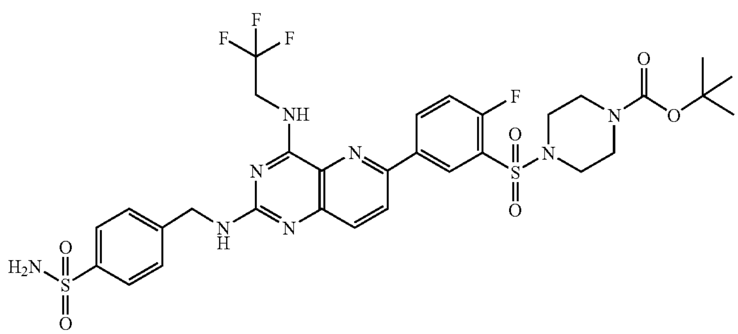 [SMILES: CC(C)(C)OC(=O)N1CCN(S(=O)(=O)c2cc(-c3ccc4nc(NCc5ccc(S(N)(=O)=O)cc5)nc(NCC(F)(F)F)c4n3)ccc2F)CC1] | 4-{2-Fluoro-5-[2-(4-sulfamoyl-benzylamino)-4-(2,2,2-trifluoro-ethylamino)-pyrido[3,2-d]pyrimidin-6-yl]-benzenesulfonyl}-piperazine-1-carboxylic acid tert-butyl ester | 755 |
| 219 | 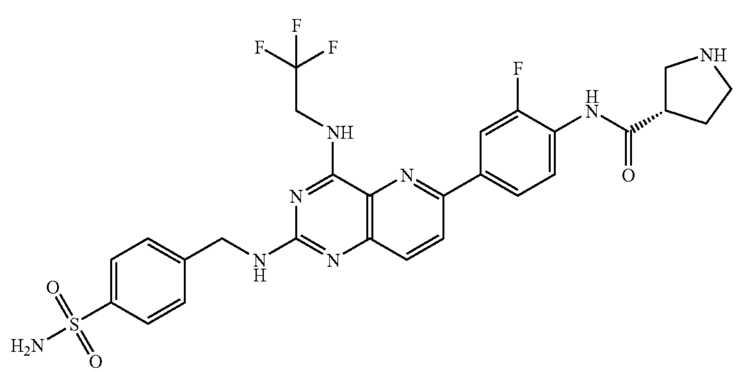 [SMILES: NS(=O)(=O)c1ccc(CNc2nc(NCC(F)(F)F)c3nc(-c4ccc(NC(=O)[C@H]5CCNC5)c(F)c4)ccc3n2)cc1] | Pyrrolidine-3-carboxylic acid {2-fluoro-4-[2-(4-sulfamoyl-benzylamino)-4-(2,2,2-trifluoro-ethylamino)-pyrido[3,2-d]pyrimidin-6-yl]-phenyl}-amide | 619.3 |

TABLE 7-continued

| No. | Structure | Name | Mass M+1 |
|---|---|---|---|
| 220 | 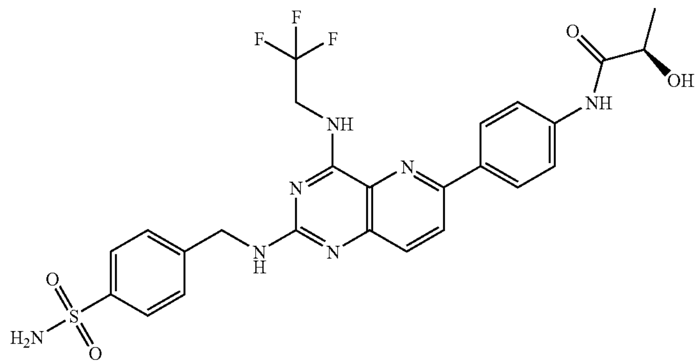 [SMILES: C[C@@H](O)C(=O)Nc1ccc(-c2ccc3nc(NCc4ccc(S(N)(=O)=O)cc4)nc(NCC(F)(F)F)c3n2)cc1] | 2-Hydroxy-N-{4-[2-(4-sulfamoyl-benzylamino)-4-(2,2,2-trifluoro-ethylamino)-pyrido[3,2-d]pyrimidin-6-yl]-phenyl}-propionamide | 576.3 |
| 221 | 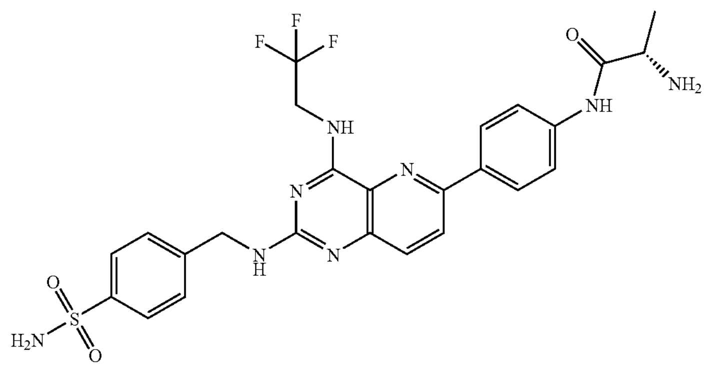 [SMILES: C[C@H](N)C(=O)Nc1ccc(-c2ccc3nc(NCc4ccc(S(N)(=O)=O)cc4)nc(NCC(F)(F)F)c3n2)cc1] | 2-Amino-N-{4-[2-(4-sulfamoyl-benzylamino)-4-(2,2,2-trifluoro-ethylamino)-pyrido[3,2-d]pyrimidin-6-yl]-phenyl}-propionamide | 575.3 |
| 222 | 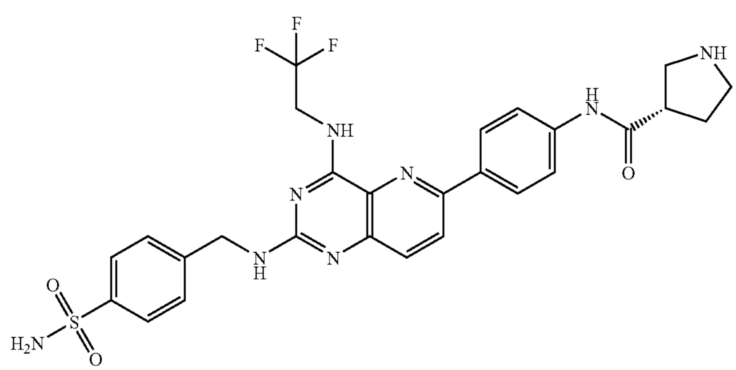 [SMILES: NS(=O)(=O)c1ccc(CNc2nc(NCC(F)(F)F)c3nc(-c4ccc(NC(=O)[C@H]5CCNC5)cc4)ccc3n2)cc1] | Pyrrolidine-3-carboxylic acid {4-[2-(4-sulfamoyl-benzylamino)-4-(2,2,2-trifluoro-ethylamino)-pyrido[3,2-d]pyrimidin-6-yl]-phenyl}-amide | 601.3 |
| 223 | 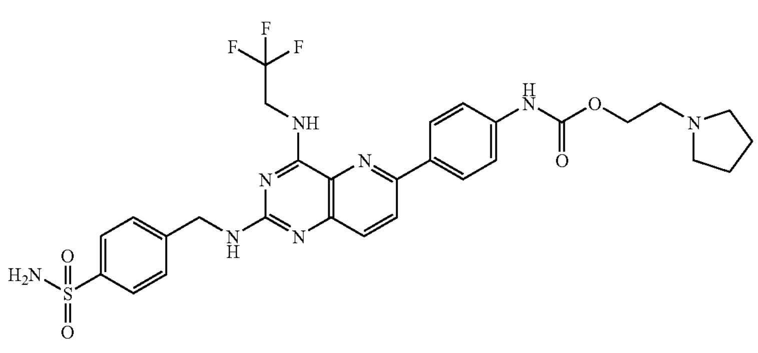 [SMILES: NS(=O)(=O)c1ccc(CNc2nc(NCC(F)(F)F)c3nc(-c4ccc(NC(=O)OCCN5CCCC5)cc4)ccc3n2)cc1] | {4-[2-(4-Sulfamoyl-benzylamino)-4-(2,2,2-trifluoro-ethylamino)-pyrido[3,2-d]pyrimidin-6-yl]-phenyl}-carbamic acid 2-pyrrolidin-1-yl-ethyl ester | 645 |

TABLE 7-continued

| No. | Structure | Name | Mass M$^{+1}$ |
|---|---|---|---|
| 224 | 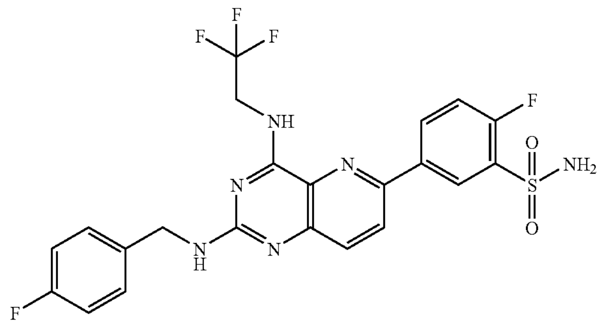 [SMILES: NS(=O)(=O)c1cc(-c2ccc3nc(NCc4ccc(F)cc4)nc(NCC(F)(F)F)c3n2)ccc1F] | 2-Fluoro-5-[2-(4-fluoro-benzylamino)-4-(2,2,2-trifluoro-ethylamino)-pyrido[3,2-d]pyrimidin-6-yl]-benzenesulfonamide | 525 |
| 225 | 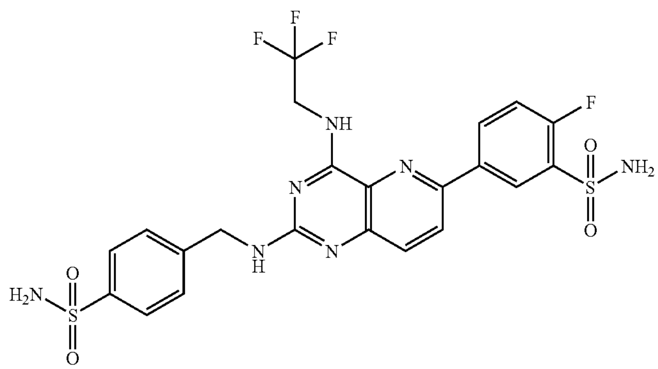 [SMILES: NS(=O)(=O)c1ccc(CNc2nc(NCC(F)(F)F)c3nc(-c4ccc(F)c(S(N)(=O)=O)c4)ccc3n2)cc1] | 2-Fluoro-5-[2-(4-sulfamoyl-benzylamino)-4-(2,2,2-trifluoro-ethylamino)-pyrido[3,2-d]pyrimidin-6-yl]-benzenesulfonamide | 586 |
| 226 | 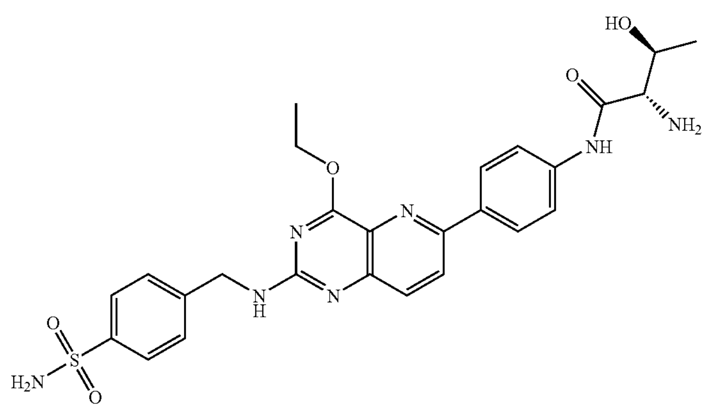 [SMILES: CCOc1nc(NCc2ccc(S(N)(=O)=O)cc2)nc2ccc(-c3ccc(NC(=O)[C@@H](N)[C@H](C)O)cc3)nc12] | 2-Amino-N-{4-[4-ethoxy-2-(4-sulfamoyl-benzylamino)-pyrido[3,2-d]pyrimidin-6-yl]-phenyl}-3-hydroxy-butyramide | 552.3 |
| 227 | 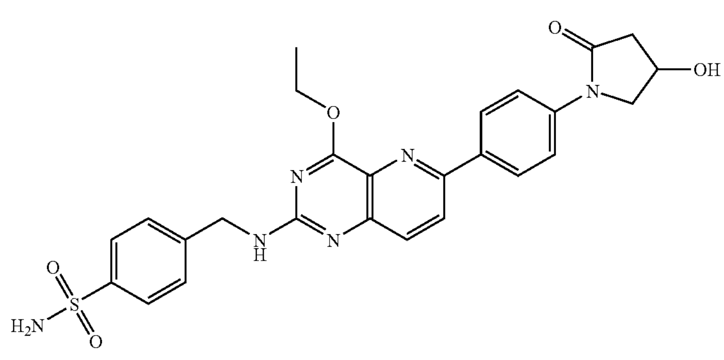 [SMILES: CCOc1nc(NCc2ccc(S(N)(=O)=O)cc2)nc2ccc(-c3ccc(N4CC(O)CC4=O)cc3)nc12] | 4-({4-Ethoxy-6-[4-(4-hydroxy-2-oxo-pyrrolidin-1-yl)-phenyl]-pyrido[3,2-d]pyrimidin-2-ylamino}-methyl)-benzenesulfonamide | 535.3 |

TABLE 7-continued

| No. | Structure | Name | Mass M$^{+1}$ |
|---|---|---|---|
| 228 | 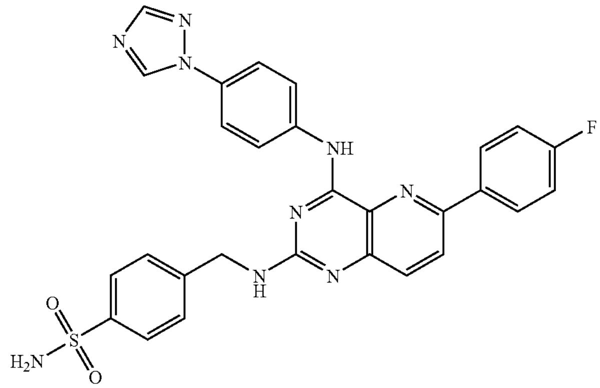 [SMILES: NS(=O)(=O)c1ccc(CNc2nc(Nc3ccc(-n4cncn4)cc3)c3nc(-c4ccc(F)cc4)ccc3n2)cc1] | 4-{[6-(4-Fluoro-phenyl)-4-(4-[1,2,4]triazol-1-yl-phenylamino)-pyrido[3,2-d]pyrimidin-2-ylamino]-methyl}-benzenesulfonamide | 568.2 |
| 229 | 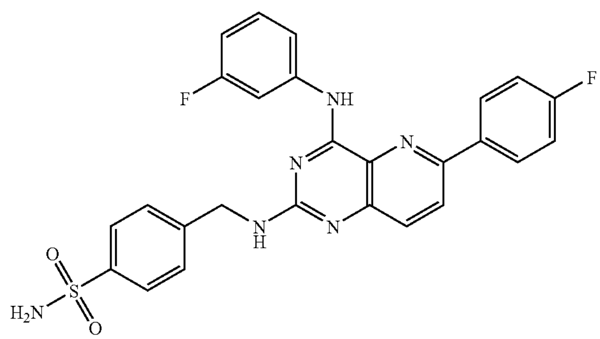 [SMILES: NS(=O)(=O)c1ccc(CNc2nc(Nc3cccc(F)c3)c3nc(-c4ccc(F)cc4)ccc3n2)cc1] | 4-{[6-(4-Fluoro-phenyl)-4-(3-fluoro-phenylamino)-pyrido[3,2-d]pyrimidin-2-ylamino]-methyl}-benzenesulfonamide | 519.2 |
| 230 | 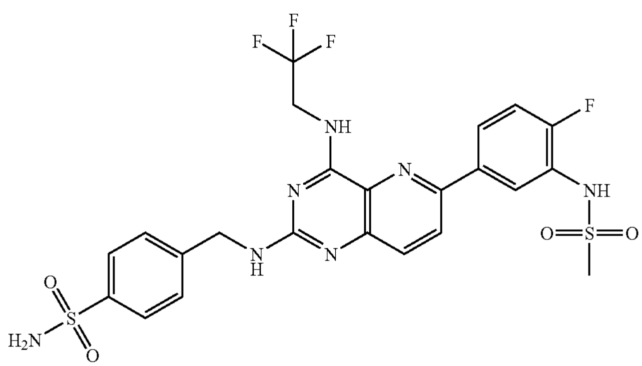 [SMILES: CS(=O)(=O)Nc1cc(-c2ccc3nc(NCc4ccc(S(N)(=O)=O)cc4)nc(NCC(F)(F)F)c3n2)ccc1F] | 4-{[6-(4-Fluoro-3-methanesulfonylamino-phenyl)-4-(2,2,2-trifluoro-ethylamino)-pyrido[3,2-d]pyrimidin-2-ylamino]-methyl}-benzenesulfonamide | 600.2 |
| 231 | 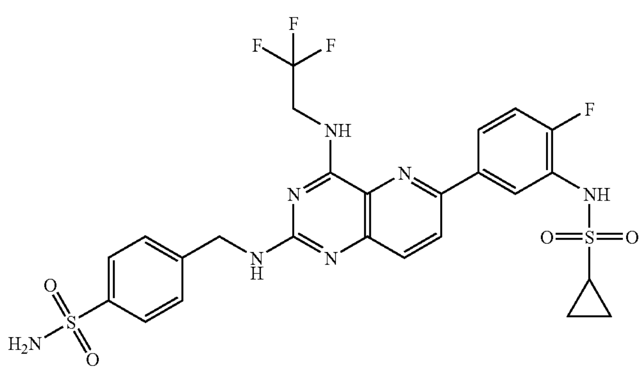 [SMILES: NS(=O)(=O)c1ccc(CNc2nc(NCC(F)(F)F)c3nc(-c4ccc(F)c(NS(=O)(=O)C5CC5)c4)ccc3n2)cc1] | 4-{[6-(3-Cyclopropanesulfonylamino-4-fluoro-phenyl)-4-(2,2,2-trifluoro-ethylamino)-pyrido[3,2-d]pyrimidin-2-ylamino]-methyl}-benzenesulfonamide | 626.1 |

TABLE 7-continued

| No. | Structure | Name | Mass M+1 |
|---|---|---|---|
| 232 | 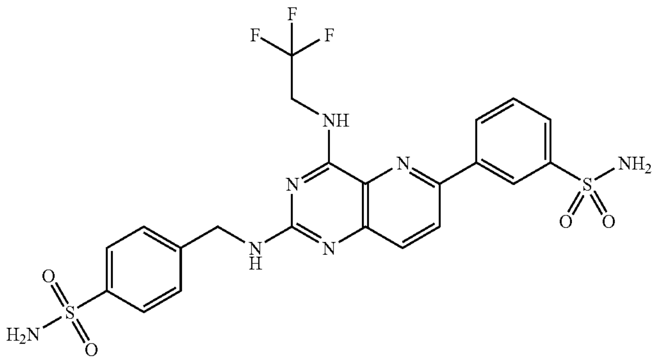 [SMILES: NS(=O)(=O)c1ccc(CNc2nc(NCC(F)(F)F)c3nc(-c4cccc(S(N)(=O)=O)c4)ccc3n2)cc1] | 3-[2-(4-sulfamoyl-benzylamino)-4-(2,2,2-trifluoro-ethylamino)-pyrido[3,2-d]pyrimidin-6-yl]-benzenesulfonamide | 568.2 |
| 233 | 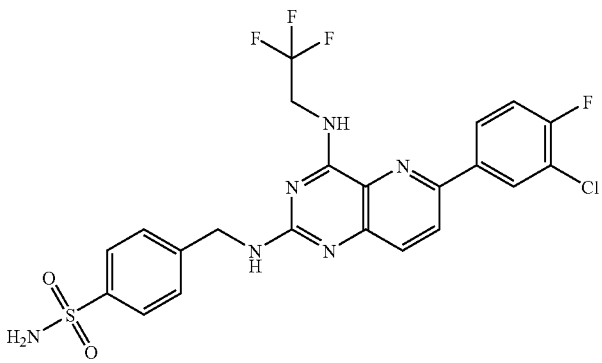 [SMILES: NS(=O)(=O)c1ccc(CNc2nc(NCC(F)(F)F)c3nc(-c4ccc(F)c(Cl)c4)ccc3n2)cc1] | 4-{[6-(3-Chloro-4-fluoro-phenyl)-4-(2,2,2-trifluoro-ethylamino)-pyrido[3,2-d]pyrimidin-2-ylamino]-methyl}-benzenesulfonamide | 541.2 |
| 234 | 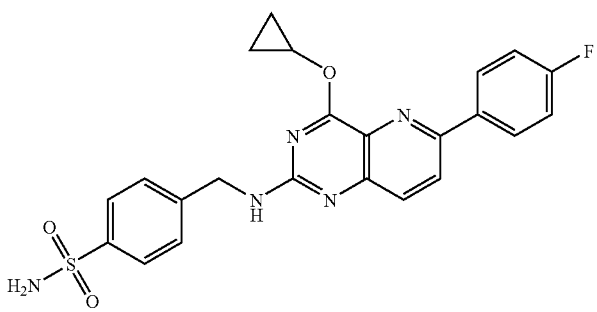 [SMILES: NS(=O)(=O)c1ccc(CNc2nc(OC3CC3)c3nc(-c4ccc(F)cc4)ccc3n2)cc1] | 4-{[4-Cyclopropoxy-6-(4-fluoro-phenyl)-pyrido[3,2-d]pyrimidin-2-ylamino]-methyl}-benzenesulfonamide | 466 |
| 235 | 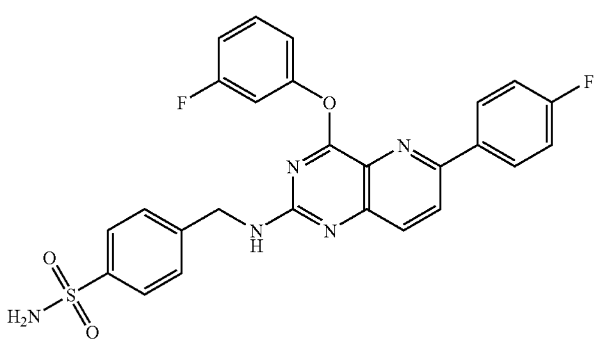 [SMILES: NS(=O)(=O)c1ccc(CNc2nc(Oc3cccc(F)c3)c3nc(-c4ccc(F)cc4)ccc3n2)cc1] | 4-{[4-(3-Fluoro-phenoxy)-6-(4-fluoro-phenyl)-pyrido[3,2-d]pyrimidin-2-ylamino]-methyl}-benzenesulfonamide | 520.2 |

TABLE 7-continued

| No. | Structure | Name | Mass M+1 |
|---|---|---|---|
| 236 | 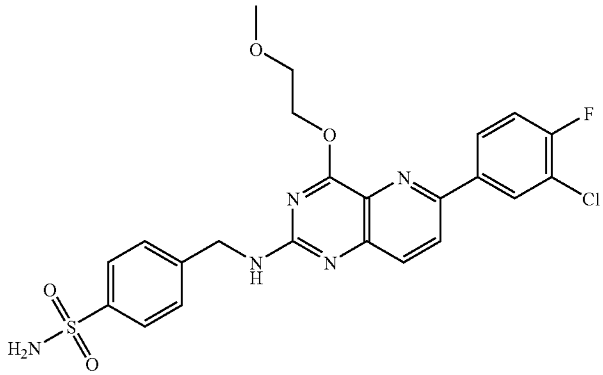 [SMILES: COCCOc1nc(NCc2ccc(S(N)(=O)=O)cc2)nc2ccc(-c3ccc(F)c(Cl)c3)nc12] | 4-{[6-(3-Chloro-4-fluoro-phenyl)-4-(2-methoxy-ethoxy)-pyrido[3,2-d]pyrimidin-2-ylamino]-methyl}-benzenesulfonamide | 518.2 |
| 237 | 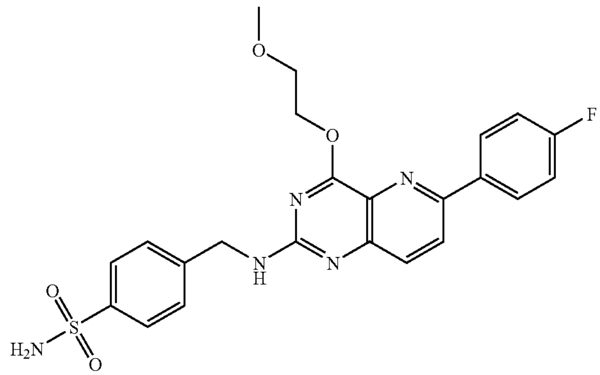 [SMILES: COCCOc1nc(NCc2ccc(S(N)(=O)=O)cc2)nc2ccc(-c3ccc(F)cc3)nc12] | 4-{[6-(4-Fluoro-phenyl)-4-(2-methoxy-ethoxy)-pyrido[3,2-d]pyrimidin-2-ylamino]-methyl}-benzenesulfonamide | 484.2 |

EXAMPLES 238 TO 261

Synthesis of N2-substituted-6-(4-Fluoro-phenyl)-N4-(2,2,2-trifluoro-ethyl)-pyrido[3,2-d]pyrimidine-2,4-diamines The compounds in Table 8 were synthesized from 2,4-dichloro-6-(4-fluorophenyl)-pyrido[3,2-d]pyrimidine according to the to the principles set forth in FIG. 1 and outlined in more details in the embodiment shown in Scheme 8 below, as exemplified by the following example.

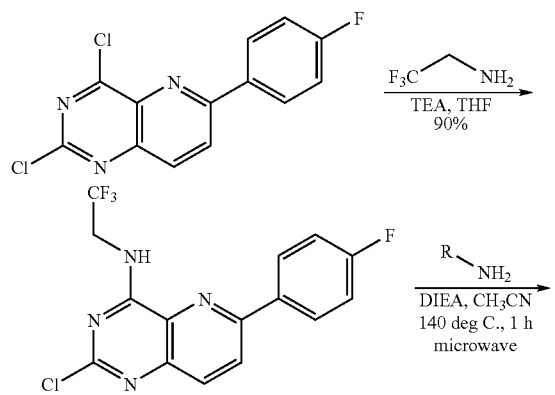

Scheme 8

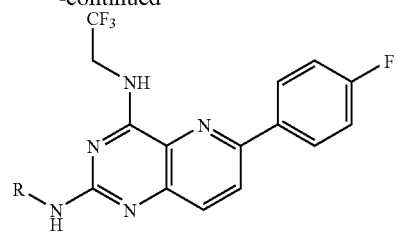

4-{[6-(4-Fluoro-phenyl)-4-(2,2,2-trifluoro-ethylamino)-pyrido[3,2-d]pyrimidin-2-ylamino]-methyl}-N,N-dimethyl-benzamide (Example 242)

Step 1: 2,4-Dichloro-6-(4-fluoro-phenyl)-pyrido[3,2-d]pyrimidine (5.00 g, 17.00 mmol, see Scheme 1 above) was suspended in THF (50 mL) and treated with triethylamine (3.60 mL, 25.5 mmol) followed by 2,2,2-trifluoro-ethylamine (2.01 mL, 25.5 mmol) and stirred at ambient temperature. After 2 h, water (approx, 75 mL) was added resulting in an oily biphasic mixture. THF was added until the mixture became homogenous. The THF was removed by evaporation resulting in an orange precipitate. A small amount of THF (10-15 mL) was added and the mixture was stirred 2-3 h. The light orange solid was filtered, washed with water, and dried to 5.45 g (90%). This material was used without further purification in the next step.

Step 2: [2-Chloro-6-(4-fluoro-phenyl)-pyrido[3,2-d]pyrimidin-4-yl]-(2,2,2-trifluoroethyl)-amine (100 mg, 0.28 mmol), 4-aminomethyl-N,N-dimethyl-benzamide (100 mg, 0.56 mmol) and diisopropylethylamine (0.097 mL, 0.56 mmol) were suspended in NMP (1.5 mL), sealed and heated by microwave to 140 deg C. for 1 h. After cooling the reaction mixture was added dropwise to a stirring mixture of water/ acetonitrile (8 mL, 3:1) to afford a yellow precipitate. The solid was filtered, washed with water, dissolved in hot dioxane and concentrated onto silica gel. Purification by flash chromatography (0-10%, EtOH (containing 11% saturated aqueous ammonium hydroxide) in dichloromethane) to afford 21 mg (15%) of the desired product as a white solid. MS (m/z) 499.3 [M+H]$^+$.

Other examples in Table 8 were synthesized using an analogous method as described for Example 242 above. In each case, a suitable amine was used in place of 4-aminomethyl-N,N-dimethyl-benzamide in the last step.

Example 238 (Table 8) required a benzyl amine which was prepared as follows:

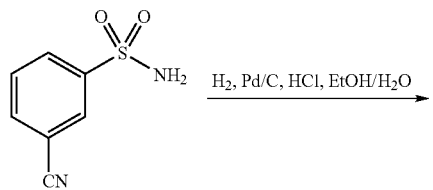 H$_2$, Pd/C, HCl, EtOH/H$_2$O

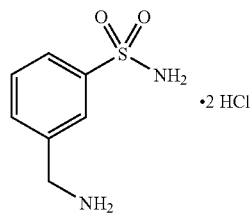

2-Cyanophenylsulfonamide (200 mg, 1.1 mmol), ethanol (3.5 mL), water (3 mL), concentrated hydrochloric acid (0.2 mL, mmol), and 10% palladium on carbon (50 mg, 0.05 mmol) were hydrogenated at atmospheric temperature and pressure over the course of 18 hours. The solution was filtered and evaporated to dryness. The residue was washed with ethanol (10 mL) to obtain 49 mg (16%) of crude product. This material was used without further purification in the next step.

TABLE 8

| No. | Structure | Name | Mass M$^{+1}$ |
|---|---|---|---|
| 238 | 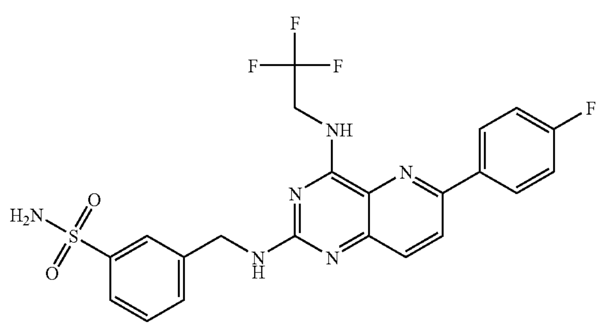 [SMILES: NS(=O)(=O)c1cccc(CNc2nc(NCC(F)(F)F)c3nc(-c4ccc(F)cc4)ccc3n2)c1] | 3-{[6-(4-Fluoro-phenyl)-4-(2,2,2-trifluoro-ethylamino)-pyrido[3,2-d]pyrimidin-2-ylamino]-methyl}-benzenesulfonamide | 507.2 |
| 239 | 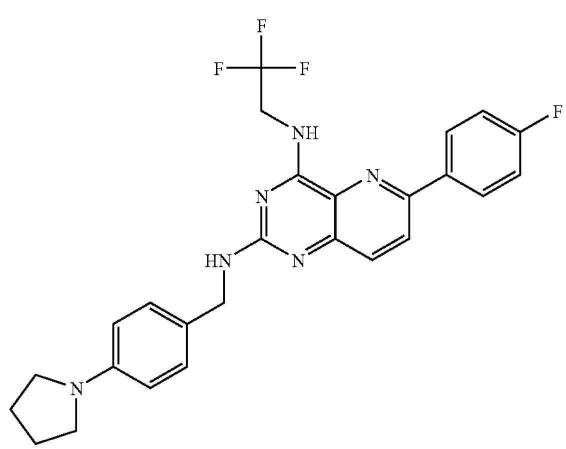 [SMILES: Fc1ccc(-c2ccc3nc(NCc4ccc(N5CCCC5)cc4)nc(NCC(F)(F)F)c3n2)cc1] | 6-(4-Fluoro-phenyl)-N2-(4-pyrrolidin-1-yl-benzyl)-N4-(2,2,2-trifluoro-ethyl)-pyrido[3,2-d]pyrimidine-2,4-diamine | 497.1 |

TABLE 8-continued

| No. | Structure | Name | Mass M+1 |
|---|---|---|---|
| 240 | 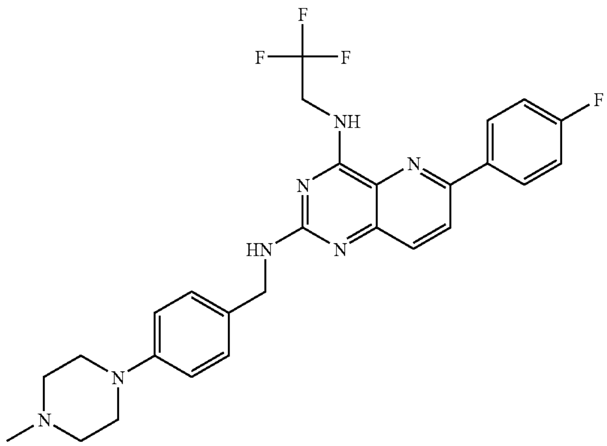 [SMILES: CN1CCN(c2ccc(CNc3nc(NCC(F)(F)F)c4nc(-c5ccc(F)cc5)ccc4n3)cc2)CC1] | 6-(4-Fluoro-phenyl)-N2-[4-(4-methyl-piperazin-1-yl)-benzyl]-N4-(2,2,2-trifluoro-ethyl)-pyrido[3,2-d]pyrimidine-2,4-diamine | 526.1 |
| 241 | 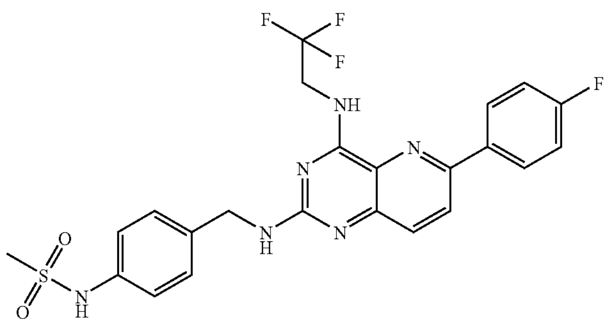 [SMILES: CS(=O)(=O)Nc1ccc(CNc2nc(NCC(F)(F)F)c3nc(-c4ccc(F)cc4)ccc3n2)cc1] | N-(4-{[6-(4-Fluoro-phenyl)-4-(2,2,2-trifluoro-ethylamino)-pyrido[3,2-d]pyrimidin-2-ylamino]-methyl}-phenyl)-methanesulfonamide | 521.5 |
| 242 | 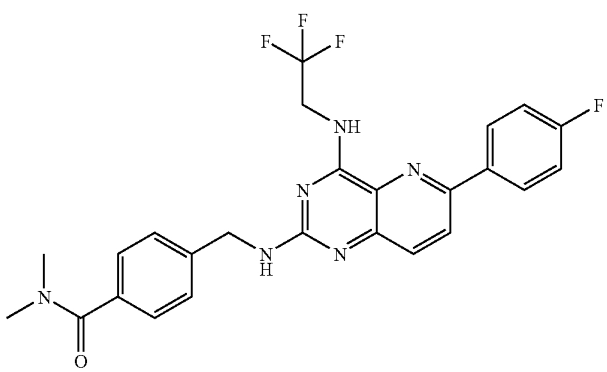 [SMILES: CN(C)C(=O)c1ccc(CNc2nc(NCC(F)(F)F)c3nc(-c4ccc(F)cc4)ccc3n2)cc1] | 4-{[6-(4-Fluoro-phenyl)-4-(2,2,2-trifluoro-ethylamino)-pyrido[3,2-d]pyrimidin-2-ylamino]-methyl}-N,N-dimethyl-benzamide | 499.3 |
| 243 | 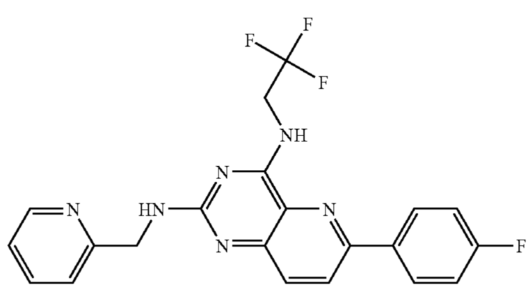 [SMILES: Fc1ccc(-c2ccc3nc(NCc4ccccn4)nc(NCC(F)(F)F)c3n2)cc1] | 6-(4-Fluoro-phenyl)-N2-pyridin-2-ylmethyl-N4-(2,2,2-trifluoro-ethyl)-pyrido[3,2-d]pyrimidine-2,4-diamine | 429.3 |

TABLE 8-continued

| No. | Structure | Name | Mass M$^{+1}$ |
|---|---|---|---|
| 244 | 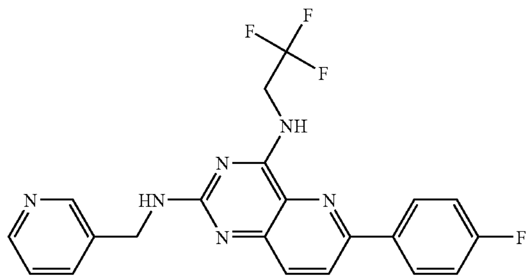 [SMILES: Fc1ccc(-c2ccc3nc(NCc4cccnc4)nc(NCC(F)(F)F)c3n2)cc1] | 6-(4-Fluoro-phenyl)-N2-pyridin-3-ylmethyl-N4-(2,2,2-trifluoro-ethyl)-pyrido[3,2-d]pyrimidine-2,4-diamine | 429.2 |
| 245 | 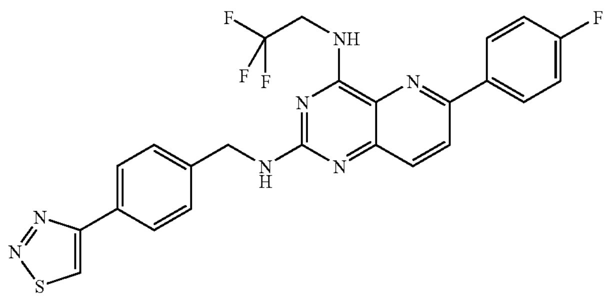 [SMILES: Fc1ccc(-c2ccc3nc(NCc4ccc(-c5csnn5)cc4)nc(NCC(F)(F)F)c3n2)cc1] | 6-(4-Fluoro-phenyl)-N2-(4-[1,2,3]thiadiazol-4-yl-benzyl)-N4-(2,2,2-trifluoro-ethyl)-pyrido[3,2-d]pyrimidine-2,4-diamine | 512.1 |
| 246 | 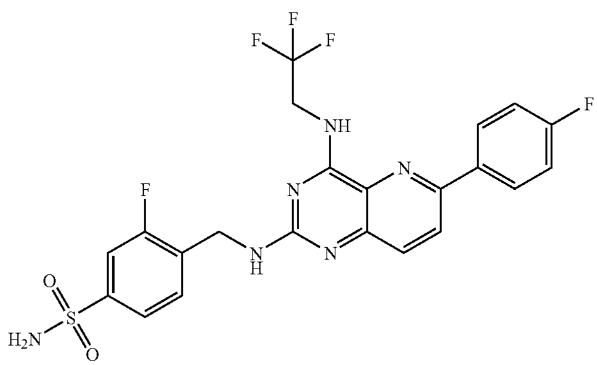 [SMILES: NS(=O)(=O)c1ccc(CNc2nc(NCC(F)(F)F)c3nc(-c4ccc(F)cc4)ccc3n2)c(F)c1] | 3-Fluoro-4-{[6-(4-fluoro-phenyl)-4-(2,2,2-trifluoro-ethylamino)-pyrido[3,2-d]pyrimidin-2-ylamino]-methyl}-benzenesulfonamide | 525.4 |
| 247 | 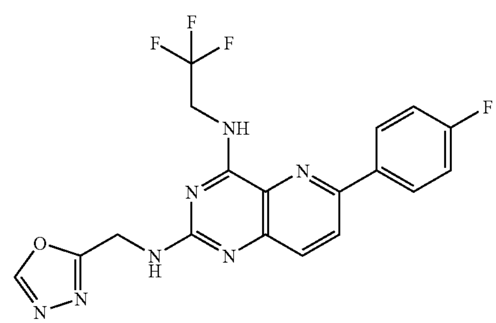 | 6-(4-Fluoro-phenyl)-N2-[1,3,4]oxadiazol-2-ylmethyl-N4-(2,2,2-trifluoro-ethyl)-pyrido[3,2-d]pyrimidine-2,4-diamine | 420.2 |
| 248 | 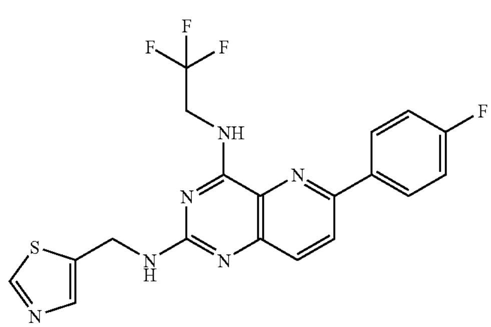 [SMILES: Fc1ccc(-c2ccc3nc(NCc4cncs4)nc(NCC(F)(F)F)c3n2)cc1] | 6-(4-Fluoro-phenyl)-N2-thiazol-5-ylmethyl-N4-(2,2,2-trifluoro-ethyl)-pyrido[3,2-d]pyrimidine-2,4-diamine | 435.2 |

TABLE 8-continued

| No. | Structure | Name | Mass M+1 |
|---|---|---|---|
| 249 | 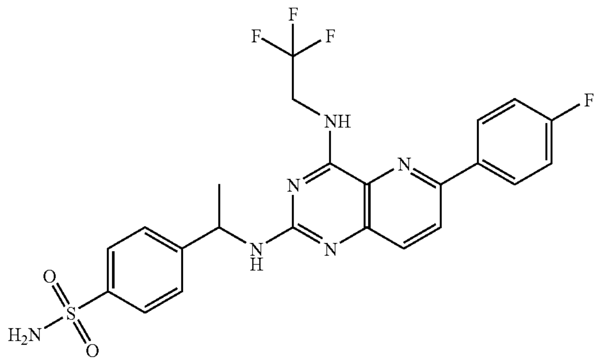 [SMILES: CC(Nc1nc(NCC(F)(F)F)c2nc(-c3ccc(F)cc3)ccc2n1)c1ccc(S(N)(=O)=O)cc1] | 4-{1-[6-(4-Fluoro-phenyl)-4-(2,2,2-trifluoro-ethylamino)-pyrido[3,2-d]pyrimidin-2-ylamino]-ethyl}-benzenesulfonamide | 521.2 |
| 250 | 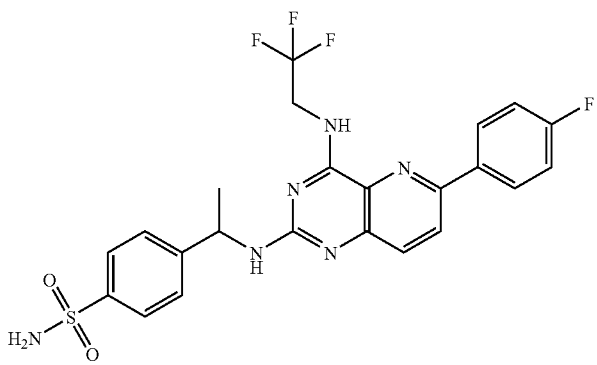 [SMILES: CC(Nc1nc(NCC(F)(F)F)c2nc(-c3ccc(F)cc3)ccc2n1)c1ccc(S(N)(=O)=O)cc1] | 4-{1-[6-(4-Fluoro-phenyl)-4-(2,2,2-trifluoro-ethylamino)-pyrido[3,2-d]pyrimidin-2-ylamino]-ethyl}-benzenesulfonamide | 521.2 |
| 251 | 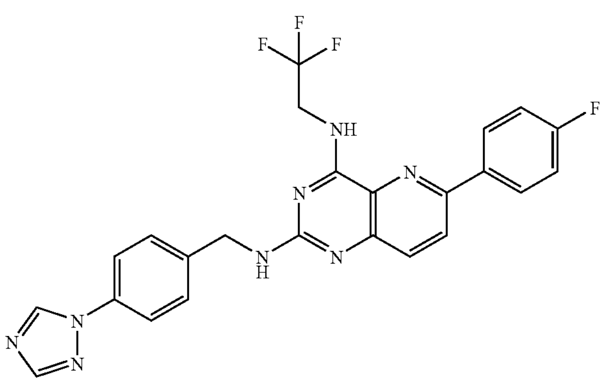 [SMILES: Fc1ccc(-c2ccc3nc(NCc4ccc(-n5cncn5)cc4)nc(NCC(F)(F)F)c3n2)cc1] | 6-(4-Fluoro-phenyl)-N2-(4-[1,2,4]triazol-1-yl-benzyl)-N4-(2,2,2-trifluoro-ethyl)-pyrido[3,2-d]pyrimidine-2,4-diamine | 495.2 |
| 252 | 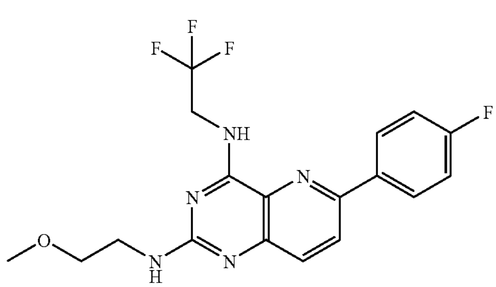 [SMILES: COCCNc1nc(NCC(F)(F)F)c2nc(-c3ccc(F)cc3)ccc2n1] | 6-(4-Fluoro-phenyl)-N2-(2-methoxy-ethyl)-N4-(2,2,2-trifluoro-ethyl)-pyrido[3,2-d]pyrimidine-2,4-diamine | 396.1 |

TABLE 8-continued

| No. | Structure | Name | Mass M$^{+1}$ |
|---|---|---|---|
| 253 | 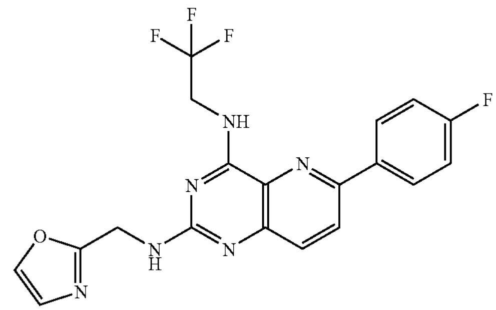 [SMILES: Fc1ccc(-c2ccc3nc(NCc4ncco4)nc(NCC(F)(F)F)c3n2)cc1] | 6-(4-Fluoro-phenyl)-N2-oxazol-2-ylmethyl-N4-(2,2,2-trifluoro-ethyl)-pyrido[3,2-d]pyrimidine-2,4-diamine | 419.1 |
| 254 | 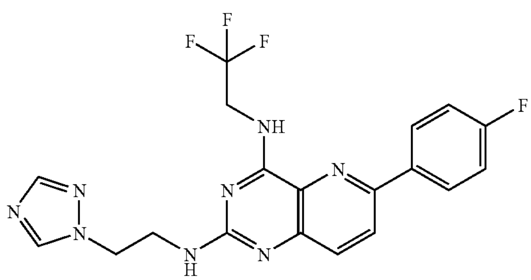 [SMILES: Fc1ccc(-c2ccc3nc(NCCn4cncn4)nc(NCC(F)(F)F)c3n2)cc1] | 6-(4-Fluoro-phenyl)-N2-(2-[1,2,4]triazol-1-yl-ethyl)-N4-(2,2,2-trifluoro-ethyl)-pyrido[3,2-d]pyrimidine-2,4-diamine | 433.1 |
| 255 | 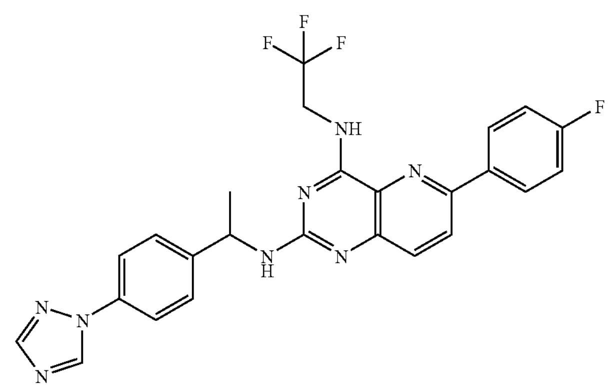 [SMILES: CC(Nc1nc(NCC(F)(F)F)c2nc(-c3ccc(F)cc3)ccc2n1)c1ccc(-n2cncn2)cc1] | 6-(4-Fluoro-phenyl)-N2-[1-(4-[1,2,4]triazol-1-yl-phenyl)-ethyl]-N4-(2,2,2-trifluoro-ethyl)-pyrido[3,2-d]pyrimidine-2,4-diamine | 509.2 |
| 256 | 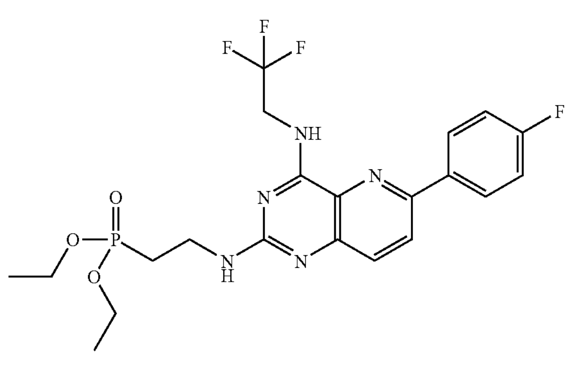 [SMILES: CCOP(=O)(CCNc1nc(NCC(F)(F)F)c2nc(-c3ccc(F)cc3)ccc2n1)OCC] | {2-[6-(4-Fluoro-phenyl)-4-(2,2,2-trifluoro-ethylamino)-pyrido[3,2-d]pyrimidin-2-ylamino]-ethyl}-phosphonic acid diethyl ester | 502.2 |

TABLE 8-continued

| No. | Structure | Name | Mass M$^{+1}$ |
|---|---|---|---|
| 257 | 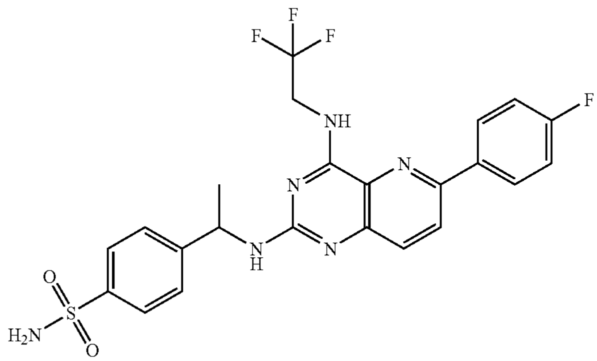 [SMILES: CC(Nc1nc(NCC(F)(F)F)c2nc(-c3ccc(F)cc3)ccc2n1)c1ccc(S(N)(=O)=O)cc1] | 4-{1-[6-(4-Fluoro-phenyl)-4-(2,2,2-trifluoro-ethylamino)-pyrido[3,2-d]pyrimidin-2-ylamino]-ethyl}-benzenesulfonamide | 521.2 |
| 258 | 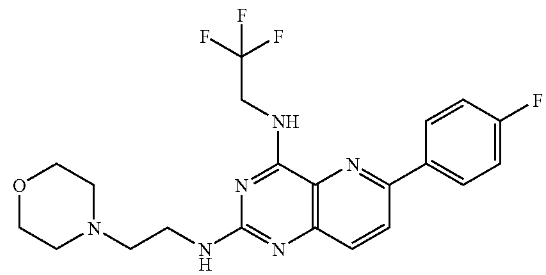 [SMILES: Fc1ccc(-c2ccc3nc(NCCN4CCOCC4)nc(NCC(F)(F)F)c3n2)cc1] | 6-(4-Fluoro-phenyl)-N2-(2-morpholin-4-yl-ethyl)-N4-(2,2,2-trifluoro-ethyl)-pyrido[3,2-d]pyrimidine-2,4-diamine | 451.2 |
| 259 | 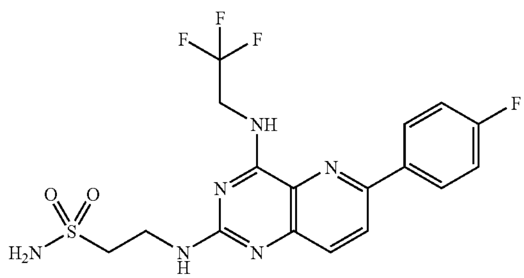 [SMILES: NS(=O)(=O)CCNc1nc(NCC(F)(F)F)c2nc(-c3ccc(F)cc3)ccc2n1] | 2-[6-(4-Fluoro-phenyl)-4-(2,2,2-trifluoro-ethylamino)-pyrido[3,2-d]pyrimidin-2-ylamino]-ethanesulfonic acid amide | 445.2 |
| 260 | 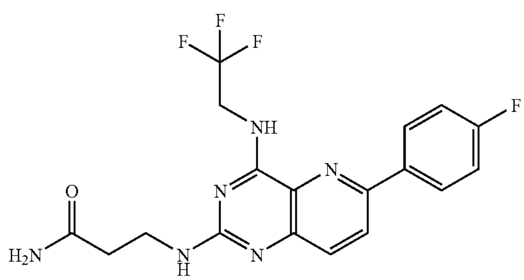 [SMILES: NC(=O)CCNc1nc(NCC(F)(F)F)c2nc(-c3ccc(F)cc3)ccc2n1] | 3-[6-(4-Fluoro-phenyl)-4-(2,2,2-trifluoro-ethylamino)-pyrido[3,2-d]pyrimidin-2-ylamino]-propionamide | 409.2 |
| 261 | 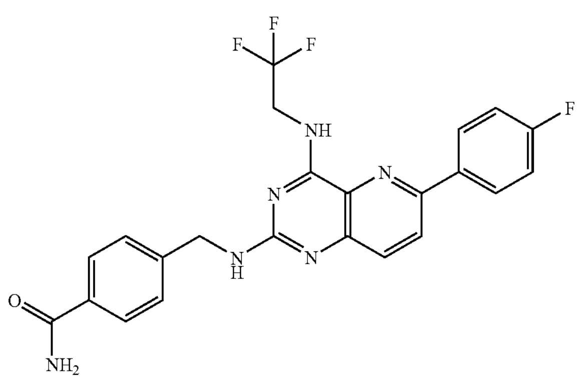 [SMILES: NC(=O)c1ccc(CNc2nc(NCC(F)(F)F)c3nc(-c4ccc(F)cc4)ccc3n2)cc1] | 4-{[6-(4-Fluoro-phenyl)-4-(2,2,2-trifluoro-ethylamino)-pyrido[3,2-d]pyrimidin-2-ylamino]-methyl}-benzamide | 471.2 |

EXAMPLES 262 TO 271

Synthesis of N2-substituted-6-(4-Fluoro-phenyl)-4-(ethoxy)-pyrido[3,2-d]pyrimidine-2-amines The compounds in Table 9 were synthesized from 2-chloro-4-hydroxy-6-(4-fluorophenyl)-pyrido[3,2-d]pyrimidine according to the to the principles set forth in FIG. 4 and outlined in more details in the embodiment shown in Scheme 9 below, as exemplified by the following example.

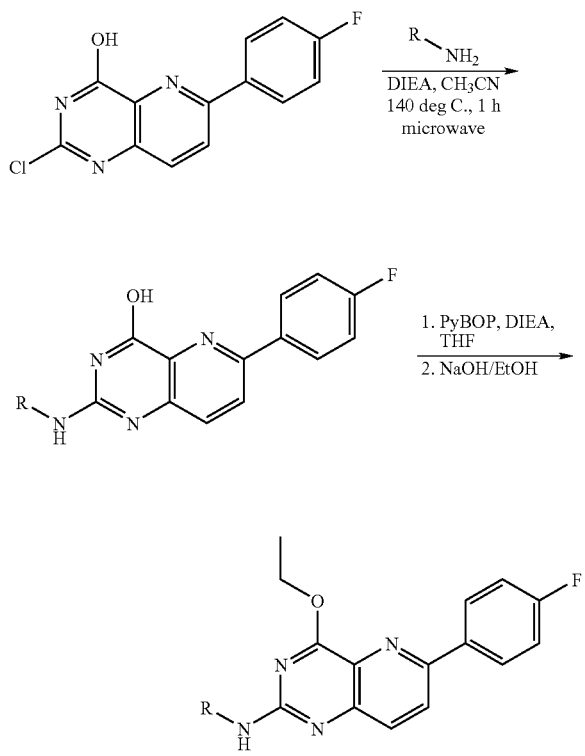

Scheme 9

3-[(6-[4-fluorophenyl]-4-ethoxy-pyrido[3,2-d]pyrimidin-2-ylamino)-methyl]-pyridine (Example 263)

Step 1: 2-Chloro-6-(4-fluorophenyl)pyrido[3,2-d]pyrimidin-4-ol (153 mg, 0.55 mmol), 3-aminomethylpyridine (70 μL, 0.68 mmol) and diisopropylethylamine (215 μL, 1.2 mmol) were suspended in NMP (2 mL), sealed and heated by microwave to 140 deg C. for 1 h. After cooling the reaction mixture was added dropwise to a stirring mixture of water/acetonitrile (8 mL, 4:1) to afford a yellow precipitate. The solid was filtered, washed with water, and dried to 121 mg (63%). This material was used without further purification in the next step.

Step 2: 3-[(6-[4-fluorophenyl]-4-hydroxy-pyrido[3,2-d]pyrimidin-2-ylamino)-methyl]-pyridine (120 mg, 0.35 mmol) and PyBOP (380 mg, 0.73 mmol) were mixed in THF (3 mL) and DIEA (90 μL, 0.51 mmol) was added. The reaction mixture was stirred at room temperature for 24 hours. Sodium ethoxide (0.7 mL, 1.9 mmol, 21 wt % in ethanol) and ethanol (3 mL) were then added. After stirring at room temperature for 24 hours, the reaction mixture was partitioned between EtOAc and $H_2O$. The aqueous layer was extracted twice with EtOAc. The combined organics were dried over $MgSO_4$, filtered, and concentrated. The residue was purified by RP HPLC using a C18 column with a 5-100% gradient of 0.1% TFA-$H_2O$/0.1% TFA-acetonitrile to afford 8 mg (6%) of the desired product as a pale yellow solid. MS (m/z) 376.1 $[M+H]^+$ Other examples in Table 9 were synthesized using an analogous method as described for Example 263 above. In each case, a suitable amine was used in place of 3-aminomethylpyridine in the first step.

TABLE 9

| No. | Structure | Name | Mass $M^{+1}$ |
|---|---|---|---|
| 262 | 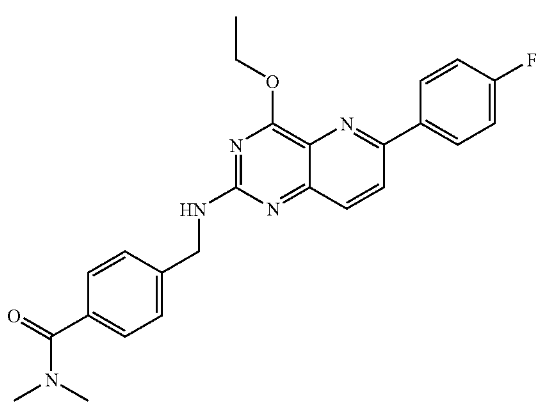 [SMILES: CCOc1nc(NCc2ccc(C(=O)N(C)C)cc2)nc2ccc(-c3ccc(F)cc3)nc12] | 4-{[4-Ethoxy-6-(4-fluoro-phenyl)-pyrido[3,2-d]pyrimidin-2-ylamino]-methyl}-N,N-dimethyl-benzamide | 446.2 |

TABLE 9-continued

| No. | Structure | Name | Mass M$^{+1}$ |
|---|---|---|---|
| 263 | 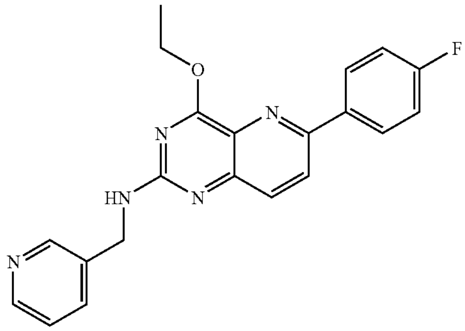 [SMILES: CCOc1nc(NCc2cccnc2)nc2ccc(-c3ccc(F)cc3)nc12] | [4-Ethoxy-6-(4-fluoro-phenyl)-pyrido[3,2-d]pyrimidin-2-yl]-pyridin-3-ylmethyl-amine | 376.1 |
| 264 | 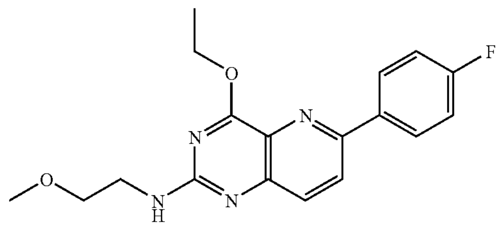 [SMILES: CCOc1nc(NCCOC)nc2ccc(-c3ccc(F)cc3)nc12] | [4-Ethoxy-6-(4-fluoro-phenyl)-pyrido[3,2-d]pyrimidin-2-yl]-(2-methoxy-ethyl)-amine | 343.3 |
| 265 | 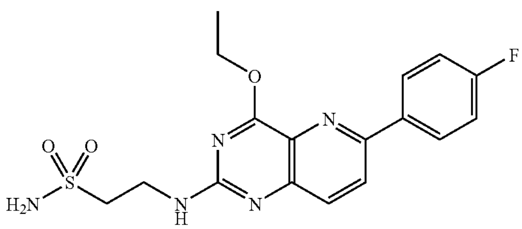 [SMILES: CCOc1nc(NCCS(N)(=O)=O)nc2ccc(-c3ccc(F)cc3)nc12] | 2-[4-Ethoxy-6-(4-fluoro-phenyl)-pyrido[3,2-d]pyrimidin-2-ylamino]-ethanesulfonic acid amide | 392.2 |
| 266 | 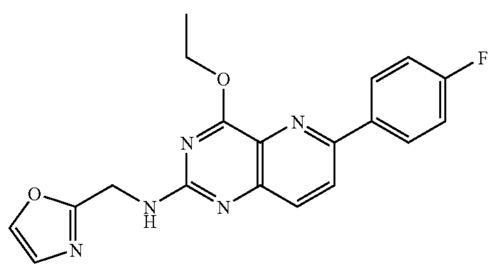 [SMILES: CCOc1nc(NCc2ncco2)nc2ccc(-c3ccc(F)cc3)nc12] | [4-Ethoxy-6-(4-fluoro-phenyl)-pyrido[3,2-d]pyrimidin-2-yl]-oxazol-2-ylmethyl-amine | 366.2 |
| 267 | 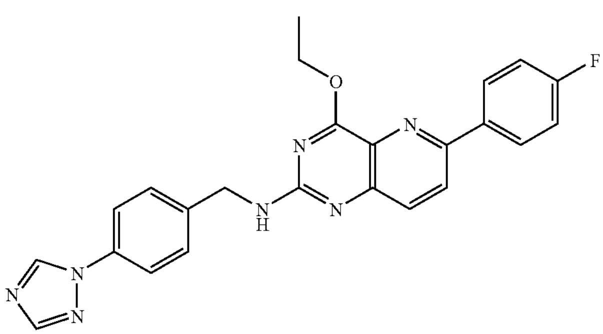 [SMILES: CCOc1nc(NCc2ccc(-n3cncn3)cc2)nc2ccc(-c3ccc(F)cc3)nc12] | [4-Ethoxy-6-(4-fluoro-phenyl)-pyrido[3,2-d]pyrimidin-2-yl]-(4-[1,2,4]triazol-1-yl-benzyl)-amine | 442.2 |

TABLE 9-continued

| No. | Structure | Name | Mass M+1 |
|---|---|---|---|
| 268 | 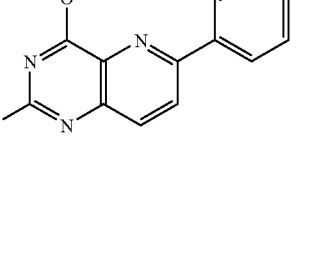 | 4-{[4-Ethoxy-6-(4-fluoro-phenyl)-pyrido[3,2-d]pyrimidin-2-ylamino]-methyl}-benzamide | 418 |
| 269 | 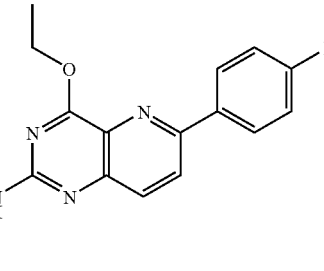 | C-(4-{[4-Ethoxy-6-(4-fluoro-phenyl)-pyrido[3,2-d]pyrimidin-2-ylamino]-methyl}-phenyl)-N-methyl-methanesulfonamide | 482.5 |
| 270 | 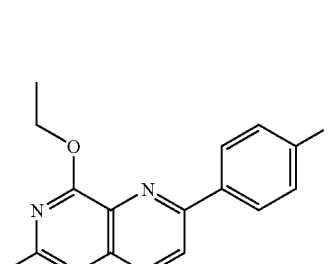 | (4-{[4-Ethoxy-6-(4-fluoro-phenyl)-pyrido[3,2-d]pyrimidin-2-ylamino]-methyl}-phenyl)-methanesulfonamide | 468.5 |
| 271 | 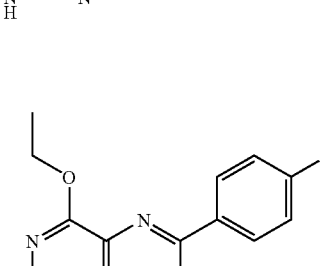 | N-(4-{[4-Ethoxy-6-(4-fluoro-phenyl)-pyrido[3,2-d]pyrimidin-2-ylamino]-methyl}-phenyl)-methanesulfonamide | 468.5 |

EXAMPLES 272 TO 283

Synthesis of 2-(4-fluoro-benzylamino)-4,6-substituted-pyrido[3,2-d]pyrimidines

The compounds in Table 10 were synthesized from 2,6-dichloro-4-hydroxypyrido[3,2-d]pyrimidine according to the to the principles set forth in FIG. 7 and outlined in more details in the embodiments shown in Scheme 10 below.

Scheme 10

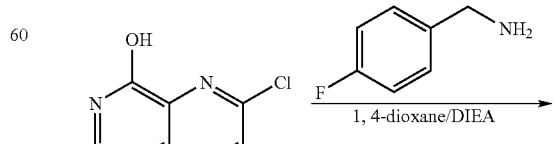

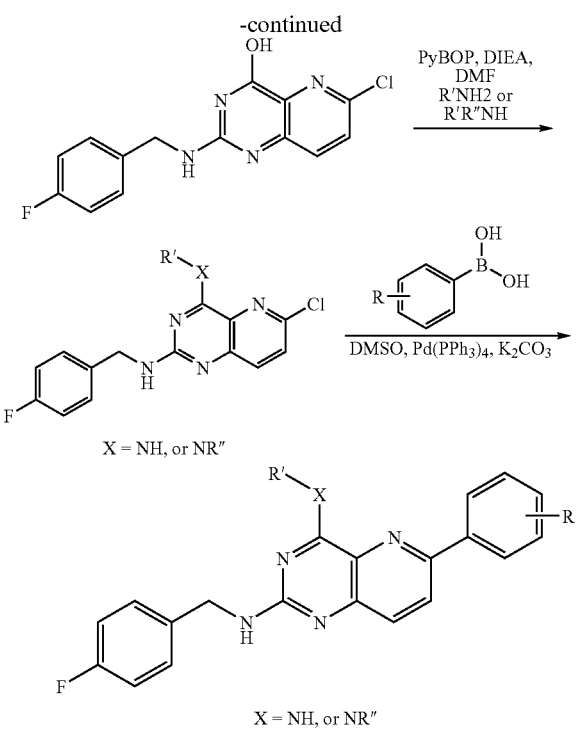

X = NH, or NR''

X = NH, or NR''

To a solution of 2,6-dichloro-pyrido[3,2-d]pyrimidin-4-ol (2.71 g, 12.55 mmol) and 4-fluorobenzylamine (1.57 g, 12.55 mmol) in 1,4-dioxane (55 mL) was added DIEA (6.5 ml, 37.65 mmol). Following heating at 90° C. overnight, the mixture was acidified with 1N HCl to pH 2~3. The resulting solid was filtered and dried in vacuo to provide 3.45 g (11.35 mm, 90%) of crude product.

6-Chloro-2-(4-fluoro-benzylamino)-pyrido[3,2-d]pyrimidin-4-ol (0.76 g, 2.5 mmol), PyBOP (1.7 g, 3.25 mmol) and the corresponding amine (3.25 mmol) were mixed in DMF (20 mL), and DIEA (1.3 mL, 7.5 mmol) was added. The reaction mixture was stirred at room temperature overnight. The corresponding 4-[(6-chloro-4-(substituted amino)-pyrido[3,2-d]pyrimidin-2-yl)-(4-fluorobenzyl)amine products were isolated by precipitation.

In the next step, the compounds in Table 10 were synthesized by introduction of the requisite substituents at the 6 position of the pyrido[3,2-d]pyrimidine ring using an analogous procedure to that described for Example 109.

TABLE 10

| No. | Structure | Name | Mass M+1 |
|---|---|---|---|
| 272 | 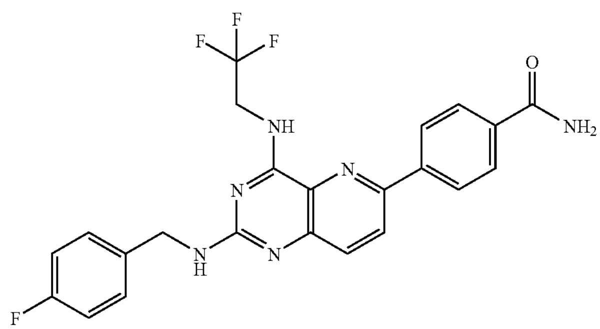 [SMILES: NC(=O)c1ccc(-c2ccc3nc(NCc4ccc(F)cc4)nc(NCC(F)(F)F)c3n2)cc1] | 4-[2-(4-Fluoro-benzylamino)-4-(2,2,2-trifluoro-ethylamino)-pyrido[3,2-d]pyrimidin-6-yl]-benzamide | 471.2 |
| 273 | 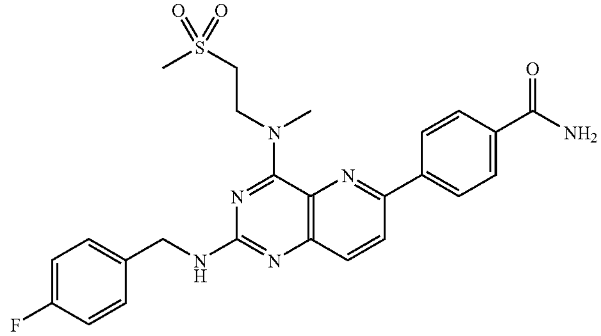 [SMILES: CN(CCS(C)(=O)=O)c1nc(NCc2ccc(F)cc2)nc2ccc(-c3ccc(C(N)=O)cc3)nc12] | 4-{2-(4-Fluoro-benzylamino)-4-[(2-methanesulfonyl-ethyl)-methyl-amino]-pyrido[3,2-d]pyrimidin-6-yl}-benzamide | 509.2 |

TABLE 10-continued

| No. | Name | Mass M+1 |
|---|---|---|
| 274 | 4-[2-(4-Fluoro-benzylamino)-4-(2-methanesulfonyl-ethylamino)-pyrido[3,2-d]pyrimidin-6-yl]-benzamide | 495.2 |
| 275 | 1-{4-[2-(4-Fluoro-benzylamino)-4-(2,2,2-trifluoro-ethylamino)-pyrido[3,2-d]pyrimidin-6-yl]-phenyl}-3-hydroxy-pyrrolidin-2-one | 527.2 |
| 276 | N-{3-[2-(4-Fluoro-benzylamino)-4-(2,2,2-trifluoro-ethylamino)-pyrido[3,2-d]pyrimidin-6-yl]-phenyl}-N-(2-hydroxy-ethyl)-methanesulfonamide | 565.1 |
| 277 | 2-Amino-N-{4-[2-(4-fluoro-benzylamino)-4-(2,2,2-trifluoro-ethylamino)-pyrido[3,2-d]pyrimidin-6-yl]-phenyl}-2-methyl-propionamide | 528.2 |

TABLE 10-continued

| No. | Name | Mass M+1 |
|---|---|---|
| 278 | 1-Hydroxy-cyclopropanecarboxylic acid {4-[2-(4-fluoro-benzylamino)-4-(2,2,2-trifluoro-ethylamino)-pyrido[3,2-d]pyrimidin-6-yl]-phenyl}-amide | 527.2 |
| 279 | N-(3-{2-(4-Fluoro-benzylamino)-4-[(2-methanesulfonyl-ethyl)-methyl-amino]-pyrido[3,2-d]pyrimidin-6-yl}-phenyl)-N-(2-hydroxy-ethyl)-methanesulfonamide | 603.2 |
| 280 | 2-Amino-N-(4-{2-(4-fluoro-benzylamino)-4-[(2-methanesulfonyl-ethyl)-methyl-amino]-pyrido[3,2-d]pyrimidin-6-yl}-phenyl)-2-methyl-propionamide | 566.2 |
| 281 | 1-Hydroxy-cyclopropanecarboxylic acid (4-{2-(4-fluoro-benzylamino)-4-[(2-methanesulfonyl-ethyl)-methyl-amino]-pyrido[3,2-d]pyrimidin-6-yl}-phenyl)-amide | 565.2 |

TABLE 10-continued

| No. | Structure | Name | Mass M+1 |
|---|---|---|---|
| 282 | 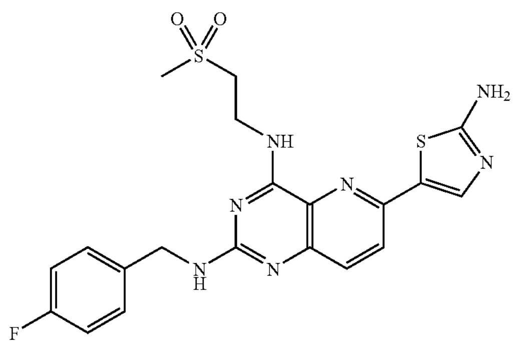 [SMILES: CS(=O)(=O)CCNc1nc(NCc2ccc(F)cc2)nc2ccc(-c3cnc(N)s3)nc12] | 6-(2-Amino-thiazol-5-yl)-N2-(4-fluoro-benzyl)-N4-(2-methanesulfonyl-ethyl)-pyrido[3,2-d]pyrimidine-2,4-diamine | 474.1 |
| 283 | 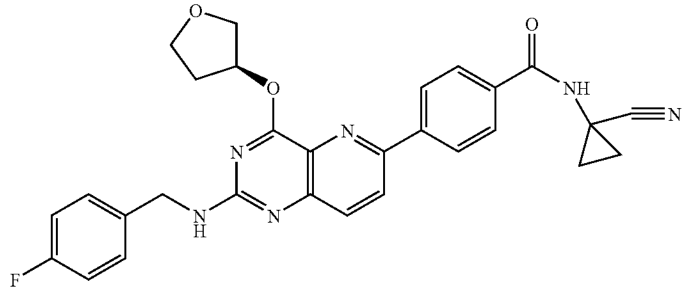 [SMILES: N#CC1(NC(=O)c2ccc(-c3ccc4nc(NCc5ccc(F)cc5)nc(O[C@H]5CCOC5)c4n3)cc2)CC1] | N-(1-Cyano-cyclopropyl)-4-[2-(4-fluoro-benzylamino)-4-(tetrahydro-furan-3-yloxy)-pyrido[3,2-d]pyrimidin-6-yl]-benzamide | 525.2 |

EXAMPLES 284 TO 286

Synthesis of 4-{[6-heteroaryl-4-(2,2,2-trifluoro-ethylamino)-pyrido[3,2-d]pyrimidin-2-ylamino]-methyl}-benzenesulfonamides The compounds in Table 11 were synthesized from 4-{[6-Chloro-4-(2,2,2-trifluoro-ethylamino)-pyrido[3,2-d]pyrimidin-2-ylamino]-methyl}-benzenesulfonamide according to the to the principles set forth in FIG. 7 and outlined in more details in the embodiment shown in Scheme 11 below, as exemplified by the following example.

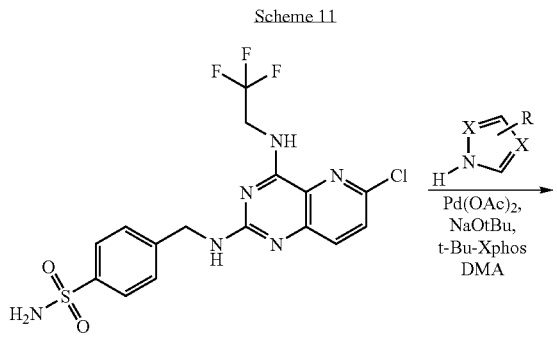

Scheme 11

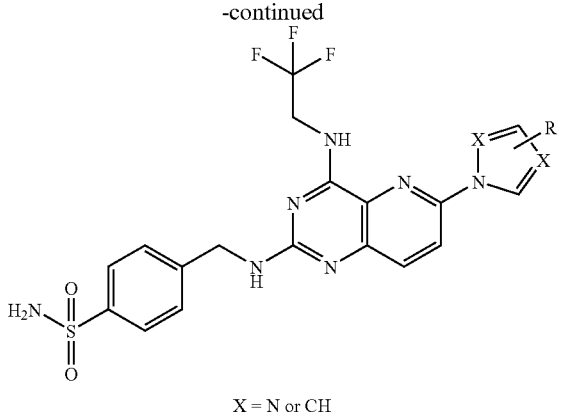

X = N or CH

A mixture of 4-{[6-Chloro-4-(2,2,2-trifluoro-ethylamino)-pyrido[3,2-d]pyrimidin-2-ylamino]-methyl}-benzenesulfonamide (45 mg, 0.1 mmol), imidazole (68 mg, 1.0 mmol), Pd(OAc)$_2$ (2.2 mg), t-Bu-XPhos (8.5 mg) and sodium tert-butoxide (38 mg, 0.4 mmol) in DMA (1.5 mL) was heated to 150° C. for 20 minutes by microwave. MeOH (1 mL) and 2N NaOH (1 mL) were added and the reaction mixture was stirred at room temperature for 2 hours, diluted with ethyl acetate (20 ml) and washed with brine (10 ml) twice. The organic layer was concentrated and purified with RP-HPLC using a C18 column with a gradient of H$_2$O, 0.05% TFA-acetonitrile to provide 15.1 mg (32%) of Example 286 as a solid.

Other examples in Table 11 were synthesized using an analogous method as described for Example 286 above. In each case, a suitable triazole or pyrazole was used in place of imidazole.

TABLE 11

| No. | Structure | Name | Mass M+1 |
|---|---|---|---|
| 284 | 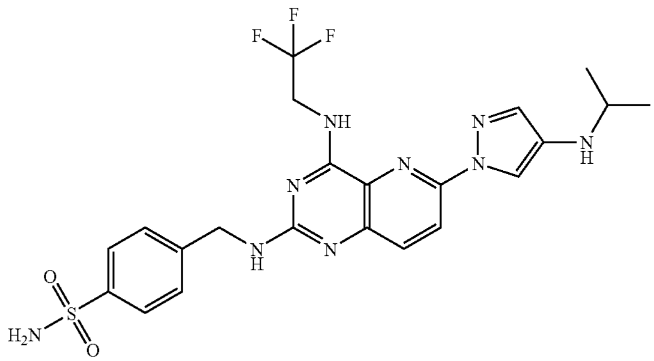 [SMILES: CC(C)Nc1cnn(-c2ccc3nc(NCc4ccc(S(N)(=O)=O)cc4)nc(NCC(F)(F)F)c3n2)c1] | 4-{[6-(4-Isopropylamino-pyrazol-1-yl)-4-(2,2,2-trifluoro-ethylamino)-pyrido[3,2-d]pyrimidin-2-ylamino]-methyl}-benzenesulfonamide | 536.3 |
| 285 | 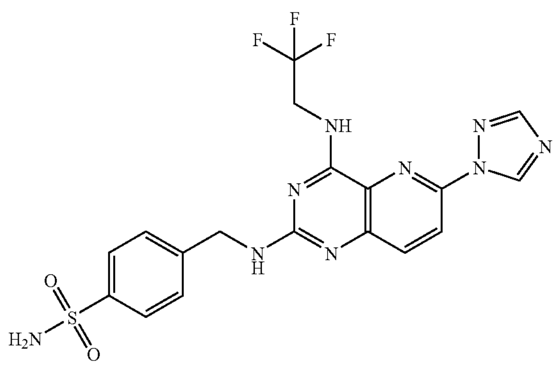 [SMILES: NS(=O)(=O)c1ccc(CNc2nc(NCC(F)(F)F)c3nc(-n4cncn4)ccc3n2)cc1] | 4-{[6-[1,2,4]Triazol-1-yl-4-(2,2,2-trifluoro-ethylamino)-pyrido[3,2-d]pyrimidin-2-ylamino]-methyl}-benzenesulfonamide | 480.2 |
| 286 | 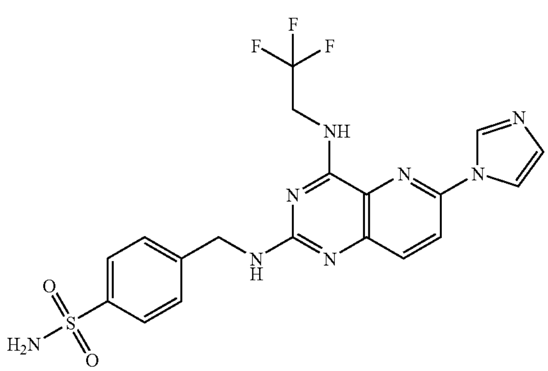 [SMILES: NS(=O)(=O)c1ccc(CNc2nc(NCC(F)(F)F)c3nc(-n4ccnc4)ccc3n2)cc1] | 4-{[6-Imidazol-1-yl-4-(2,2,2-trifluoro-ethylamino)-pyrido[3,2-d]pyrimidin-2-ylamino]-methyl}-benzenesulfonamide | 479.2 |

EXAMPLES 287 AND 288

Synthesis of 4-{[6-heteroaryl-4-(2,2,2-trifluoro-ethylamino)-pyrido[3,2-d]pyrimidin-2-ylamino]-methyl}-benzenesulfonamides Scheme 12

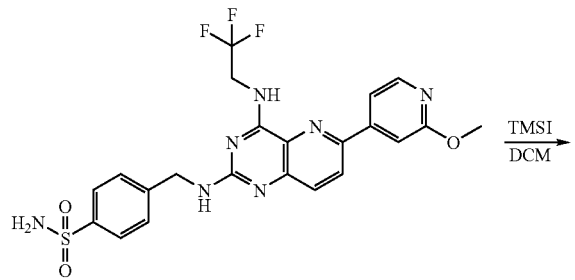

TMSI / DCM

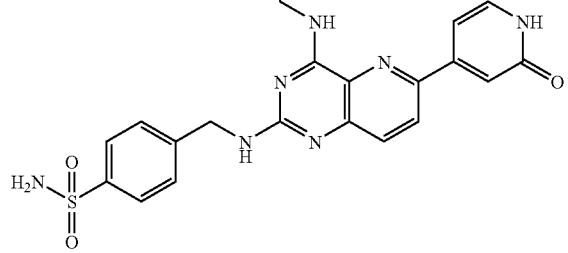

The compounds in Table 12 were synthesized according to the general synthetic sequence outlined in Scheme 12 as exemplified by the following example:

Iodotrimethylsilane (0.19 mL, 1.4 mmol) was added to a solution of 4-{[6-(2-Methoxy-pyridin-4-yl)-4-(2,2,2-trifluoro-ethylamino)-pyrido[3,2-d]pyrimidin-2-ylamino]-methyl}-benzenesulfonamide (90 mg, 0.14 mmol) in DCM (10 mL). The mixture was heated to 100° C. for 15 minutes by microwave. After removal of solvent, the crude residue was purified by RP-HPLC using a C18 column with a gradient of H₂O, 0.05% TFA-acetonitrile, to provide 47 mg (67% yield) of Example 287.

TABLE 12

| No. | Structure | Name | Mass $M^{+1}$ |
|---|---|---|---|
| 287 | (structure) | 4-{[6-(6-Oxo-1,6-dihydro-pyridin-3-yl)-4-(2,2,2-trifluoro-ethylamino)-pyrido[3,2-d]pyrimidin-2-ylamino]-methyl}-benzenesulfonamide | 506.2 |
| 288 | (structure) | 4-{[6-(2-Oxo-1,2-dihydro-pyridin-4-yl)-4-(2,2,2-trifluoro-ethylamino)-pyrido[3,2-d]pyrimidin-2-ylamino]-methyl}-benzenesulfonamide | 506.2 |

EXAMPLES 289 TO 295

Synthesis of 4-{[4,6-(substituted)-pyrido[3,2-d]pyrimidin-2-ylamino]-methyl}-benzenesulfonamides The compounds in Table 13 were synthesized from 2,4,6-trichloro-pyrido[3,2-d]pyrimidine according to the to the principles set forth in FIG. 8 and outlined in more details in the embodiments shown in Scheme 13 below. For Example 295, n-propyl magnesium bromide was used instead of cyclopropyl magnesium bromide in the first step.

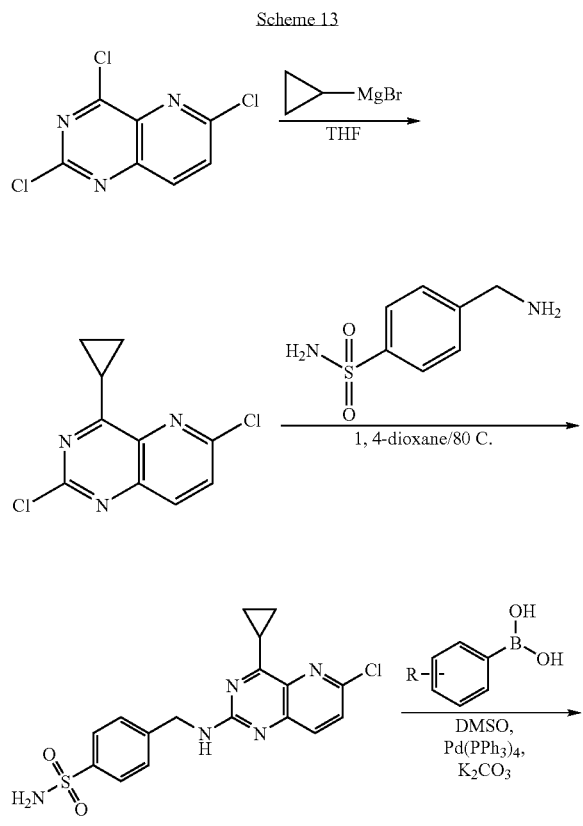

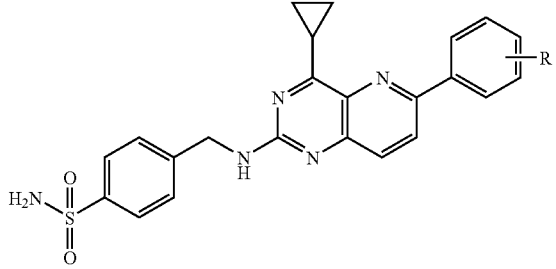

A mixture of 2,4,6-trichloro-pyrido[3,2-d]pyrimidine (500 mg, 2.13 mmol) cyclopropyl magnesium bromide (4.26 ml, 2.13 mmol) in THF (5 mL) was stirred at room temperature for 14 hrs. The reaction was neutralized with HCl (1N) and extracted twice with ethyl acetate. The organic layer was dried and concentrated. The crude product was further purified by flash column chromatography (Rf: 0.3, 10% of ethyl acetate/hexane). The yield was 150 mg.

DIEA (0.44 ml, 2.5 mmol) was added to a solution of 2,6-dichloro-4-cyclopropyl-pyrido[3,2-d]pyrimidine (150 mg, 0.625 mmol) and 4-aminomethyl-benzenesulfonamide (278 mg, 1.25 mmol) in 1,4-dioxane (2 mL). The mixture was heated at 90° C. overnight, acidified with 1N HCl to pH 2~3 and diluted with ethyl acetate (50 ml). The organic layer was washed twice with 1N HCl, dried and concentrated, to give 130 mg of the desired product, which was used without further purification.

A mixture of 4-[(6-Chloro-4-cyclopropyl-pyrido[3,2-d]pyrimidin-2-ylamino)-methyl]-benzenesulfonamide (26 mg, 0.067 mmol), potassium carbonate (0.33 ml, 1.3 mmol), tetrakis(triphenylphosphine) palladium (0) (10 mg) and a suitable aryl boronic acid (1.1 eq) in DMSO (1 mL) was heated to 120° C. for 5 minutes by microwave. The mixture was separated by RP HPLC using a C18 column with a gradient of $H_2O$, 0.05% TFA-acetonitrile, to provide the desired product. This procedure provided the desired products with yields ranging from 40% to 70% depending upon the aryl group introduced at the 6-position of the pyrido[3,2-d]pyrimidine ring.

TABLE 13

| No. | Structure | Name | Mass $M^{+1}$ |
|---|---|---|---|
| 289 | ![structure] | 5-[4-Cyclopropyl-2-(4-sulfamoyl-benzylamino)-pyrido[3,2-d]pyrimidin-6-yl]-2-fluoro-benzenesulfonamide | 529 |

TABLE 13-continued

| No. | Structure | Name | Mass M[+1] |
|---|---|---|---|
| 290 | 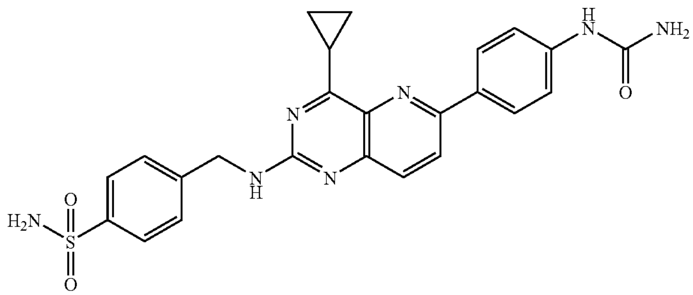 [SMILES: NC(=O)Nc1ccc(-c2ccc3nc(NCc4ccc(S(N)(=O)=O)cc4)nc(C4CC4)c3n2)cc1] | 4-{[4-Cyclopropyl-6-(4-ureido-phenyl)-pyrido[3,2-d]pyrimidin-2-ylamino]-methyl}-benzenesulfonamide | 490 |
| 291 | 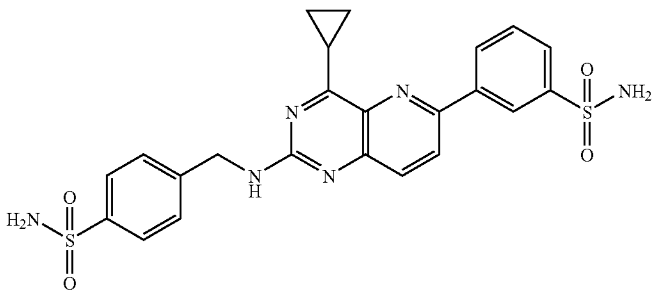 [SMILES: NS(=O)(=O)c1ccc(CNc2nc(C3CC3)c3nc(-c4cccc(S(N)(=O)=O)c4)ccc3n2)cc1] | 4-{[4-Cyclopropyl-6-(3-(aminosulfonyl)-phenyl)-pyrido[3,2-d]pyrimidin-2-ylamino]-methyl}-benzenesulfonamide | 511 |
| 292 | 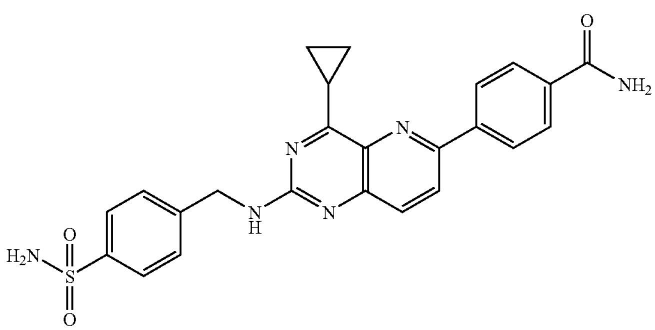 [SMILES: NC(=O)c1ccc(-c2ccc3nc(NCc4ccc(S(N)(=O)=O)cc4)nc(C4CC4)c3n2)cc1] | 4-[4-Cyclopropyl-2-(4-sulfamoyl-benzylamino)-pyrido[3,2-d]pyrimidin-6-yl]-benzamide | 475 |
| 293 | 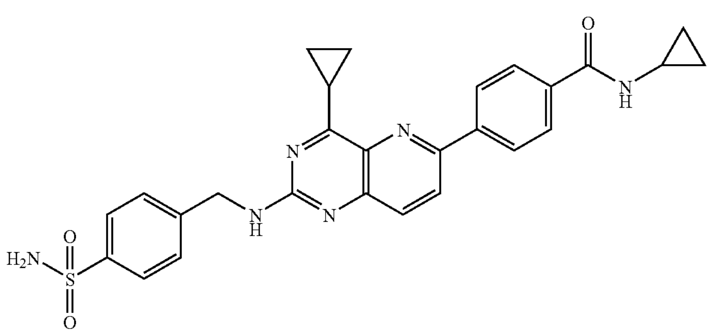 [SMILES: NS(=O)(=O)c1ccc(CNc2nc(C3CC3)c3nc(-c4ccc(C(=O)NC5CC5)cc4)ccc3n2)cc1] | N-Cyclopropyl-4-[4-cyclopropyl-2-(4-sulfamoyl-benzylamino)-pyrido[3,2-d]pyrimidin-6-yl]-benzamide | 515 |
| 294 | 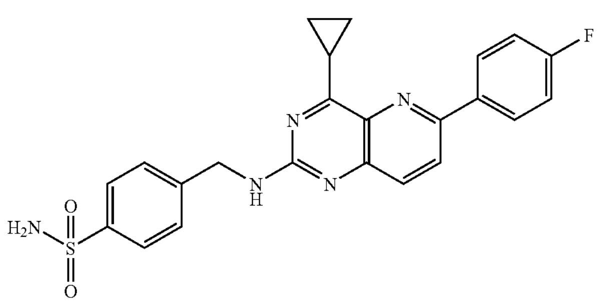 [SMILES: NS(=O)(=O)c1ccc(CNc2nc(C3CC3)c3nc(-c4ccc(F)cc4)ccc3n2)cc1] | 4-{[4-Cyclopropyl-6-(4-fluoro-phenyl)-pyrido[3,2-d]pyrimidin-2-ylamino]-methyl}-benzenesulfonamide | 450 |

TABLE 13-continued

| No. | Structure | Name | Mass M+1 |
|---|---|---|---|
| 295 | 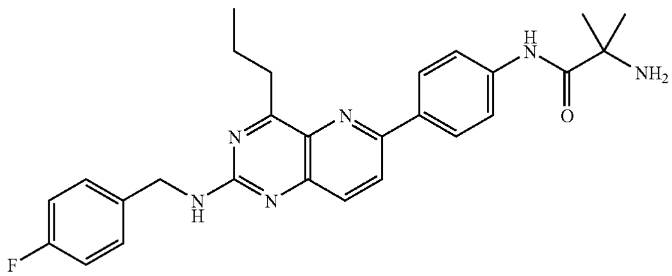 | 2-Amino-N-{4-[2-(4-fluoro-benzylamino)-4-propyl-pyrido[3,2-d]pyrimidin-6-yl]-phenyl}-2-methyl-propionamide | 473.2 |

EXAMPLES 296 TO 299

Synthesis of N2,N4-substituted-6-(4-fluoro-phenyl)-pyrido[3,2-d]pyrimidine-2,4-diamines The compounds in Table 14 were synthesized from 2-(substituted benzyl)amino-4-hydroxy-6-chloro-pyrido[3,2-d]pyrimidine according to the to the principles set forth in FIG. 5 and outlined in more details in the embodiments shown in Scheme 14 below, as exemplified by the following example.

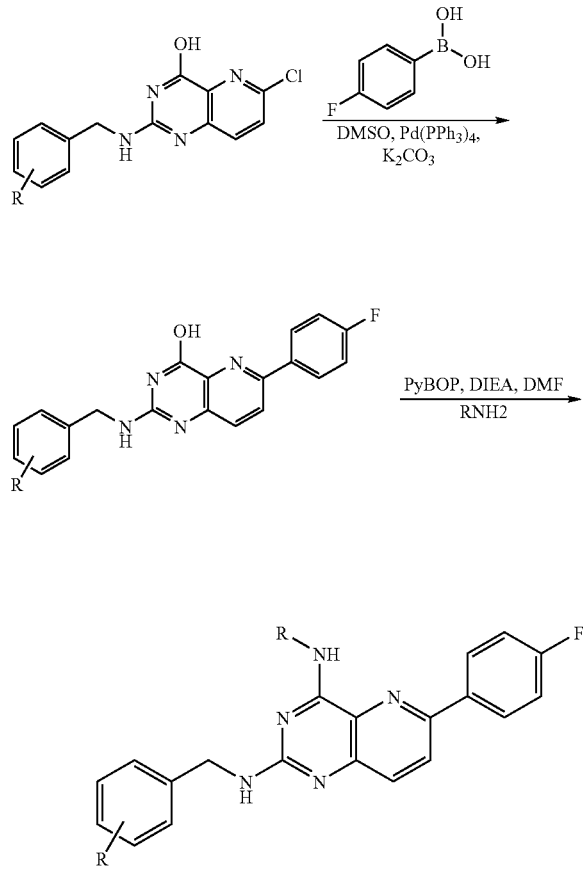

4-{[4-Ethylamino-6-(4-fluoro-phenyl)-pyrido[3,2-d]pyrimidin-2-ylamino]-methyl}-benzenesulfonamide (Example 297)

Step 1

A mixture of 4-[(6-chloro-4-hydroxy-pyrido[3,2-d]pyrimidin-2-ylamino)-methyl]-benzenesulfonamide (1.0 g, 2.73 mmol), potassium carbonate (0.754 g, 5.46 mmol), tetrakis (triphenylphosphine) palladium (0) (94 mg) and 4-fluorophenyl boronic acid (0.457 g, 3.27 mmol) in DMSO (25 mL) and water (8 mL) was heated to 120° C. for 5 minutes by microwave. The reaction mixture was diluted with ethyl acetate (200 ml) and washed twice with brine (100 ml). The organic layer was concentrated and purified with RP HPLC using a C18 column with a gradient of H$_2$O, 0.1% TFA-acetonitrile (0-60%), to provide the desired product. The yield was 904 mg (78%).

Step 2

4-{[6-(4-Fluoro-phenyl)-4-hydroxy-pyrido[3,2-d]pyrimidin-2-ylamino]-methyl}-benzenesulfonamide (100 mg, 0.23 mmol) and PyBOP (119 mg, 0.23 mmol) were taken up in DMF (2 mL) and DIEA (0.07 mL, 0.46 mmol) was added, followed by ethylamine (2.0M in THF) (0.115 mL, 0.23 mmol) This solution was stirred at room temperature overnight. The DMF was removed in vacuo and the residue diluted with ethyl acetate (2 mL) and washed with water and brine. The organic layer was dried over sodium sulfate and concentrated to afford an oily residue. The residue was purified by RP HPLC using a C18 column with a 0-60% gradient of 0.1% TFA-H$_2$O/0.1% TFA-acetonitrile to afford 55 mg (52%) of Example 297. MS (m/z) 453.4 [M+H]$^+$.

Other examples in Table 14 were synthesized using an analogous method as described for Example 297 above. In each case, a suitable boronic acid or boronate ester was used in place of 4-fluorophenyl boronic acid in the first step, and suitable amine was used in place of ethyl amine in the second step.

TABLE 14

| No. | Structure | Name | Mass M + 1 |
|---|---|---|---|
| 296 | 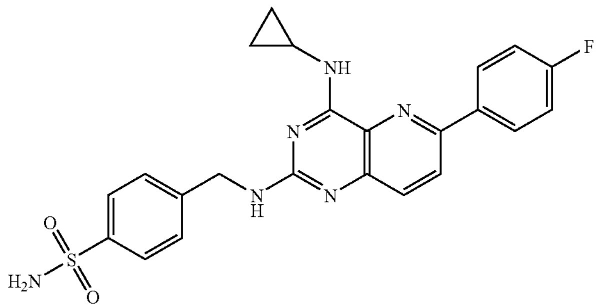 | 4-{[4-Cyclopropylamino-6-(4-fluoro-phenyl)-pyrido[3,2-d]pyrimidin-2-ylamino]-methyl}-benzenesulfonamide | 464.9 |
| 297 | 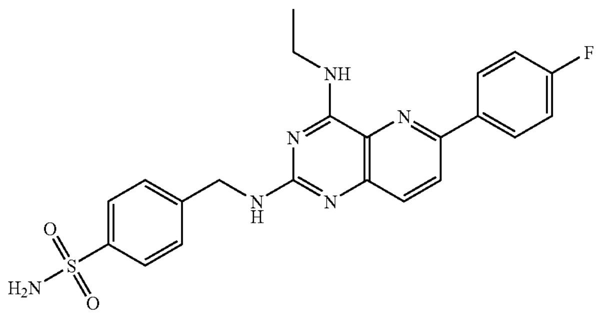 [SMILES: CCNc1nc(NCc2ccc(S(N)(=O)=O)cc2)nc2ccc(-c3ccc(F)cc3)nc12] | 4-{[4-Ethylamino-6-(4-fluoro-phenyl)-pyrido[3,2-d]pyrimidin-2-ylamino]-methyl}-benzenesulfonamide | 453.4 |
| 298 | 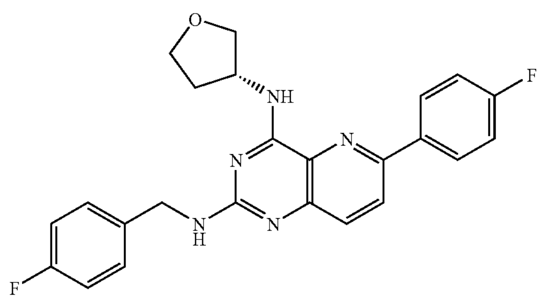 [SMILES: Fc1ccc(CNc2nc(N[C@@H]3CCOC3)c3nc(-c4ccc(F)cc4)ccc3n2)cc1] | N2-(4-Fluoro-benzyl)-6-(4-fluoro-phenyl)-N4-(tetrahydro-furan-3-yl)-pyrido[3,2-d]pyrimidine-2,4-diamine | 434.4 |
| 299 | 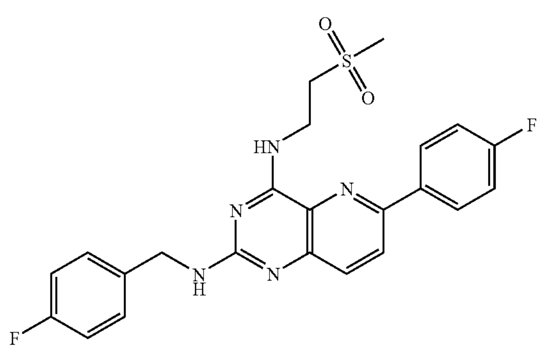 [SMILES: CS(=O)(=O)CCNc1nc(NCc2ccc(F)cc2)nc2ccc(-c3ccc(F)cc3)nc12] | N2-(4-Fluoro-benzyl)-6-(4-fluoro-phenyl)-N4-(2-methanesulfonyl-ethyl)-pyrido[3,2-d]pyrimidine-2,4-diamine | 470.5 |

EXAMPLES 300 TO 303

Synthesis of 4-{[4-substituted-6-(4-fluoro-phenyl)-pyrido[3,2-d]pyrimidin-2-ylamino]-methyl}-benzenesulfonamides The compounds in Table 15 were synthesized from 4-{[6-(4-Fluoro-phenyl)-4-hydroxy-pyrido[3,2-d]pyrimidin-2-ylamino]-methyl}-benzenesulfonamide according to the to the principles set forth in FIG. 5 and outlined in more details in the embodiments shown in Scheme 15 below, as exemplified by the following example.

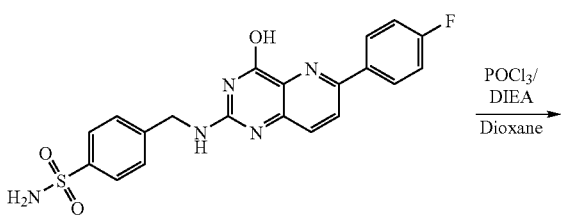

Scheme 15

-continued

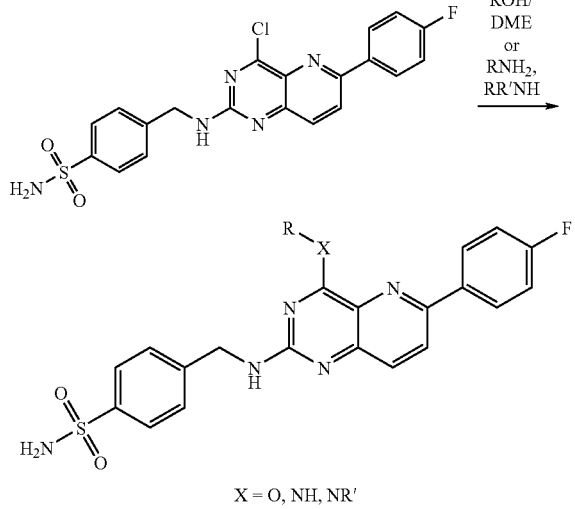

X = O, NH, NR'

In a first step, POCl$_3$ (1 mL, 10.92 mmol) was added to a suspension of 4-{[6-(4-Fluoro-phenyl)-4-hydroxy-pyrido[3,2-d]pyrimidin-2-ylamino]-methyl}-benzenesulfonamide (1.25 g, 2.94 mmol) and DIEA (1.0 mL, 5.88 mmol) in Dioxane (50 mL). The resulting mixture was heated at 100° C. for 1 hour. After removal of volatiles, the residue was triturated with dichloromethane. The solid was filtered and dried in vacuo to provide 1.24 g (2.8 mm, 95%) of crude product.

To a mixture of 4-{[4-Chloro-6-(4-fluoro-phenyl)-pyrido[3,2-d]pyrimidin-2-ylamino]-methyl}-benzenesulfonamide (0.16 g, 0.35 mmol) and 1-Methyl-cyclopropanol (0.15 mg, 2.1 mmol) in DME (5 mL) was added dropwise a solution of potassium tert-butoxide (1M in THF, 0.7 mL, 0.7 mmol). The reaction mixture was stirred at room temperature for 1 hour. Ethyl acetate (20 mL) was added to the mixture and washed with water and brine. The organic layer was dried over sodium sulfate and concentrated to afford crude material which was purified by RP-HPLC using a C18 column with a gradient of H$_2$O, 0.1% TFA-acetonitrile, to provide 75 mg (44% yield) of Example 301.

Other examples in Table 15 were synthesized using an analogous method as described for Example 301 above. In each case, a suitable alcohol or amine in a suitable solvent was used in place of 1-methyl-cyclopropanol in the second step.

TABLE 15

| No. | Structure | Name | Mass M$^{+1}$ |
|---|---|---|---|
| 300 | 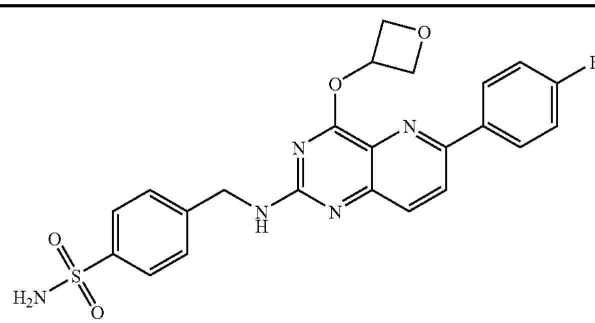 | 4-{[6-(4-Fluoro-phenyl)-4-(oxetan-3-yloxy)-pyrido[3,2-d]pyrimidin-2-ylamino]-methyl}-benzenesulfonamide | 482.1 |
| 301 | 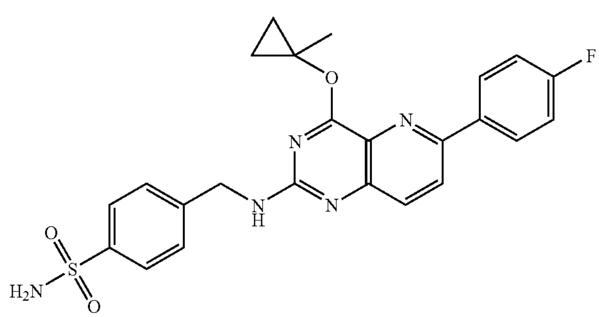 [SMILES: CC1(Oc2nc(NCc3ccc(S(N)(=O)=O)cc3)nc3ccc(-c4ccc(F)cc4)nc23)CC1] | 4-{[6-(4-Fluoro-phenyl)-4-(1-methyl-cyclopropoxy)-pyrido[3,2-d]pyrimidin-2-ylamino]-methyl}-benzenesulfonamide | 480.2 |
| 302 | 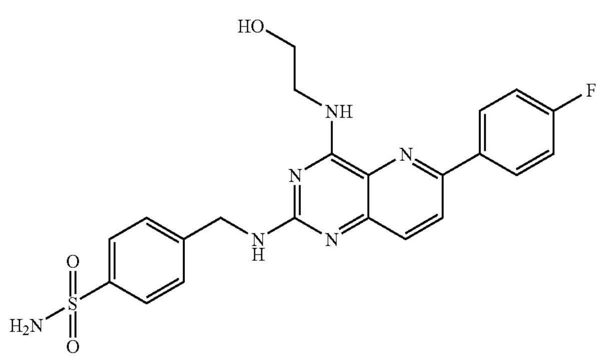 [SMILES: NS(=O)(=O)c1ccc(CNc2nc(NCCO)c3nc(-c4ccc(F)cc4)ccc3n2)cc1] | 4-{[6-(4-Fluoro-phenyl)-4-(2-hydroxy-ethylamino)-pyrido[3,2-d]pyrimidin-2-ylamino]-methyl}-benzenesulfonamide | 469.2 |

TABLE 15-continued

| No. | Structure | Name | Mass M+1 |
|---|---|---|---|
| 303 | 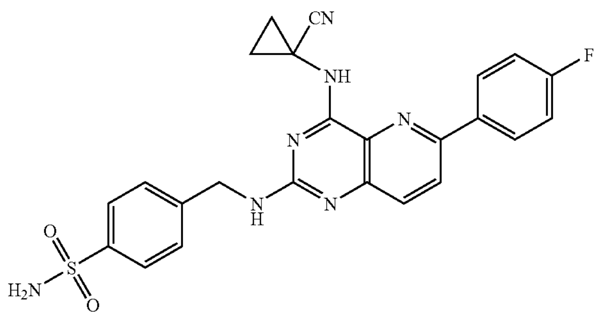 [SMILES: N#CC1(Nc2nc(NCc3ccc(S(N)(=O)=O)cc3)nc3ccc(-c4ccc(F)cc4)nc23)CC1] | 4-{[4-(1-Cyano-cyclopropylamino)-6-(4-fluoro-phenyl)-pyrido[3,2-d]pyrimidin-2-ylamino]-methyl}-benzenesulfonamide | 490.2 |

EXAMPLE 304

Anti-HCV Assay/Replicon Assay

The anti-HCV activity of the pyrido[3,2-d]pyrimidine derivatives of this invention was tested in a human hepatoma Huh-7 cell line harboring a HCV replicon. The assay comprised the following steps:

Step 1: Compound Preparation and Serial Dilution 1. for water soluble pyrido[3,2-d]pyrimidine derivatives, a volume of 500 μL of solution in cell media (DMEM, 10% FBS, P/S, L-Glutamine) was prepared with a concentration being twice the concentration of the starting final serial dilution concentration. A volume of 150 μL of the solution was added to the pre-specified wells in column 1 of a 96-well cell culture plate (PerkinElmer, white plate, cat. #6005181, for EC50 assay; black plate, cat. #6005182 for CC50 assay). The rest of the plate, columns 2-12, was filled with 100 μL of cell media. The plate was then placed on a Precision 2000 Workstation to start the serial dilution. Compounds were diluted three times each step from column 1 to column 10. Column 11 was used as a blank control (no compound added).

2. for pyrido[3,2-d]pyrimidine derivatives requiring DMSO to dissolve, serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 μL of the solution was transferred from the 384-well plate to a 96-well cell culture plate containing 100 μL of cell media on a Biomek FX Workstation. The DMSO concentration in the final assay condition was 0.5% after cells are added to the plate and the total volume in each well is brought to 200 μL.

Step 2: to each well of the serial dilution plate prepared above, 100 μL of cell media containing 6000 suspended Huh-7 HCV replicon cells was added with a Multidrop workstation. The plates were incubated for 3 days at 37° C. with 5% $CO_2$.

Step 3: Detection:

a) for the $EC_{50}$ assay, the media in a 96-well cell culture plate was aspirated with a Biotek EL405 plate-washer. A volume of 200 μL of a solution containing a 1:1 mixture of cell-lysis buffer (Promega, Luciferase Cell Culture Lysis 5× Reagent, cat. #E1531) and luciferase substrate solution (Promega, Luciferase Assay, cat.#E4550) was added to each well of the plate with Multidrop. The plate was incubated for 30 minutes at room temperature before the luminescence signal was measured with a TopCount plate-reader.

b) for the $CC_{50}$ assay, a volume of 100 μL of pre-mixed CellTiter-Glo (Promega, cat.#G7572) solution is added directly to the cell culture in each well of the plate and the luminescence signal is measured with a TopCount plate-reader after 10 minutes of incubation at room temperature.

Table 16 below shows $EC_{50}$ and CC50 ranges of derivatives tested in this assay. Results in table 16 are expressed by the following data:

the 50% effective concentration ($EC_{50}$), i.e. the concentration that protects 50% of the cell monolayer from virus-induced cythopathic effect, is valued by "A" when below 0.1 μM, by "B" when between 0.1 and 0.25 μM, and indicated by "C" when between 0.25 and 2 μM; and the 50% cytostatic concentration ($CC_{50}$), i.e. the concentration that results in 50% inhibition of cell growth, is valued by "A" when below 5 μM, by "B" when between 5 and 25 μM, and by "C" when higher than 25 μM.

TABLE 16

| No. | $EC_{50}$ | $CC_{50}$ |
|---|---|---|
| 20 | A | C |
| 21 | A | B |
| 23 | A | B |
| 24 | A | B |
| 25 | A | A |
| 26 | A | C |
| 27 | A | A |
| 28 | A | C |
| 29 | A | A |
| 30 | A | B |
| 31 | A | B |
| 32 | A | B |
| 33 | A | B |
| 34 | A | A |
| 35 | A | B |
| 36 | A | B |
| 37 | A | B |
| 38 | A | B |
| 39 | A | B |
| 40 | A | B |
| 41 | A | B |
| 42 | A | B |
| 43 | A | C |
| 44 | A | B |

TABLE 16-continued

| No. | EC$_{50}$ | CC$_{50}$ |
|---|---|---|
| 45 | A | B |
| 46 | A | B |
| 47 | A | B |
| 48 | A | C |
| 49 | C | C |
| 50 | C | C |
| 51 | C | C |
| 52 | C | B |
| 53 | B | B |
| 54 | B | B |
| 55 | A | B |
| 56 | C | B |
| 57 | C | A |
| 58 | C | A |
| 59 | A | B |
| 60 | A | C |
| 62 | A | C |
| 63 | A | A |
| 64 | A | B |
| 65 | A | C |
| 66 | A | A |
| 67 | A | B |
| 68 | A | B |
| 69 | A | C |
| 70 | A | A |
| 71 | A | A |
| 72 | A | B |
| 73 | A | B |
| 74 | A | B |
| 75 | A | C |
| 76 | A | B |
| 77 | A | B |
| 78 | A | B |
| 79 | A | B |
| 80 | A | B |
| 81 | A | A |
| 82 | A | A |
| 83 | A | B |
| 84 | A | A |
| 85 | A | B |
| 86 | A | A |
| 87 | A | A |
| 88 | A | B |
| 89 | A | A |
| 90 | A | A |
| 91 | A | A |
| 92 | A | A |
| 93 | A | A |
| 94 | A | B |
| 95 | A | A |
| 96 | A | A |
| 97 | A | B |
| 98 | A | C |
| 99 | A | A |
| 100 | A | A |
| 101 | A | B |
| 102 | A | B |
| 103 | A | A |
| 104 | A | B |
| 105 | A | A |
| 107 | A | B |
| 108 | A | B |
| 109 | A | B |
| 110 | A | B |
| 111 | A | B |
| 112 | A | A |
| 113 | A | C |
| 114 | A | B |
| 115 | A | B |
| 116 | A | C |
| 117 | A | B |
| 118 | A | B |
| 119 | A | A |
| 120 | A | B |
| 121 | A | C |
| 122 | A | C |
| 123 | A | B |
| 124 | A | B |

TABLE 16-continued

| No. | EC$_{50}$ | CC$_{50}$ |
|---|---|---|
| 125 | A | A |
| 126 | A | A |
| 127 | A | A |
| 128 | A | B |
| 129 | A | C |
| 130 | A | B |
| 131 | A | B |
| 132 | A | A |
| 133 | A | B |
| 134 | A | B |
| 135 | A | A |
| 136 | A | B |
| 137 | A | B |
| 138 | A | B |
| 139 | A | A |
| 140 | B | C |
| 141 | A | A |
| 142 | A | A |
| 143 | A | B |
| 144 | A | B |
| 145 | A | B |
| 146 | A | B |
| 147 | A | A |
| 148 | A | B |
| 149 | A | B |
| 150 | A | A |
| 151 | A | A |
| 152 | A | A |
| 153 | A | A |
| 154 | B | C |
| 155 | B | C |
| 156 | A | A |
| 157 | A | C |
| 158 | A | B |
| 159 | A | C |
| 160 | A | B |
| 161 | A | C |
| 162 | B | C |
| 164 | B | C |
| 165 | A | A |
| 166 | A | C |
| 167 | A | A |
| 168 | A | C |
| 169 | A | C |
| 170 | A | A |
| 171 | A | C |
| 172 | A | B |
| 173 | A | C |
| 174 | A | C |
| 175 | A | C |
| 176 | A | C |
| 177 | A | B |
| 178 | A | B |
| 179 | A | C |
| 180 | A | C |
| 181 | A | A |
| 182 | A | B |
| 183 | A | B |
| 184 | A | A |
| 185 | A | B |
| 186 | A | C |
| 187 | A | C |
| 188 | A | B |
| 189 | A | B |
| 190 | A | A |
| 191 | A | A |
| 192 | A | B |
| 193 | A | A |
| 194 | A | A |
| 195 | A | A |
| 196 | A | A |
| 197 | A | A |
| 198 | A | B |
| 199 | A | A |
| 200 | A | A |
| 201 | A | B |
| 202 | A | A |
| 203 | A | C |

TABLE 16-continued

| No. | EC$_{50}$ | CC$_{50}$ |
|---|---|---|
| 204 | A | A |
| 205 | A | A |
| 206 | A | A |
| 207 | A | A |
| 208 | A | B |
| 209 | A | A |
| 210 | A | C |
| 211 | A | B |
| 212 | A | B |
| 213 | A | A |
| 214 | A | B |
| 215 | A | B |
| 216 | A | A |
| 217 | A | A |
| 218 | A | B |
| 219 | A | A |
| 220 | A | B |
| 221 | A | C |
| 222 | A | B |
| 223 | A | B |
| 224 | A | C |
| 225 | A | C |
| 226 | A | C |
| 227 | A | C |
| 228 | A | A |
| 229 | A | A |
| 230 | A | B |
| 231 | A | C |
| 232 | A | C |
| 233 | A | B |
| 234 | A | B |
| 235 | A | B |
| 236 | A | B |
| 237 | A | A |
| 238 | A | A |
| 239 | A | B |
| 240 | A | A |
| 241 | A | B |
| 242 | A | C |
| 243 | A | B |
| 244 | A | B |
| 245 | A | C |
| 246 | A | B |
| 247 | A | B |
| 248 | A | B |
| 249 | A | A |
| 250 | A | A |
| 251 | A | C |
| 252 | A | B |
| 253 | A | A |
| 254 | A | C |
| 255 | A | B |
| 256 | A | B |
| 257 | A | B |
| 258 | A | A |
| 259 | A | B |
| 260 | A | B |
| 261 | A | A |
| 262 | A | C |
| 263 | A | C |
| 264 | A | C |
| 265 | A | B |
| 266 | A | C |
| 267 | A | C |
| 268 | A | B |
| 269 | A | B |
| 270 | A | B |
| 271 | A | B |
| 272 | A | A |
| 273 | A | B |
| 274 | A | A |
| 275 | A | A |
| 276 | A | B |
| 277 | A | A |
| 278 | A | B |
| 279 | A | B |
| 280 | A | B |
| 281 | A | B |
| 282 | A | C |
| 283 | A | A |
| 284 | A | C |
| 285 | A | C |
| 286 | A | B |
| 287 | A | C |
| 288 | A | C |
| 289 | A | B |
| 290 | A | B |
| 291 | A | A |
| 292 | A | B |
| 293 | A | A |
| 294 | A | A |
| 295 | A | C |
| 296 | A | C |
| 297 | A | A |
| 298 | A | B |
| 299 | A | B |
| 301 | A | A |
| 303 | A | B |

All publications and patent applications mentioned in this specification are herein incorporated by reference to the same extent as if each independent publication or patent application was specifically and individually indicated to be incorporated by reference.

What is claimed is:

1. A pyrido(3,2-d)pyrimidine derivative represented by the structural formula (I):

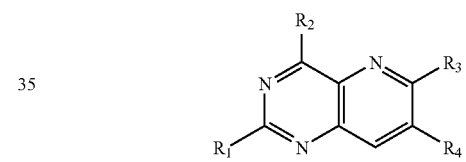

wherein:

R$_1$ is selected from the group consisting of 2,2,2-trifluoro-ethylamino, 4-fluorobenzylamino, 3,4-difluorobenzylamino, 2,6-difluoro-4-methoxybenzyl-amino, 4-chloro-2,6-difluorobenzylamino, 4-chloro-2-fluorobenzylamino, 2,4,6-trifluoro-benzylamino, 4-chloro-3-fluorobenzylamino, 2,3,4-trifluorobenzylamino, 3-chloro-4-fluorobenzylamino, 2-chloro-4-fluorobenzylamino, 3-fluoro-4-trifluoromethyl-amino, 3,5-difluorobenzylamino, 3,4,5-trifluoro-benzylamino, 3-fluorobenzylamino, 3-chloro-2-fluorobenzylamino, 4-fluorophenylamino, phenylamino, 6-methyl-pyridazin-3-ylamino, pyridin-2-ylmethylamino, pyridin-3-ylmethylamino, 2-morpholin-4-ylethylamino, 2,2-difluoroethyl-amino, 2-methoxyethylamino, 4-sulfamoylbenzylamino, 3-sulfamoylbenzylamino, 1-(4-fluorophenyl)-cyclopropyl-amino, 2,4-difluorobenzylamino, 1-phenylethyl-amino, thiazol-2-ylmethylamino, oxazol-4-ylmethylamino, isoxazol-3-ylmethylamino, 4-(N-isopropylsulfamoylmethyl) benzylamino, phenethylamino, 4-methanesulfonyl-benzylamino, 4-pyrrolidin-1-yl-benzylamino, 4-(4-methylpiperazin-1-yl)benzylamino, (N,N-dimethylcarbamoyl)benzylamino, 4-[1,2,3]thiadiazol-4-ylbenzylamino, 2-fluoro-4-sulfamoylbenzylamino, 4-[1,3,4]oxadiazol-2-ylmethylamino, thiazol-5-ylmethyl-amino, 1-(4-sulfamoylphenyl)ethylamino, 4-([1,2,4](triazol-1-yl)benzylamino, oxazol-2-ylmethylamino, 2-([1,2,4]triazol-1-yl)ethylamino, 1-(4-[1,2,4]triazol-1-yl-phenyl)-ethylamino, 2-(diethylphosphono)ethylamino, 2-sulfamoylethylamino, 2-carbamoylethylamino, 4-carbamoylbenzylamino, 4-(N,N-dimethylcarboxamido)-benzylamino, 4-(N-methylmethanesulfonamido)-benzylamino, 4-(methanesulfonylamino)benzylamino, 4-(N-methylsulfamoylmethyl)benzylamino, 4-(sulfamoylmethyl)benzylamino, —NH—CHR$_5$R$_6$ and —NH—R$_8$, R$_5$ and R$_6$ are independently selected from the group consisting of hydrogen, C$_{1-6}$ alkyl, C$_{3-10}$ cycloalkyl, aryl and heterocyclyl selected from imidazol-2-yl and thien-2-yl, with the proviso that both R$_5$ and R$_6$ are not hydrogen;
  wherein said aryl is optionally substituted with one or more substituents independently selected from the group consisting of halogen, hydroxy, amino, nitro, cyano, trifluoromethyl, trifluoromethoxy, C$_{1-4}$ alkyl C$_{1-4}$ alkoxy, C$_{1-4}$ alkylthio, di-C$_{1-4}$ alkylamino, mono-C$_{1-4}$ alkylamino, —SO$_2$NHR$_{13}$, CON(R$_{13}$)$_2$, —NR$_{12}$COR$_{10}$, SO$_2$R$_{13}$, NHSO$_2$R$_{13}$, and phenoxy, wherein said C$_{1-4}$ alkyl is optionally substituted with SO$_2$NHR$_{13}$;
  wherein said C$_{1-6}$ alkyl is substituted with one or more substituents independently selected from the group consisting of halogen, C$_{1-4}$ alkoxy, aryl, P(O)(OR$_{13}$)$_2$, carbamoyl, and —SO$_2$NHR$_{13}$;

R$_8$ is selected from the group consisting of C$_{3-10}$ cycloalkyl, heteroaryl selected from pyridazinyl and pyrazolyl, and aryl
  wherein said heteroaryl or aryl is optionally substituted with one or more substituents independently selected from the group consisting of halogen and C$_{1-4}$ alkyl and
  wherein said C$_{3-10}$ cycloalkyl is optionally substituted at the carbon position adjacent to the N atom of —NHR$_8$ with aryl wherein said aryl is optionally substituted with halogen;

R$_2$ is XR$_7$ or is selected from the group consisting of tetrahydrofuran-3-yloxy, ethoxy, hydroxy, 2-carbamoylethylamino, 2-methyl-2-hydroxy-propylamino, methoxy, 3-methanesulfonylpyrrolidin-1-yl, N-methanesulfonylethyl-N-methyl-amino, 1-isopropyl-piperidin-4-ylamino, ethylamino, pyridin-3-ylmethylamino, N-morpholin-4-ylethylamino, 2,2,2-trifluoroethylamino, 2-methoxyethylamino, isopropylamino, dimethylamino, diethylamino, cyclopentoxy, cyclobutoxy, propyl, methanesulfonylethylamino, 2,2-difluoroethylamino, cyclopropoxy, cyclopropyl-amino, 4-([1,2,4]triazol-1-yl)phenylamino, 3-fluorophenylamino, 2-methoxy-ethoxy, N-(methanesulfonylethyl)-amino, 1-propyl, tetrahydrofuran-3-ylamino, oxetan-3-yloxy, 1-methylcyclopropoxy, 2-hydroxyethylamino, 1-cyano-cyclopropylamino, N-morpholinyl, N-thiomorpholinyl, N-thiomorpholinyl dioxide, cyclopropyl, N-piperidinyl and N-pyrrolidinyl, wherein said N-pyrrolidinyl is optionally substituted with C$_{1-4}$ alkylsulfonyl;

X is selected from the group consisting of O, S, NR$_{13}$ and CH$_2$;

R$_7$ is selected from the group consisting of C$_{1-20}$ alkyl, C$_{3-10}$ cycloalkyl, aryl, and aryl-C$_{1-4}$ alkyl;
  wherein said C$_{1-20}$ alkyl is optionally substituted with one or more substituents independently selected from the group consisting of methylsulfonyl, hydroxy, carbamoyl, halogen and C$_{1-4}$ alkoxy when X is NR$_{13}$ or said C$_{1-20}$ alkyl is optionally substituted with one or more substituents independently selected from the group consisting of C$_{1-4}$ alkoxy, and halo-C$_{1-4}$ alkoxy when X is O; and
  wherein said C$_{3-10}$ cycloalkyl is optionally substituted with one or more C$_{1-20}$ alkyl or cyano; and
  wherein said aryl is optionally substituted with one or more halogen;

R$_4$ is hydrogen;

R$_3$ is selected from the group consisting of halogen, 4-fluorophenyl, 5-amino-pyrazin-2-yl, 4-(N-(2-dimethylaminoethyl)carbamoyl)phenyl, 3-chloro-4-fluoro-phenyl, 4-(N-cyclopropylcarbamoyl)phenyl, 3-(N-methylsulfonyl-amino)phenyl, 4-(cyclopropanecarboxamido)phenyl, 3-sulfamoyl-4-fluorophenyl, 4-(2-hydroxy-acetamido)-phenyl, 4-(2-amino-acetamido)phenyl, 4-[3-(2-morpholin-4-yl-ethyl)-ureido]phenyl, 4-(morpholin-4-carboxamido)phenyl, 4-(pyrrolidine-1-carboxamido)phenyl, 4-(3-cyclopropylureido)phenyl, 4-ureidophenyl, 4-[(4-hydroxy-2-oxo-pyrrolidin-1-yl)]phenyl, 1H-indazol-5-yl, 2-oxo-indolin-5-yl, 6-cyclopropanecarboxamido-pyridin-3-yl, 2-cyclopropanecarboxamido-pyrimidin-5-yl, 3-(2-pyrrolidin-1-yl-ethanesulfonamido)phenyl, 3-(cyclopropanesulfonamido)-phenyl, 4-sulfamoylphenyl, 3-(dimethylaminesulfonamido)phenyl, 3-sulfamoylphenyl, 4-(3-hydroxy-2-oxo-pyrrolidin-1-yl)phenyl, 2-fluoropyridin-5-yl, 4-(4-hydroxypyrrolidin-2-carboxamido)phenyl, 4-(pyrrolidin-2-carboxamido)phenyl, 4-[3-(2-pyrrolidin-1-yl-ethyl)ureido]phenyl, 4-(pyrrolidin-3-carboxamido)-3-fluoro-phenyl, 4-(pyrrolidin-3-carboxamido)phenyl, 4-(2-(pyrrolidin-1-yl)-ethoxycarbonyl-amino)phenyl, 3-(4-(tert-butoxycarbonylamino)-piperidin-1-sulfonyl)-4-chloro-phenyl, 3-(N-(1-(tert-butoxycarbonyl)-pyrrolidin-3-yl)-sulfamoyl)-4-fluoro-phenyl, 4-(methoxycarbonylamino)phenyl, 3-(N-(1-(tert-butoxycarbonyl)-piperidin-4-yl)-sulfamoyl)-4-chloro-phenyl, 3-(N-(1-(tert-butoxycarbonyl)-piperidin-4-yl)-sulfamoyl)-4-fluoro-phenyl, 4-(N-(2-hydroxy-1,1-dimethylethyl)carbamoyl)phenyl, 4-(N-(2-(pyrrolidin-1-yl)-1,1-dimethyl-ethyl)carbamoyl)phenyl, 2-amino-thiazol-5-yl, 5-hydroxymethylfuran-2-yl, 4-(N-pyrrolidin-2-one)-phenyl, 4-carbamoyl-phenyl, 4-(N-1-cyano-1-cyclopropyl-carbamoyl)phenyl, 4-(N-1-amino-1-cyclopropylcarbamoyl)phenyl, 4-(N-1-hydroxy-1-cyclopropylcarboxamido)phenyl, 3-(N-(2-hydroxyethyl)methylsulfonamido)-phenyl, 4-(N-(2-(morpholin-4-yl)-1,1-dimethyl-ethyl)carbamoyl) phenyl, 4-(2-oxo-pyrrolidin-1-yl)phenyl, 4-(2-amino-2-methylpropionamido)phenyl, 4-(N-cyclopropylcarbamoyl)phenyl, 4-(3-hydroxy-2-aminopropionamido)phenyl, 3-cyclopropanesulfonamido-4-fluorophenyl, 4-(2-amino-propionamido)-phenyl, 4-(3-hydroxy-2-aminobutyramido)phenyl, 3,5-dimethyl-isoxazol-4-yl, 1-methyl-1H-pyrazol-4-yl, 5-pyrrolidin-1-ylpyrazin-2-yl, 2-trifluoromethylpyridin-4-yl, 2-aminopyridin-4-yl, 4-hydroxyphenyl, 2-pyrrolidin-1-yl-thiazol-4-yl, 2-methoxypyridin-4-yl, 2-cyanopyridin-4-yl, 2-aminopyrimidin-5-yl, 3-cyanophenyl, 4-(1-methylpyrrolidine-3-carboxamido)-3-fluorophenyl, 4-(1-methylpyrrolidine-3-carboxamido)-phenyl, 3-cyclopropanesulfonamido-4-fluorophenyl, 1H-pyrazol-4-yl, 3-(N-(1-isopropyl-piperidin-4-yl)sulfamoyl)-4-chlorophenyl, 3-(N-(2-pyrrolidin-1-yl-ethyl)sulfamoyl)-4-chlorophenyl, 3-(4-isopropyl-piperazin-1-sulfonyl)-4-chloro-phenyl, 3-(N-pyrrolidin-3-ylsulfamoyl)-4-chlorophenyl, 3-(N-pyrrolidin-3-yl-sulfamoyl)-4-fluorophenyl, 3-(N-(2-methoxyethyl)-sulfamoyl)-4-chlorophenyl, 3-(N-piperidin-4-ylsulfamoyl)-4-chlorophenyl, 3-(N-piperidin-4-ylsulfamoyl)-4-fluorophenyl, pyridazin-4-yl, 4-cyanophenyl, 4-fluoro-3-(piperazin-1-sulfonyl)-phenyl, 4-fluoro-3-(4-tert-butoxycarbonyl-piperazin-1-sulfonyl)-phenyl, 4-isopropylamino-pyrazol-1-yl, [1,2,4]triazol-1-yl, imidazol-1-yl, imidazol-2-yl, 6-oxo-1,6-dihydro-pyridin-3-yl, 2-oxo-1,2-dihydro-pyridin-4-yl, 3-hydroxy-2-oxo-pyrrolidin-1-yl, 4-chlorophenyl, and optionally mono-substituted or disubstituted aryl,
    wherein each substituent of said aryl is independently selected from the group consisting of halogen, hydroxy, amino, $C_{1-4}$ alkylamino, cyano, $C_{1-6}$ alkyl, $C_{1-6}$ alkoxy, $C_{1-6}$ alkylthio, —$CONHR_9$, —$NR_{12}COR_{10}$, —$NR_{12}SO_2R_{11}$, —$SO_2NH_2$, and —$SO_2NHR_{14}$;
    wherein said $C_{1-6}$ alkyl is optionally substituted with one or more substituents independently selected from the group consisting of halogen and hydroxyl;
$R_9$ is selected from the group consisting of hydrogen, $C_{3-10}$ cycloalkyl, $C_{1-6}$ alkyl, $C_{1-6}$ alkoxy, and phenyl;
    wherein said $C_{3-10}$ cycloalkyl is optionally substituted with one or more substituents independently selected from the group consisting of cyano, halogen, hydroxy, oxo, amino, $C_{1-6}$ alkyl and $C_{1-6}$ alkoxy;
    wherein said $C_{1-6}$ alkyl is optionally substituted with one or more substituents independently selected from the group consisting of amino, alkylamino, cyano, dialkylamino, halogen, and hydroxy; and
wherein said phenyl is optionally and independently substituted with one or more halogens;
$R_{10}$ and $R_{11}$ are each independently selected from the group consisting of $C_{1-6}$ alkyl, $C_{1-6}$ alkoxy, $C_{3-10}$ cycloalkyl, and amino,
    wherein said $C_{1-6}$ alkyl is optionally substituted with one or more substituents independently selected from the group consisting of amino, cyano, halogen, and hydroxy;
    wherein said $C_{1-6}$ alkoxy is optionally substituted with one or more substituents independently selected from the group consisting of amino, $C_{1-4}$ alkylamino, cyano, di-$C_{1-4}$ alkylamino, and halogen;
    wherein said $C_{3-10}$ cycloalkyl is optionally substituted with one or more substituents independently selected from the group consisting of cyano, amino, and hydroxy; and
    wherein said amino is optionally substituted with one or more substituents independently selected from the group consisting of $C_{3-10}$ cycloalkyl, and $C_{1-6}$ alkyl optionally substituted with one or more substituents independently selected from the group consisting of amino, $C_{1-4}$ alkylamino, cyano, di-$C_{1-4}$ alkylamino, and halogen;
$R_{12}$ is selected from the group consisting of hydrogen and $C_{1-6}$ alkyl,
    wherein said $C_{1-6}$ alkyl is optionally substituted with one or more substituents independently selected from the group consisting of cyano, halogen and hydroxy;
each $R_{13}$ is independently selected from the group consisting of hydrogen and $C_{1-20}$ alkyl; and
$R_{14}$ is $C_{1-4}$ alkyl optionally substituted with one or more $C_{1-4}$ alkoxy;
or a pharmaceutically acceptable addition salt or a stereochemical isomeric form thereof or a N-oxide thereof.

2. A pyrido(3,2-d)pyrimidine derivative according to claim 1, wherein
$R_2$ is $XR_7$ or is selected from the group consisting of N-morpholinyl, N-thiomorpholinyl, N-thiomorpholinyl dioxide, cyclopropyl, N-piperidinyl and N-pyrrolidinyl, wherein said N-pyrrolidinyl is optionally substituted with $C_{1-4}$ alkylsulfonyl;
X is selected from the group consisting of O, S, $NR_{13}$ and $CH_2$; and
$R_7$ is selected from the group consisting of $C_{1-20}$ alkyl, $C_{3-10}$ cycloalkyl, aryl, and aryl-$C_{1-4}$ alkyl;
    wherein said $C_{1-20}$ alkyl is substituted with one or more substituents independently selected from the group consisting of methylsulfonyl, carbamoyl, halogen and $C_{1-4}$ alkoxy when X is $NR_{13}$, or said $C_{1-20}$ alkyl is optionally substituted with one or more substituents independently selected from the group consisting of $C_{1-4}$ alkoxy, and halo-$C_{1-4}$ alkoxy when X is O;
    wherein said $C_{3-10}$ cycloalkyl is substituted with one or more substituents independently selected from the group consisting of $C_{1-20}$ alkyl and cyano when X is O, S, $CH_2$ or $NR_{13}$;
    wherein said aryl is optionally substituted with one or more halogen when X is O, S or $CH_2$;
or a pharmaceutically acceptable addition salt or a stereochemical isomeric form thereof or a N-oxide thereof.

3. A pyrido(3,2-d)pyrimidine derivative according to claim 1, wherein:
$R_1$ is selected from the group consisting of —NH—$CHR_5R_6$ and —NH—$R_8$,
$R_5$ and $R_6$ are independently selected from the group consisting of hydrogen, $C_{1-6}$ alkyl, $C_{3-10}$ cycloalkyl, aryl and heterocyclyl selected from imidazol-2-yl and thien-2-yl, with the proviso that both $R_5$ and $R_6$ are not hydrogen, and
    wherein said aryl is substituted with one or more substituents selected from the group consisting of cyano, trifluoromethoxy, $C_{1-4}$ alkyl, $C_{1-4}$ alkoxy, di-$C_{1-4}$ alkylamino, mono-$C_{1-4}$ alkylamino, —$SO_2NHR_{13}$, —$CON(R_{13})_2$, —$NR_{12}COR_{10}$, —$SO_2R_{13}$, —$NHSO_2R_{13}$, and phenoxy, wherein said $C_{1-4}$ alkyl is optionally substituted with —$SO_2NHR_{13}$, and
    said aryl is optionally further substituted with one or more substituents selected from the group consisting of halogen, hydroxy, amino, nitro and trifluoromethyl;
    wherein said $C_{1-6}$ alkyl is substituted with one or more substituents selected from the group consisting of halogen, $C_{1-4}$ alkoxy, aryl, —$P(O)(OR_{13})_2$, carbamoyl, and —$SO_2NHR_{13}$; and
$R_8$ is selected from the group consisting of $C_{3-10}$ cycloalkyl substituted at the carbon position adjacent to the N atom of —$NHR_8$ with aryl
    wherein said aryl is optionally substituted with halogen; phenyl; and 4-fluorophenyl,
or a pharmaceutically acceptable addition salt or a stereochemically isomeric form thereof or a N-oxide thereof.

4. A pyrido(3,2-d)pyrimidine derivative according to claim 1, wherein:
$R_3$ is mono-substituted or disubstituted aryl,
    wherein at least one substituent of said aryl is independently selected from the group consisting of $C_{1-6}$ alkyl, —$CONHR_9$, —$NR_{12}COR_{10}$, —$NR_{12}SO_2R_{11}$, and —$SO_2NHR_{14}$,
    wherein said $C_{1-6}$ alkyl is substituted with one or more hydroxy and optionally further substituted with one or more halogen;

and wherein a further substituent of said aryl is independently selected from the group consisting of halogen, amino, $C_{1-4}$ alkylamino, hydroxy, cyano, $C_{1-6}$ alkyl, $C_{1-6}$ alkoxy, —CONNR$_9$, —NR$_{12}$COR$_{10}$, —NR$_{12}$SO$_2$R$_{11}$, —SO$_2$NH$_2$, and —SO$_2$NHR$_{14}$, wherein said $C_{1-6}$ alkyl is optionally substituted with one or more substituents independently selected from the group consisting of halogen and hydroxy; and each R$_{10}$ is independently selected from the group consisting of $C_{1-6}$ alkyl; $C_{1-6}$ alkoxy; $C_{3-10}$ cycloalkyl and amino, wherein said $C_{1-6}$ alkyl is substituted with one or more substituents independently selected from the group consisting of amino, cyano, halogen, and hydroxy;

wherein said $C_{1-6}$ alkoxy is substituted with one or more substituents independently selected from the group consisting of amino, $C_{1-4}$ alkylamino, cyano, di-$C_{1-4}$ alkylamino, and halogen;

wherein said $C_{3-10}$ cycloalkyl is substituted with one or more substituents independently selected from the group consisting of cyano, amino, and hydroxy; and wherein said amino is optionally substituted with one or more substituents independently selected from the group consisting of $C_{3-10}$ cycloalkyl and $C_{1-6}$ alkyl optionally substituted with one or more substituents independently selected from the group consisting of amino, $C_{1-4}$ alkylamino, cyano, di-$C_{1-4}$ alkylamino, and halogen or a pharmaceutically acceptable addition salt or a stereochemical isomeric form thereof or a N-oxide thereof.

5. A pyrido(3,2-d)pyrimidine derivative according to claim 1, wherein

R$_2$ is XR$_7$;

X is selected from the group consisting of O, S, and NR$_{13}$ wherein R$_{13}$ is H; and R$_7$ is selected from the group consisting of $C_{2-20}$ alkyl, $C_{3-10}$ cycloalkyl, and aryl $C_{1-4}$ alkyl that is benzyl when X is NR$_{13}$; and R$_7$ is $C_{1-4}$ alkyl when X is O or S;

or a pharmaceutically acceptable addition salt or a stereochemical isomeric form thereof or a N-oxide thereof.

6. A pyrido(3,2-d)pyrimidine derivative according to claim 1, wherein R$_2$ is selected from the group consisting of ethoxy, isopropylamino, 2,2,2-trifluoroethylamino, 2,2-difluoroethylamino, methanesulfonylethylamino, cyclo-propylamino and cyclopropyl, or a pharmaceutically acceptable addition salt or a stereochemical isomeric form thereof or a N-oxide thereof.

7. A pyrido(3,2-d)pyrimidine derivative according to claim 1, wherein R$_3$ is a mono-substituted or disubstituted aryl that is a phenyl group, wherein at least one substituent of said phenyl group is located in para position with respect to the carbon atom to which R$_3$ is bound, or a pharmaceutically acceptable addition salt or a stereochemical isomeric form thereof or a N-oxide thereof.

8. A pyrido(3,2-d)pyrimidine derivative according to claim 1, wherein R$_3$ is a mono-substituted or disubstituted aryl that is a phenyl group, wherein at least one substituent of said phenyl group is located in meta position with respect to the carbon atom to which R$_3$ is bound, or a pharmaceutically acceptable addition salt or a stereochemical isomeric form thereof or a N-oxide thereof.

9. A pyrido(3,2-d)pyrimidine derivative according to claim 1, wherein R$_3$ is selected from the group consisting of phenyl, 4-fluorophenyl, 4-methylphenyl, 3-chloro-4-ethoxyphenyl, 3-ethoxy-4-fluorophenyl, 3-methyl-4-fluorophenyl, 3,4-dichlorophenyl and 3,4-methylenedioxy-phenyl, or a pharmaceutically acceptable addition salt or a stereochemical isomeric form thereof or a N-oxide thereof.

10. A pyrido(3,2-d)pyrimidine derivative according to claim 1, wherein

R$_5$ is hydrogen and

R$_6$ is selected from the group consisting of $C_{3-10}$ cycloalkyl, heterocyclyl selected from imidazol-2-yl and thien-2-yl, and phenyl, wherein said phenyl is optionally substituted with one or more substituents selected from the group consisting of halogen, hydroxy, amino, nitro, cyano, trifluoromethyl, trifluoromethoxy, $C_{1-4}$ alkyl, $C_{1-4}$ alkoxy, dimethylamino, diethylamino and phenoxy, or a pharmaceutically acceptable addition salt or a stereochemical isomeric form thereof or a N-oxide thereof.

11. A pyrido(3,2-d)pyrimidine derivative according to claim 1, wherein R$_1$ is selected from the group consisting of 4-fluorobenzylamino, 2,2,2-trifluoroethylamino and 4-sulfamoylbenzylamino, or a pharmaceutically acceptable addition salt or a stereochemical isomeric form thereof or a N-oxide thereof.

12. A pyrido(3,2-d)pyrimidine derivative according to claim 1, wherein

R$_5$ is hydrogen and

R$_6$ is selected from the group consisting of $C_{1-6}$ alkyl that is trifluoromethyl, aryl that is naphthyl, imidazol-2-yl and thien-2-yl, or a pharmaceutically acceptable addition salt or a stereochemical isomeric form thereof or a N-oxide thereof.

13. A pyrido(3,2-d)pyrimidine derivative according to claim 1, wherein R$_8$ is selected from the group consisting of phenyl, pyridazinyl and pyrazolyl and wherein said R$_8$ is optionally substituted with a substituent selected from the group consisting of halogen and methyl, or a pharmaceutically acceptable addition salt or a stereochemical isomeric form thereof or a N-oxide thereof.

14. A pyrido(3,2-d)pyrimidine derivative according to claim 1, wherein:

R$_1$ is selected from the group consisting of 2,2,2-trifluoroethylamino, 4-fluorobenzylamino, 3,4-difluorobenzylamino, 2,6-difluoro-4-methoxybenzyl-amino, 4-chloro-2,6-difluorobenzylamino, 4-chloro-2-fluorobenzylamino, 2,4,6-trifluoro-benzylamino, 4-chloro-3-fluorobenzylamino, 2,4,4-trifluoro-benzylamino, 3-chloro-4-fluorobenzylamino, 2-chloro-4-fluorobenzylamino, 3-fluoro-4-trifluoromethyl-amino, 3,5-difluorobenzylamino, 3,4,5-trifluoro-benzylamino, 3-fluorobenzylamino, 3-chloro-2-fluorobenzylamino, 4 fluorophenylamino, phenylamino, 6-methyl-pyridazin-3-ylamino, pyridin-2-ylmethylamino, pyridin-3-ylmethylamino, 2-morpholin-4-ylethylamino, 2,2-difluoroethyl-amino, 2-methoxyethylamino, 4-sulfamoylbenzylamino, 1-(4 fluorophenyl)-cyclopropyl-amino, 2,4-difluorobenzylamino, 1-phenylethyl-amino, thiazol-2-ylmethylamino, oxazol-4-ylmethylamino, isoxazol-3-ylmethylamino, 4-(N-isopropylsulfamoylmethyl)benzylamino, phenethylamino, 4-methanesulfonyl-benzylamino, 4-pyrrolidin-1-yl-benzylamino, 4-(4-methylpiperazin-1-yl)benzylamino, (N,N-dimethylcarboxamido)-benzylamino, 4-[1,2,3]thiadiazol-4-ylbenzylamino, 2 fluoro-4-sulfamoylbenzylamino, 4-[1,3,4]-oxadiazol-2-ylmethylamino, thiazol-5-ylmethyl-amino 1-(4-sulfamoylphenyl)ethylamino, 4-([1,2,4](triazol-1-yl)benzylamino oxazol-2-ylmethylamino, 2-([1,2,4]-triazol-1-yl)ethylamino 1-(4-[1,2,4]triazol-1-yl-phenyl)-ethylamino, 2-(diethylphosphono)ethylamino, 2-sulfamoylethylamino, 2-carbamoylethylamino, 4-carbamoylbenzylamino, 4-(N,N-dimethylcarboxamido)-benzylamino, and 4-(N-methylmethanesulfonamido)-benzylamino;

$R_2$ is selected from the group consisting of tetrahydrofuran-3-yloxy, ethoxy, hydroxy, n-propionamido-amino, 2-methyl-2-hydroxy-propylamino, methoxy, 3-methanesulfonyl-pyrrolidin-1-yl, N-methanesulfonylethyl-N-methylamino, 1-isopropyl-piperidin-4-ylamino, ethylamino, pyridin-3-ylmethylamino, N-morpholin-4-ylethylamino, 2,2,2-trifluoroethylamino, 2-methoxyethylamino, isopropylamino, dimethylamino, diethylamino, cyclopentoxy, cyclobutoxy, propyl, methanesulfonylethylamino, 2,2-difluoroethylamino, cyclopropoxy, cyclopropyl-amino, 4-([1,2,4]triazol-1-yl)phenylamino, 3-fluorophenylamino, 2-methoxyethoxy, tetrahydro-furan-3-ylamino, oxetan-3-yloxy, 1-methylcyclopropoxy, 2-hydroxyethylamino, 1-cyano-cyclopropylamino, N-morpholinyl, N-thiomorpholinyl, N-thiomorpholinyl dioxide, cyclopropyl, N-piperidinyl and N-pyrrolidinyl, wherein said N-pyrrolidinyl is optionally substituted with $C_{1-4}$ alkylsulfonyl;

$R_3$ is selected from the group consisting of optionally mono-substituted or disubstituted aryl,
wherein each substituent of said aryl is independently selected from the group consisting of halogen, hydroxy, amino, $C_{1-4}$ alkylamino, cyano, $C_{1-6}$ alkyl, $C_{1-6}$ alkoxy, —CONHR$_9$, —NR$_{12}$COR$_{10}$, —NR$_{12}$SO$_2$R$_{11}$, —SO$_2$NH$_2$, and —SO$_2$NHR$_{14}$;
wherein said $C_{1-6}$ alkyl is optionally substituted with hydroxy;

$R_9$ is selected from the group consisting of hydrogen; $C_{3-10}$ cycloalkyl; $C_{1-6}$ alkyl; $C_{1-6}$ alkoxy; and phenyl,
wherein said $C_{3-10}$ cycloalkyl is optionally substituted with one or more substituents independently selected from the group consisting of cyano, halogen, hydroxy, oxo, amino, $C_{1-6}$ alkyl and $C_{1-6}$ alkoxy;
wherein said $C_{1-6}$ alkyl is optionally substituted with one or more substituents independently selected from the group consisting of amino, alkylamino, cyano, di-$C_{1-4}$ alkylamino, and halogen; and
wherein said phenyl is optionally and independently substituted with one or more halogen;

$R_{10}$ and $R_{11}$ are each independently selected from the group consisting of $C_{1-6}$ alkyl optionally substituted with one or more substituents independently selected from the group consisting of amino, cyano, halogen, and hydroxy; $C_{1-6}$ alkoxy; $C_{3-10}$ cycloalkyl; and amino
wherein said $C_{1-6}$ alkyl is optionally substituted with one or more substituents independently selected from the group consisting of amino, cyano, halogen, and hydroxy;
wherein said $C_{1-6}$ alkoxy is optionally substituted with one or more substituents independently selected from the group consisting of amino, $C_{1-4}$ alkylamino, cyano, di-$C_{1-4}$ alkylamino, and halogen;
wherein said $C_{3-10}$ cycloalkyl is optionally substituted with one or more substituents independently selected from the group consisting of amino and hydroxy;
wherein said amino is optionally substituted with one or more substituents independently selected from the group consisting of $C_{3-10}$ cycloalkyl and $C_{1-6}$ alkyl optionally substituted with one or more substituents independently selected from the group consisting of amino, $C_{1-4}$ alkylamino, cyano, di-$C_{1-4}$ alkylamino, and halogen;

$R_{12}$ is selected from the group consisting of hydrogen and $C_{1-6}$ alkyl,
wherein said $C_{1-6}$ alkyl is optionally substituted with one or more substituents independently selected from the group consisting of cyano, halogen and hydroxy; and
$R_{14}$ is $C_{1-4}$ alkyl optionally substituted with one or more $C_{1-4}$ alkoxy;

or a pharmaceutically acceptable addition salt or a stereochemical isomeric form thereof or a N-oxide thereof.

15. A pyrido(3,2-d)pyrimidine derivative according to claim 1, wherein:
$R_1$ is selected from the group consisting of —NH—CHR$_5$R$_6$ and —NH—R$_8$;
$R_5$ and $R_6$ are independently selected from the group consisting of hydrogen, $C_{1-6}$ alkyl, $C_{3-10}$ cycloalkyl, aryl and heterocyclyl selected from imidazol-2-yl and thien-2-yl, with the proviso that both $R_5$ and $R_6$ are not hydrogen, and
wherein said aryl is optionally substituted with one or more substituents selected from the group consisting of halogen, hydroxy, amino, nitro, cyano, trifluoromethyl, trifluoromethoxy, $C_{1-4}$ alkyl optionally substituted with —SO$_2$NHR$_{13}$, wherein R$_{13}$ is $C_{1-4}$ alkyl, $C_{1-4}$ alkoxy, di-$C_{1-4}$ alkylamino, mono-$C_{1-4}$ alkylamino, —SO$_2$NHR$_{13}$ wherein R$_{13}$ is hydrogen, —CON(R$_{13}$)$_2$ wherein R$_{13}$ is hydrogen, —SO$_2$R$_{13}$ wherein R$_{13}$ is $C_{1-4}$alkyl, —NHSO$_2$R$_{13}$ wherein R$_{13}$ is hydrogen, —NHSO$_2$R$_{13}$ wherein R$_{13}$ is $C_{1-4}$ alkyl, and phenoxy;
wherein said $C_{1-6}$ alkyl is substituted with one or more substituents selected from the group consisting of halogen, $C_{1-4}$ alkoxy, aryl, —P(O)(OR$_{13}$)$_2$ wherein R$_{13}$ is $C_{1-6}$ alkyl, carbamoyl, —SO$_2$NHR$_{13}$ wherein R$_{13}$ is hydrogen and —SO$_2$NHR$_{13}$ wherein R$_{13}$ is $C_{1-4}$ alkyl;

$R_8$ is selected from the group consisting of $C_{3-10}$ cycloalkyl, heteroaryl selected from pyridazinyl and pyrazolyl and aryl
wherein said heteroaryl or aryl is optionally substituted with one or more substituents selected from the group consisting of halogen and $C_{1-4}$ alkyl and wherein said $C_{3-10}$ cycloalkyl is optionally substituted at the carbon position adjacent to the N atom of —NHR$_8$ with aryl wherein said aryl is optionally substituted with halogen;

$R_2$ is selected from the group consisting of tetrahydrofuran-3-yloxy, ethoxy, hydroxy, n-propionamido-amino, 2-methyl-2-hydroxy-propylamino, methoxy, 3-methanesulfonyl-pyrrolidin-1-yl, N-methanesulfonylethyl-N-methylamino, 1-isopropyl-piperidin-4-ylamino, ethylamino, pyridin-3-ylmethylamino, N-morpholin-4-ylethylamino, 2,2,2-trifluoroethylamino, 2-methoxyethylamino, isopropylamino, dimethylamino, diethylamino, cyclopentoxy, cyclobutoxy, propyl, methanesulfonyl-ethylamino, 2,2-difluoroethylamino, cyclopropoxy, cyclopropylamino, 4-[1,2,4]triazol-1-yl-anilino, 3-fluoroanilino, 2-methoxy-ethoxy, tetrahydro-furan-3-ylamino, oxetan-3-yloxy, 1-methylcyclopropoxy, 2-hydroxy-ethylamino, 1-cyano-cyclopropylamino, N-morpholinyl, N-thiomorpholinyl, N-thiomorpholinyl dioxide, cyclopropyl, N-piperidinyl and N-pyrrolidinyl, wherein said N-pyrrolidinyl is optionally substituted with $C_{1-4}$ alkylsulfonyl; and $R_3$ is selected from the group consisting of optionally mono-substituted or disubstituted aryl,
wherein each substituent of said aryl is independently selected from the group consisting of halogen, hydroxy amino, $C_{1-4}$ alkylamino, cyano, $C_{1-6}$ alkyl, $C_{1-6}$ alkoxy, —CONHR$_9$, —NR$_{12}$COR$_{10}$, —NR$_{12}$SO$_2$R$_{11}$, —SO$_2$NH$_2$, and —SO$_2$NHR$_{14}$; and
wherein said $C_{1-6}$ alkyl is optionally substituted with hydroxyl;

$R_9$ is selected from the group consisting of hydrogen, $C_{3-10}$ cycloalkyl; $C_{1-6}$ alkyl; $C_{1-6}$ alkoxy; and phenyl
wherein said $C_{3-10}$ cycloalkyl is optionally substituted with one more substituents independently selected from the group consisting of cyano, halogen, hydroxy, oxo, amino, $C_{1-6}$ alkyl and $C_{1-6}$ alkoxy;
wherein said $C_{1-6}$ alkyl is optionally substituted with one or more substituents independently selected from the group consisting of amino, alkylamino, cyano, dialkylamino, and halogen; $C_{1-6}$ alkoxy; and
wherein said phenyl is optionally and independently substituted with one or more halogen;

$R_{10}$ and $R_{11}$ are each independently selected from the group consisting of $C_{1-6}$ alkyl; $C_{1-6}$ alkoxy; $C_{3-10}$ cycloalkyl; and amino
wherein said $C_{1-6}$ alkyl is optionally substituted with one or more substituents independently selected from the group consisting of amino, cyano, halogen, and hydroxy;
wherein said $C_{1-6}$ alkoxy is optionally substituted with one or more substituents independently selected from the group consisting of amino, $C_{1-4}$ alkylamino, cyano, di-$C_{1-4}$ alkylamino, and halogen;
wherein said $C_{3-10}$ cycloalkyl is optionally substituted with one or more substituents independently selected from the group consisting of amino and hydroxy; and
wherein said amino is optionally substituted with one or more substituents independently selected from the group consisting of $C_{3-10}$ cycloalkyl and $C_{1-6}$ alkyl optionally substituted with one or more substituents independently selected from the group consisting of amino, $C_{1-4}$ alkylamino, cyano, di-$C_{1-4}$ alkylamino, and halogen;

$R_{12}$ is selected from the group consisting of hydrogen and $C_{1-6}$ alkyl, wherein said $C_{1-6}$ alkyl is optionally substituted with one or more substituents independently selected from the group consisting of cyano, halogen and hydroxy; and $R_{14}$ is $C_{1-4}$ alkyl optionally substituted with one or more substituents independently selected from the group consisting of $C_{1-4}$ alkoxy;

or a pharmaceutically acceptable addition salt or a stereochemical isomeric form thereof or a N-oxide thereof.

16. A pyrido(3,2-d)pyrimidine derivative according to claim 1, wherein:

$R_1$ is selected from the group consisting of —NH—CHR$_5$R$_6$ and —NH—R$_8$;

$R_5$ and $R_6$ are independently selected from the group consisting of hydrogen, $C_{1-6}$ alkyl, $C_{3-10}$ cycloalkyl, aryl and heterocyclyl selected from imidazol-2-yl and thien-2-yl, with the proviso that both $R_5$ and $R_6$ are not hydrogen, and
wherein said aryl is optionally substituted with one or more substituents selected from the group consisting of halogen, hydroxy, amino, nitro, cyano, trifluoromethyl, trifluoromethoxy, $C_{1-4}$ alkyl optionally substituted with —SO$_2$NHR$_{13}$, wherein $R_{13}$ is $C_{1-4}$ alkyl, $C_{1-4}$ alkoxy, di-$C_{1-4}$ alkylamino, mono-$C_{1-4}$ alkylamino, —SO$_2$NHR$_{13}$ wherein $R_{13}$ is hydrogen, —CO$_2$NHR$_{13}$ wherein $R_{13}$ is hydrogen, —SO$_2$R$_{13}$ wherein $R_{13}$ is $C_{1-4}$ alkyl, —NHSO$_2$R$_{13}$ wherein $R_{13}$ is hydrogen, —NHSO$_2$R$_{13}$ wherein $R_{13}$ is $C_{1-4}$ alkyl, and phenoxy;
wherein said $C_{1-6}$ alkyl is substituted with one or more substituents selected from the group consisting of halogen, $C_{1-4}$ alkoxy, aryl, —P(O)(OR$_{13}$)$_2$ wherein $R_{13}$ is $C_{1-6}$ alkyl, carbamoyl, —SO$_2$NHR$_{13}$ wherein $R_{13}$ is hydrogen and —SO$_2$NHR$_{13}$ wherein $R_{13}$ is $C_{1-4}$ alkyl;

$R_8$ is selected from the group consisting of $C_{3-10}$ cycloalkyl, heteroaryl selected from pyridazinyl and pyrazolyl and aryl
wherein said heteroaryl or aryl is optionally substituted with one or more substituents selected from the group consisting of halogen and $C_{1-4}$ alkyl and
wherein said $C_{3-10}$ cycloalkyl is optionally substituted at the carbon position adjacent to the N atom of —NHR$_8$ with aryl wherein said aryl is optionally substituted with halogen;

$R_2$ is selected from the group consisting of tetrahydrofuran-3-yloxy, ethoxy, hydroxy, 2 carbamoylethylamino, 2-methyl-2-hydroxy-propylamino, methoxy, 3-methanesulfonyl-pyrrolidin-1-yl, N-methanesulfonylethyl-N-methylamino, 1-isopropylpiperidin-4-ylamino, ethylamino, pyridin-3-ylmethylamino, N-morpholin-4-ylethylamino, 2,2,2-trifluoroethylamino, 2-methoxyethylamino, isopropylamino, dimethylamino, diethylamino, cyclopentoxy, cyclobutoxy, propyl, methane-sulfonylethylamino, 2,2-difluoroethylamino, cyclopropoxy, cyclopropylamino, 4-[1,2,4]triazol-1-yl-anilino, 3-fluoroanilino, 2-methoxy-ethoxy, tetrahydrofuran-3-ylamino, oxetan-3-yloxy, 1-methylcyclopropoxy, 2-hydroxyethylamino, 1-cyano-cyclopropylamino, N-morpholinyl, N-thiomorpholinyl, N-thiomorpholinyl dioxide, cyclopropyl, N-piperidinyl and N-pyrrolidinyl, wherein said N-pyrrolidinyl is optionally substituted with $C_{1-4}$ alkylsulfonyl; and $R_3$ is selected from the group consisting of 4-fluorophenyl, 5-amino-pyrazin-2-yl, 4-(N-(2-dimethylaminoethyl)carbamoyl)phenyl, 3-chloro-4-fluorophenyl, 4-(N-cyclopropylcarbamoyl)phenyl, 3-(N-methylsulfonylamino)phenyl, 4-(cyclopropanecarboxamido)phenyl, 3-sulfamoyl-4-fluorophenyl, 4-(2-hydroxy-acetamido)-phenyl, 4-(2-amino-acetamido)phenyl, 4-[3-(2-morpholin-4-yl-ethyl)-ureido]phenyl, 4-(morpholine-4-carboxamido)phenyl, 4-(pyrrolidine-1-carboxamido)phenyl, 4-(3-cyclopropylureido)phenyl, 4-ureidophenyl, 4-[(4-hydroxy-2-oxo-pyrrolidin-1-yl)]phenyl, 1H-indazol-5-yl, 2-oxo-indol-5-yl, 2-cyclopropanecarboxamido-pyrimidin-5-yl, 3-(2-pyrrolidin-1-yl-ethanesulfonamido)phenyl,
3-(cyclopropanesulfonamido)-phenyl, 4-sulfamoylphenyl, 3-(dimethylaminesulfonamido)phenyl 3-sulfamoylphenyl, 4-(3-hydroxy-2-oxo-pyrrolidin-1-yl)phenyl, 2-fluoropyridin-5-yl, 4-(4-hydroxypyrrolidin-2-carboxamido)phenyl, 4-(pyrrolidin-2-carboxamido)phenyl, 4-(pyrrolidin-3-carboxamido)-3-fluoro-phenyl, 4-(pyrrolidin-3-carboxamido)phenyl, 4-(2-(pyrrolidin-1-yl)-ethoxycarbonyl-amino)-phenyl, 3-(4-(tert-butoxycarbonylamino)-piperidin-1-sulfonyl)-4-chlorophenyl, 3-(N-(1 (tert-butoxycarbonyl)-pyrrolidin-3-yl)-sulfamoyl)-4-fluoro-phenyl,
4-(methoxycarbonylamino)-phenyl, 3-(N-(1-(tert-butoxycarbonyl)-piperidin-4-yl)-sulfamoyl)-4-chloro-phenyl, 3-(N-(1-(tert-butoxycarbonyl)-piperidin-4-yl)-sulfamoyl)-4-fluoro-phenyl, 4-[3-(2 pyrrolidin-1-yl-ethyl)ureido]phenyl, 4-(N-(2-hydroxy-1,1-dimethylethyl)-carbamoyl)phenyl 4-(N-(2-(pyrrolidin-1-yl)-1,1-dimethyl-ethyl)carbamoyl)phenyl, 2-amino-thiazol-5-yl, 5-hydroxymethylfuran-2-yl, 4-(N-pyrrolidin-2-one)-phenyl, 4-carbamoyl-phenyl, 4-(N-1 cyano-1-cyclopropyl-carbamoyl)-phenyl, 4-(N-1 amino-1-cyclopropylcarbamoyl)-phenyl, 4-(N-1-hydroxy-1-cyclopropylcarboxamido)-phenyl, 3-(N-(2-hydroxyethyl)methylsulfonamido)-phenyl, 4-(N-(2-(morpholin-4-yl)-1,1-dimethyl-ethyl)carbamoyl) phenyl, 4-(2-oxo-pyrrolidin-1-yl)phenyl, 4-(2-amino-2-methylpropionamido)phenyl, 4-(N-cyclopropylcarbamoyl)phenyl, 4-(3-hydroxy-2-aminopropionamido)phenyl, 3-cyclopropanesulfonamido-4-fluoro-phenyl, 4-(2-amino-propionamido)-phenyl, 4-(3-hydroxy-2-amino-butyramido)phenyl, 3,5-dimethyl-isoxazol-4-yl, 1-methyl-1H-pyrazol-4-yl, 5-pyrrolidin-1-ylpyrazin-2-yl, 2-trifluoromethylpyridin-4-yl, 2-aminopyridin-4-yl, 4-hydroxyphenyl, 2-pyrrolidin-1-yl-thiazol-4-yl, 2-methoxypyridin-4-yl, 2-cyanopyridin-4-yl, 2-aminopyrimidin-5-yl, 3-cyanophenyl, 4-(1-methylpyrrolidine-3-carboxamido)-3-fluorophenyl, 4-(1-methylpyrrolidine-3-carboxamido)-phenyl, 3-cyclopropanesulfonamido-4-fluoro-phenyl, 1H-pyrazol-4-yl, 3-(N (1 isopropyl-piperidin-4-yl)sulfamoyl)-4-chlorophenyl, 3-(N-(2-pyrrolidin-1-yl-ethyl)sulfamoyl)-4-chlorophenyl, 3-(4-isopropyl-piperazin-1-sulfonyl)-4-chloro-phenyl 3-(N-pyrrolidin-3-ylsulfamoyl)-4-chlorophenyl, 3-(N-(2-methoxyethyl) sulfamoyl)-4-chlorophenyl, 3-(N-piperidin-4-ylsulfamoyl)-4-chlorophenyl, pyridazin-4-yl, 4-cyanophenyl, 4-fluoro-3-(piperazin-1-sulfonyl)-phenyl, 4-fluoro-3-(4-tert-butoxycarbonyl-piperazin-1-sulfonyl)-phenyl, 4-isopropylamino-pyrazol-1-yl, [1,2,4] triazol-1-yl, imidazol-1-yl, imidazol-2-yl, 6-oxo-1,6-dihydro-pyridin-3-yl, 2-oxo-1,2-dihydro-pyridin-4-yl, 3-hydroxy-2-oxo-pyrrolidin-1-yl, and 4-chlorophenyl, or a pharmaceutically acceptable addition salt or a stereochemical isomeric form thereof or a N-oxide thereof.

17. A pharmaceutical composition comprising:
one or more pharmaceutically acceptable carriers,
a pyrido(3,2-d)pyrimidine derivative according to claim 1, or a pharmaceutically acceptable addition salt or a stereochemical isomeric form thereof or a N-oxide thereof, and
optionally one or more antiviral agents.

* * * * *